United States Patent
Geist et al.

(10) Patent No.: US 10,463,481 B2
(45) Date of Patent: Nov. 5, 2019

(54) PROSTHETIC VALVE FOR REPLACING MITRAL VALVE

(71) Applicant: Edwards Lifesciences Corporation, Irvine, CA (US)

(72) Inventors: Stephen C. Geist, Costa Mesa, CA (US); Robert C. Taft, Irvine, CA (US); Travis Zenyo Oba, Yorba Linda, CA (US); Sam Sok, Santa Ana, CA (US); Matthew A. Peterson, Costa Mesa, CA (US); Kevin M. Golemo, Mission Viejo, CA (US); Mark Chau, Aliso Viejo, CA (US); Seung-Beom Yi, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 127 days.

(21) Appl. No.: 15/259,988

(22) Filed: Sep. 8, 2016

(65) Prior Publication Data

US 2017/0231759 A1    Aug. 17, 2017

Related U.S. Application Data

(63) Continuation of application No. 14/171,603, filed on Feb. 3, 2014, now Pat. No. 9,439,763.

(Continued)

(51) Int. Cl.
*A61F 2/24* (2006.01)
*A61B 6/00* (2006.01)
*A61B 8/12* (2006.01)

(52) U.S. Cl.
CPC .......... *A61F 2/2418* (2013.01); *A61F 2/2409* (2013.01); *A61F 2/2412* (2013.01);

(Continued)

(58) Field of Classification Search
CPC .... A61F 2/2418; A61F 2/2409; A61F 2/2412; A61F 2/2436; A61F 2/2466
See application file for complete search history.

(56) References Cited

U.S. PATENT DOCUMENTS 3,409,013 A   11/1968   Berry
3,472,230 A   10/1969   Fogarty
(Continued)

FOREIGN PATENT DOCUMENTS

DE   2246526 A1   3/1973
DE   19532846 A1  3/1997
(Continued)

OTHER PUBLICATIONS

International Search Report, dated May 1, 2014.
(Continued)

*Primary Examiner* — Christopher D. Prone
*Assistant Examiner* — Tiffany P Shipmon
(74) *Attorney, Agent, or Firm* — Klarquist Sparkman LLP

(57) ABSTRACT

A prosthetic heart valve includes a collapsible and expandable frame having a main body, an atrial portion, and at least one ventricular anchor. The atrial portion extends radially outwardly relative to the main body and the ventricular anchor extends from a ventricular end of the main body. The main body and the atrial portion are preferably separate metal components that are coupled together via sutures or a fabric member. The prosthetic heart valve also includes a valve structure that is supported in the main body of the frame. The valve structure has a plurality of leaflets for regulating the flow of blood in one direction.

20 Claims, 81 Drawing Sheets

Related U.S. Application Data

(60) Provisional application No. 61/914,648, filed on Dec. 11, 2013, provisional application No. 61/760,577, filed on Feb. 4, 2013.

(52) U.S. Cl.
CPC .......... *A61F 2/2436* (2013.01); *A61F 2/2466* (2013.01); *A61B 6/4441* (2013.01); *A61B 8/12* (2013.01); *A61F 2210/0014* (2013.01); *A61F 2220/0008* (2013.01); *A61F 2220/0016* (2013.01); *A61F 2220/0075* (2013.01); *A61F 2230/005* (2013.01); *A61F 2230/0054* (2013.01); *A61F 2230/0078* (2013.01); *A61F 2250/0018* (2013.01); *A61F 2250/0029* (2013.01); *A61F 2250/0069* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,287,339 B1 | 9/2001 | Vazquez et al. |
| 6,299,637 B1 | 10/2001 | Shaolian |
| 6,302,906 B1 | 10/2001 | Goicoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,436,120 B1 | 8/2002 | Meglin |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |

(56) References Cited

U.S. PATENT DOCUMENTS

| | | |
|---|---|---|
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,892,281 B2 | 2/2011 | Seguin et al. |
| 7,914,575 B2 | 3/2011 | Guyenot et al. |
| 7,993,394 B2 | 8/2011 | Hariton et al. |
| 8,007,992 B2 | 8/2011 | Tian et al. |
| 8,029,556 B2 | 10/2011 | Rowe |
| 8,092,521 B2 | 1/2012 | Figulla et al. |
| 8,118,866 B2 | 2/2012 | Herrmann et al. |
| 8,167,932 B2 | 5/2012 | Bourang et al. |
| 8,206,437 B2 | 6/2012 | Bonhoeffer et al. |
| 8,216,174 B2 | 7/2012 | Wilk et al. |
| 8,317,858 B2 | 11/2012 | Straubinger et al. |
| 8,398,704 B2 | 3/2013 | Straubinger et al. |
| 8,407,380 B2 | 3/2013 | Matsunaga et al. |
| 8,416,643 B2 | 4/2013 | Magee |
| 8,449,599 B2 | 5/2013 | Chau et al. |
| 8,460,370 B2 | 6/2013 | Zakay |
| 9,439,763 B2 | 9/2016 | Geist et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0092858 A1 | 5/2004 | Wilson et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0137688 A1 | 6/2005 | Salahieh et al. |
| 2005/0137698 A1 | 6/2005 | Salahieh et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0025857 A1 | 2/2006 | Bergheim et al. |
| 2006/0058872 A1 | 3/2006 | Salahieh et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0195134 A1 | 8/2006 | Crittenden |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0027534 A1 | 2/2007 | Bergeim et al. |
| 2007/0066863 A1 | 3/2007 | Rafiee et al. |
| 2007/0088431 A1 | 4/2007 | Bourang et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0270943 A1 | 11/2007 | Solem |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082166 A1 | 4/2008 | Styrc et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0174364 A1 | 7/2010 | Hoffman et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2011/0015616 A1 | 1/2011 | Straubinger et al. |
| 2011/0015729 A1 | 1/2011 | Jimenez et al. |
| 2011/0029072 A1 | 2/2011 | Gabbay |
| 2011/0137397 A1* | 6/2011 | Chau ............... A61F 2/2418 623/1.11 |
| 2011/0137410 A1 | 6/2011 | Hacohen |
| 2011/0153008 A1 | 6/2011 | Marchand et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0238159 A1 | 9/2011 | Guyenot et al. |
| 2011/0288634 A1 | 11/2011 | Tuval et al. |
| 2011/0319989 A1 | 12/2011 | Lane et al. |
| 2012/0035722 A1 | 2/2012 | Tuval |
| 2012/0046741 A1 | 2/2012 | Tuval et al. |
| 2012/0046742 A1 | 2/2012 | Tuval et al. |
| 2012/0101570 A1 | 4/2012 | Tuval et al. |
| 2012/0101572 A1* | 4/2012 | Kovalsky ............ A61F 2/2418 623/2.19 |
| 2012/0123529 A1 | 5/2012 | Levi et al. |
| 2012/0185039 A1 | 7/2012 | Tuval et al. |
| 2012/0197386 A1 | 8/2012 | Von Segesser et al. |

(56) References Cited

U.S. PATENT DOCUMENTS

| | | |
|---|---|---|
| 2012/0209374 A1 | 8/2012 | Bonhoeffer et al. |
| 2012/0283823 A1 | 11/2012 | Bonhoeffer et al. |
| 2012/0310336 A1 | 12/2012 | Figulla et al. |
| 2013/0073035 A1 | 3/2013 | Tuval et al. |
| 2013/0079869 A1 | 3/2013 | Straubinger et al. |
| 2013/0310928 A1 | 11/2013 | Morriss et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1469797 A1 | 10/2004 |
| EP | 1570809 A1 | 9/2005 |
| EP | 1653888 A2 | 5/2006 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 1991017720 A1 | 11/1991 |
| WO | 9217118 A1 | 10/1992 |
| WO | 93001768 A1 | 2/1993 |
| WO | 9724080 A1 | 7/1997 |
| WO | 1998029057 A1 | 7/1998 |
| WO | 9933414 A1 | 7/1999 |
| WO | 1999040964 A1 | 8/1999 |
| WO | 1999047075 A1 | 9/1999 |
| WO | 0018333 A1 | 4/2000 |
| WO | 2000041652 A1 | 7/2000 |
| WO | 2000047139 A1 | 8/2000 |
| WO | 0128459 A1 | 4/2001 |
| WO | 0135878 A2 | 5/2001 |
| WO | 01049213 A2 | 7/2001 |
| WO | 0154624 A1 | 8/2001 |
| WO | 0154625 A1 | 8/2001 |
| WO | 2001062189 | 8/2001 |
| WO | 2001064137 A1 | 9/2001 |
| WO | 01076510 A1 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 0347468 A1 | 6/2003 |
| WO | 2005034812 A1 | 4/2005 |
| WO | 2005087140 A1 | 9/2005 |
| WO | 2005102015 A2 | 11/2005 |
| WO | 2006014233 A2 | 2/2006 |
| WO | 2006034008 A2 | 3/2006 |
| WO | 2006108090 A2 | 10/2006 |
| WO | 2006111391 A1 | 10/2006 |
| WO | 2006138173 A2 | 12/2006 |
| WO | 2008005405 A2 | 1/2008 |
| WO | 2008/029296 A2 | 3/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009024859 A2 | 2/2009 |
| WO | 2009116041 A2 | 9/2009 |
| WO | 2009132187 A1 | 10/2009 |
| WO | 2010057262 A1 | 5/2010 |
| WO | 2010/127041 A1 | 11/2010 |
| WO | 2011/057087 A1 | 5/2011 |
| WO | 2011072084 A2 | 6/2011 |
| WO | 2012177942 A2 | 12/2012 |

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Transluminal Placement of Endovascular Stent-Grafts for the Treatment of Descending Thoracic Aortic Aneurysms, New Engl. J.Med., 1994; 331:1729-34.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, http://www.nytimes.com/1991/01/03/health/device-that-opens-clogged-arteri- es-gets-a-faili . . . , Jul. 29, 2009, 2 pages.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschlu.beta. des Ductus Arteriosus Persistens ohne Thorakotomie," Thoraxchirurgie Vaskulare Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rosch, M.D., Josef, "The Birth, Early Years and Future of Interventional Radiology," J Vasc Intery Radiol 2003; 14:841-853.

Ross, F.R.C.S., D.N., "Aortic Valve Surgery," Guys Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

(56) References Cited

OTHER PUBLICATIONS

Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, Ulrich, "An Overview of Intravascular Stents: Old and New," Chapter 48, Textbook of Interventional Cardiology, 2.sup.nd Edition, W.B. Saunders Company, Philadelphia, PA, .COPYRGT. 1994, 1990, pp. 803-815.
Uchida, Barry T., et al., "Modifications of Gianturco Expandable Wire Stents," AJR;150, May 1988, Dec. 3, 1987, pp. 1185-1187.
Urban, M.D., Philip, "Coronary Artery Stenting," Editions Medecine et Hygiene, Geneve, 1991, pp. 5-47.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Wheatley, M.D., David J., "Valve Prostheses," Rob & Smith's Operative Surgery, Fourth Edition, pp. 415-424, Butterworths 1986.

\* cited by examiner

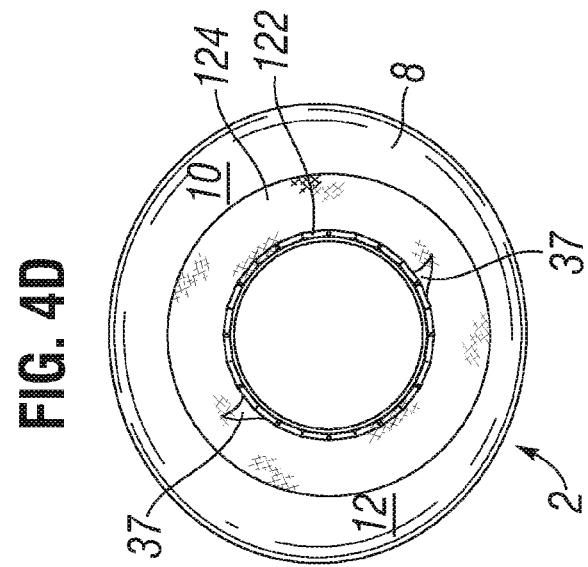
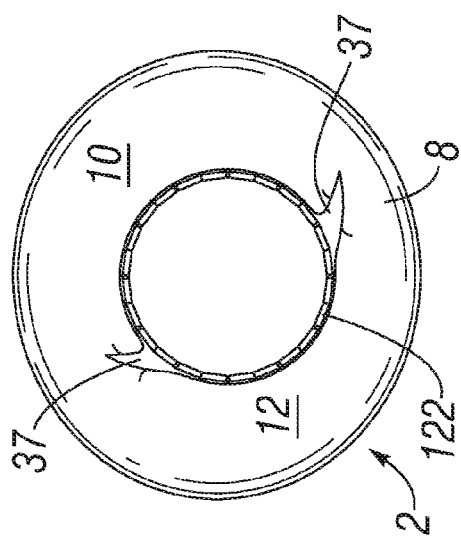
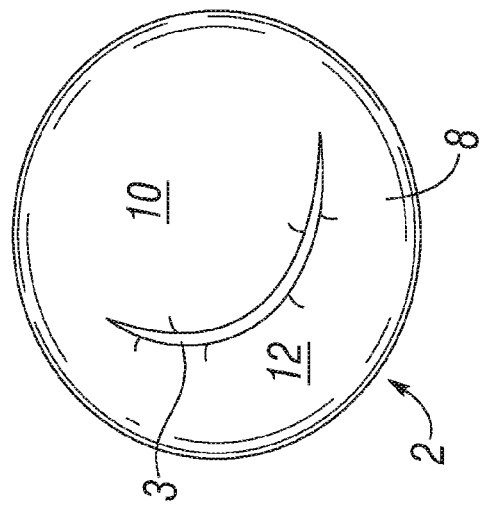

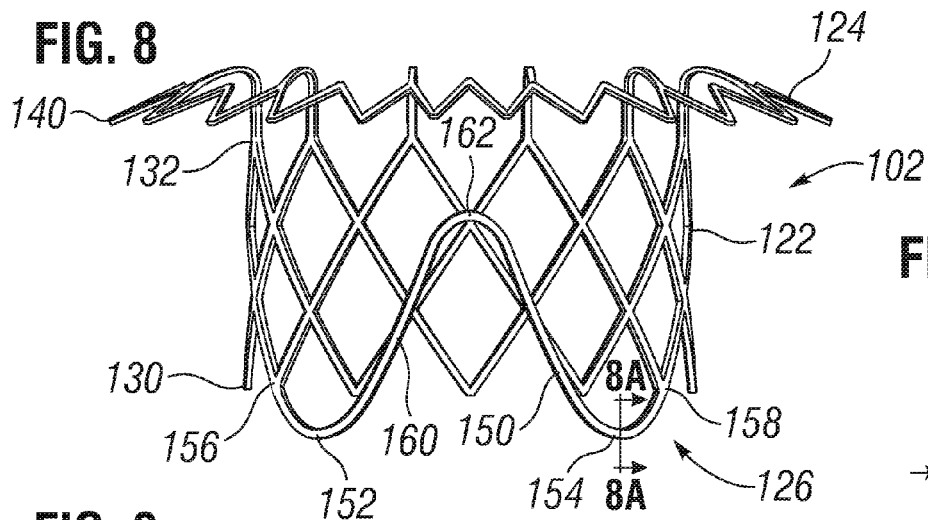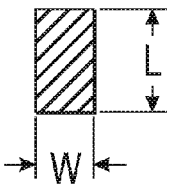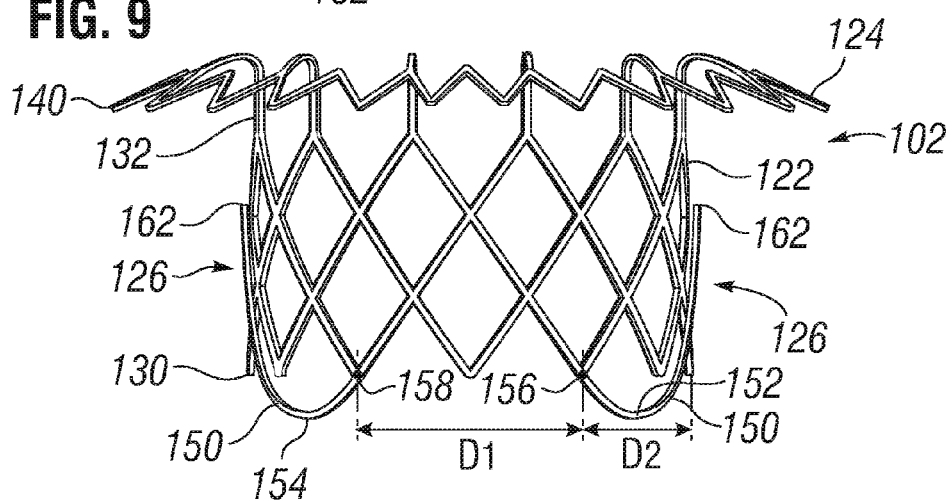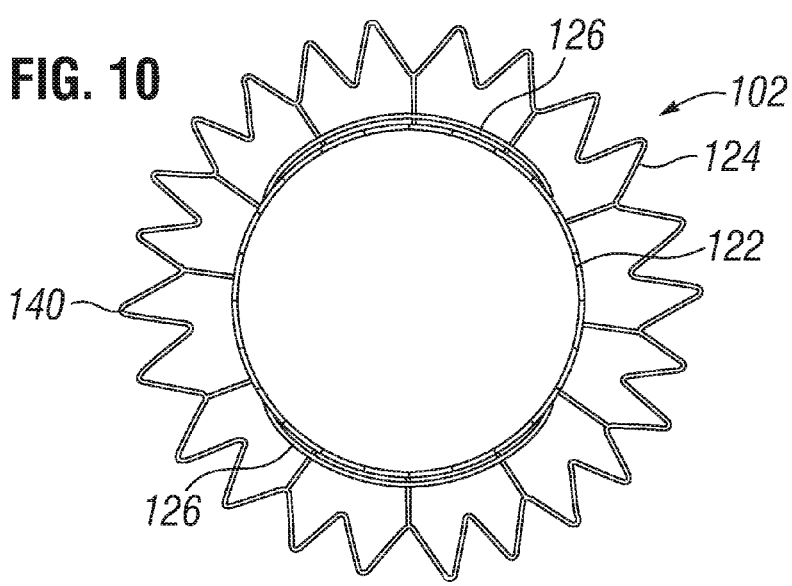

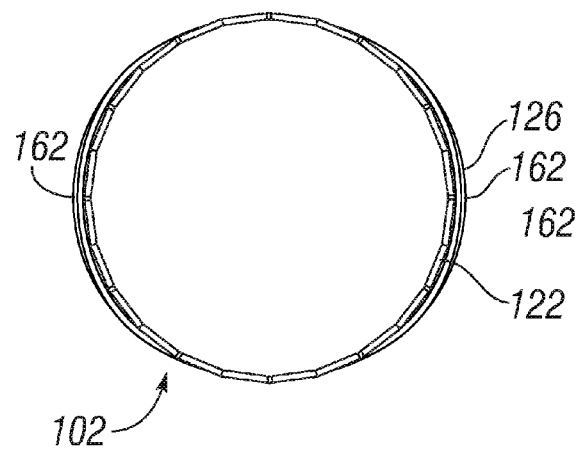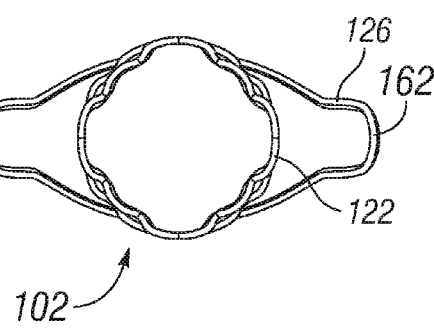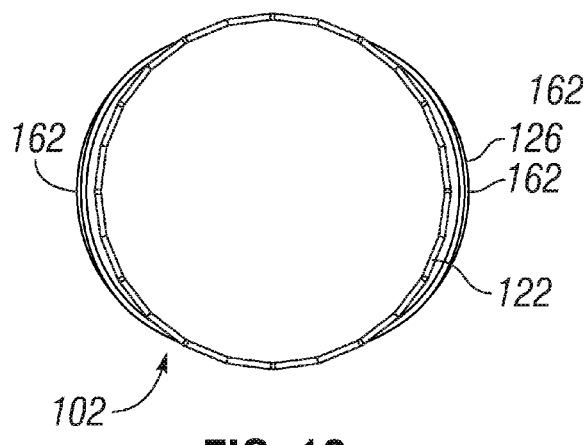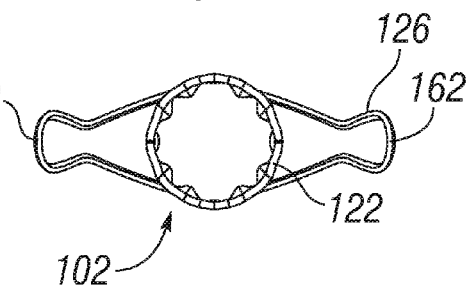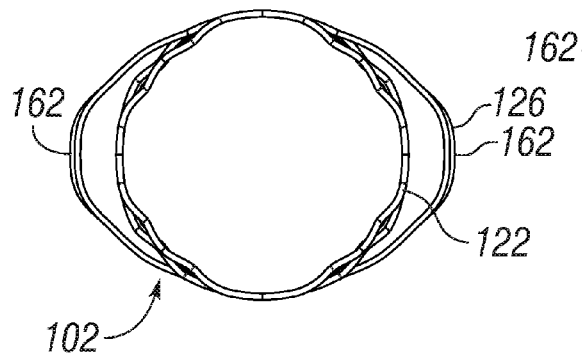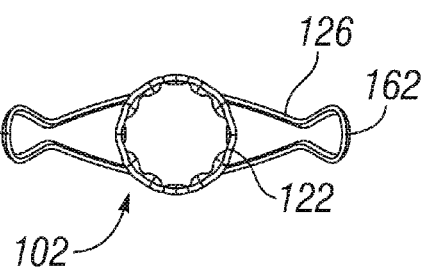

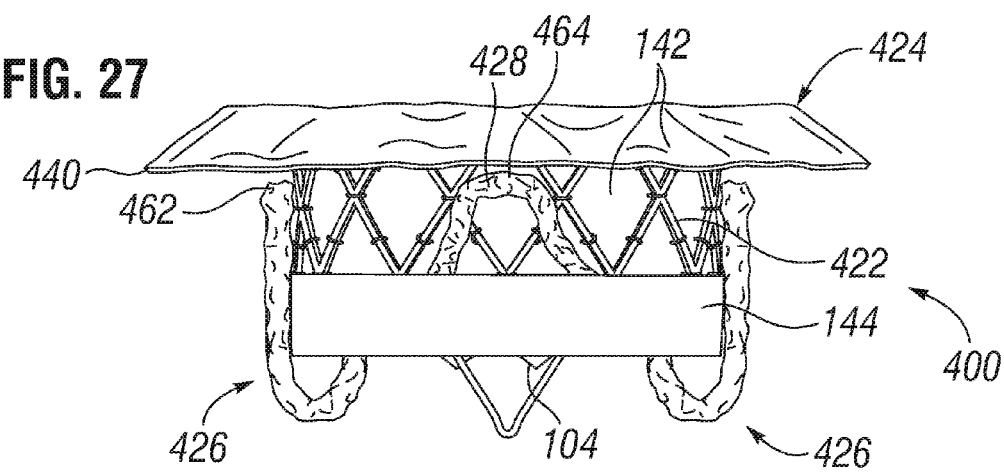
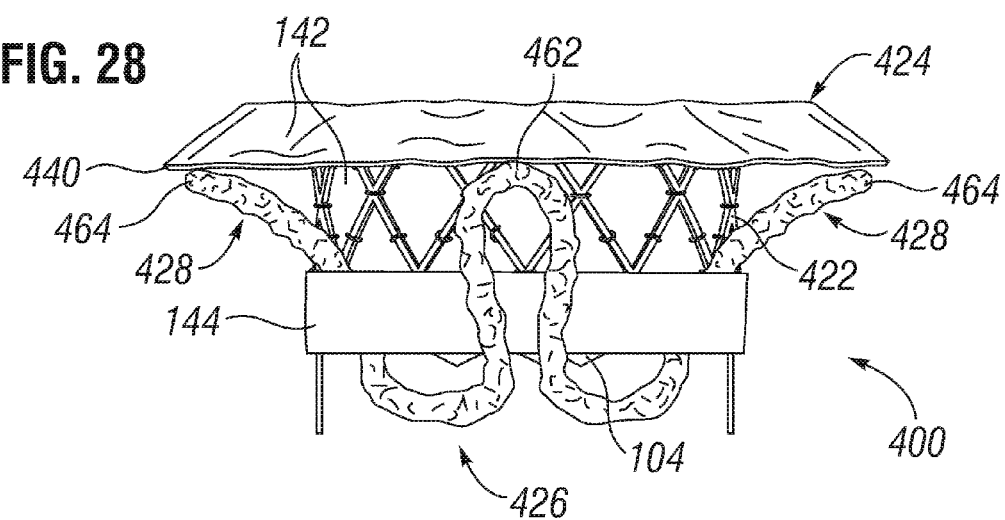
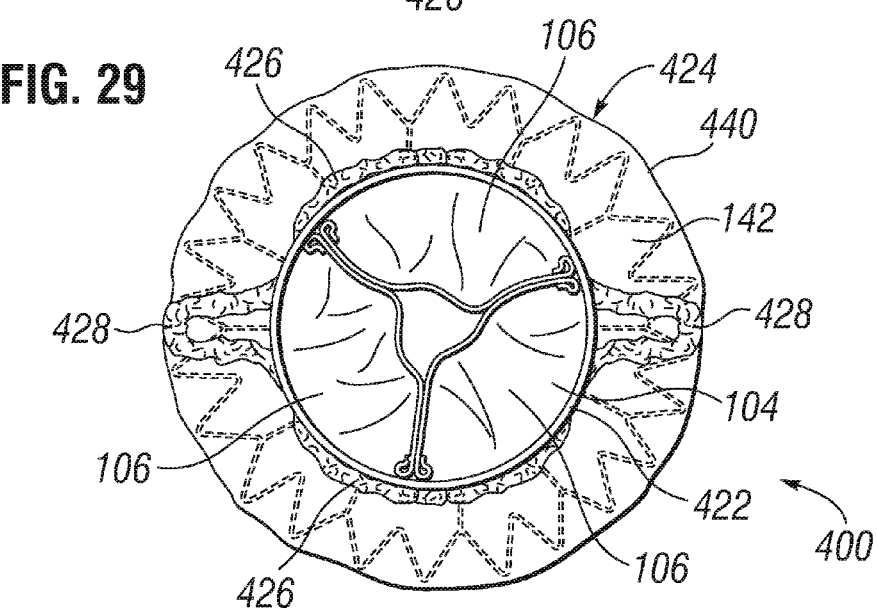

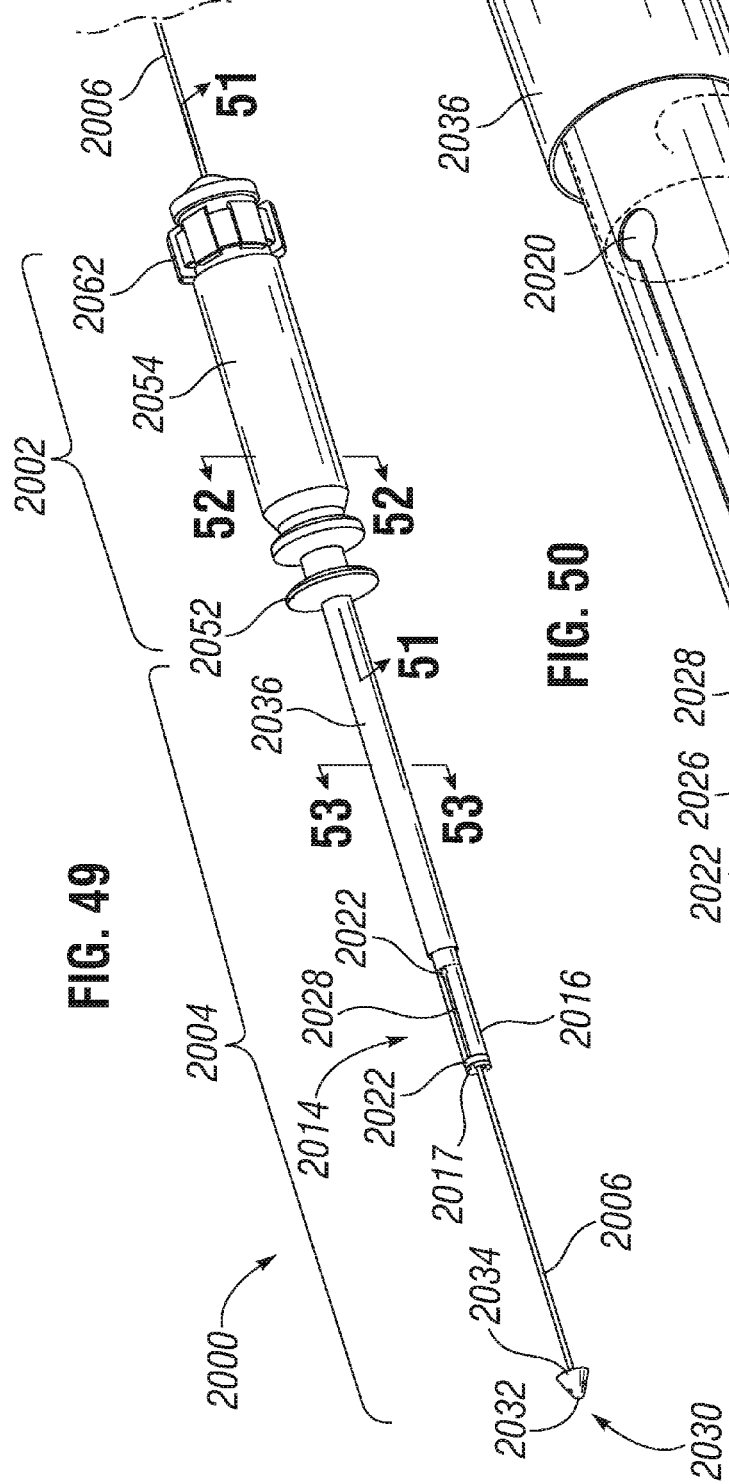

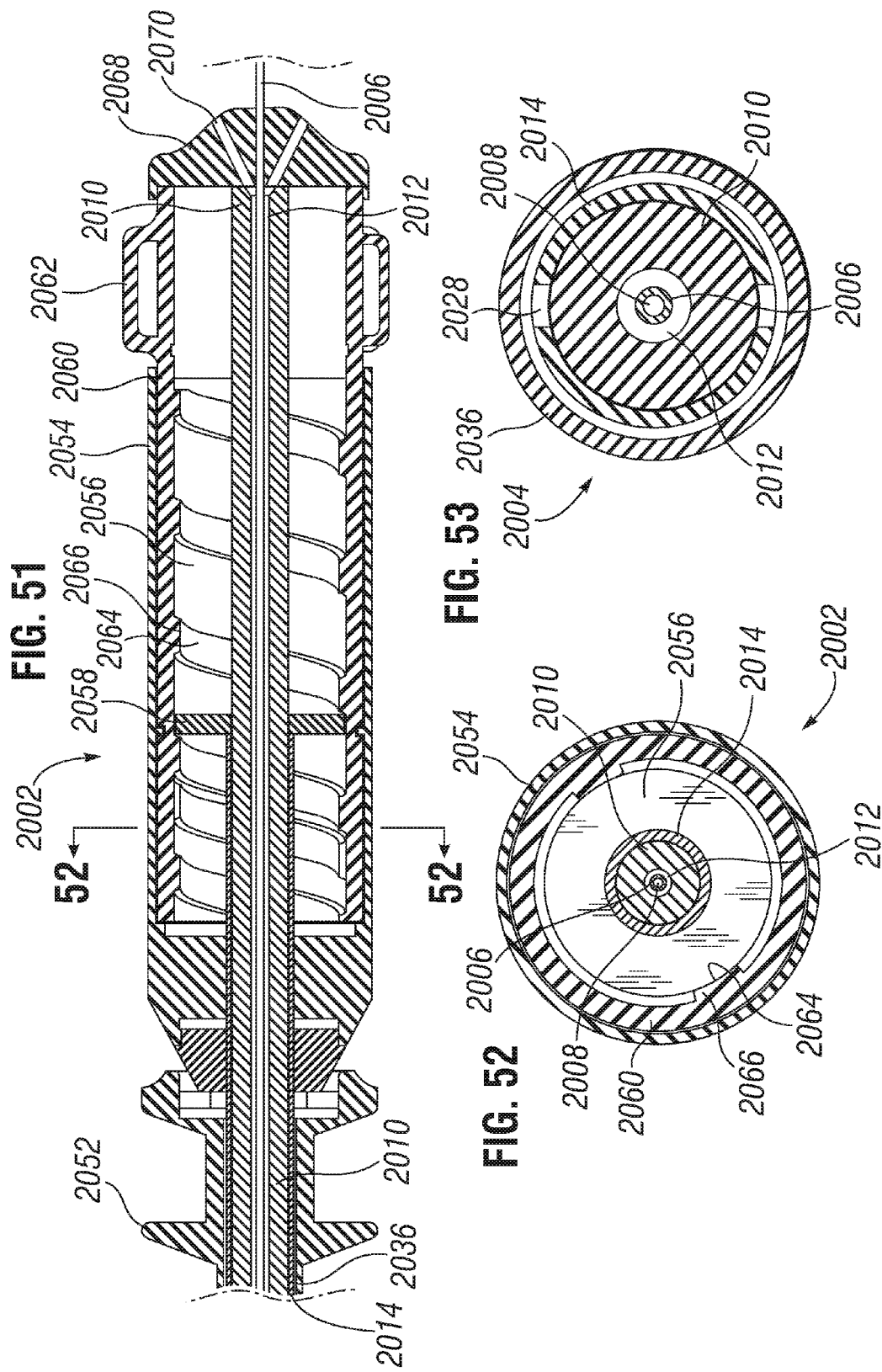

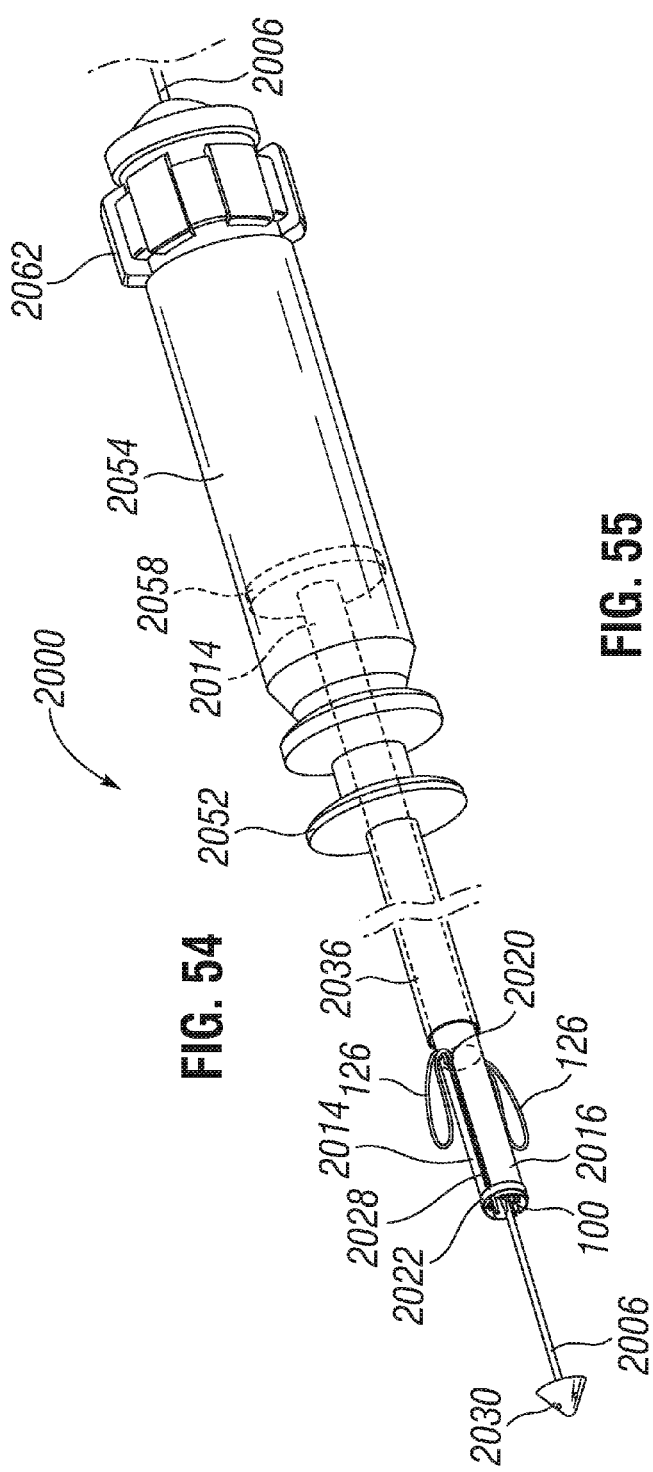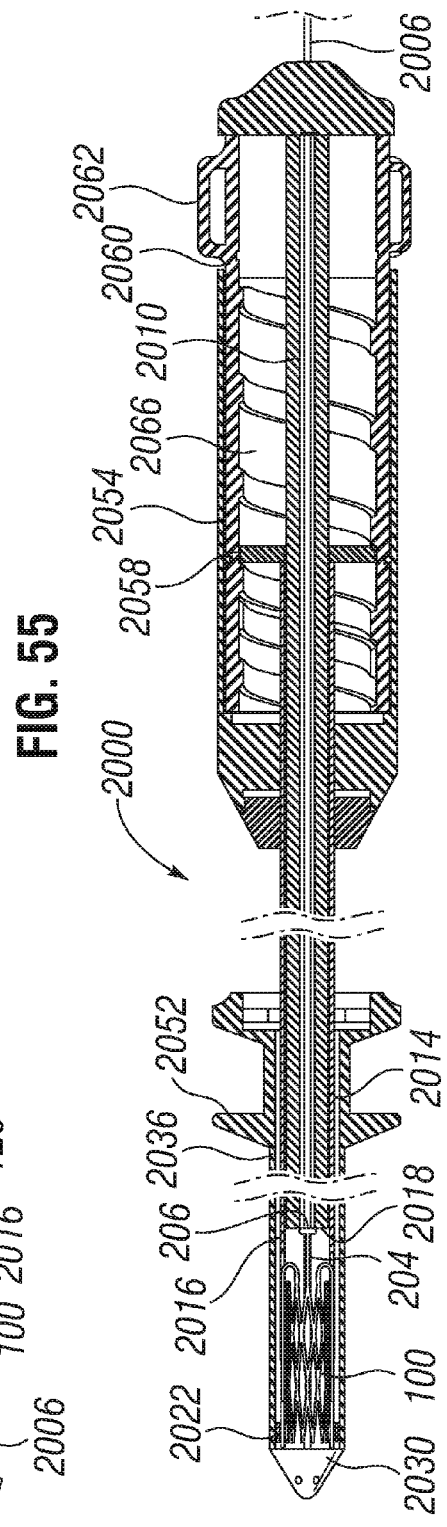

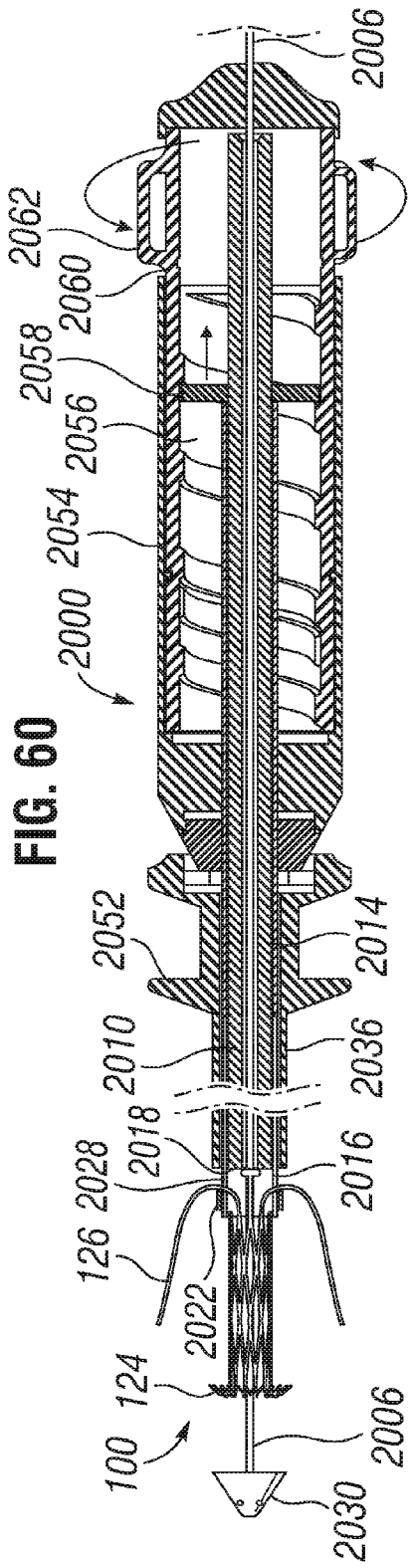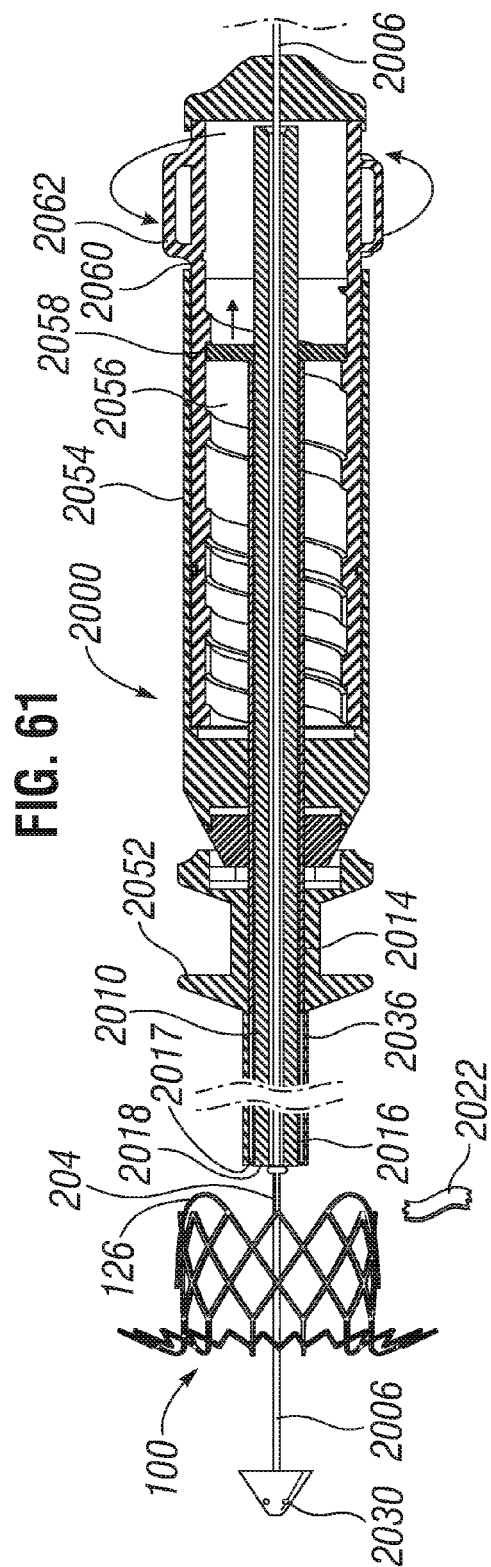

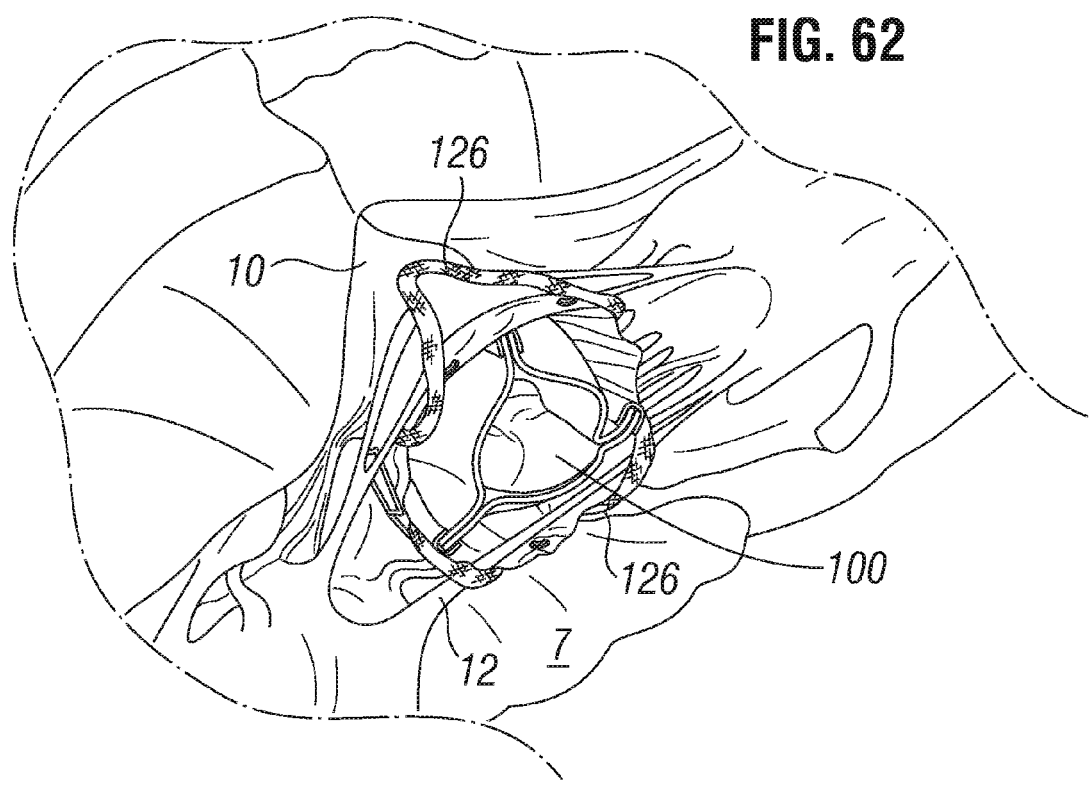

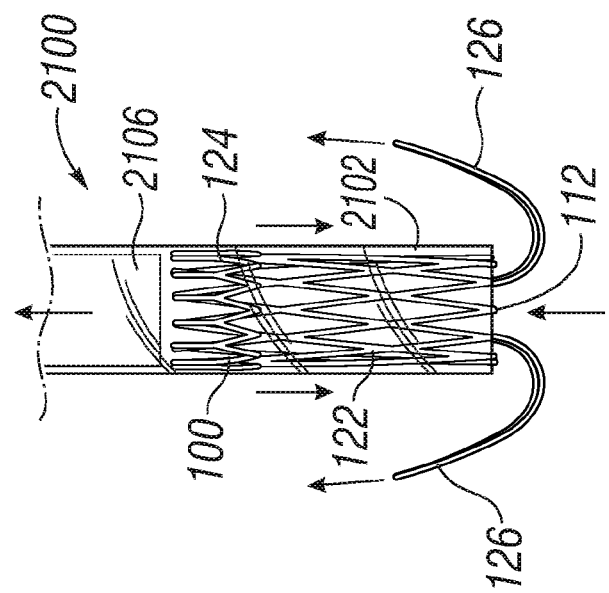
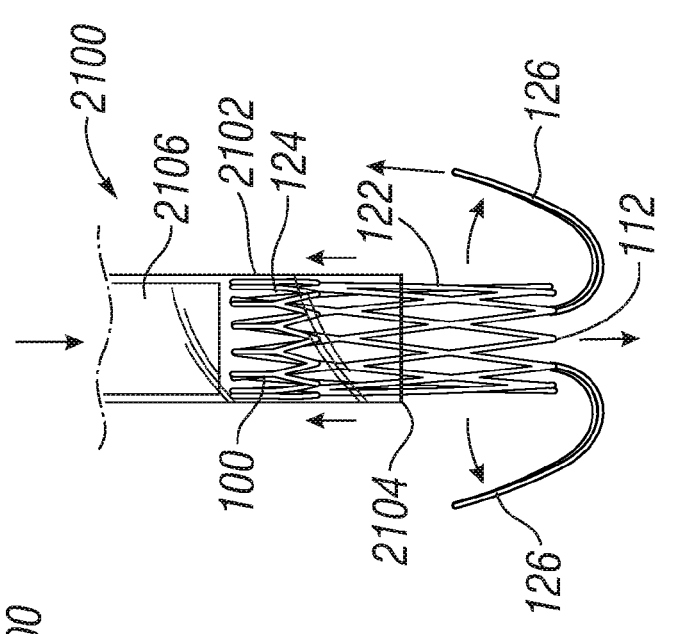
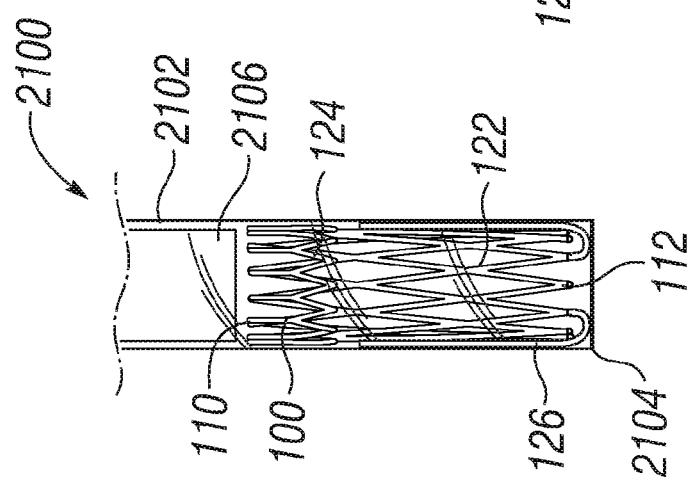

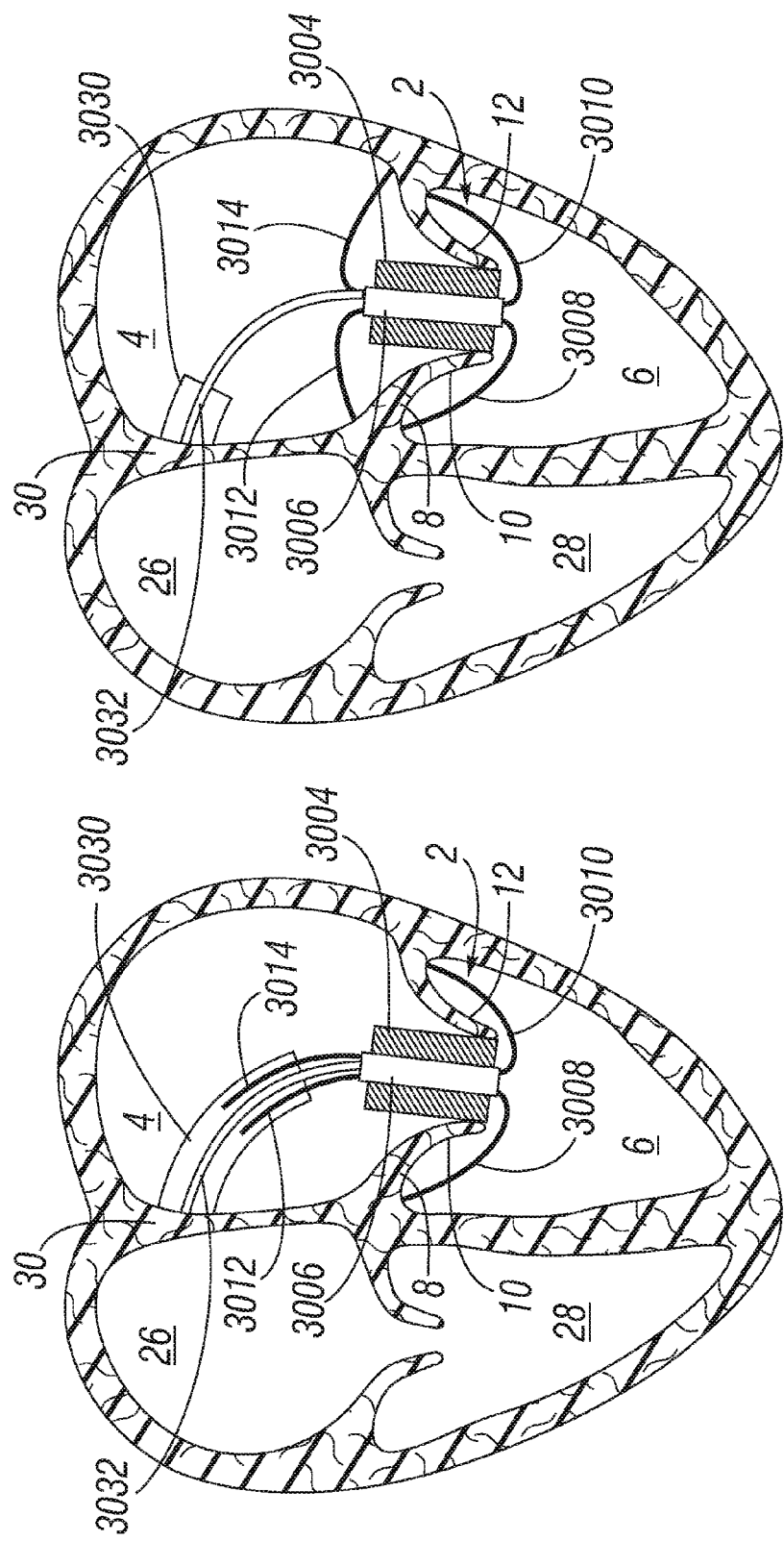

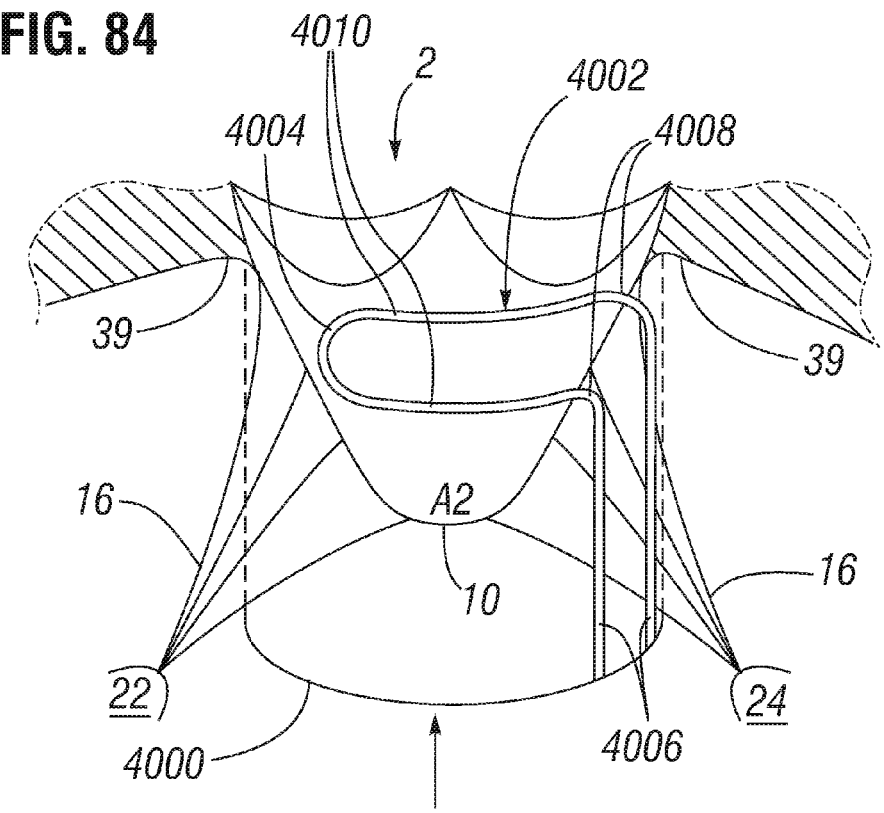
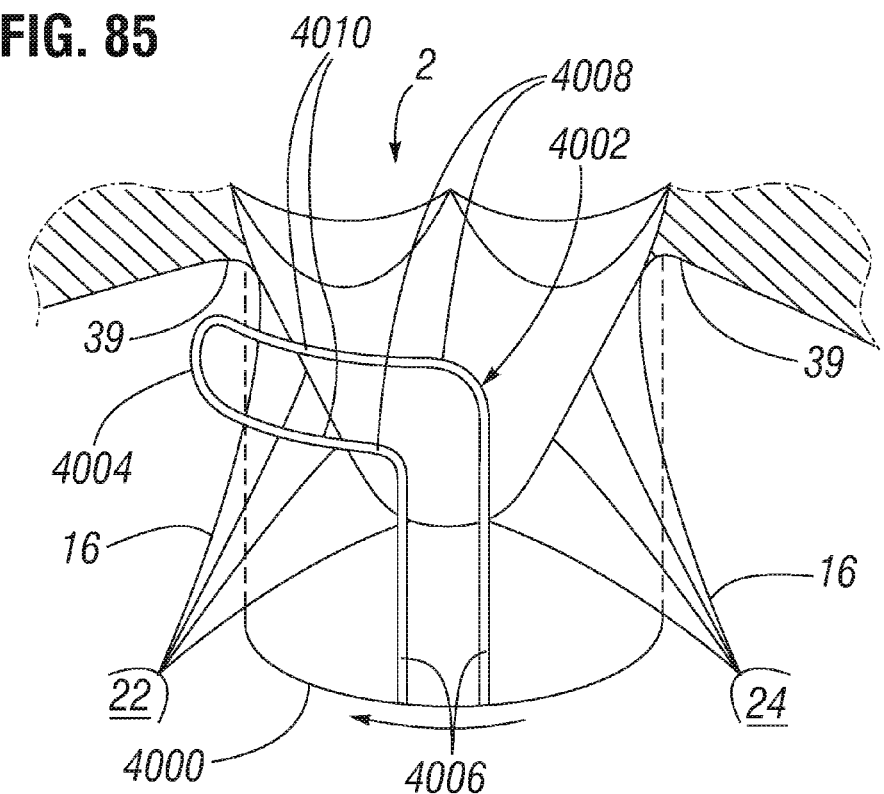

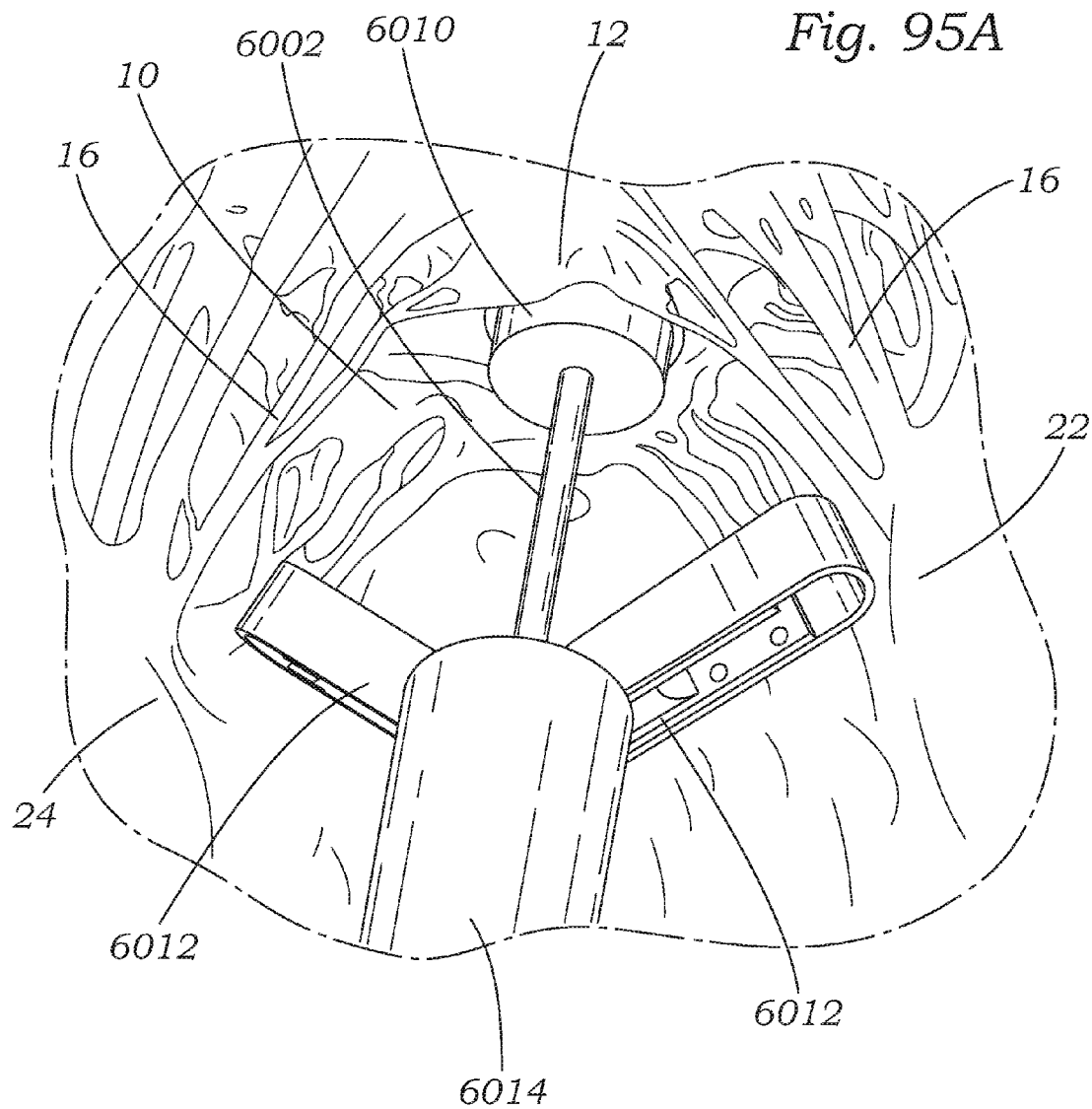

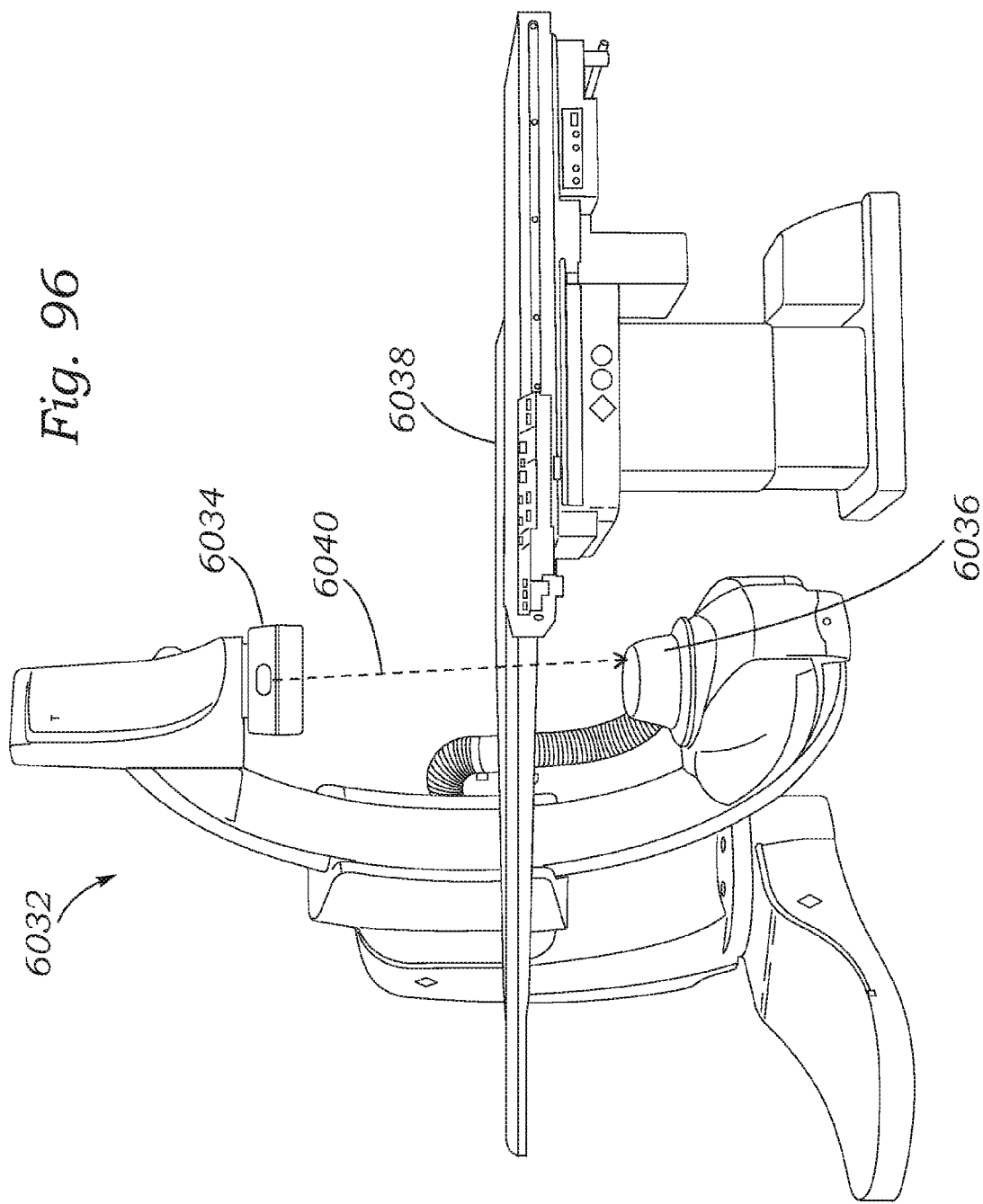

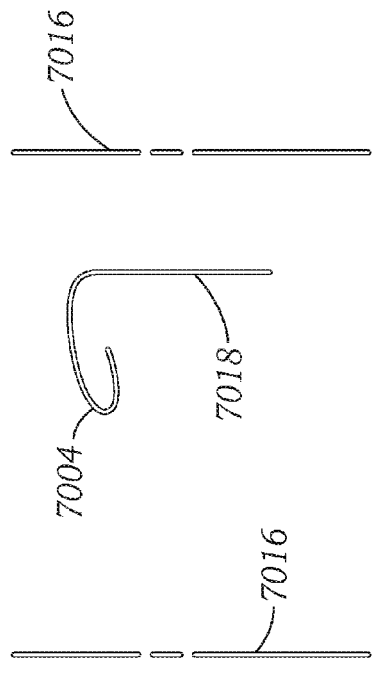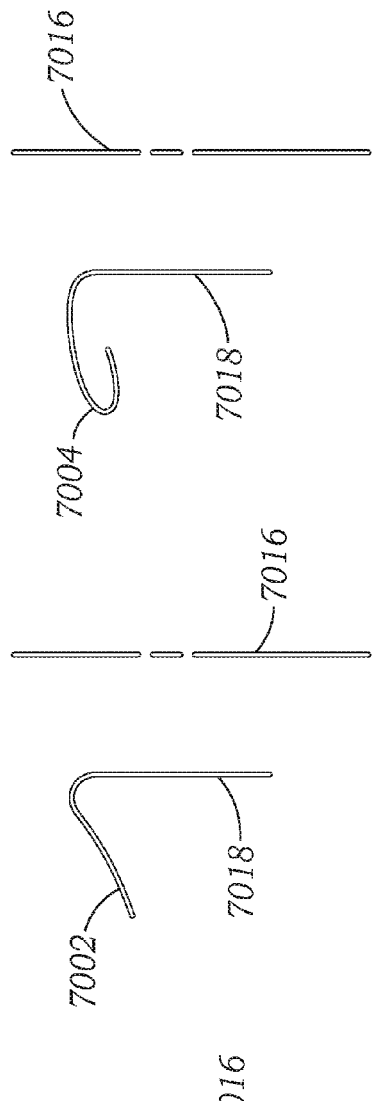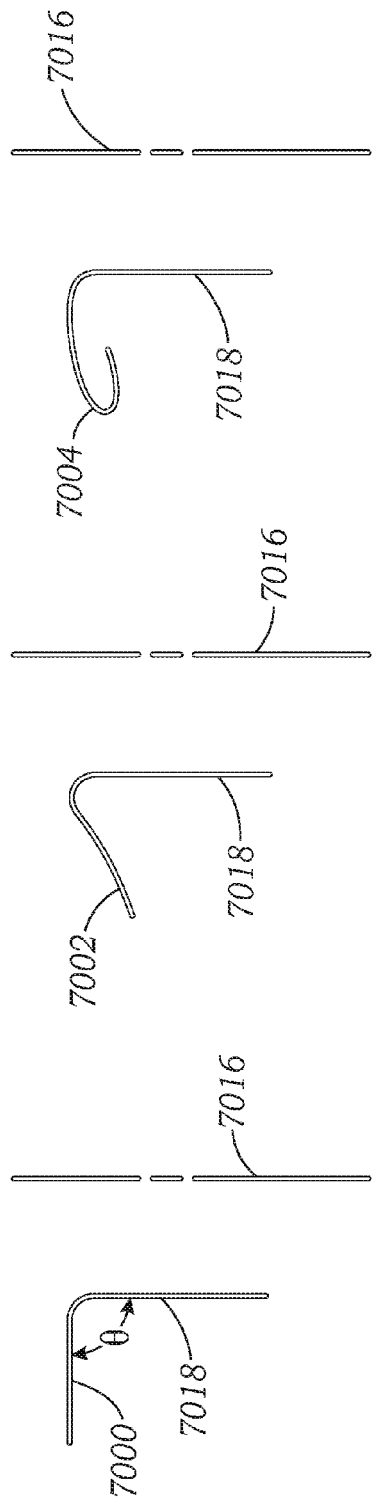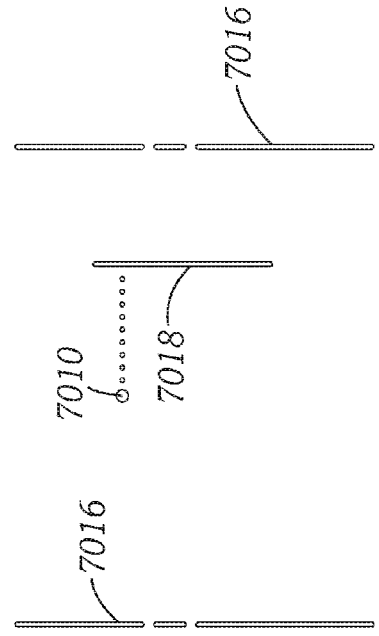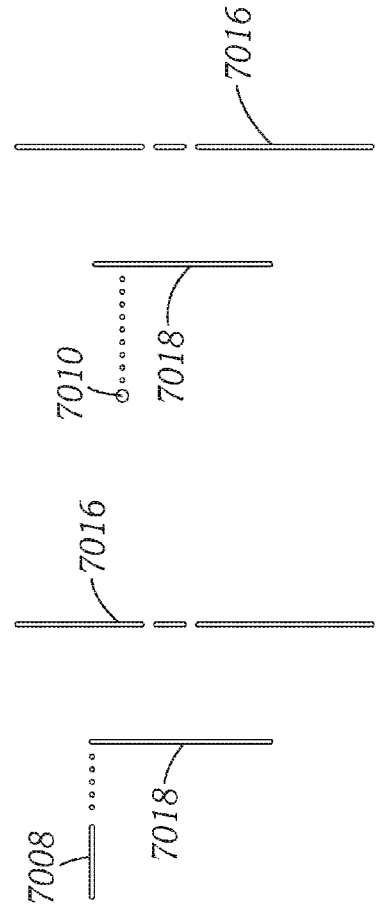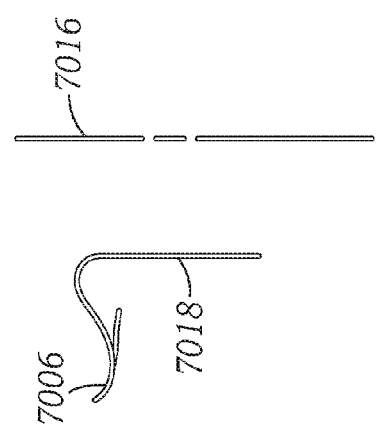

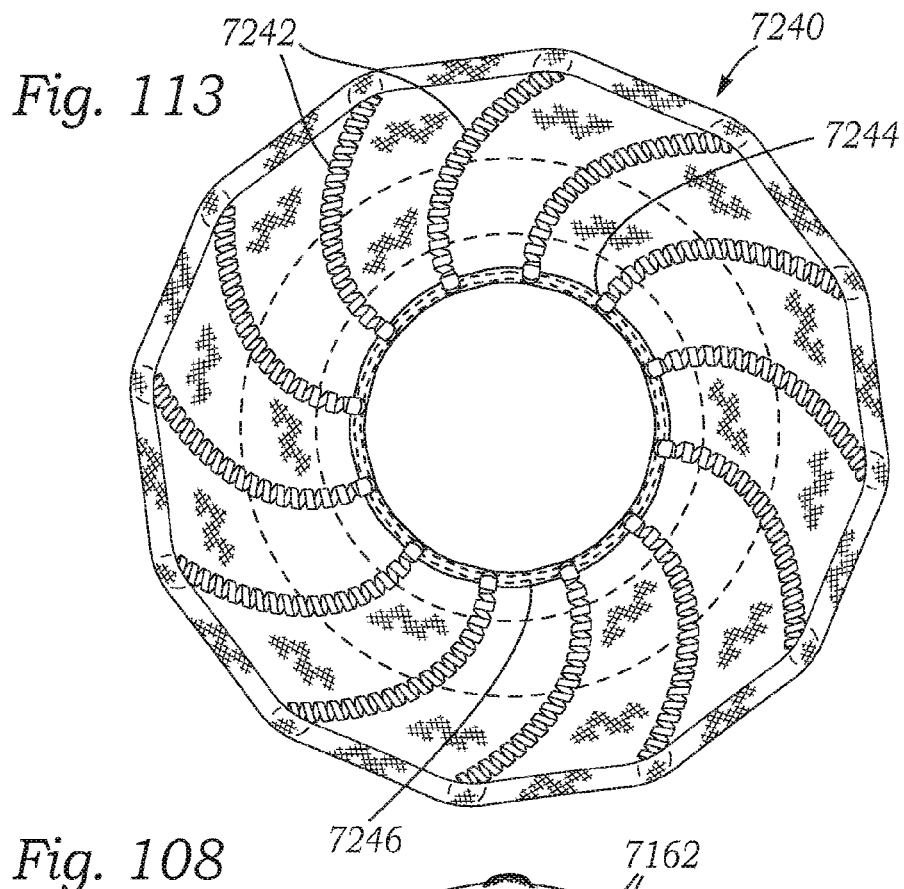
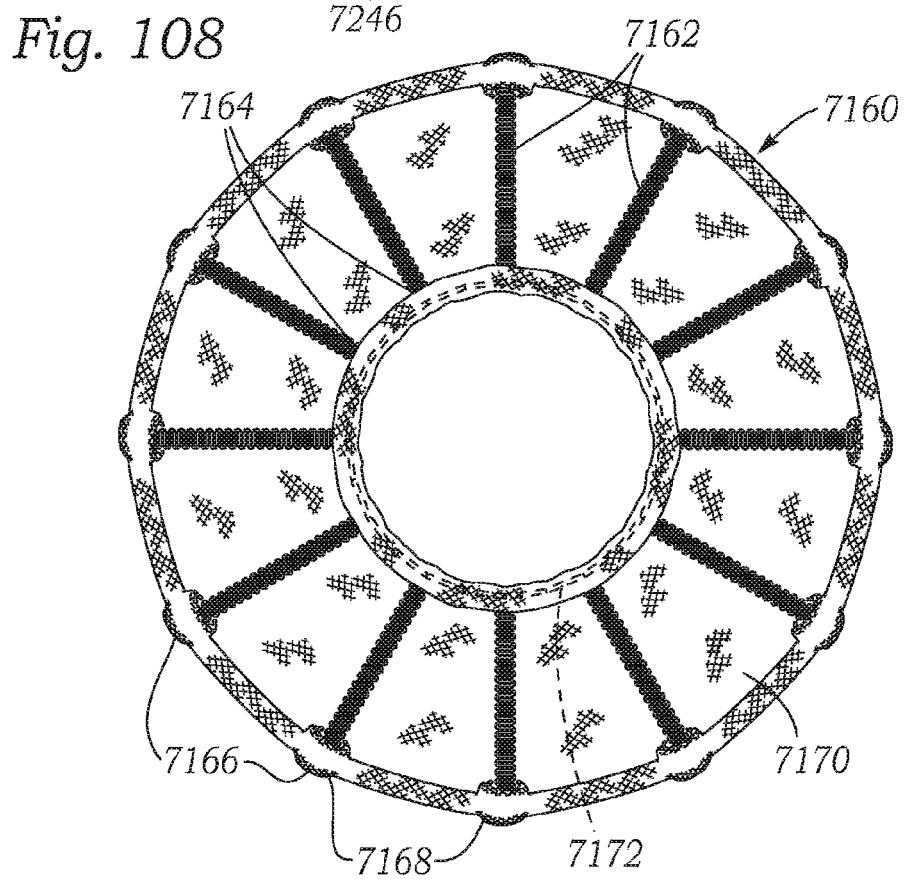

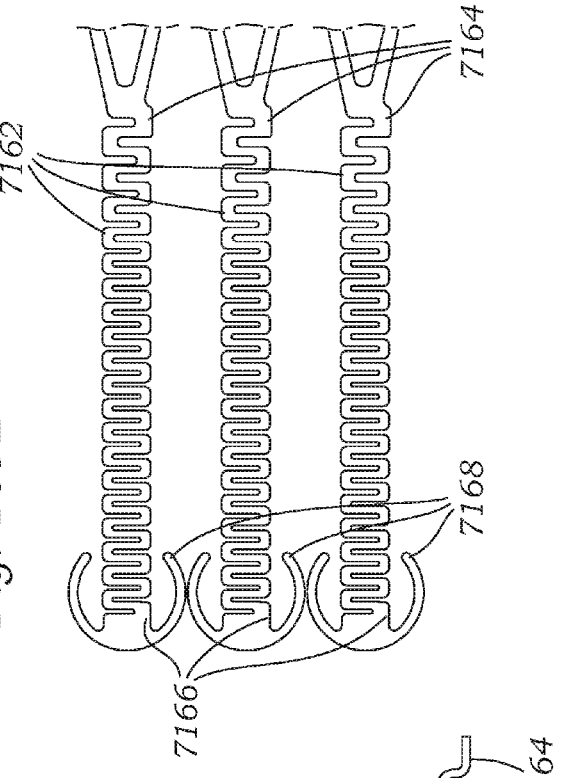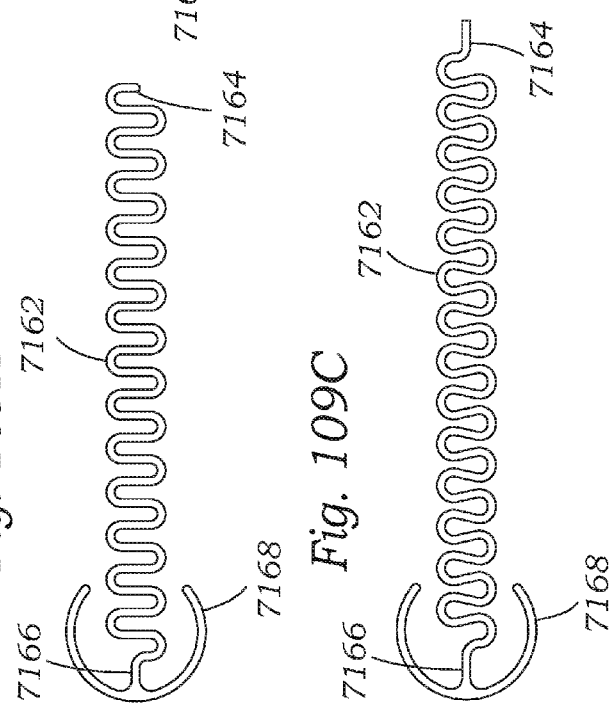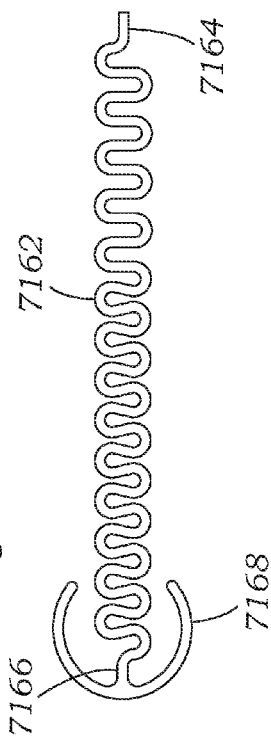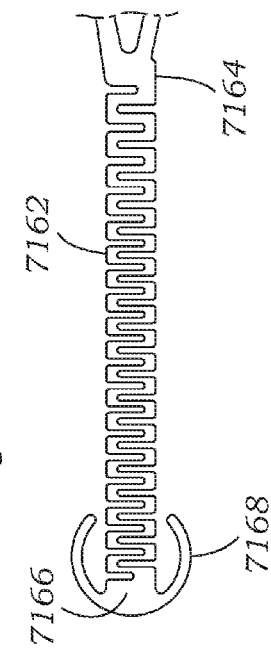
Fig. 109A  Fig. 109B  Fig. 109C  Fig. 109D  Fig. 109E

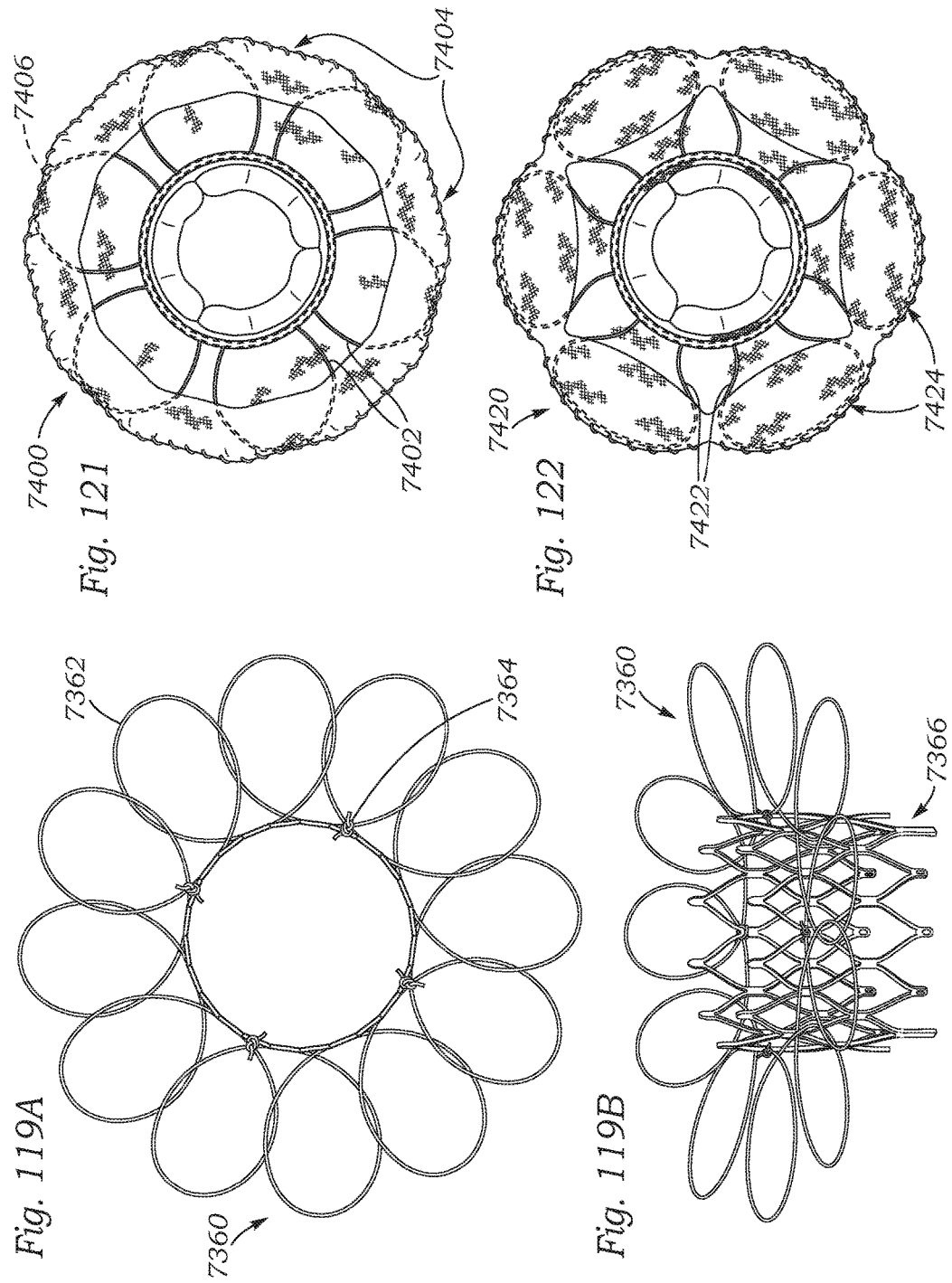

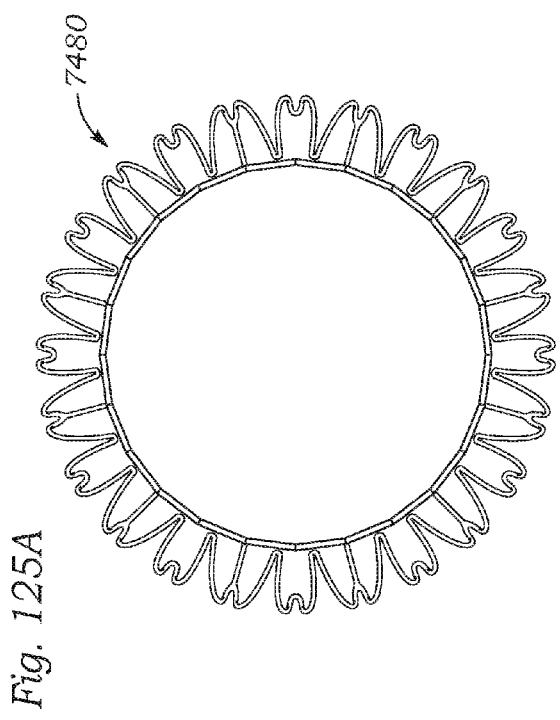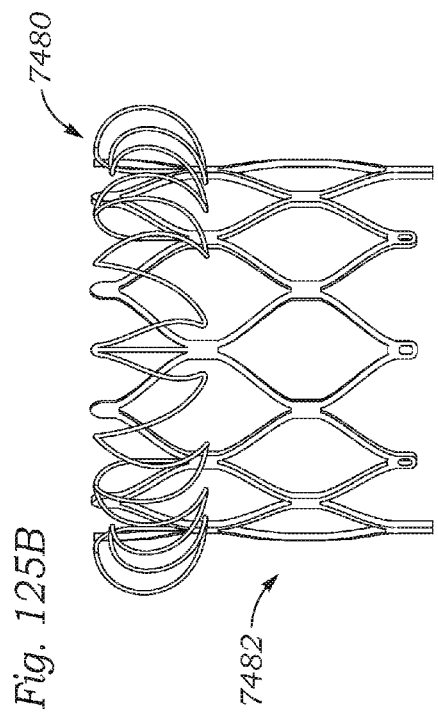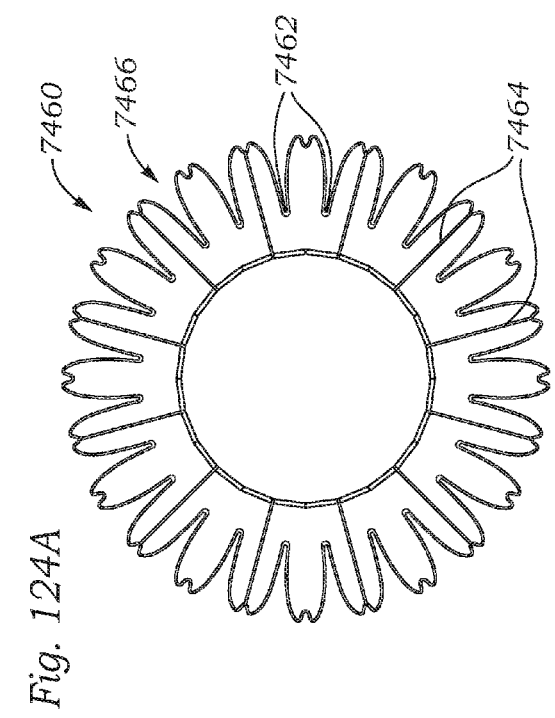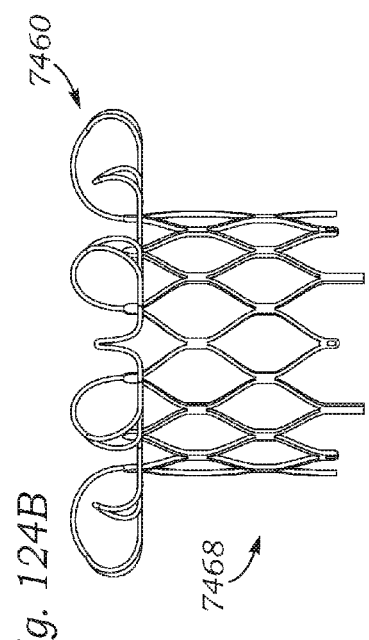
Fig. 124A / Fig. 124B / Fig. 125A / Fig. 125B

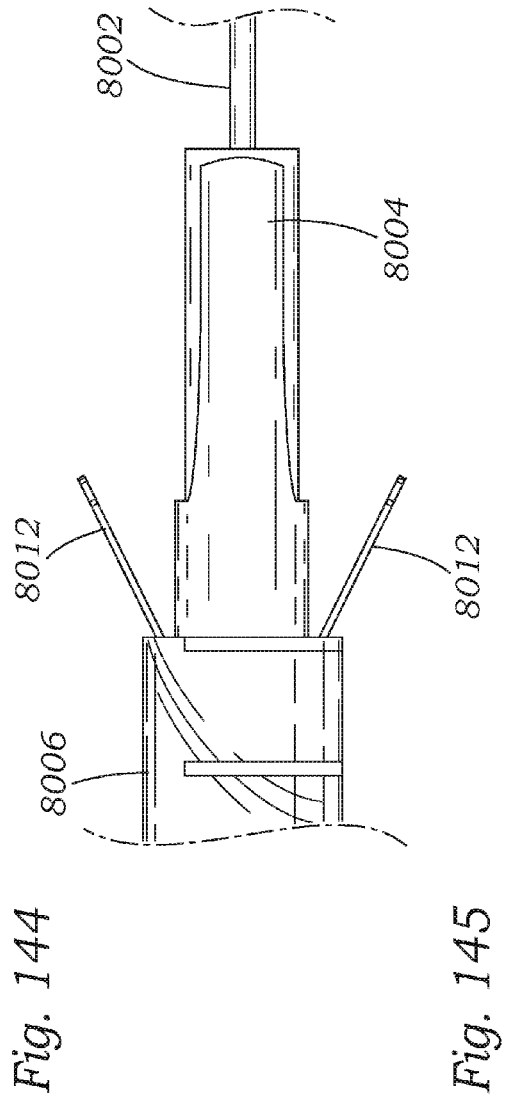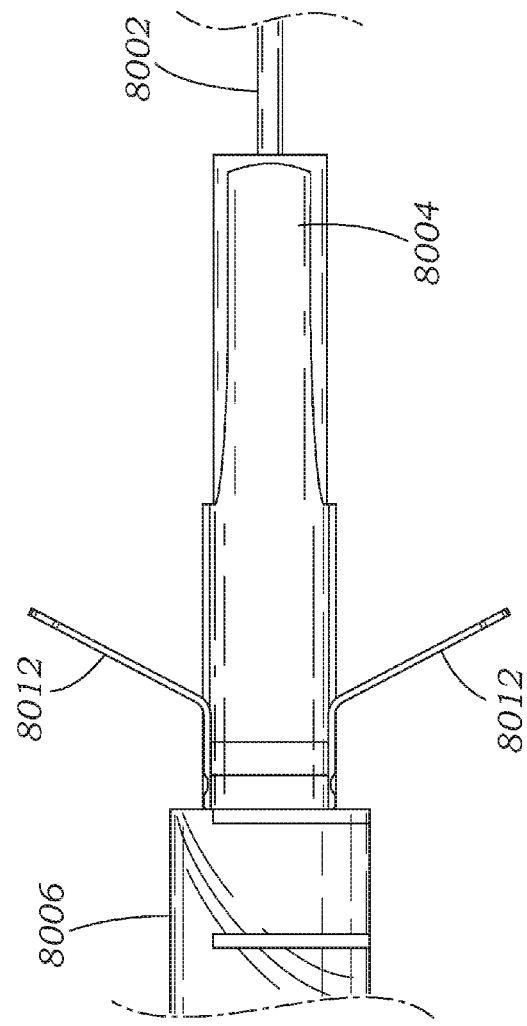

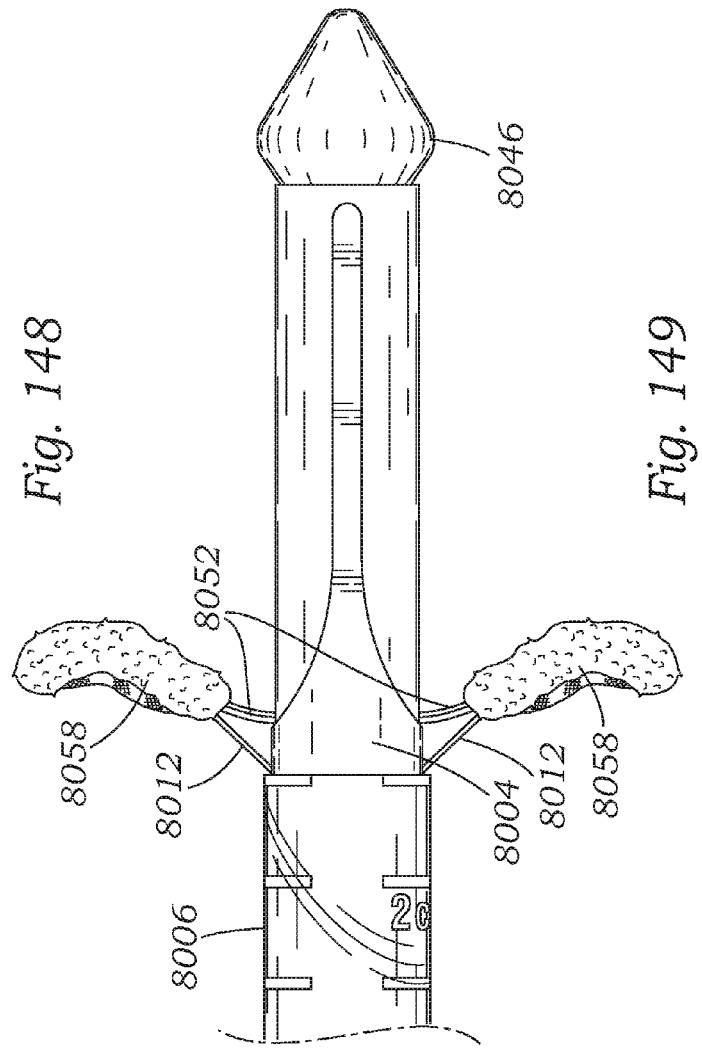
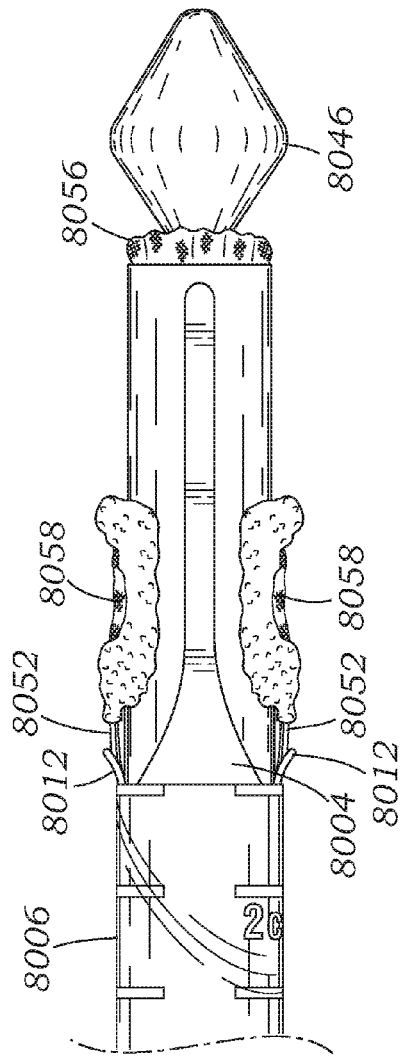

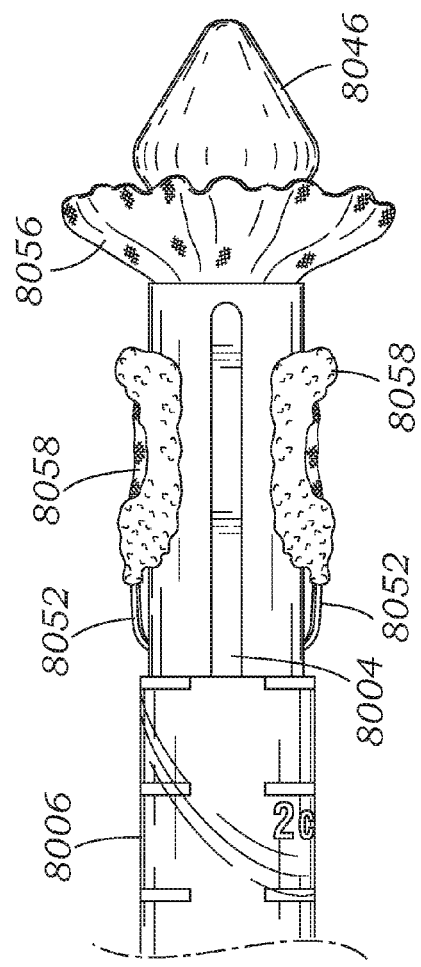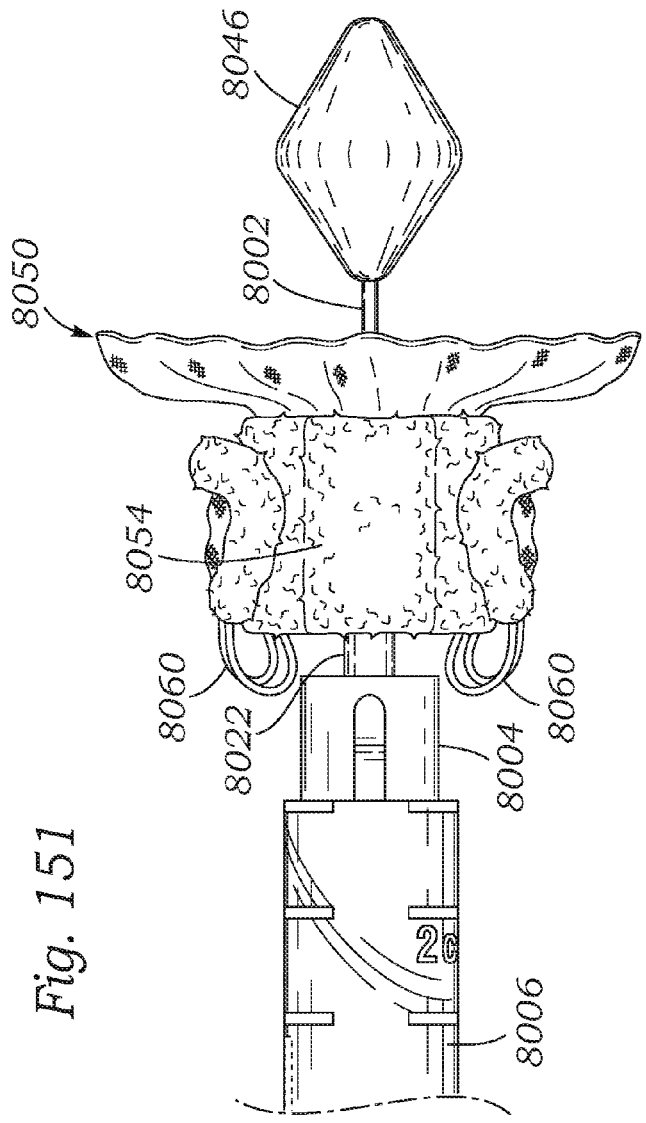

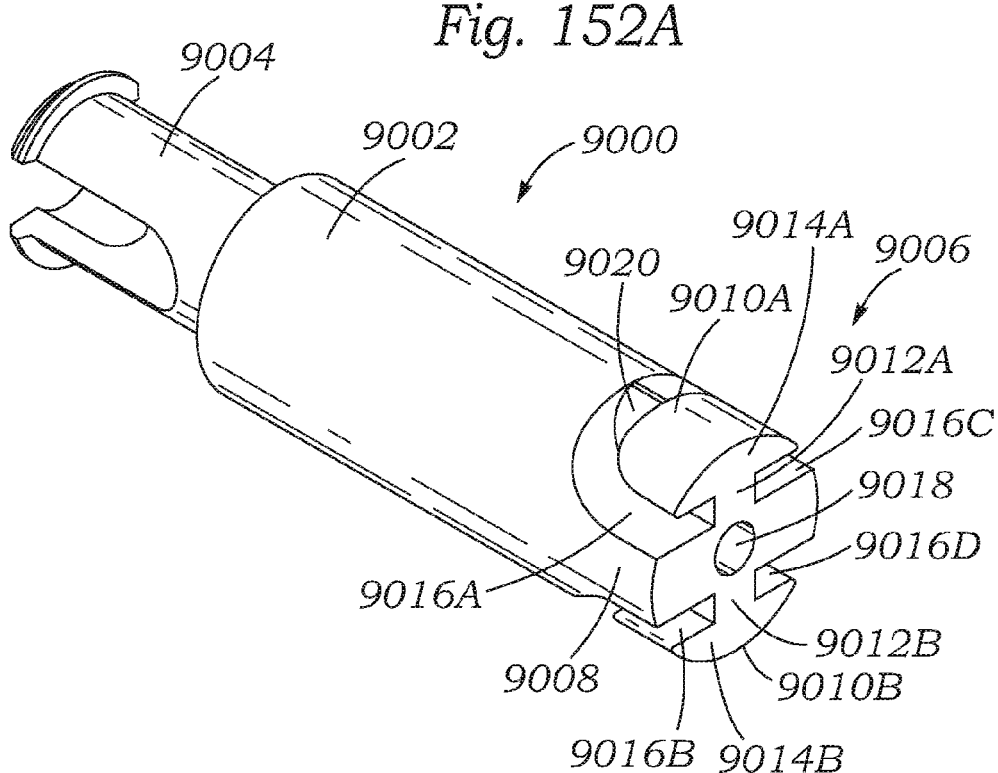
Fig. 152A
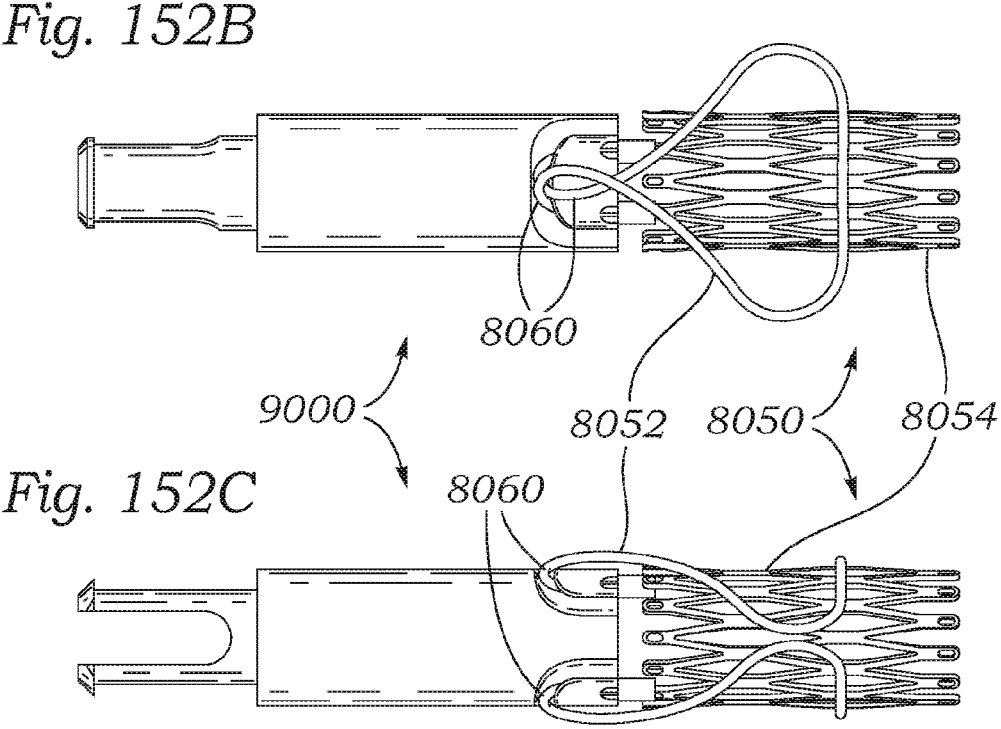
Fig. 152B
Fig. 152C

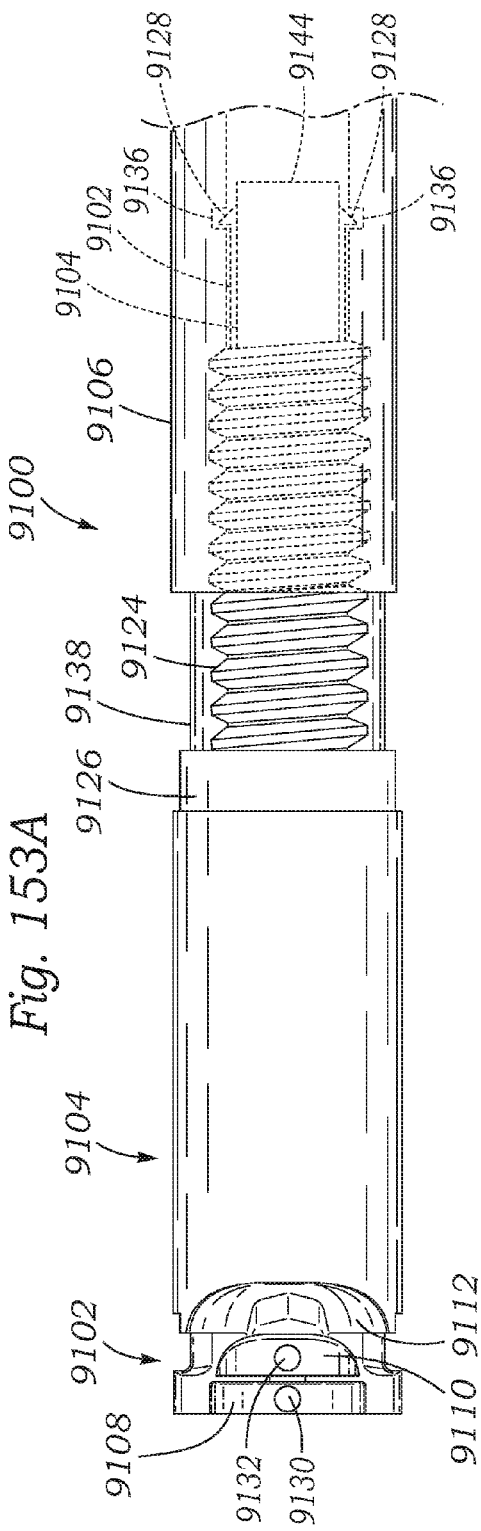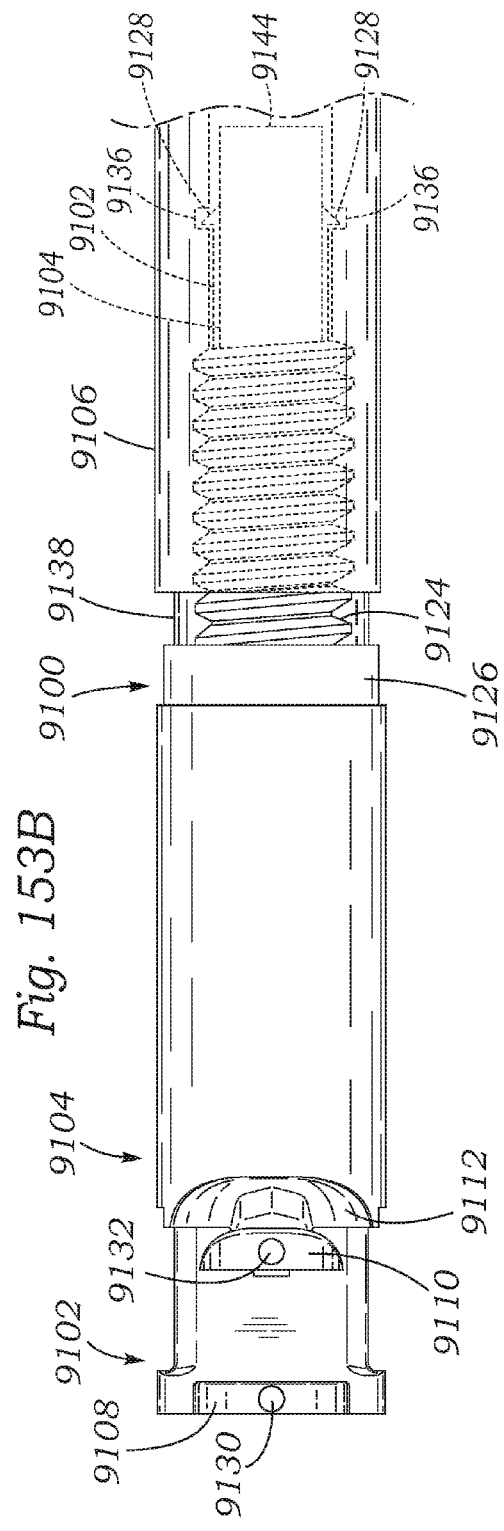

PROSTHETIC VALVE FOR REPLACING MITRAL VALVE

CROSS-REFERENCE TO RELATED APPLICATIONS

This application is a continuation of U.S. patent application Ser. No. 14/171,603, filed Feb. 3, 2014, now U.S. Pat. No. 9,439,763, which claims the benefit of U.S. Provisional Application No. 61/760,577, filed Feb. 4, 2013, and U.S. Provisional Application No. 61/914,648, filed Dec. 11, 2013, which are hereby incorporated herein by reference in their entireties.

FIELD

This disclosure pertains generally to prosthetic devices for repairing and/or replacing native heart valves, and in particular to prosthetic valves for replacing defective mitral valves, as well as methods and devices for delivering and implanting the same within a human heart.

BACKGROUND

Prosthetic valves have been used for many years to treat cardiac valvular disorders. The native heart valves (i.e., the aortic, pulmonary, tricuspid and mitral valves) serve critical functions in assuring the forward flow of an adequate supply of blood through the cardiovascular system. These heart valves can be rendered less effective by congenital malformations, inflammatory processes, infectious conditions or disease. Such damage to the valves can result in serious cardiovascular compromise or death. For many years the definitive treatment for such disorders was the surgical repair or replacement of the valve during open heart surgery. However, such surgeries are highly invasive and are prone to many complications. Therefore, elderly and frail patients with defective heart valves often go untreated. More recently a transvascular technique has been developed for introducing and implanting a prosthetic heart valve using a flexible catheter in a manner that is much less invasive than open heart surgery.

In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

Another known technique for implanting a prosthetic aortic valve is a transapical approach where a small incision is made in the chest wall of a patient and the catheter is advanced through the apex (i.e., bottom tip) of the heart. Transapical techniques are disclosed in U.S. Patent Application Publication No. 2007/0112422, which is hereby incorporated by reference. Like the transvascular approach, the transapical approach can include a balloon catheter having a steering mechanism for delivering a balloon-expandable prosthetic heart valve through an introducer to the aortic annulus. The balloon catheter can include a deflecting segment just proximal to the distal balloon to facilitate positioning of the prosthetic heart valve in the proper orientation within the aortic annulus.

The above techniques and others have provided numerous options for high operative risk patients with aortic valve disease to avoid the consequences of open heart surgery and cardiopulmonary bypass. While devices and procedures for the aortic valve are well-developed, such catheter-based procedures are not necessarily applicable to the mitral valve due to the distinct differences between the aortic and mitral valve. The mitral valve has complex subvalvular apparatus, i.e., chordae tendineae, which are not present in the aortic valve.

Surgical mitral valve repair techniques (e.g., mitral annuloplasty) have increased in popularity due to their high success rates, and clinical improvements noted after repair. In addition to the existing mitral valve repair technologies, there are a number of new technologies aimed at making mitral valve repair a less invasive procedure. These technologies range from iterations of the Alfieri stitch procedure to coronary sinus-based modifications of mitral anatomy to subvalvular plications or ventricular remodeling devices, which would incidentally correct mitral regurgitation.

However, for mitral valve replacement, few less-invasive options are available. There are approximately 25,000 mitral valve replacements (MVR) each year in the United States. However, it is estimated that over 300,000 patients who meet guidelines for treatment are denied treatment based on their age and/or co-morbidities. Thus, a need exists for minimally invasive techniques for replacing the mitral valve.

SUMMARY

Prosthetic mitral valves, components thereof, and methods and devices for implanting the same are described herein.

A prosthetic apparatus is described that is configured for implanting at the native mitral valve region of the heart and includes a main body that is radially compressible to a radially compressed state and self-expandable from the compressed state to a radially expanded state. The prosthetic apparatus also comprises at least one ventricular anchor coupled to the main body and disposed outside of the main body such that when the main body is compressed to the compressed state, a leaflet-receiving space between the ventricular anchor and an outer surface of the main body increases to receive a native valve leaflet therebetween. When the main body self-expands to the expanded state in the absence of any substantial external inward forces on the main body or the ventricular anchor, the space decreases to capture the leaflet between the main body and the ventricular anchor.

In some embodiments, a prosthetic apparatus, for implanting at the native mitral valve region of the heart, includes a frame having a main body and at least one ventricular anchor coupled to and disposed outside of the main body. The prosthetic apparatus also includes a plurality of leaflets supported by the main body that form a one-way valve for the flow of blood through the main body. The main body is radially compressible to a radially compressed state for delivery into the body and self-expandable from the compressed state to a radially expanded state. The ventricular anchor comprises a base that is fixedly secured to the main body, a free end portion opposite the base, and an intermediate portion defining a leaflet-receiving space between the ventricular anchor and the main body for receiving a leaflet of the native valve. Expansion of the main body from its compressed state to its radially expanded state in the absence of any radial inward forces on the ventricular anchor causes the leaflet-receiving space to decrease.

In other embodiments, a prosthetic apparatus for implanting at the native mitral valve region includes a main body, at least one ventricular anchor and at least one atrial anchor.

The main body is configured for placement within the native mitral valve and is compressible to a compressed state for delivery into the heart and self-expandable from the compressed state to an expanded state. At least one ventricular anchor is coupled to and disposed outside of the main body such that, in the expanded state, a leaflet-receiving space exists between the ventricular anchor and an outer surface of the main body to receive a free edge portion of a native valve leaflet. The ventricular anchor comprises an engagement portion configured to extend behind the received native leaflet and contact a ventricular surface of the native mitral annulus, the annulus connection portion of the received native leaflet, or both the ventricular surface of the native annulus and the annulus connection portion of the received native leaflet. At least one atrial sealing member is coupled to and disposed outside of the main body and is configured to contact an atrial portion of the native mitral annulus, the annulus connection portion of the received native leaflet, or both the atrial surface of the native annulus and the annulus connection portion of the received native leaflet at a location opposite from the engagement portion of the ventricular anchor for retention of the prosthetic apparatus and/or prevention of paravalvular leakage.

Exemplary delivery systems are also described for delivering a prosthetic apparatus into the heart. Some embodiments include an inner sheath having a distal end portion having at least one longitudinal slot extending proximally from a distal end of the inner sheath. The distal end portion of the inner sheath is configured to contain the prosthetic apparatus in a radially compressed state. An outer sheath is positioned concentrically around the inner sheath and at least one of the inner sheath and outer sheath is movable axially relative to the other between a first position in which the outer sheath extends over at least a portion of the longitudinal slot and a second position in which the at least a portion of the longitudinal slot is uncovered by the outer sheath so to allow a portion of the prosthetic apparatus contained within the inner sheath to expand radially outward through the slot.

Exemplary methods are also described for implanting a prosthetic apparatus at the native mitral valve region of the heart. One such method includes delivering the prosthetic apparatus into the heart in a radially compressed state; allowing a ventricular anchor to self-expand away from a main body of the frame while the main body is held in the compressed state, thereby increasing a gap between the ventricular anchor and an outer surface of the main body; positioning the main body in the annulus of the native mitral valve and the ventricular anchor adjacent the ventricular side of a native mitral valve leaflet such that the leaflet is disposed in the gap between the ventricular anchor and the outer surface of the main body; and allowing the main body to self-expand to an expanded state such that the gap decreases to capture the leaflet between the outer surface of the main body and the ventricular anchor.

In some cases, an implantable prosthetic valve comprises a radially collapsible and radially expandable annular frame and a valve member supported within an interior of the frame. In some cases, the frame comprises an annular main body defining a lumen therethrough, at least one ventricular anchor coupled to a ventricular end portion of the main body, and an atrial portion coupled to the main body and extending radially away from the main body, wherein the atrial portion comprises a plurality of radially extending arms, and wherein at least one of the arms comprises a serpentine or coiled segment.

In some cases, at least one of the arms comprises a serpentine segment comprising a plurality of substantially straight, parallel segments. In some cases, at least one of the arms comprises a serpentine segment comprising a plurality of substantially curved portions. In some cases, at least one of the arms comprises a serpentine segment comprising a plurality of substantially straight, parallel segments at a portion of the arm proximate to the main body and a plurality of substantially curved portions at a terminal portion of the arm. In some cases, at least one of the arms comprises a serpentine segment having a thickness which increases from a terminal end portion of the arm to a portion of the arm proximate the main body.

In some cases, the plurality of arms are connected to the main body independently of each other without metal segments interconnecting adjacent arms. In some cases, each arm has a free end portion comprising a curved or rounded element. In some cases, the curved or rounded element comprises a horseshoe shaped element comprising two terminal end portions pointing radially inward toward the main body. In some cases, each of the two terminal end portions comprise a loop having a hole formed therethrough. In some cases, each arm comprises a single metal wire or coil that is flexible relative to the main body and to adjacent arms. In some cases, at least one of the arms comprises a coiled segment.

In some cases, a method for implanting a prosthetic apparatus at the native mitral valve region of a heart comprises delivering the prosthetic apparatus to the native mitral valve region within a distal end portion of a delivery apparatus, retracting an outer sheath of the delivery apparatus to expose a ventricular anchor of the prosthetic apparatus, forcibly expanding the ventricular anchor radially away from the delivery apparatus, advancing the prosthetic apparatus through the native mitral valve so the ventricular anchor moves behind a native mitral valve leaflet, contracting the ventricular anchor radially toward the delivery apparatus, and retracting an inner sheath of the delivery apparatus, thereby allowing a main body of the prosthetic apparatus to radially expand within the native mitral valve.

In some cases, the act of retracting the outer sheath exposes an anchor spreader which forcibly expands the anchor. In some cases, the anchor spreader is coupled to the inner sheath and the act of retracting the outer sheath allows the anchor spreader to resiliently extend radially from the inner sheath, thereby forcibly expanding the anchor. In some cases, the act of retracting the inner sheath comprises partially retracting the inner sheath, thereby allowing an atrial portion of the prosthetic apparatus to radially expand prior to the main body being expanded. In some cases, the act of retracting the inner sheath further comprises completely retracting the inner sheath, thereby allowing the main body portion of the prosthetic apparatus to radially expand.

In some cases, a method comprises introducing an orientation device to the native mitral valve region of a patient's heart, deploying an echogenic arm of the orientation device, viewing the echogenic arm of the orientation device within the native mitral valve region using echocardiography, orienting the arm of the orientation device to align with the A2 and P2 regions of the native mitral valve, aligning a fluoroscope axis of a fluoroscope along a line extending through the orientation device when the arm is aligned with the A2 and P2 regions, removing the orientation device from the patient's heart, introducing a prosthetic apparatus to the native mitral valve region, and positioning an anchor of the prosthetic apparatus behind one of the native mitral valve leaflets at one of the A2 or P2 regions, the anchor being visible on the fluoroscope.

In some cases, the echogenic arm comprises two echogenic arms extending radially away from a distal end portion of a shaft of the orientation device. In some cases, the distal end portion of the shaft further comprises a fluoroscopic marker band having first and second apertures disposed therein and the act of aligning the fluoroscope axis comprises aligning the fluoroscope axis with a line extending from the first to the second aperture.

The foregoing and other objects, features, and advantages of the invention will become more apparent from the following detailed description, which proceeds with reference to the accompanying figures.

BRIEF DESCRIPTION OF THE DRAWINGS

FIG. 4B shows a native mitral valve with a gap between the leaflets.

FIGS. 4C and 4D show an exemplary prosthetic valve positioned within a native mitral valve.

FIGS. 8-10 are views corresponding to FIGS. 5-7, showing an exemplary embodiment of a frame of the prosthetic valve of FIGS. 5-7.

FIGS. 17-22 are a series of end views corresponding to FIGS. 11-16, respectively.

FIGS. 27-29 show an exemplary embodiment of a prosthetic valve having a frame with four ventricular anchors.

FIG. 49 shows an exemplary embodiment of a delivery system for delivering and implanting a prosthetic valve at a native mitral valve region of the heart.

FIG. 50 is a detailed view of the distal portion of the delivery system of FIG. 49.

FIG. 51 is a cross-sectional view of a handle portion of the delivery system of FIG. 49, taken along section line 51-51.

FIG. 52 is a cross sectional view of the handle portion of the delivery system of FIG. 49, taken along section line 52-52.

FIG. 53 is a cross sectional view of an insertable portion of the delivery system of FIG. 49, taken along section line 53-53.

FIG. 54 shows the delivery system of FIG. 49 with a prosthetic valve loaded within a slotted inner sheath with the ventricular anchors extending outward through slots of the inner sheath.

FIG. 55 is a cross-sectional view of the delivery system of FIG. 49 in a delivery position containing the prosthetic valve within inner and outer sheaths and between a nose cone and a tip of a pusher shaft.

FIG. 60 is a cross-sectional view of the delivery system of FIG. 49 showing the slotted inner sheath retracted to a point where the ventricular anchors of the prosthetic valve contact a notched retaining band around the slotted inner sheath.

FIG. 61 is a cross-sectional view of the delivery system of FIG. 49 showing the slotted inner sheath fully retracted after the band has been broken, and the prosthetic valve in an expanded state after being fully deployed from the sheath.

FIG. 62 is a view of the mitral valve region of the heart from the left ventricle showing an exemplary embodiment of a prosthetic valve fully implanted with the mitral leaflets captured between a main body and ventricular anchors.

FIG. 63 shows an exemplary embodiment of a prosthetic valve within a catheter sheath for delivering to a native valve region of the heart, according to another embodiment.

FIG. 64 shows the prosthetic valve of FIG. 63 with the catheter sheath pulled back such that the ventricular anchors are free to expand but the main body remains compressed.

FIG. 65 shows the prosthetic valve of FIG. 63 with the outer sheath recapturing the main body such that only the ventricular anchors are exposed.

FIGS. 75-79 are cross-sectional views of the heart showing a transeptal delivery of the prosthetic apparatus of FIG. 71.

FIGS. 84 and 85 show an exemplary method for implanting an exemplary prosthetic apparatus having "L" shaped ventricular anchors.

FIGS. 95A and 95B shows the orientation device of FIG. 89 deployed in the native mitral valve region of a heart.

FIG. 96 shows an exemplary embodiment of a fluoroscope device.

FIGS. 100A-100F show various exemplary axial configurations of atrial portions of prosthetic devices.

FIGS. 101A-125B show various exemplary atrial portions of prosthetic devices having various axial and radial configurations, and various components thereof.

FIGS. 143-146 show partial views of the distal end portion of the delivery device of FIG. 141.

FIGS. 147-151 show an exemplary deployment sequence of the delivery device of FIG. 141.

FIGS. 152A-152E show an exemplary prosthetic valve retaining device for a delivery apparatus.

FIGS. 153A-153G show another exemplary prosthetic valve retaining device.

DETAILED DESCRIPTION

Described herein are embodiments of prosthetic valves and components thereof that are primarily intended to be implanted at the mitral valve region of a human heart, as well as apparatus and methods for implanting the same. The prosthetic valves can be used to help restore and/or replace the functionality of a defective native valve.

The Human Heart

Figure 1:
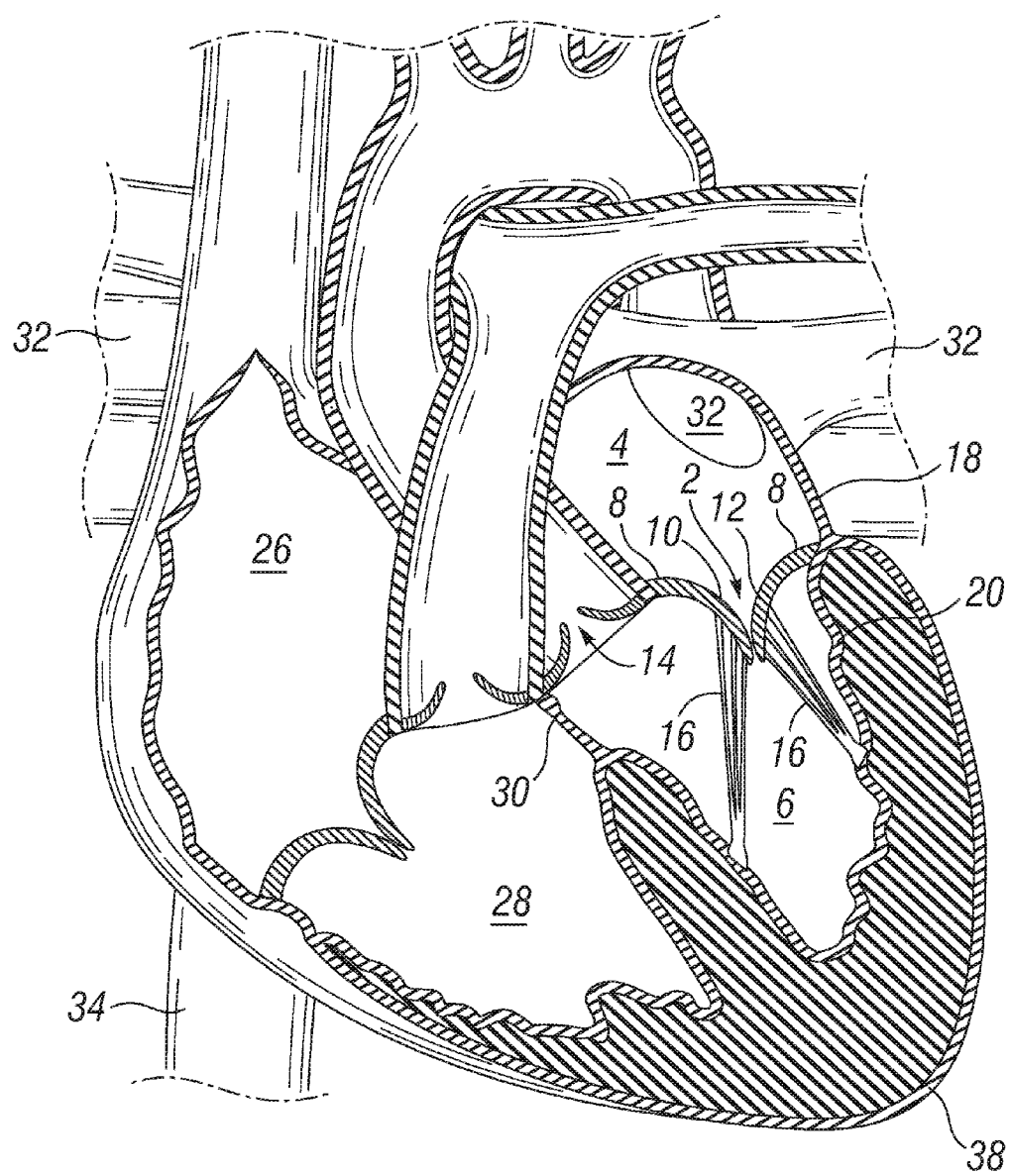
FIG. 1 is a cross sectional view of the human heart.
Figure 2:
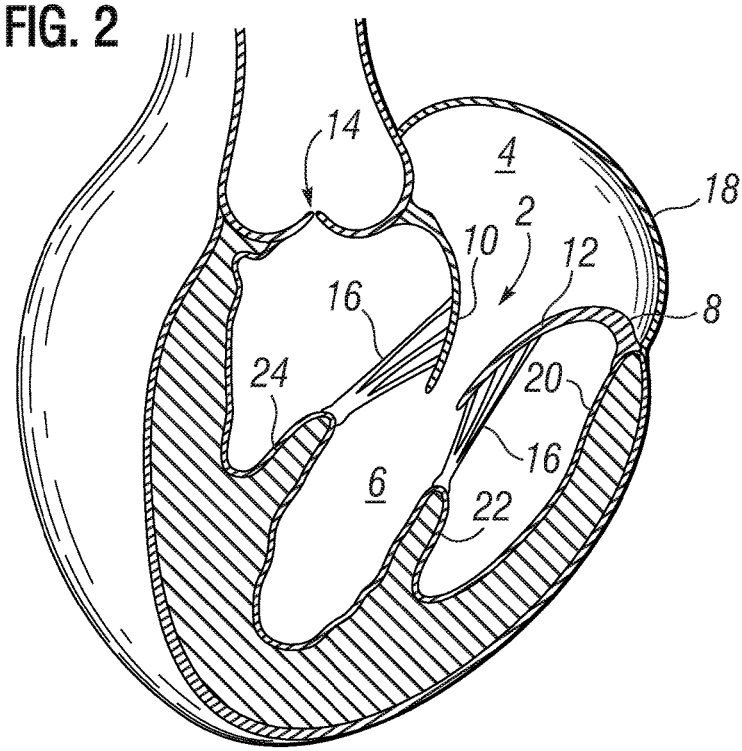
FIG. 2 is another cross sectional view of the human heart showing the mitral valve region.

Relevant portions of the human heart are shown in FIGS. 1 and 2. A healthy heart has a generally conical shape that tapers to a lower apex 38. The heart is four-chambered and comprises the left atrium 4, right atrium 26, left ventricle 6, and right ventricle 28. The left and right sides of the heart are separated by a wall generally referred to as the septum 30. The native mitral valve 2 of the human heart connects the left atrium 4 to the left ventricle 6. The mitral valve 2 has a very different anatomy than other native heart valves, such as the aortic valve 14.

Figure 4A:
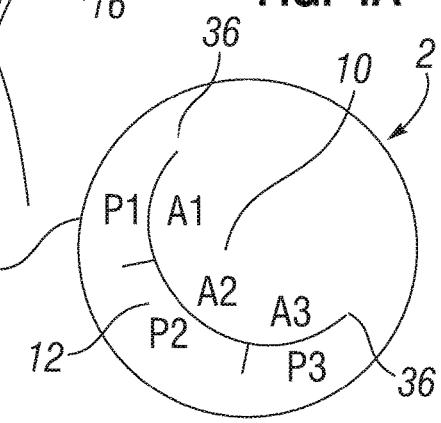
FIG. 4A is a diagram of native mitral valve showing Carpentier nomenclature.

The mitral valve 2 includes an annulus portion 8, which is an annular portion of the native valve tissue surrounding the mitral valve orifice, and a pair of cusps, or leaflets, 10, 12 extending downward from the annulus 8 into the left ventricle 6. The mitral valve annulus 8 can form a "D" shaped, oval, or otherwise out-of-round cross-sectional shape having major and minor axes. The anterior leaflet 10 can be larger than the posterior leaflet 12, as shown schematically in FIG. 4A, forming a generally "C" shaped boundary between the abutting free edges of the leaflets when they are closed together. FIG. 4B shows the native mitral valve 2 with a slight gap 3 between the leaflets 10, 12, such as with a defective native mitral valve that fails to completely close, which can lead to mitral regurgitation and/or other undesirable conditions.

When operating properly, the anterior leaflet 10 and the posterior leaflet 12 function together as a one-way valve to allow blood to flow only from the left atrium 4 to the left ventricle 6. The left atrium 4 receives oxygenated blood from the pulmonary veins 32. When the muscles of the left atrium 4 contract and the left ventricle dilates, the oxygenated blood that is collected in the left atrium 4 flows into the left ventricle 6. When the muscles of the left atrium 4 relax and the muscles of the left ventricle 6 contract, the increased blood pressure in the left ventricle urges the two leaflets together, thereby closing the one-way mitral valve so that blood cannot flow back to the left atrium and is instead expelled out of the left ventricle through the aortic valve 14.

Figure 3:
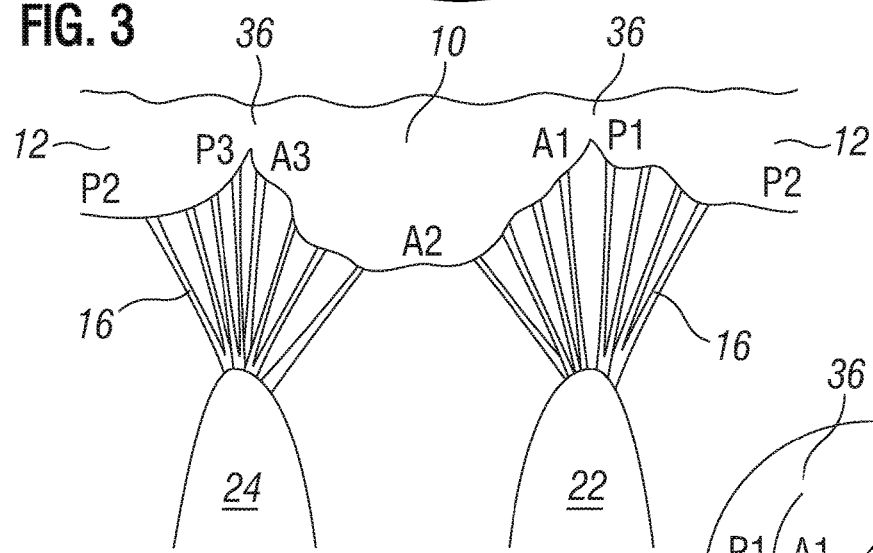
FIG. 3 is a schematic view of the native mitral valve anatomy showing the mitral leaflets attached to the papillary muscles via chordae tendineae.

To prevent the two leaflets 10, 12 from prolapsing under pressure and folding back through the mitral annulus 8 toward the left atrium 4, a plurality of fibrous cords called chordae tendineae 16 tether the leaflets 10, 12 to papillary muscles in the left ventricle 6. Referring to FIGS. 3 and 4, chordae 16 are attached to and extend between the postero-medial papillary muscle 22 and the postero-medial margins of both the anterior leaflet 10 and the posterior leaflet 12 (A1 and P1 areas, respectively, as identified by Carpentier nomenclature). Similarly, chordae 16 are attached to and extend between the antero-lateral papillary muscle 24 and the antero-lateral margins of both the anterior leaflet 10 and the posterior leaflet 12 (A3 and P3 areas, respectively, as identified by Carpentier nomenclature). The A2 and P2 areas are relatively free of chordae attachment points and provide a region where a prosthetic mitral valve can be anchored (see FIG. 3). In addition, the organization of the chordae provides an approach path to deliver a prosthetic mitral valve with minimal risk of chordae entanglement.

Prosthetic Valve

When the native mitral valve fails to function properly, a prosthetic valve replacement can help restore the proper functionality. Compared to the aortic valve 14, however, which has a relatively round and firm annulus (especially in the case of aortic stenosis), the mitral valve annulus 8 can be relatively less firm and more unstable. Consequently, it may not be possible to secure a prosthetic valve that is designed primarily for the aortic valve within the native mitral valve annulus 8 by relying solely on friction from the radial force of an outer surface of a prosthetic valve pressed against the native mitral annulus 8. Accordingly, the prosthetic valves described herein can rely on ventricular anchors instead of, or in addition to, radial friction forces, to secure the prosthetic valve within the native mitral valve annulus 8 (see FIG. 23, for example).

In addition to providing an anchoring means for the prosthetic valve, the ventricular anchors can also remodel the left ventricle 6 to help treat an underlying cause of mitral regurgitation—left ventricle enlargement/dilation. The ventricular anchors can pull the native mitral valve leaflets 10, 12 closer together and toward the left atrium and, via the chordae 16, thereby pull the papillary muscles 22, 24 closer together, which can positively remodel the ventricle acutely and prevent the left ventricle from further enlarging. Thus, the ventricular anchors can also be referred to as tensioning members or reshaping members.

Figure 5:
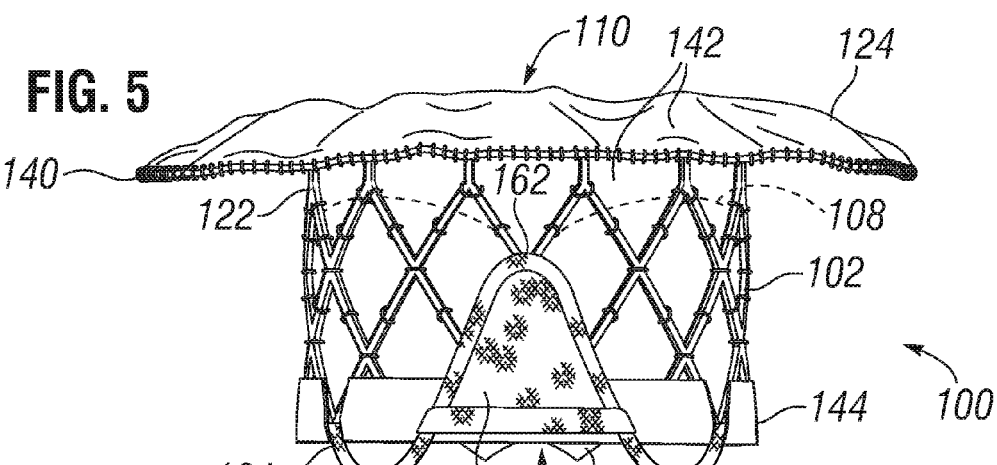
FIG. 5 is a side view of an exemplary embodiment of a prosthetic valve.
Figure 6:
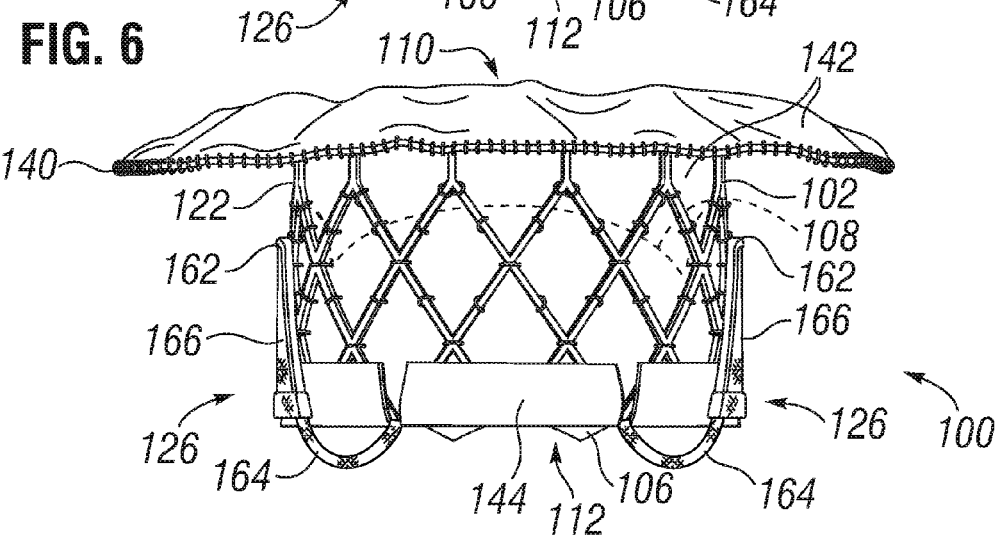
FIG. 6 shows the prosthetic valve of FIG. 5 rotated 90 degrees with respect to a longitudinal axis of the value.
Figure 7:
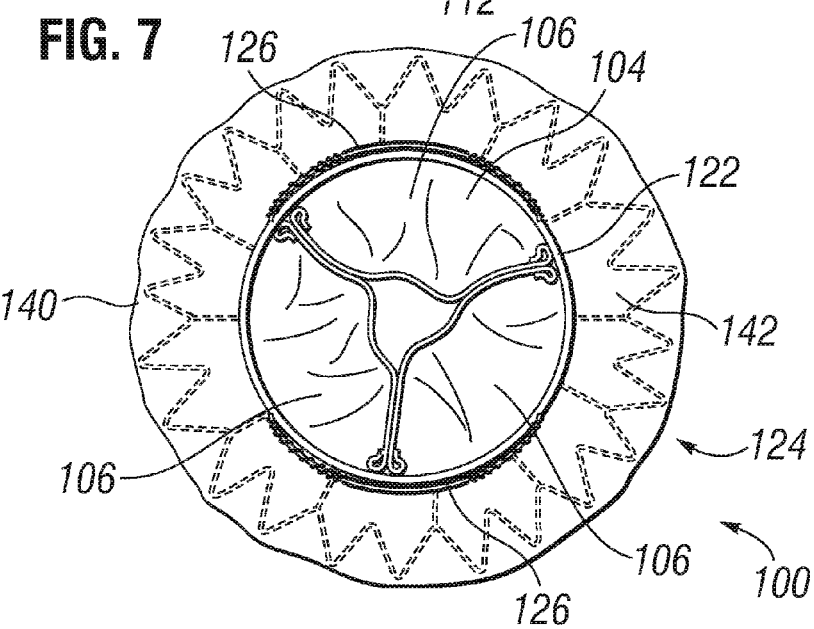
FIG. 7 is a ventricular (outflow) view of the prosthetic valve shown of FIG. 5.
Figure 11:
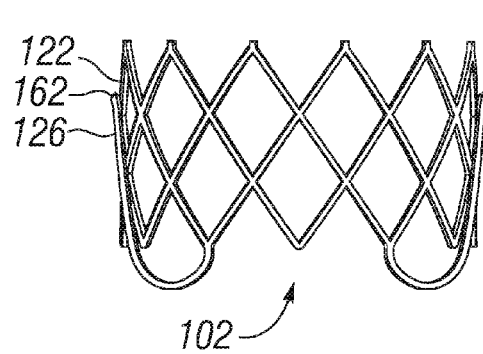
FIGS. 11-16 are a series of side views of the frame of FIG. 9, without the atrial sealing member, showing the leaflet-receiving spaces between the ventricular anchors and the main body increasing as the main body is radially compressed.
Figure 12:
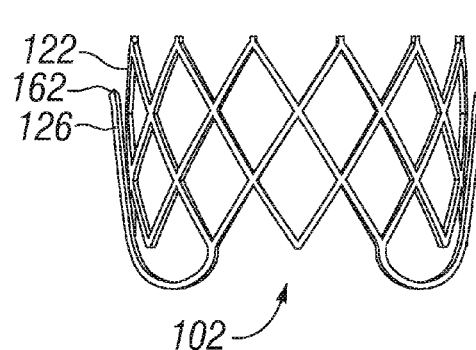
Figure 13:
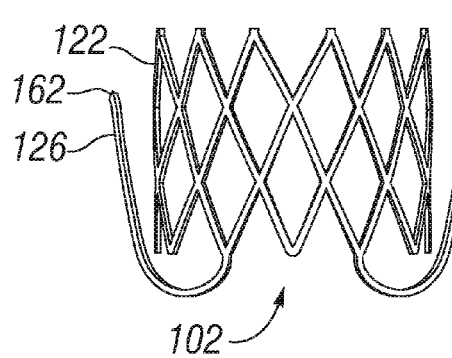
Figure 14:
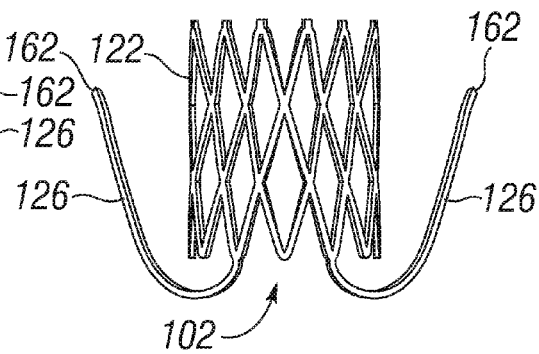
Figure 15:
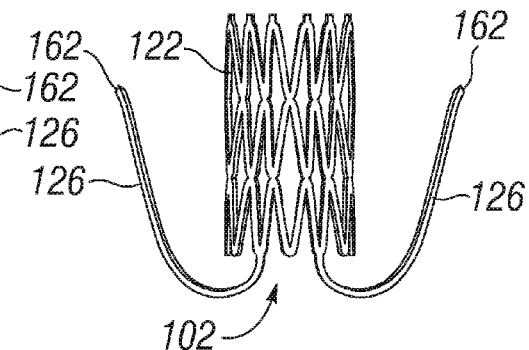
Figure 16:
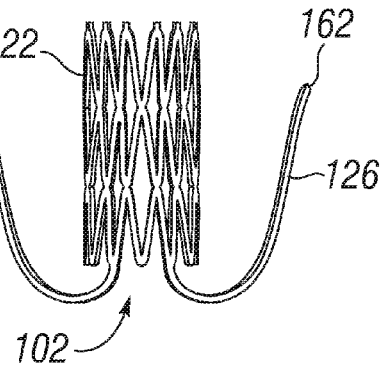

FIGS. 5-7 illustrate an exemplary prosthetic valve 100, according to one embodiment, that can be implanted in the native mitral valve region of the heart to replace the functionality of the native mitral valve 2. The prosthetic valve 100 comprises a frame 102 and a valve structure 104 supported by and/or within the frame. The valve structure 104 can include a plurality of prosthetic leaflets 106 (three in the illustrated embodiment) and/or other components for regulating the flow of blood in one direction through the prosthetic valve 100. In FIGS. 5 and 6, for example, valve structure 104 is oriented within the frame 102 such that an upper end 110 of the valve structure is the inflow end and a lower end 112 of the valve structure is the outflow end. The valve structure 104 can comprise any of various suitable materials, such as natural tissue (e.g., bovine pericardial tissue) or synthetic materials. The valve structure 104 can be mounted to the frame 102 using suitable techniques and mechanisms. In the illustrated embodiment, for example, the leaflets 106 are sutured to the frame 102 in a tricuspid arrangement, as shown in FIG. 7.

Additional details regarding components and assembly of prosthetic valves (including techniques for mounting leaflets to the frame) are described, for example, in U.S. Patent Application Publication No. 2009/0276040 A1 and U.S. patent application Ser. No. 12/393,010, which are incorporated by reference herein.

Figure 23:
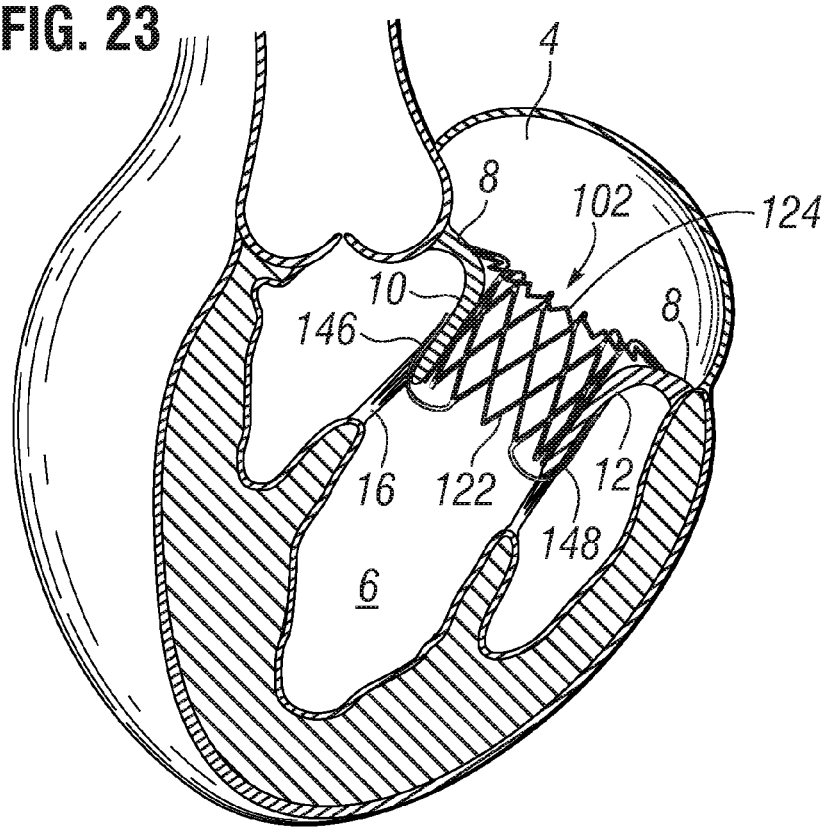
FIG. 23 is a cross-sectional view of the heart showing the frame of FIG. 9 implanted in the mitral valve region, wherein the native mitral valve leaflets are captured between the main body and the ventricular anchors.

As shown in FIGS. 8-10, the frame 102 can comprise a tubular main body 122, one or more ventricular anchors 126 extending from a ventricular end 130 of the main body and optionally an atrial sealing member 124 extending radially outward from an atrial end 132 of the main body. When the frame 102 is implanted in the native mitral valve region of the heart, as shown in FIG. 23, the main body 122 is positioned within the native mitral valve annulus 8 with the ventricular end 130 of the main body 122 being a lower outlet end, the atrial end 132 of the main body 132 being an upper inlet end, the ventricular anchors 126 being located in the left ventricle 6, and the atrial sealing member 124 being located in the left atrium 4.

The frame 102 can be made of a wire mesh and can be radially collapsible and expandable between a radially expanded state and a radially compressed state (as shown schematically in a series of successive stages in FIGS. 11-16 and 17-22) to enable delivery and implantation at the mitral valve region of the heart (or within another native heart valve). The embodiments of the frame 102 shown in FIGS. 11-22 do not include an atrial sealing member 124, though other embodiments of the frame 102 do include an atrial sealing member 124. The wire mesh can include metal wires or struts arranged in a lattice pattern, such as the sawtooth or zig-zag pattern shown in FIGS. 8-10 for example, but other patterns may also be used. The frame 102 can comprise a shape-memory material, such as Nitinol for example, to enable self-expansion from the radially compressed state to the expanded state. In alternative embodiments, the frame 102 can be plastically expandable from a radially compressed state to an expanded state by an expansion device, such as an inflatable balloon (not shown) for example. Such plastically expanding frames can comprise stainless steel, chromium alloys, and/or other suitable materials.

In an expanded state, as shown in FIGS. 8-10, the main body 122 of the frame 102 can form an open-ended tube. The valve structure 104 can be coupled to an inner surface of the frame 102, such as via a material layer 142 on the inner surface of the frame, as discussed below, and can be retained within the lumen formed by the main body 122, as shown in FIG. 7. An outer surface of the main body 122 can have dimensions similar to that of the mitral orifice, i.e., the inner surface of the mitral annulus 8, but not necessarily. In some embodiments, for example, the outer surface of the main body 122 can have diametrical dimensions that are smaller than the diametrical dimensions of the native mitral orifice, such that the main body 122 can fit within the mitral orifice in the expanded state without substantially stretching the native mitral annulus 8, such as in FIG. 23. In such embodiments, the frame 102 need not rely on a pressure fit, or friction fit, between the outer surface of the main body 122 and the inner surface of the mitral annulus 8 for prosthetic valve retention. Instead, the frame 102 can rely on the ventricular anchors 126 and/or the atrial sealing member 124 for retention, as further described below. In other embodiments, however, the main body 122 can be configured to expand to an equal or greater size than the native mitral orifice and thereby create a pressure fit when implanted.

In embodiments wherein the main body 122 comprises diametrical dimensions that are smaller than the diametrical dimensions of the native mitral orifice, the main body can sit loosely, or "float," between the native leaflets 10, 12. As shown in FIG. 4C, this loose fit can create gaps 37 between the leaflets 10, 12 and the main body 122 of the frame. To prevent blood flow between the outside of the prosthetic valve 100 and the native valve tissue, such as through the gaps 37, the annular atrial sealing member 124 can create a fully annular contact area, or seal, with the native tissue on the atrial side of the mitral annulus 8. Accordingly, as shown in FIG. 4D, the atrial sealing member 124 can be sized to fully cover the gaps 37.

The ends of the frame 102 can have a saw-toothed or zig-zag pattern, as shown in FIGS. 8-10, comprising a series of side-by-side "V" shaped portions connected together at their upper ends, for example. This pattern can facilitate compression and can help maximize a surface area with which the frame connects to the native tissue. Alternatively, the ends of the frame 102 can have a straight edge, or some other pattern.

Figure 25:
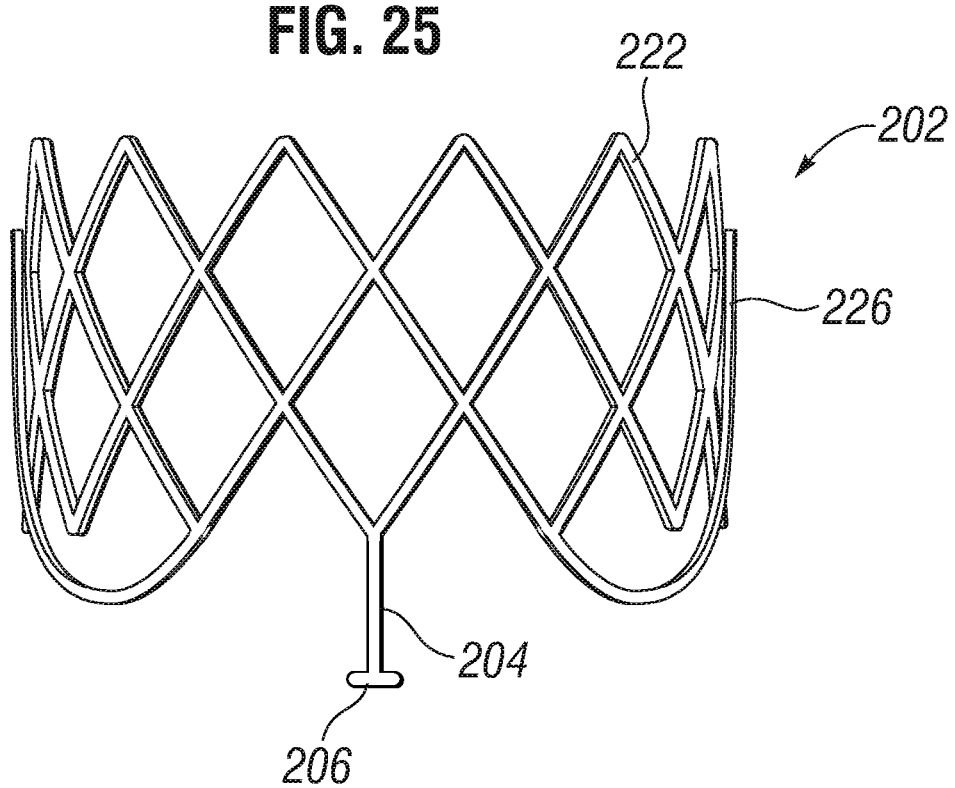
FIG. 25 shows an exemplary embodiment of a frame, with the atrial sealing member excluded, comprising a "T" shaped pushing member extending downward from a ventricular end of the main body.
Figure 26:
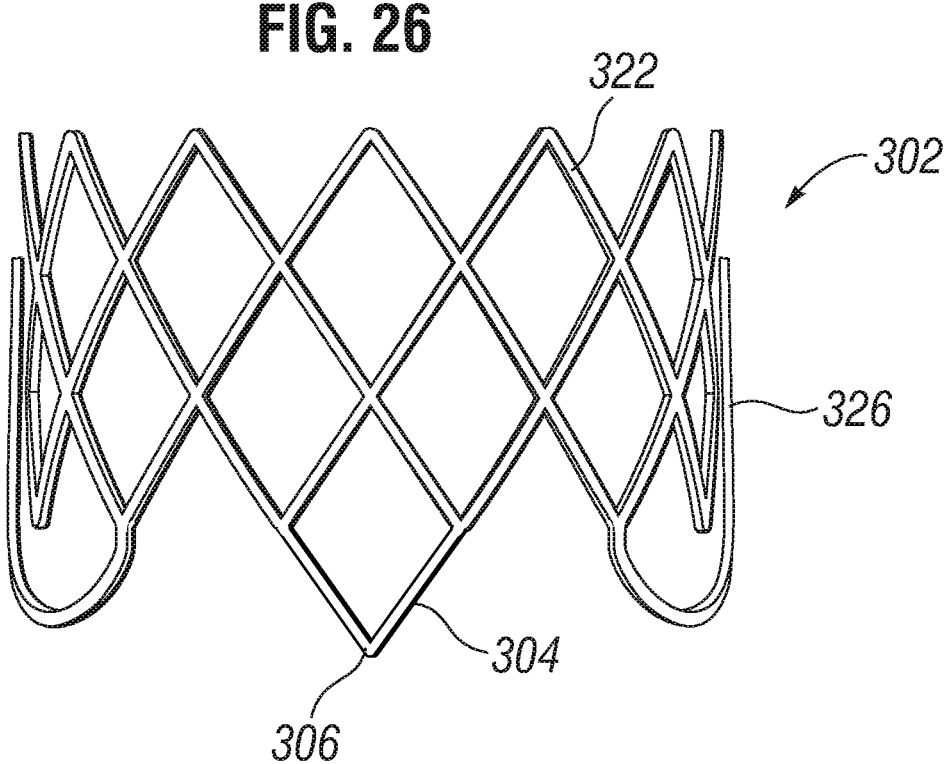
FIG. 26 shows an exemplary embodiment of a frame, with the atrial sealing member excluded, comprising a "V" shaped pushing member extending downward from the ventricular end of the main body.
Figure 30:
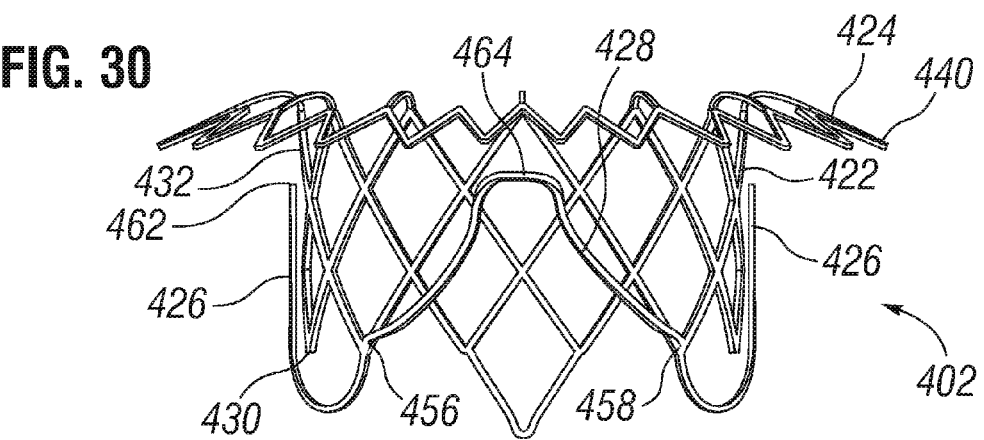
FIGS. 30-32 show the frame of the prosthetic valve shown in FIGS. 27-29.
Figure 31:
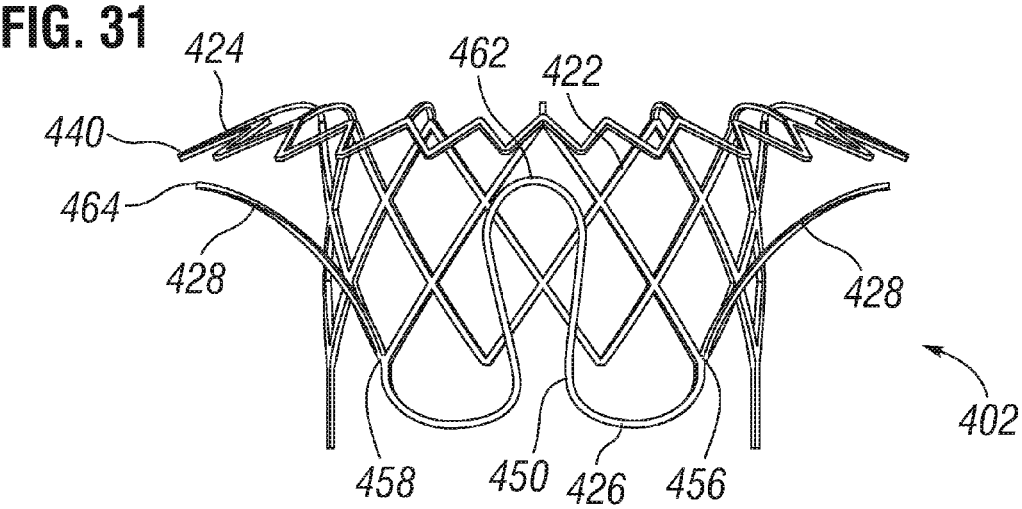
Figure 32:
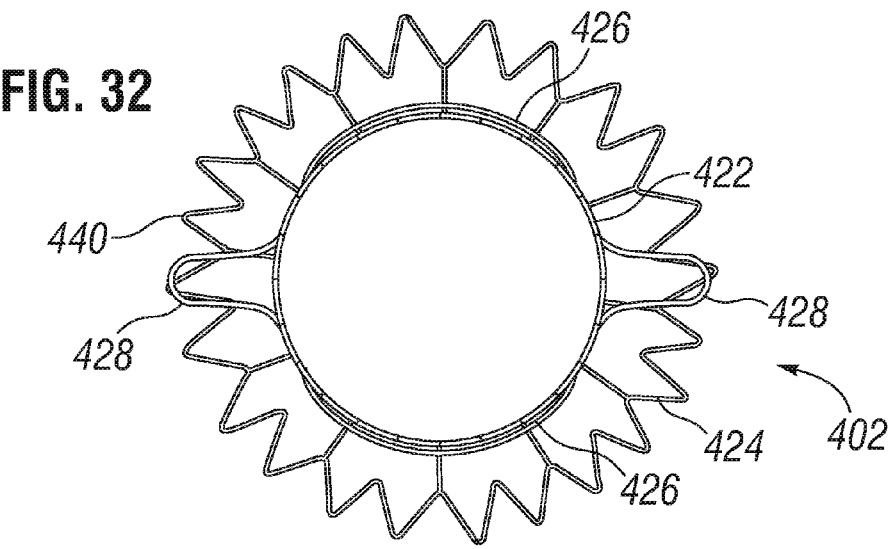

In some embodiments, the main body 122 can comprise at least one extension member, or pushing member, that extends downward from the ventricular end 130 of the main body 122. The frame 202 shown in FIG. 25, for example, comprises an extension member in the form of a prong 204 that extends from the lower vertex of one of the "V" shaped portions of a main body 222. The prong 204 can have an upside-down "T" shape comprising a lower pushing surface 206. In another embodiment, the frame 302 shown in FIG. 26 comprises a "V" shaped pushing member 304 that extends from two adjacent lower vertices of a main body 322 and comprises a pushing surface 306. The pushing surfaces 206 and 306 can comprise the lowermost points on the frames 202 and 302, respectively, and can provide a pushing surface for the frame to be expelled out of a delivery device without contacting the ventricular anchors 226, 326, as described in more detail below.

With reference again to the embodiment shown in FIGS. 8-10, the atrial sealing member 124 of the frame 102 can be integral with the main body 122 and can be comprised of the same wire mesh lattice as the main body 122 such that the atrial sealing member 124 can also be radially collapsible and expandable. In the expanded state, the atrial sealing member 124 can be generally frustoconical and extend from the atrial end 132 of main body 122 both radially outward and axially downward toward the ventricular end 130 of the main body 122. An outer rim 140 of the atrial sealing member 124 can be sized and shaped to contact the atrial side of the mitral annulus and tissue of the left atrium 8 when the frame 102 is implanted, as shown in FIG. 23. The end view profile of the outer rim 140, as shown in FIG. 10, can have a generally circular, oval, or other shape that generally corresponds to the native geometry of the atrial walls 18 and the mitral annulus 8. The contact between the atrial sealing member 124 and the tissue of the atrial walls 18 and/or the mitral annulus 8 can promote tissue in-growth with the frame, which can improve retention and reduce paravalvular leakage.

The atrial sealing member 124 desirably is sized such that when the prosthetic valve 100 is implanted in the native mitral valve, as shown in FIG. 23, the outer rim 140 contacts the native annulus 8 around the entire native valve and therefore completely covers the opening between the native leaflets 10, 12. The atrial sealing member 124 desirably includes a sealing layer 142 that is impervious to the flow of blood. In this manner, the atrial sealing member 124 is able to block blood from flowing back into the left atrium between the outer surfaces of the prosthetic valve 100 and the native valve tissue. The atrial sealing member also ensures that all, or substantially all, of the blood passes through the one-way valve as it flows from the left atrium to the left ventricle.

As shown in FIGS. 5-7, at least one biocompatible sheet or layer 142 can be connected to the inner and/or outer surfaces of the main body 122 and the atrial sealing member 124 to form at least one layer or envelope covering the openings in the wire mesh. The layer 142 can be connected to the frame 102 by sutures, for example. The layer 142 can form a fluid-occluding and/or sealing member that can at least partially block the flow of blood through the wire mesh to reduce paravalvular leakage and can promote tissue in-growth with the frame 102. The layer 142 can provide a mounting surface, or scaffold, to which the portions of the valve structure 104, such as the leaflets 106, can be secured. For example, the dashed line 108 in FIGS. 5 and 6 represents where the inlet ends of the leaflets 106 can be sewn, sutured, or otherwise secured to the layer 142. This seam between the inlet ends of the leaflets 106 and the layer 142 can form a seal that is continuous around the inner perimeter of the layer 142 and can block blood flow between the inner surface of the layer 142 and the outer surface of the leaflets 106. This seal can allow the prosthetic valve 100 to direct blood to flow between the plurality of leaflets 106.

The same layer 142 and/or one or more separate cuffs 144 can also wrap around, or cover, the end edges of the frame 102, such as the ventricular end 130 of the main body 122 and/or the outer rim 140 of the atrial sealing member 124. Such a cuff 144 can cover and protect sharp edges at the ends of the frame 102. For example, in the embodiment shown in FIG. 5, the layer 142 extends from the outer rim 140 across the upper surface of the atrial sealing member 124 and downward along the inner surface of the main body 122 and comprises a cuff 144 that wraps around and covers a ventricular end portion of the main body 122. The layer 142 can be sutured to the outer rim 140 and to the inner surface of the main body 122.

The layer 142 can comprise a semi-porous fabric that blocks blood flow but can allow for tissue in-growth. The layer 142 can comprise synthetic materials, such as polyester material or a biocompatible polymer. One example of a polyester material is polyethylene terephthalate (PET). Alternative materials can be used. For example, the layer can comprise biological matter, such as natural tissue, pericardial tissue (e.g., bovine, porcine, or equine pericardium) or other biological tissue.

With reference to FIGS. 8 and 9, one or more ventricular anchors 126 can extend from the main body 122 of the frame 102, such as from the ventricular end 130 of the main body. The ventricular anchors 126 can function to retain the frame 102, with or without the valve structure 104, within a native valve region of the heart. In the embodiment shown in FIGS. 8 and 9, the frame 102 comprises two diametrically opposed ventricular anchors 126 that can function to secure the frame 102 to the anterior and posterior mitral leaflets 10, 12, respectively, when the frame 102 is implanted in the mitral valve region, as shown in FIG. 23. In alternate embodiments, the frame 102 can have three or more ventricular anchors 126, which can be angularly spaced around the main body 122 of the frame.

When the frame 102 is in an expanded state, as in FIG. 9, the geometry of the frame can cause the ventricular anchors 126 to be urged against the outer surface of the main body 122. Alternatively, the ventricular anchors 126 can be configured to be spaced apart from the outer surface of the main body 122 when the frame 102 is in the expanded state (see FIG. 39, for example). In any case, when the frame 102 is radially compressed to the compressed state, the space or gap between the ventricular anchors 126 and the outer surface of the main body 122 can increase, as shown in FIGS. 11-16.

Figure 59:
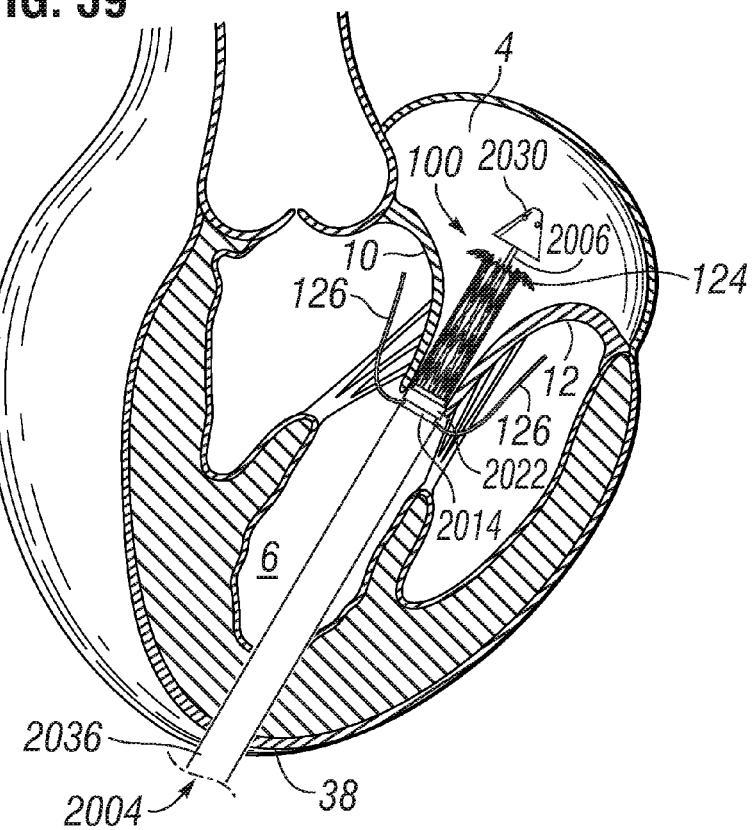
FIG. 59 is a cross-sectional view of the heart showing the prosthetic valve being implanted in the mitral valve region using the delivery system of FIG. 49 with the native leaflets positioned between the ventricular anchors and the inner sheath.

While the main body 122 and the atrial sealing member 124 are in the compressed state, the frame 102 can be inserted into the mitral valve orifice such that the spaced apart ventricular anchors 126 wrap around the leaflets 10, 12 and extend upward between the leaflets and the ventricular walls 20 (see FIG. 59, for example). With reference to FIG. 23, an anterior ventricular anchor 146 can be located behind the anterior leaflet 10 and a posterior ventricular anchor 148 can be located behind the posterior leaflet 12. With reference to FIGS. 3 and 4, the two ventricular anchors are desirably located behind the respective leaflets near the middle portions of the leaflets A2, P2 about midway between the commissures 36 where the two leaflets meet. These middle portions A2, P2 of the leaflets 10,12 are desirable ventricular anchor locations because the chordae tendineae 16 attachments to the leaflets are sparser in these locations compared to locations nearer to the commissures 36.

When the main body 122 is subsequently expanded or allowed to self-expand to the expanded state, as shown in FIGS. 11-16 in reverse order, the ventricular anchors are configured to pivot radially inward relative to the main body 122, without external compressive forces on the ventricular anchors. This causes the gaps between the ventricular anchors 126 and the outer surface of the main body 122 to decrease, thereby enabling the capture of the leaflets 10, 12 between the ventricular anchors and the main body. Conversely, compressing the main body 122 causes the ventricular anchors 126 to pivot away from the main body to increase the gaps between the outer surface of the main body and the ventricular anchors. In some embodiments, the free ends, or apexes, 162 of the ventricular anchors 126 can remain substantially the same distance apart from one another as the main body 122 is radially compressed or expanded free of external forces on the ventricular anchors. In some embodiments, such as the embodiment shown in FIG. 23, the frame is configured to compress the native mitral leaflets 10, 12 between the main body and the ventricular anchors when the frame expands to the expanded state. In other embodiments, such as the embodiment shown in FIG. 39, the ventricular anchors do not compress or clamp the native leaflets against the main body but still prevent the prosthetic valve from migrating toward the left atrium by the hooking of the ventricular anchors around the native leaflets 10, 12. In such embodiments, the prosthetic valve 100 can be retained in place against migration toward the left ventricle by the atrial sealing member 124 as further described below.

With reference to the embodiment shown in FIGS. 8-10, each ventricular anchor 126 can comprise a flexible, elongate member, or wire, 150 comprised of a shape memory material, such as, for example, Nitinol. In some embodiments, as shown in FIG. 8, each wire 150 can comprise a first end portion 152 coupled to a first attachment location 156 of the main body 122, and a second end portion 154 coupled to a second attachment location 158 of the main body. The first and second end portions 152, 154 form a base of the ventricular anchor. The first and second attachment locations 152, 154 of the main body can be at, or adjacent to, the ventricular end 130 of the main body 122. The two end portions 152, 154 of each wire 150 can be extensions of the wires or struts that make up the lattice mesh of the main body 122. Each wire 150 further comprises an intermediate portion 160 extending in a direction lengthwise of the main body between the end portions 152, 154. The intermediate portion 160 includes a bend 162 that forms the free end portion, or apex, of the ventricular anchor.

The wire 150 can have a circular or non-circular cross-sectional profile perpendicular to a length of the wire, such as a polygonal cross-sectional profile. With reference to FIG. 8A, the wire 150 can comprise a rectangular cross-sectional shape having a length "L" and a relatively narrower width "W" such that when the two end portions 152, 154 of the ventricular anchor 126 attached to the frame 102 are moved toward each other, such as when the frame is compressed, the wire 150 bends primarily in the width direction. This promotes bending of the ventricular anchor 126 in a direction radially outward away from the main body 122, widening the gap between the ventricular anchor 126 and the main body 122. This feature can help to capture a leaflet between the ventricular anchor 126 and the main body 122 during implantation.

Ventricular anchors can comprise various shapes or configurations. Some frame embodiments, such as the frame 102 shown in FIG. 8, comprise generally "U" or "V" shaped ventricular anchors 126 that connect to the main body 122 at two attachment locations 156, 158. The upper apex 162 of the ventricular anchors 126 can function like a wedge to facilitate moving the ventricular anchors behind respective leaflets while minimizing the risk of chordae entanglement. The end portions 152, 154 of each wire 150 can extend downward from attachment locations 156, 158, respectively, at the ventricular end 130 of the main body 122. The wire 150 can then curve back upward from each end portion 152, 154 toward the apex 162.

The wires 150 can be covered by biocompatible materials, such as in the embodiment shown in FIGS. 5-7. A first material 164 can be wrapped around, or coat, at least some portion of the wire 150. A second material 166 can span across two portions of the wire 150 to form a web, which can improve tissue in-growth. The first and second materials 164, 166 can comprise the same material or different materials, such as a biocompatible semi-porous fabric, for example. The covering materials 164, 166 can increase tissue in-growth with the ventricular anchor 126 to improve retention. Furthermore, the covering materials can decrease the frictional properties of the ventricular anchors 126 to facilitate implantation and/or increase the frictional properties of the ventricular anchors to improve retention.

Figure 24:
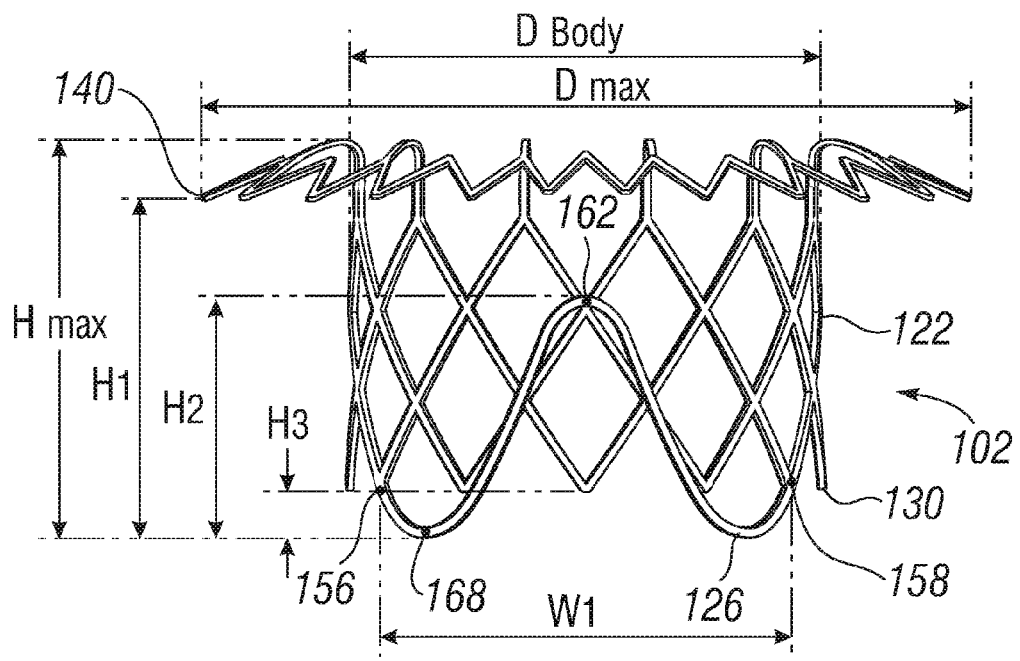
FIG. 24 shows exemplary dimensions of the atrial sealing member, main body and ventricular anchors of FIG. 9.

FIG. 24 shows exemplary dimensions of the embodiment of the frame 102 shown in FIG. 9. The diameter "Dmax" of the outer rim 140 of the atrial sealing member 124 can range from about 50 mm to about 70 mm, and is about 50 mm in one example. The diameter "Dbody" of the outer surface of the main body 122 can range from about 23 mm to about 50 mm, and is about 29 mm in one example. The distance "W1" between the two attachment points 156, 158 for one ventricular anchor 126 can range from about 8 mm to about 50 mm, and is about 25 mm in one example. The overall axial height "Hmax" of the frame 102 can range from about 20 mm to about 40 mm, and is about 30 mm in one example. The axial height "H1" from the outer rim 140 to the lowermost portion 168 of the ventricular anchors 126 can range from about 10 mm to about 40 mm, and is about 23 mm in one example. The axial distance "H2" from the apex 162 of the ventricular anchor 126 to the lowermost portion 168 of the ventricular anchor 126 can range from about 10 mm to about 40 mm, and is about 18 mm in one example. The axial distance "H3" from the lower end 130 of the main body 122 to the lowermost portion 168 of the ventricular anchor 126 can range from about 0 mm to about 10 mm, and is about 5 mm in one example.

Some frame embodiments comprise more than two ventricular anchors. For example, a frame can have two or more ventricular anchors configured to attach to multiple locations along a single leaflet of a native valve. In some such embodiments (not shown), the frame can comprise two ventricular anchors that attach to the anterior mitral leaflet 10 and/or two ventricular anchors that attach to the posterior mitral leaflet 12. Ventricular anchors can also attach to other regions of the leaflets instead of, or in addition to, the A2 and P2 regions.

Figure 33:
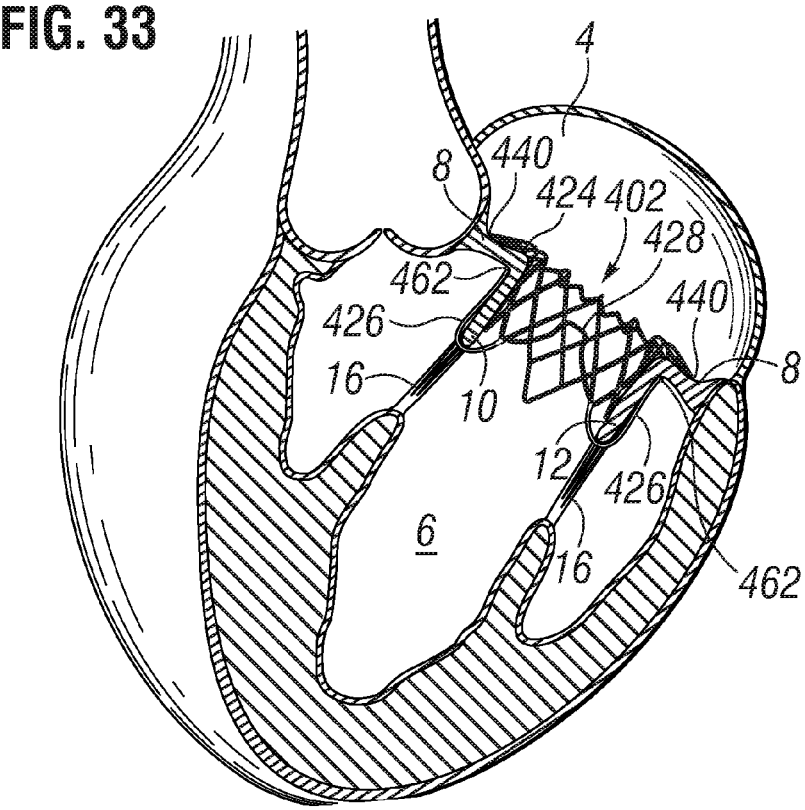
FIG. 33 is a cross-sectional view of the heart showing the frame of FIGS. 30-32 implanted in the mitral valve region.

Some prosthetic valve embodiments comprise four ventricular anchors spaced evenly apart around a main body. FIGS. 27-32 show one such prosthetic valve embodiment 400 comprising a frame 402 that comprises a pair of ventricular anchors 426 on diametrically opposed sides of a main body 422 and a pair of diametrically opposed commissure anchors 428 located about midway between the ventricular anchors 426. The ventricular anchors 426 extend downward from attachment points 456 and 458 and comprise a neck portion 450 (see FIG. 31). These ventricular anchors 426 can function similarly to the ventricular anchors 126 of the frame 102 to capture leaflets and retain the frame 402 within the mitral orifice, as shown in FIG. 33. The commissure anchors 428 can extend upward from the same attachment locations 456, 458 on the main body 422 (see FIG. 30). While the ventricular anchors 426 can clip the mitral leaflets 10, 12 at the A2 and P2 regions, respectively, the commissure anchors 428 can hook around and extend upward behind the mitral commissures 36, not compressing the leaflets. The apexes 464 of the commissure anchors 428 can extend upward to abut the ventricular side of the mitral annulus 8 and compress the mitral annulus 8 between the outer rim 440 of the atrial sealing member 424 and the apexes 464 of the commissure anchors 428. This compression of the mitral annulus 8 can provide additional retention against both atrial and ventricular movement.

Other frame embodiments can comprise more than four ventricular anchors. For example, a frame can comprise six or more ventricular anchors that can engage multiple locations on the leaflets 10, 12 and/or the commissures 36.

Figure 34:
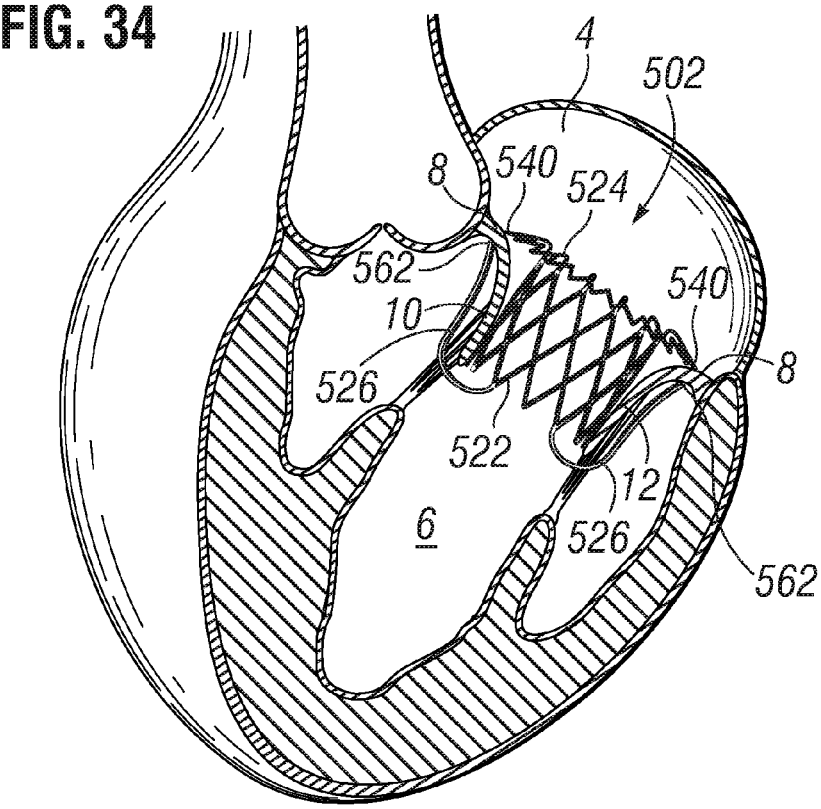
FIG. 34 is a cross-sectional view of the heart showing an embodiment of a frame, comprising extended ventricular anchors and an atrial sealing member, implanted in the mitral valve region such that the mitral annulus and/or native leaflets are compressed between the ends of the extended ventricular anchors and the atrial sealing member.

FIG. 34 shows a frame embodiment 502 that comprises extended ventricular anchors 526 that are configured to extend around the ends of the leaflets 10, 12 and extend upward behind the leaflets to locations proximate the outer rim 540 of a downwardly extending frustoconical atrial sealing member 524. The upper apexes 562 of the extended ventricular anchors 526 contact the ventricular surface of the mitral annulus 8 and/or portions of the native leaflets 10, 12 adjacent to the annulus, or annulus connection portions of the leaflets, while the outer rim 540 of the atrial sealing member 524 contacts the atrial surface of the mitral annulus and/or the annulus connection portions of the leaflets. The extended ventricular anchors 526 and the atrial sealing member 524 can be configured to oppose one another and desirably compress the mitral annulus 8 and/or annulus connection portions of the leaflets 10, 12 to retain the frame 502 from movement in both the atrial and ventricular directions. Thus, in this embodiment, the ventricular anchors 526 need not compress the native leaflets 10, 12 against the outer surface of the main body 522 of the frame. Instead, as shown in FIG. 34, the leaflets 10, 12 can be captured loosely between the extended ventricular anchors 526 and the outer surface of the main body 522.

Figure 35:
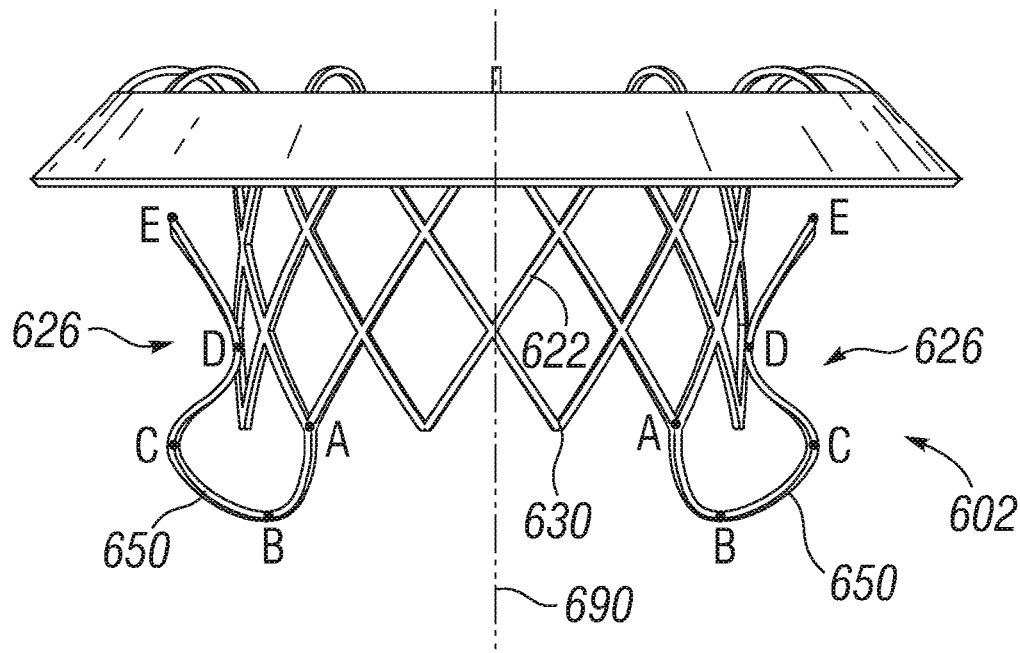
FIGS. 35 and 36 are side views of an exemplary embodiment of a frame comprising "S" shaped ventricular anchors.
Figure 36:
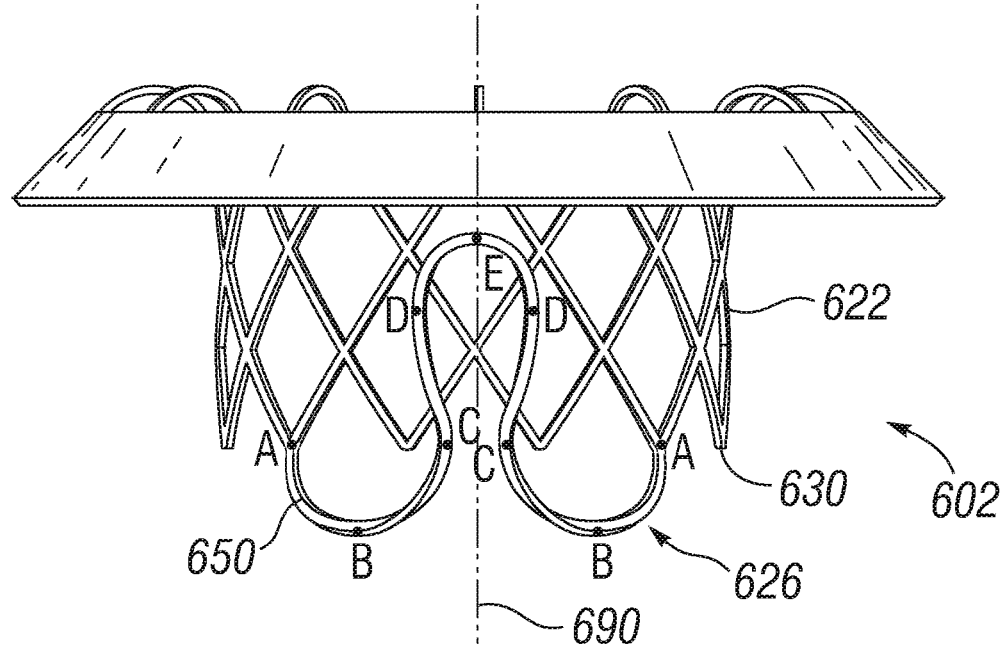

FIGS. 35 and 36 show a frame embodiment 602 comprising necked, "S" shaped ventricular anchors 626. From the side view of FIG. 35, the "S" shape of the ventricular anchors 626 is apparent. Starting from one attachment point A on the ventricular end 630 of the main body 622, the ventricular anchor wire 650 extends downward and radially outward from the main body to a point B, then curves upward and outward to a point C, then curves upward and inward to a point D, and then curves upward and back outward to an uppermost point, or apex, E. The ventricular anchor wire 650 then continues to extend back to the second attachment point following a similar, but mirrored path. From the frontal view of FIG. 36, the ventricular anchor wire 650 forms a necked shape that is symmetrical about a longitudinal center axis 690 extending through the center of the main body 622, forming two mirrored halves. Each half of ventricular anchor wire 650 begins at an attachment point A on the ventricular end 630 of the main body 622, curves downward and inward (toward the other half) to point B, then curves upward and inward to a necked portion at point C, then curves upward and outward (away from the other half) to a point D, then curves upward and inward again to an uppermost point, or apex, E where the two halves join together. Referring to FIG. 35, the radial distances from a longitudinal center axis 690 of the main body 622 to points C and E are both greater than the radial distances from the axis 690 to points D. Furthermore, the distance between the two points C is less than the distance between the two points D. The "S" shaped ventricular anchor 626 can help distribute stresses more evenly along the wire 650 and reduce stress concentrations at certain locations, such as the attachment points A.

Figure 37:
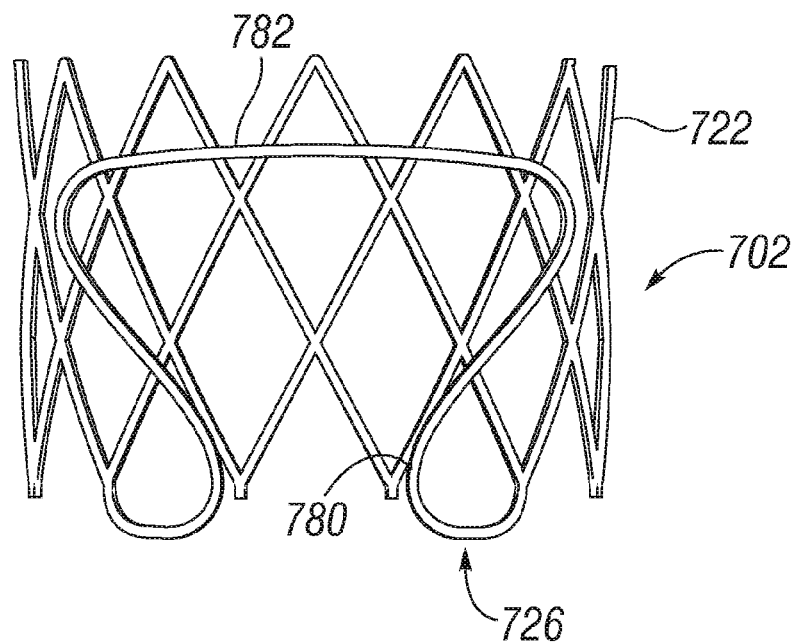
FIGS. 37 and 38 are side and top views, respectively, of an exemplary embodiment of a frame, with the atrial sealing member excluded, comprising wider shaped ventricular anchors.
Figure 38:
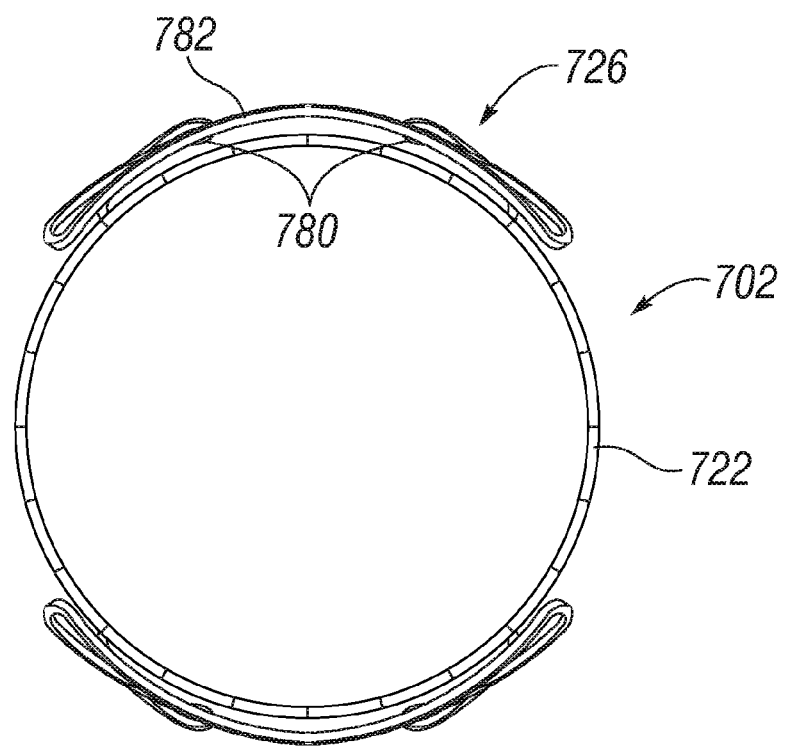

FIGS. 37 and 38 show a frame embodiment 702 that comprises two wider shaped ventricular anchors 726. Each wider shaped ventricular anchors 726 comprises a necked mid portion 780 and a broad upper portion 782. The upper portion 782 can extend generally parallel to the inflow opening of the frame 702 and can be curved around the outer surface of a main body 722. This wider shape can increase surface contact with the native leaflet and/or other cardiac tissue to reduce pressure and thereby reduce abrasion. In some embodiments, the broad upper portion 782 of the wider shaped ventricular anchors 726 can have a curvature that corresponds to the curvature of the outer surface of the main body 722 (see FIG. 38) to further improve tissue contact. The wider shaped ventricular anchor can have a longer surface contact with the atrial sealing member; thereby increasing retention performance and reducing paravalvular leak.

Figure 39:
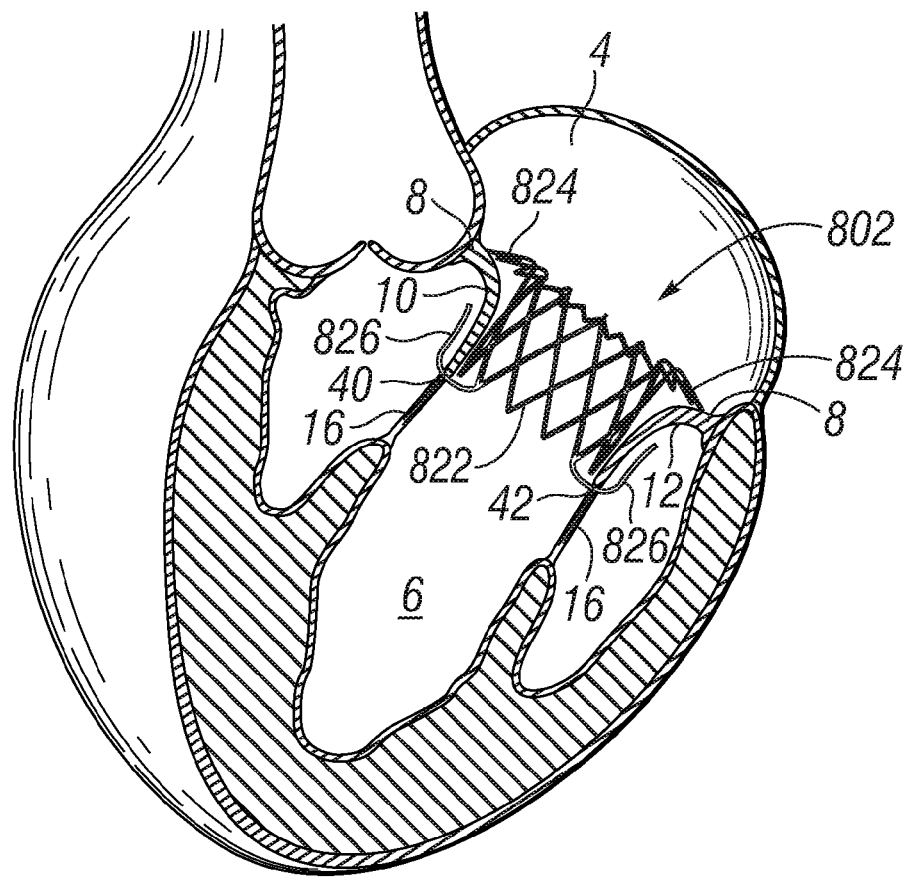
FIG. 39 is a cross-sectional view of the heart showing an embodiment of a frame implanted in the mitral valve region, wherein the ventricular anchors remain separated from the body of the frame after expansion and the ventricular anchors contact the lower ends of the mitral leaflets to utilize tension from the chordae tendineae to retain the frame.

FIG. 39 shows a frame embodiment 802 comprising ventricular anchors 826 that are configured to define a separation, or gap, between the anchors and the main body 822 even after the frame 802 expands (although the anchors 826 can otherwise function similar to ventricular anchors 126, such that the gaps between the anchors 826 and the frame main body 822 can increase and decrease upon compression and expansion of the main body, respectively, to facilitate placement of the anchors 826 behind the native leaflets). The gap can be sized to facilitate capturing the native leaflets 10, 12 with little or no compression of the native leaflets. Since little or no leaflet compression occurs, this frame embodiment 802 can minimize trauma to the native leaflets. Instead of compressing the leaflets 10, 12 for valve retention, the ventricular anchors 826 can hook the ventricular edges 40, 42 of the leaflets 10, 12, respectively, while an atrial sealing member 824 of the frame presses downwardly on the atrial side of the mitral valve annulus 8. The contact between the atrial sealing member 824 and the annulus 8 causes the main body 822 to shift slightly upwardly pulling the ventricular anchors 826 upwardly against the ventricular edges of the leaflets 10, 12. The upward force of the ventricular anchors in conjunction with downward tension on the leaflets from the chordae tendineae 16 restrain the implant from moving upward toward the left atrium 4.

Figure 40:
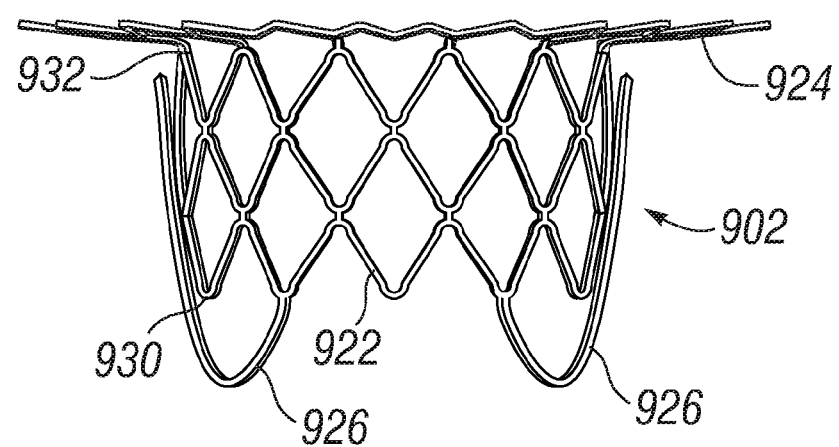
FIG. 40 shows an exemplary embodiment of a frame comprising a substantially flat atrial sealing member.

FIG. 40 shows a frame embodiment 902 that comprises a main body 922, ventricular anchors 926 and a disk-like atrial sealing member 924 that extends radially outward from the upper end 932 of the main body 922. In this embodiment, the atrial sealing member 924 extends substantially perpendicular to the frame opening defined by the upper and 932 rather than downwardly toward the frame's lower end 930. The disk-like atrial sealing member 924 can be positioned flat across the top surface of the mitral annulus 8 and provide increased surface area contact for tissue in-growth.

Figure 41:
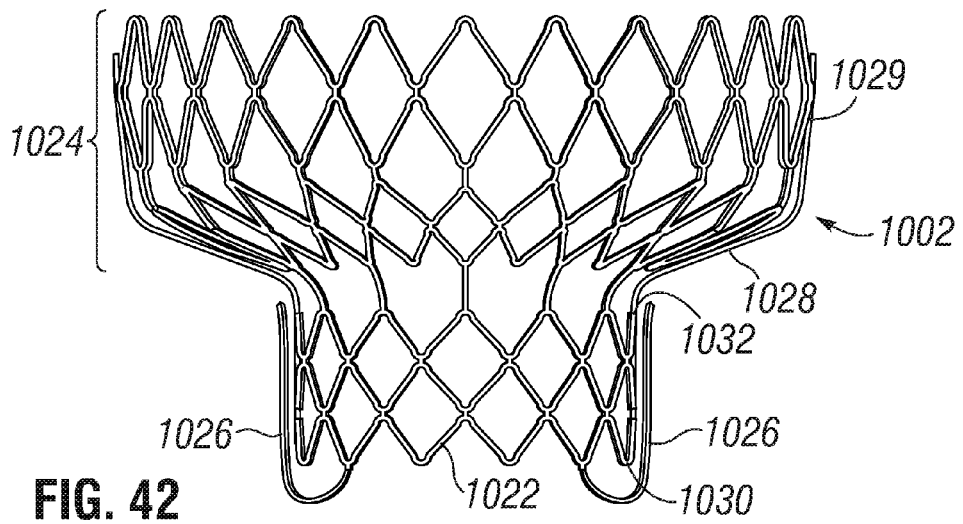
FIG. 41 shows an exemplary embodiment of a frame comprising an upwardly extending atrial sealing member.
Figure 42:
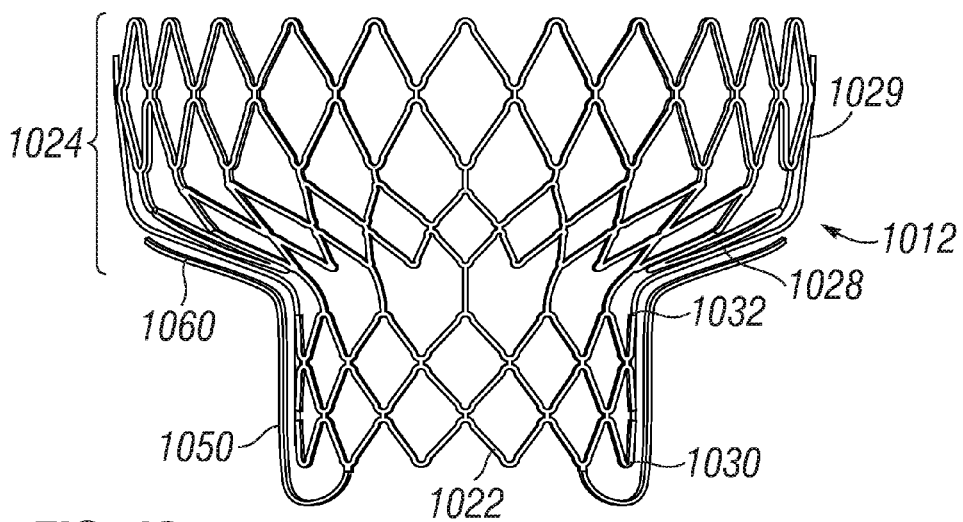
FIG. 42 shows an exemplary embodiment of a frame comprising an upwardly extending atrial sealing member and extended ventricular anchors.

FIGS. 41 and 42 show frame embodiments 1002 and 1012, respectively, that comprise an atrial sealing member 1024 having a generally frustoconical portion 1028 that extends from the upper end 1032 of a main body 1022 both radially outward and axially upward away from the main body. The atrial sealing member 1024 can also include a generally cylindrical upper, or inlet, portion 1029 that extends further upward from the frustoconical portion 1028 opposite the upper end 1032 of the main body 1022. The atrial sealing member 1024 can generally correspond to the shape of the atrial walls 18 adjacent to the mitral annulus 8 and provide for increased contact area between the atrial wall tissue and the atrial sealing member 1024. The frame 1002 includes ventricular anchors 1026 that extend from a ventricular end 1030 of the main body 1022 and along the majority of the length of the main body.

The frame 1012 shown in FIG. 42 comprises extended ventricular anchors 1050. The extended anchors 1050 can extend from the ventricular end 1030 of the main body 1022 along the outer surface of the main body and bend radially outward to form upper portions 1060 that extend along the lower surface of the frustoconical portion 1028. This configuration can allow the extended ventricular anchors 1050 to trap more of the leaflets 10, 12 and/or the mitral annulus 8 against the frame, thereby reducing paravalvular leakage and improving tissue in-growth and retention.

Figure 43:
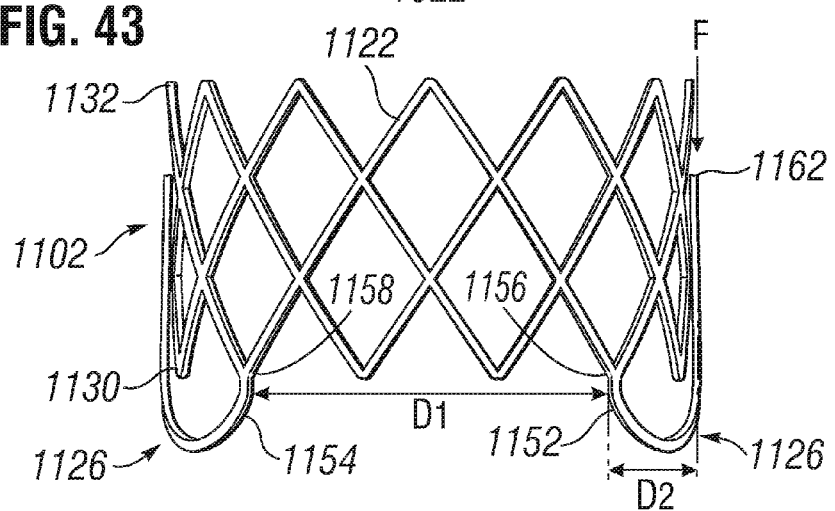
FIG. 43 shows an exemplary embodiment of a frame, with the atrial sealing member excluded, comprising wide-set ventricular anchors.

FIG. 43 shows a frame embodiment 1102 having ventricular anchors 1126 that have shorter moment arms D2 compared to the ventricular anchors 126 of the frame 102 shown in FIG. 9. The shorter moment arms D2 can result in reduced torque at the ventricular anchor attachment points 1156, 1158. The distance D2 can be reduced by increasing the distance D1 between the attachment points 1158 and 1156 on the main body 1122 of neighboring ventricular anchors 1126. The distance D1 between the ventricular anchors 1126 of the frame 1102 is greater than the distance D1 between the attachment points 158 and 156 of frame 102 (see FIG. 9), thus shortening the moment arm D2 of the force F relative to the attachment point 1156. The reduced torque at the attachment points 1156 and 1158 can reduce fatigue and thus improve the durability of the frame 1102.

Some embodiments of ventricular anchors can optionally also comprise one or more barbs (not shown) that can protrude radially from a ventricular anchor toward the ventricular walls 20 or toward the leaflets 10, 12. Such barbs can help retain a frame, particularly against movement towards the left ventricle 6.

Figure 44:
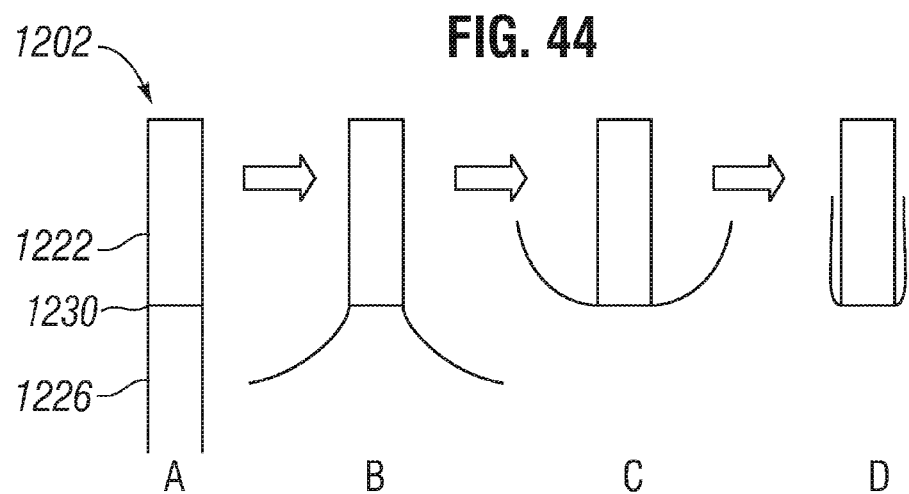
FIG. 44 depicts a series of side views of an exemplary embodiment of a frame, with the atrial sealing member excluded, having ventricular anchors that flip up into a final configuration.

FIGS. 44A-44D illustrate a frame embodiment 1202 comprising "flip-up" ventricular anchors 1226. Each ventricular anchor 1226 can be finger-like and can extend from only one attachment point on the lower end 1230 of the main body 1222. Alternatively, each ventricular anchor can comprise a wire or similar element that extends from two attachment points on the main body 1222. In the illustrated embodiment, the ventricular anchors 1226 can be pre-formed to extend along the outer side of the main body 1222 in the functional, deployed state, as shown in FIG. 44D. During delivery, the ventricular anchors 1226 can be partially or completely straightened, as shown in FIG. 44A, and retained in that state by a delivery device, such as a sheath. As the frame 1202 is advanced from the sheath, for example, the ventricular anchors 1226 spring back to their pre-formed shape, as shown in FIGS. 44B-44D, capturing the leaflets 10, 12 between the ventricular anchors 1226 and the main body 1222.

Figure 45:
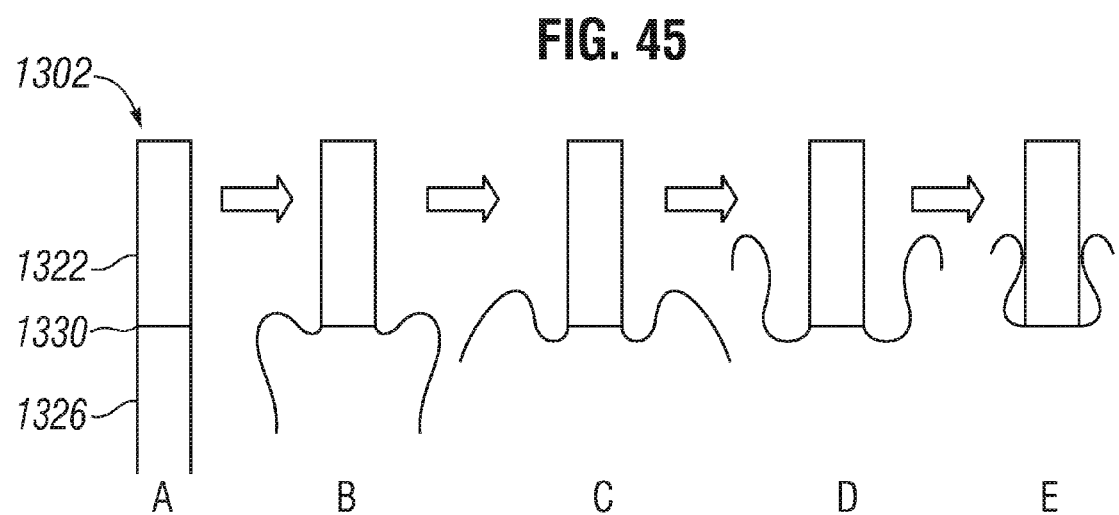
FIG. 45 depicts a series of side views of an exemplary embodiment of a frame, with the atrial sealing member excluded, having ventricular anchors that curl up into a final configuration.

FIGS. 45A-45E represent a frame embodiment 1302 comprising "curl-up" ventricular anchors 1326. As with the ventricular anchors 1226 of FIG. 44, each ventricular anchor 1326 can be finger-like and can extend from two or more points on lower end 1330 of the main body 1322. The ventricular anchors 1326 can be pre-formed in a curved shape, as shown in FIG. 45E, that extends along the side of the main body 1322 in the deployed state. During delivery, the ventricular anchors 1326 can be partially or completely straightened, as shown FIG. 45A, and retained in that state by a delivery device, such as a sheath. As the frame 1302 is advanced from the sheath, for example, the ventricular anchors 1326 are allowed to spring back to their pre-formed curved shape, as shown in FIGS. 45B-45E, capturing the leaflets 10, 12 between the ventricular anchors 1326 and the main body 1322.

Figure 46A:
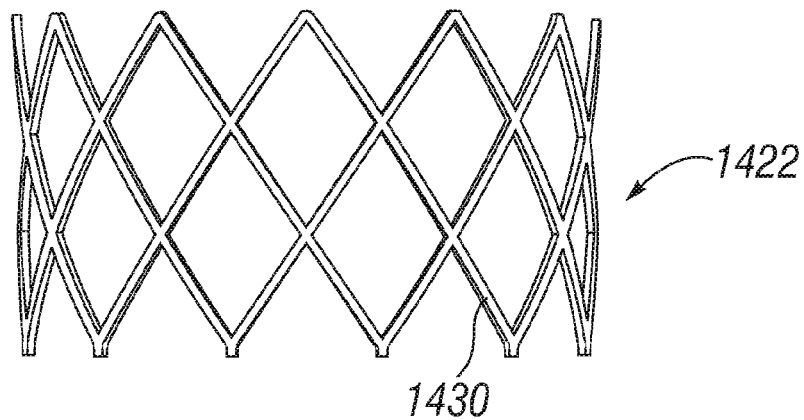
FIGS. 46A-46C show an exemplary embodiment of a frame, with the atrial sealing member excluded, wherein the main body is manufactured separately from the ventricular anchors.
Figure 46B:
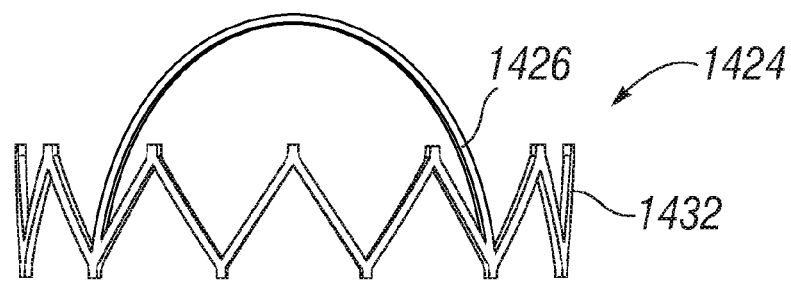
Figure 46C:
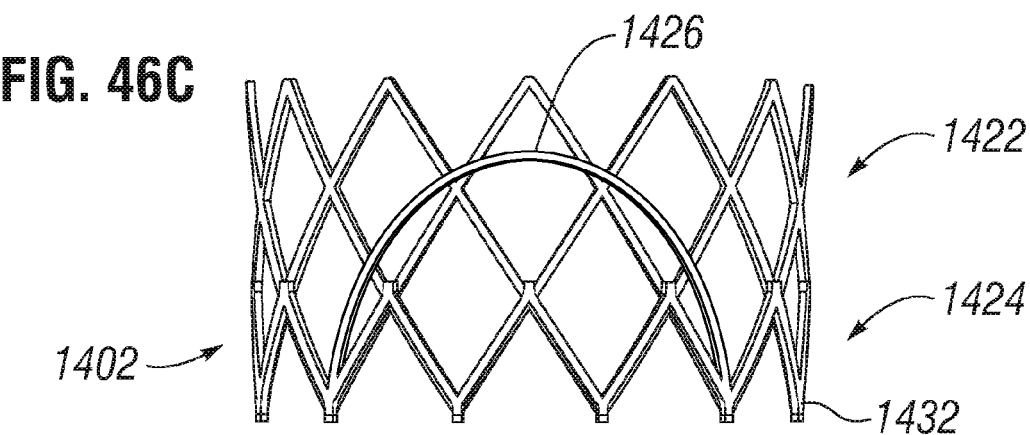
Figure 47A:
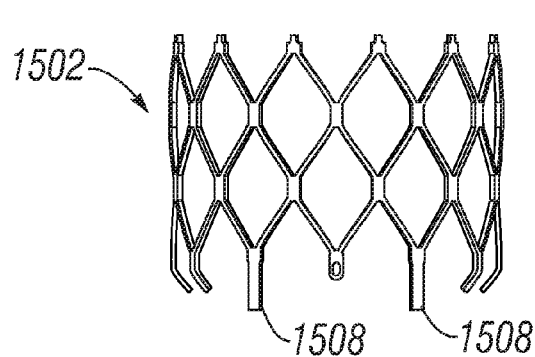
FIGS. 47A-47D show another embodiment of a frame, with the atrial sealing member excluded, wherein the main body is manufactured separately from the ventricular anchors and attached using a sleeve.
Figure 47B:
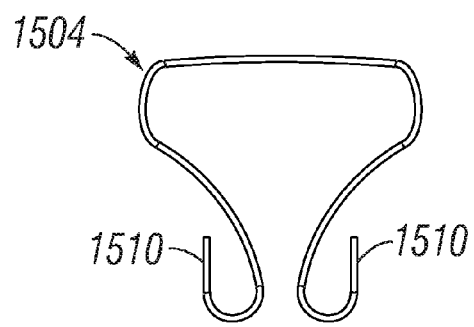
Figure 47C:
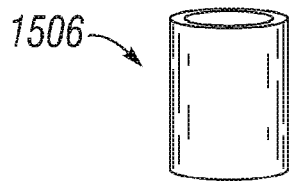
Figure 47D:
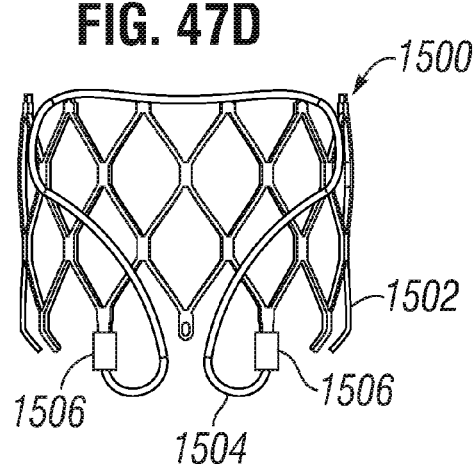

In some frame embodiments, one or more ventricular anchor components can be formed separately from the main body and later assembled together to form a frame. In one such frame embodiment 1402, as shown in FIGS. 46A-46C, a main body 1422 is formed separately from at least one ventricular anchor portion 1424. The ventricular anchor portions 1424 can comprise one or more ventricular anchors 1426 extending from an at least partially annular base 1432, which can comprise side-by-side "V" shaped strut portions connected together at their upper ends. The lower ends of the ventricular anchors 1426 in the illustrated embodiment are connected to the base 1432 at the lower vertexes of the "V" shaped portions. After the main body and the ventricular anchor portions are separately formed, the ventricular anchor portions 1424 can be attached to the lower portion 1430 of the main body 1422. For example, the bases 1432 can be placed on opposite sides of the outer surface of the main body 1422 and then sewn, welded, or otherwise attached to the lower portion 1430 of the main body 1422 in a suitable manner, such as by using a locking mechanism. The bases 1432 can be attached to the main body 1422 such that the "V" shaped portions of the bases overlap with corresponding "V" shaped portions of the lower end 1430 of the main body 1422. In some embodiments, the ventricular anchor portion 1424 can comprise a complete ring having all of the ventricular anchors 1426 extending from one annular base such that the ventricular anchors are pre-spaced relative to one another. The annular base can then be attached around the lower end 1430 of the main body 1422. In other embodiments, multiple ventricular anchor portions 1424, each having one or more ventricular anchors 1426 extending from a respective base 1432 comprising a partial ring, are secured to the main body 1422.

Figure 48A:
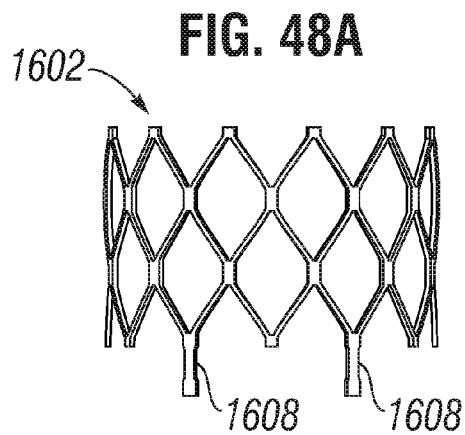
FIGS. 48A-48C show another embodiment of a frame, with the atrial sealing member excluded, wherein the main body is manufactured separately from the ventricular anchors and attached using a sleeve with a mechanical lock.
Figure 48B:
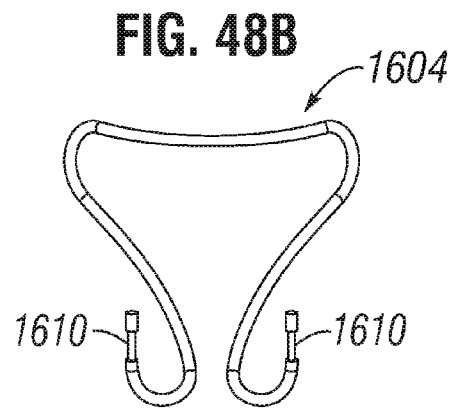
Figure 48C:
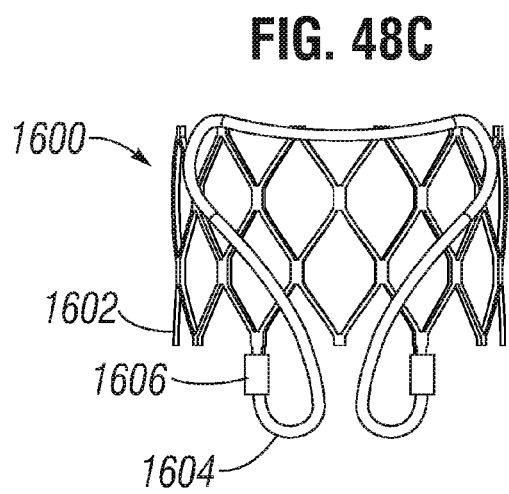

FIGS. 47A-47D and FIGS. 48A-48C show alternative frame embodiments wherein one or more ventricular anchor components are formed separately from a main body and later assembled together to form a frame. In these frame embodiments, the main body can comprise attachment portions to which anchor portions can be attached using sleeves. For example, FIGS. 47A-47D show an exemplary frame 1500 comprising a main body 1502 having at least two ventricular anchor attachment portions 1508 and at least one ventricular anchor 1504 having two attachment portions 1510 connected to respective attachment portions 1508 with respective sleeves 1506. Similarly, FIG. 48A-48C show an exemplary frame 1600 comprising a main body 1602 having at least two ventricular anchor attachment portions 1608 and at least one ventricular anchor 1604 having two attachment portions 1610 connected to respective attachment portions 1608 with respective sleeves 1606. The sleeves can comprise, for example, a metal material, such as Nitinol, having superelastic and/or shape-memory characteristics. In some embodiments, the sleeves can comprise metal of an anneal state suitable for a crimping process. The sleeves can be attached to the anchor portions and to the attachment portions of the main body by any suitable attachment means, such as by welding. As shown in FIGS. 48A-48C, the attachment portion 1610 of the anchors 1604 and the attachment portions 1608 of the main body 1602 can comprise geometric features, such as narrow regions, or cut-outs, which allow the sleeves 1606 to integrate the anchor portions 1604 to the main body 1602, such as by forming a mechanical lock.

Multi-part construction of a frame, as shown in FIG. 46-48, can reduce strain and fatigue at the ventricular anchor attachment locations compared to a unibody, or one-piece, construction. By contrast, in some embodiments comprising a unibody construction, the ventricular anchors are initially laser cut and expanded such that they extend downward from the lower end of the main body, and are then formed, or bent, to a desired configuration adjacent to the outside of the main body of the frame. Such bending can strain and weaken the bent portion.

To avoid strain caused by plastic deformation of the ventricular anchors, the ventricular anchors can be pre-formed in a desired implantation (deployed) shape without plastically bending the ventricular anchors. The ventricular anchors can then be elastically deformed, such as straightened and/or compressed, to fit into a delivery device for delivery through the body to the mitral valve region of the heart. The deformed ventricular anchors can resiliently regain their pre-formed shape once freed from the axial constraint of a delivery device to facilitate capturing the leaflets 10, 12 between the ventricular anchors and the main body of the frame.

Figure 70:
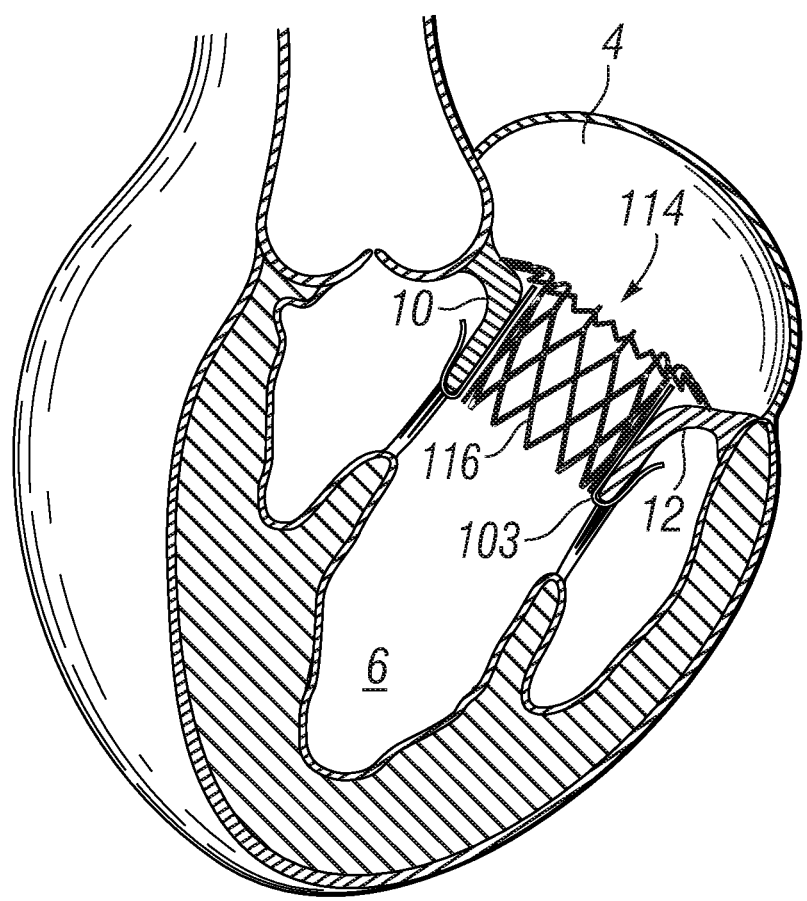
FIG. 70 is a cross-sectional view of the heart showing an embodiment of a docking frame that is secured to the native tissue of mitral valve region and a separately deployed prosthetic valve that is secured to the docking frame within the lumen of the docking frame.

Any of the various embodiments of frames described above can be combined with a fluid-occluding member, such as valve structure 104, to form a fully assembled prosthetic valve that can be implanted within the native mitral valve. In other embodiments, any of the frames described above can be provided without a fluid-occluding member and can be used as a scaffolding or docking structure for receiving a separate prosthetic valve in a two-stage delivery process. With reference to the exemplary embodiment shown in FIG. 70, a docking frame 103 (which can have a construction similar to the frame 102) can be deployed first, for example by any of the anchoring techniques discussed above. Then, a separate prosthetic valve 114 can be delivered and deployed within the lumen formed by the previously deployed docking frame 103. The separate prosthetic valve 114 desirably comprises a radially compressible and expandable frame 116 that mounts a fluid-occluding member (not shown in FIG. 70), such as the valve structure 104 (see FIG. 7) having a plurality of leaflets 106. When expanded inside the docking frame 103, the frame 116 of the prosthetic valve 114 engages the inside surface of the docking frame 103 so as to retain, such by friction or mechanical locking feature, the prosthetic valve 114 within the docking frame 103. Examples of prosthetic valves that can be used in such a two-stage process are disclosed in U.S. Pat. No. 7,510,575, which is incorporate herein by reference. In particular embodiments, the prosthetic valve can comprise any of various transcatheter heart valves, such as the Sapien valve, available from Edwards Lifesciences LLC (Irvine, Calif.).

The technique of capturing the leaflets 10, 12 between a ventricular anchor and the main body of a frame, such as shown in FIG. 23, can provide several advantages. First, this can allow for anchoring onto the native leaflets 10, 12 for retention within the mitral valve region. Second, this technique can utilize the native chordae 16 for retention. Third, this technique can prevent the anterior leaflet 10 from being "pulled" toward the aortic valve 14 when the left ventricle 6 contracts and blood rushes out through the aortic valve (systolic anterior motion). Fourth, this technique tends to force the native leaflets 10, 12 to collapse around the main body of the frame, which can reduce leakage between the outside of the prosthetic valve 100 and the native mitral valve 2. Fifth, this technique allows for implantation from either the left atrium 4 or from the left ventricle 6, as described in detail below.

As described above, various frame embodiments can utilize one or more anchoring techniques other than compressing the leaflets 10, 12 to retain the prosthetic valve 100 in a desired position within the mitral valve orifice. These anchoring techniques can include, for example, utilizing tension of the native chordae 16, extending the ventricular anchor length such that the apex of the ventricular anchor is pressed up against the mitral annulus 8 so as to form a stop, and compressing the mitral annulus 8 and/or atrial tissue between the apex of an ventricular anchor and the outer rim of an atrial sealing member of the frame.

Delivery Approaches

The various methods and apparatus described hereinafter for delivery and implantation at the native mitral valve region are described with respect to the prosthetic valve 100, though it should be understood that similar methods and apparatus can be used to deliver and/or implant a component of the prosthetic valve 100, such as the frame 102 without the valve structure 104, or other prosthetic apparatus.

The prosthetic valve 100 can be delivered to the mitral valve region from the left ventricle 6 or from the left atrium 4. Because of the anatomy of the native mitral valve 2, different techniques and/or equipment can be used depending on the direction the prosthetic valve 100 is delivered.

Figure 57:
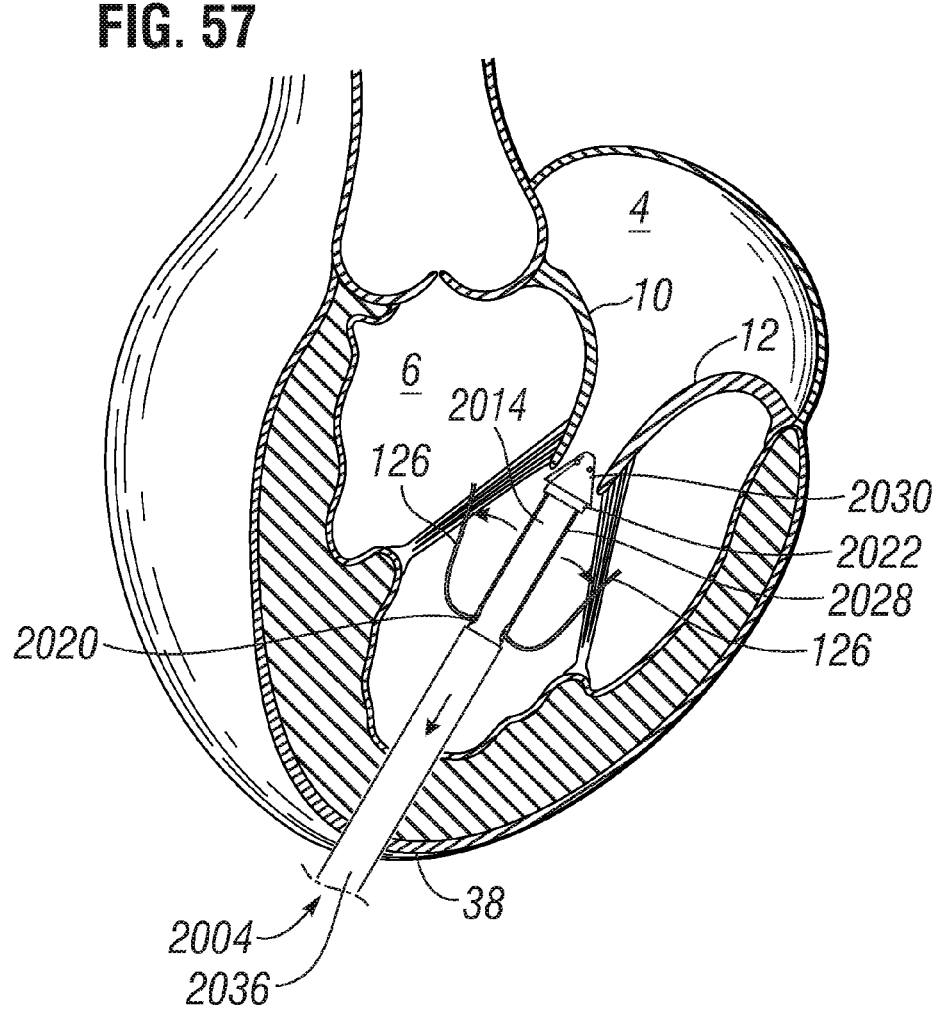
FIG. 57 is a cross-sectional view of the heart showing the ventricular anchors of the prosthetic valve being pre-deployed in the left ventricle using the delivery system of FIG. 49.

Delivery from the ventricular side of the mitral annulus 8 can be accomplished in various manners. For example, the prosthetic valve 100 can be delivered via a transapical approach in which access is made to the left ventricle 6 via the heart apex 38, as shown in FIG. 57.

Figure 66:
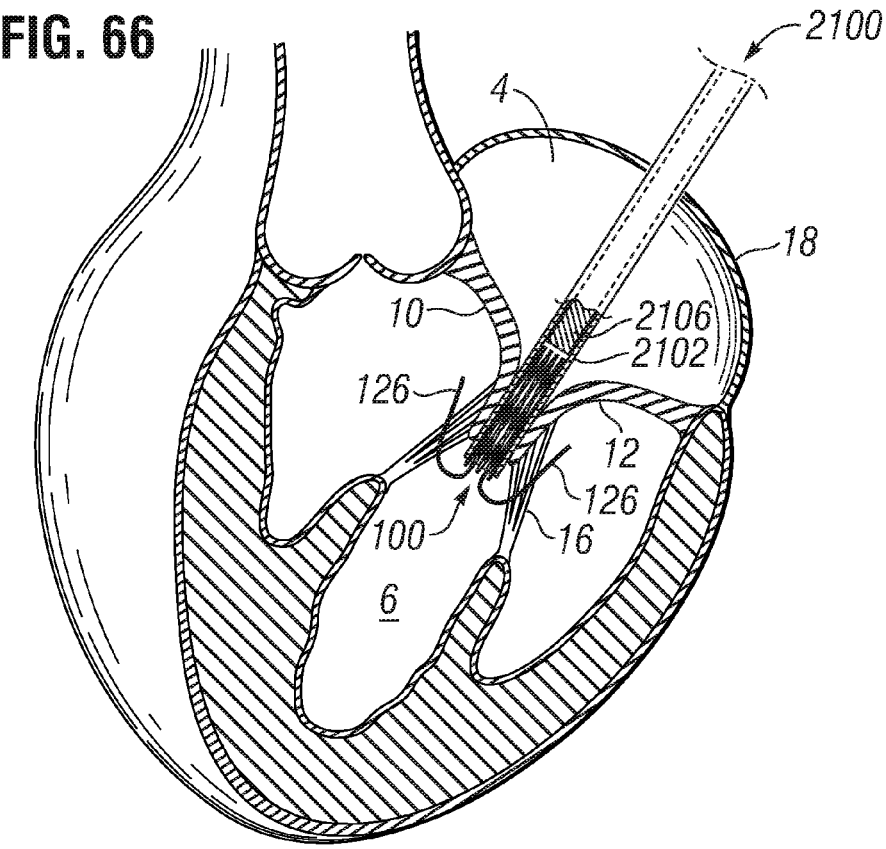
FIG. 66 is a cross-sectional view of the heart showing the prosthetic valve of FIG. 65 being implanted in the native mitral valve region using a transatrial approach.
Figure 67:
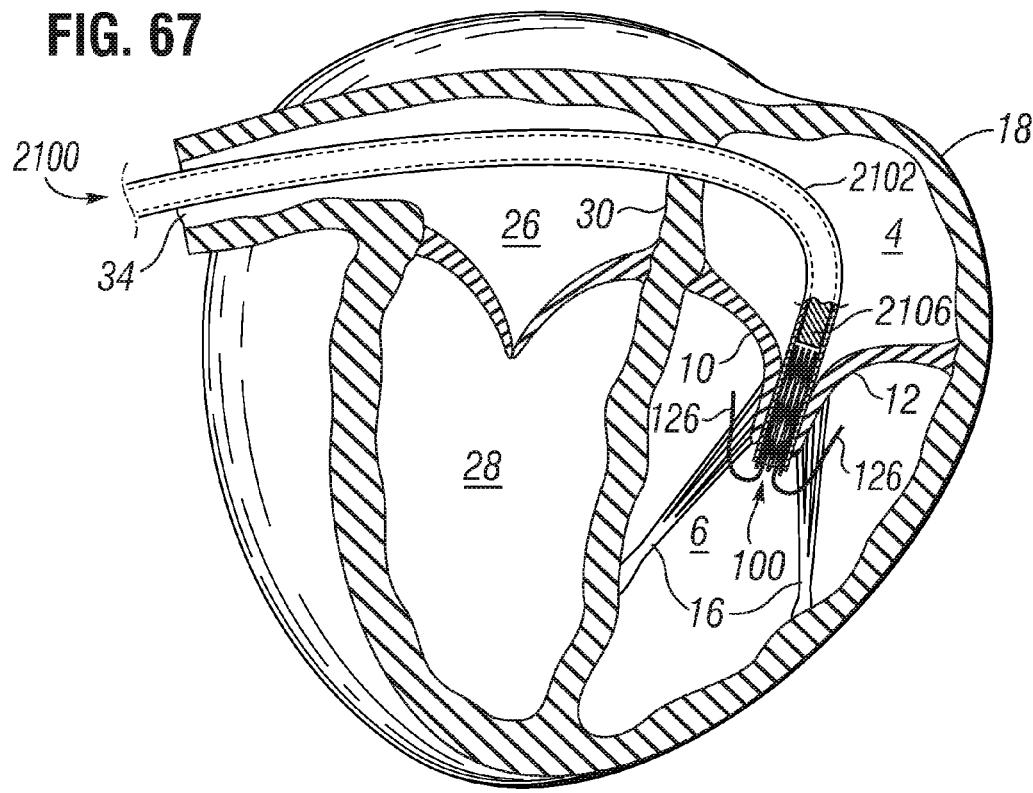
FIG. 67 is a cross-sectional view of the heart showing the prosthetic valve of FIG. 65 being implanted in the native mitral valve region using a transeptal approach.

Delivery from the atrial side of the mitral annulus 8 can also be accomplished in various manners. For example, a transatrial approach can be made through an atrial wall 18, as shown in FIG. 66, for example by an incision through the chest. An atrial delivery can also be made from a pulmonary vein 32 (see FIG. 1). In addition, atrial delivery can be made via a transeptal approach, as shown in FIG. 67, wherein an incision is made in the atrial portion of the septum 30 to allow access from the right atrium 26, such as via the inferior or superior vena cava 34.

Ventricular Approaches

One technique for delivering a compressed prosthetic apparatus, such as the prosthetic valve 100, to the mitral valve region includes accessing the native mitral valve region from the left ventricle 6, one example being the transapical approach. Alternatively, access to the left ventricle 6 can be made through the aortic valve 14. In the transapical approach, access to the left ventricle 6 can be made through an incision in the chest and an incision at the heart apex 38, as shown in FIG. 57. A transapical delivery system can be used with the transapical approach.

FIGS. 49-53 show an exemplary transapical delivery system, or delivery tool, 2000 that is configured to deliver and implant the prosthetic valve 100. The delivery system 2000 can comprise a series of concentric shafts and sheaths aligned about a central axis and slidable relative to one another in the axial directions. The delivery system 2000 can comprise a proximal handle portion 2002 for physician manipulation outside of the body while a distal end portion, or insertion portion, 2004 is inserted into the body.

The delivery system 2000 can comprise an inner shaft 2006 that runs the length of the delivery system and comprises a lumen 2008 through which a guidewire (not shown) can pass. The inner shaft 2006 can be positioned within a lumen of a pusher shaft 2010 and can have a length that extends proximally beyond the proximal end of the pusher shaft and distally beyond the distal end of the pusher shaft. The delivery system 2000 can comprise an annular space 2012 between the outer surface of the inner shaft 2006 and the inner surface of the pusher shaft 2010. This annular space can be used for flushing with saline or for allowing blood to be expelled distally.

The delivery system 2000 further comprises an inner sheath 2014 positioned concentrically around at least a distal portion of the pusher shaft 2010. The inner sheath 2014 is axially slidable relative to the pusher shaft 2010 between a delivery position (see FIG. 55) and a retracted position (see FIG. 50). In the delivery position, a distal end portion 2016 of the inner sheath 2014 is positioned distal to a distal end, or pusher tip 2018, of the pusher shaft 2010. In the delivery position, the distal end portion 2016 of the inner sheath 2014 forms an inner cavity that can contain a compressed prosthetic valve 100. In the retracted position (see FIG. 50), the distal end 2017 of the inner sheath 2014 is positioned proximal to or aligned axially with the pusher tip 2018. As the inner sheath 2014 moves from the delivery position toward the retracted position (either by retracting the inner sheath 2014 proximally relative to the pusher shaft 2010 or advancing the pusher shaft distally relative to the inner sheath), the pusher tip 2018 can force the prosthetic valve 100 out of the distal end portion 2016 of the inner sheath.

As shown in FIG. 50, the inner sheath 2014 comprises one or more longitudinally disposed slots 2028 extending proximally from a distal end 2017 of the inner sheath. These slots 2028 can allow ventricular anchors 126 of a prosthetic valve 100 contained within the inner sheath 2014 to extend radially outward from the compressed main body of the prosthetic valve while the main body is retained in the compressed state within the inner sheath. In the embodiment shown in FIG. 50, two slots 2028 are shown oriented on diametrically opposed sides of a longitudinal central axis of the inner sheath 2014. This embodiment corresponds to the prosthetic valve 100, which comprises two opposed ventricular anchors 126. In other embodiments, the inner sheath 2014 can comprise a different number of slots 2028, for example four slots, that correspond to the number and location of ventricular anchors on a selected prosthetic valve. In some embodiments, such as shown in FIG. 50, the proximal end portion 2020 of the each slot 2028 comprises a rounded opening that has a greater angular width than the rest of the slot.

A break-away, or frangible, retaining band 2022 can be positioned around the distal end portion 2016 of the inner sheath 2014, as shown in FIG. 50. The band 2022 can help retain the distal end portion 2016 of the inner sheath 2014 from splaying apart from the force of a compressed prosthetic valve 100 contained within the inner sheath 2014. The band 2022 comprises a proximal edge 2024 that can comprise at least one notch 2026 located over a slot 2028 in the inner sheath 2014. The band 2022 can comprise a frangible material and can be configured to tear or break apart at the notch location when a sufficient axial force is applied at the notch 2026. In use, the band 2022 is configured to break at notches 2026 under the force of the ventricular anchors 126 of the valve 100 as it is deployed from the inner sheath 2014, as further described below.

An outer sheath 2036 is positioned concentrically around a portion of the inner sheath 2014 and is slidable axially relative to the inner sheath. The outer sheath 2036 can be positioned to cover at least a portion of the distal end portion 2016 of the inner sheath 2014. In such a covered position, such as shown in FIG. 55, the ventricular anchors can be contained between the inner and outer sheath. The outer sheath 2036 is in this covered position while the loaded delivery system 2000 is inserted through the body and into the left ventricle 6. The outer sheath 2036 can be retracted proximally relative to the sheath 2014 to uncover the slots 2028 and allow the ventricular anchors 126 to spring outward through the slots in the inner sheath 2014 during deployment. Alternatively, the inner sheath 2014 can be advanced distally relative to the outer sheath 2036 to uncover the slots 2028.

With reference to FIG. 51, the handle portion 2002 of the delivery system 2000 can comprise components that facilitate sliding the inner sheath 2014 and the outer sheath 2036 back and forth along their respective ranges of axial movement to load, deliver, and deploy the prosthetic valve 100. An outer sheath grip 2052 can be attached to the proximal end of the outer sheath 2036. A physician can grasp the outer sheath grip 2052 and push or pull the outer sheath 2036 proximally or distally relative to the rest of the delivery system 2000. The outer sheath can also be mounted on a lead screw (not shown). The handle portion 2002 of the delivery system 2000 can further comprise a housing 2054 that provides a hand grip or handle for the physician to hold the delivery system 2000 steady while she uses the other hand to actuate the sheaths. A sliding lead screw 2056 can be fixed (e.g., bonded, mechanically locked, etc.) to a proximal end portion 2058 of the inner sheath 2014 and be positioned within the housing 2054. The lead screw 2056 can be fixed rotationally relative to the housing 2054 and can be constrained to an axial sliding range within the housing. A rotatable sleeve 2060 can be positioned concentrically between the outer housing 2054 and the inner lead screw 2056 and can comprise a proximal knob portion 2062 that extends free of the housing 2054 to provide a hand grip for the physician to rotate the rotatable sleeve 2060. The rotatable sleeve 2060 can be free to rotate relative to the housing 2054, but be fixed axially relative to the housing. The lead screw 2056 can comprise an outer helical groove 2064 that interacts with inwardly projecting ridges 2066 on the rotatable sleeve 2060 such that when the knob 2062 is rotated relative to the lead screw 2056 and the housing 2054, the ridges 2066 cause the lead screw 2056 to slide axially, thereby causing the inner sheath 2014 to also slide axially. Thus, the physician can move the inner sheath 2014 proximally by rotating the knob 2062 one direction relative to the housing 2054 and distally by rotating the knob the opposite direction relative to the housing. The housing 2054 can be fixed relative to the pusher shaft 2010 such that when the knob 2062 is rotated relative to the housing, the lead screw 2056 and the inner sheath 2014 slide axially together relative to the pusher shaft 2010 and the housing 2054.

As shown in FIG. 51, the inner shaft 2006 passes all the way through the handle portion 2002 of the delivery system 2000 and the pusher shaft 2010 can terminate at or near a proximal end cap 2068 of the handle portion 2002. The annular space 2012 between the outer surface of the inner shaft 2006 and the inner surface of the pusher shaft 2010 (see FIGS. 52 and 53) can be fluidly connected to at least one flushing port 2070 in the end cap 2068 of the handle portion 2002. The flushing port 2070 can provide access to inject fluid into the annular space 2012 and/or allow fluid to escape from the annular space.

As shown in FIG. 49, a nose cone 2030 can be attached to the distal end of the inner shaft 2006. The nose cone 2030 can be tapered from a proximal base 2034 to a distal apex 2032. The base 2034 can have a diameter about equal to the diameter of the outer sheath 2036. The nose cone 2030 can be retracted proximally, by sliding the inner shaft 2006 proximally relative to the rest of the delivery system 2000, to mate against the distal end of the outer sheath 2036 and/or the inner sheath 2014 to further contain the compressed prosthetic valve 100, as shown in FIG. 55. The nose cone 2030 can also be moved distally away from the sheaths to provide space for the prosthetic valve 100 to be loaded and/or deployed. During insertion of the delivery system 2000 through the body, the tapered nose cone 2030 can act as a wedge to guide the insertion portion 2004 of the delivery system 2000 into the body and provides an atraumatic tip to minimize trauma to surrounding tissue as the delivery system is advanced through the body.

Figure 56:
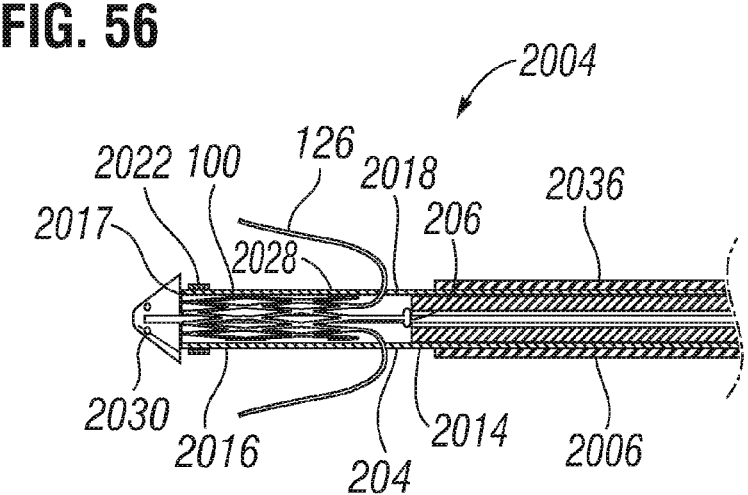
FIG. 56 is a cross-sectional view of a distal end portion of the delivery system of FIG. 49 showing the outer sheath of the delivery system retracted such that ventricular anchors extend outward through slots of the inner sheath.

To load the prosthetic valve 100 into the delivery system 2000, the nose cone 2030 must be moved distally away from the sheaths and the inner sheath 2014 must be advanced distally to the delivery position, as shown in FIG. 54 (without retaining band 2022). The outer sheath 2036 can be retracted to expose the slots 2028 in the inner sheath 2014. The prosthetic valve 100 is then positioned between the nose cone 2030 and the inner sheath 2014 and around the inner shaft 2006. The prosthetic valve 100 is then compressed to the compressed state and slid into the inner sheath 2014 such that the proximal, or lower, end of the prosthetic valve is adjacent to or contacting the pusher tip, as shown in FIG. 56. A loading cone or equivalent mechanism can be used to insert the valve 100 into the inner sheath 2014. In embodiments of the prosthetic valve 100 comprising a pusher member 204, such as in FIG. 25, the bottom end 206 of the pusher member 204 can contact the pusher tip 2018, as shown in FIG. 56. The ventricular anchors 126 can be allowed to extend out through the rounded proximal end portions 2020 of the respective slots 2028, as shown in FIG. 54. The proximal end portion 2020 of each slot can have sufficient angular width to allow the two end portions of the ventricular anchor 126 to reside side-by-side within the slot, which can cause the intermediate portion of the ventricular anchor to assume a desired shape for implanting behind the leaflets 10, 12. The break-away retaining band 2022 can be placed around the distal end portion of the inner sheath 2014 such that each notch 2026 in the band 2022 is located over a respective slot, as shown in FIG. 50. The outer sheath 2036 is then advanced distally to cover the slots 2028, as shown in FIG. 55, thereby compressing the ventricular anchors 126 and constraining the ventricular anchors within the outer sheath 2036. Alternatively, the prosthetic valve can be inserted into the inner sheath 2014 while the outer sheath 2036 is covering the slots 2028, such that the ventricular anchors 126 are positioned in the slots, but cannot extend out of the slots. The ventricular anchors 126 can also be constrained between the outer surface of the inner sheath 2014 and inner surface of the outer sheath 2036. In any case, the ventricular anchors 126 are free to spring radially outward once the outer sheath 2036 is retracted. After the prosthetic valve 100 is within the inner sheath 2014, the inner shaft 2006 can be retracted to pull the nose cone 2030 against the distal end of the inner sheath 2014 and/or the outer sheath 2036, as shown in FIG. 55. With the prosthetic valve 100 within the inner shaft 2006, the nose cone 2030 retracted and the outer sheath 2036 constraining the ventricular anchors 126, the delivery system 2000 is in the loaded configuration and ready for insertion into the body.

Figure 58:
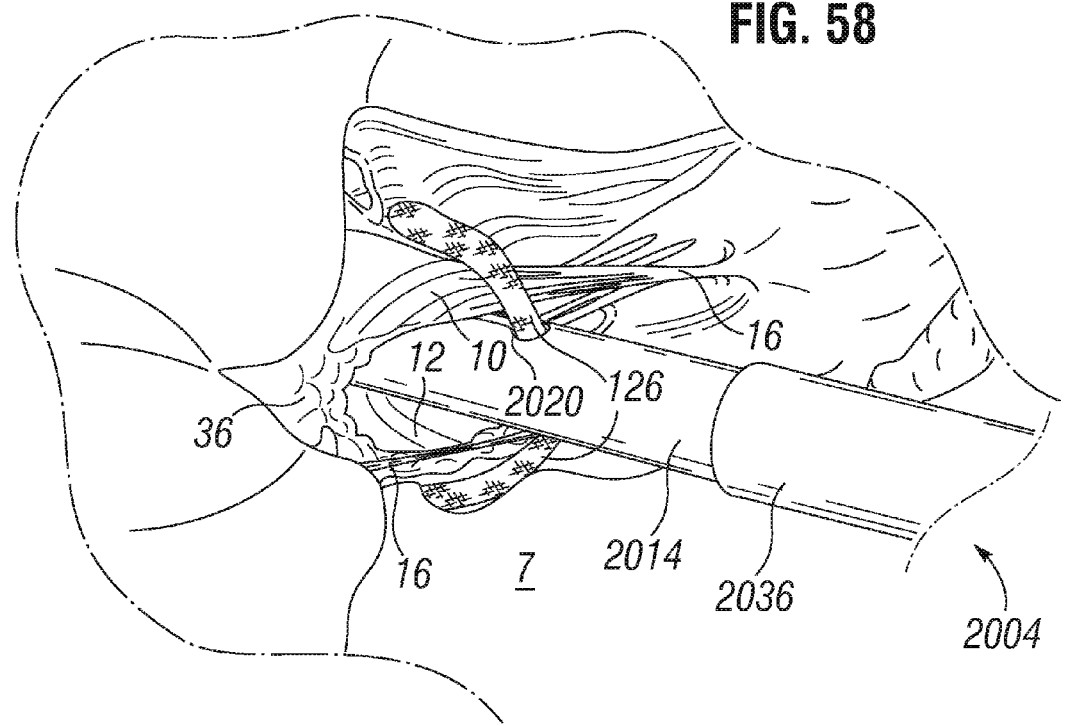
FIG. 58 is a view of the mitral valve region of the heart from the left ventricle showing the ventricular anchors extending from the slots in the delivery system and showing the ventricular anchors positioned between respective mitral leaflets and the ventricular walls.

In the loaded configuration shown in FIG. 55, the loaded delivery system 2000 can be inserted, nose cone 2030 first, through heart apex 38 into the left ventricle 6 and positioned near the mitral valve region for deployment. An introducer sheath (not shown) can be initially inserted through an incision in the heart to provide a port for introducing the delivery system 2000 into the heart. In addition, the delivery system 2000 can be advanced over a conventional guide wire (not shown) that is advanced into the heart ahead of the delivery system 2000. The grip 2052 can then be moved proximally relative to the rest of the delivery system to retract the outer sheath 2036 relative to the inner sheath 2014 and allow the ventricular anchors 126 to spring outwardly away from the inner sheath 2014, as shown in FIGS. 56 and 57, such that the ventricular anchors extend through the rounded proximal end portion 2020 of the slots 2028. The delivery system desirably is oriented rotationally such that each ventricular anchor 126 is positioned between sets of chordate tendineae 16 attached to one of the native mitral valve leaflets 10, 12. Next, the delivery system 2000 can be advanced atrially such that the nose cone 2030 enters the native mitral valve orifice and the protruding ventricular anchors 126 move between respective leaflets 10, 12 and the ventricular walls 20, as shown in FIG. 58. Then, while holding a housing 2054 of the delivery system 2000 steady, the physician can rotate the knob 2062 of the rotatable sleeve 2060 relative to the housing to retract the inner sheath 2014 proximally. The pusher tip 2018 remains stationary while the inner sheath 2014 retracts, thereby leaving the compressed prosthetic valve 100 in the same axial location as it is uncovered and deployed from the inner sheath 2014. Alternatively, the inner sheath 2014 can be held stationary while the pusher tip 2060 is moved distally to push the valve 100 out of the inner sheath 2014. While the inner sheath 2014 is being retracted relative to the pusher tip 2018, the pusher tip can exert an axial force in the distal direction upon the proximal, or lowermost, surface of the prosthetic valve 100. In embodiments of the prosthetic valve having a pusher member 204, the pusher member 204 can direct this axial force directly to the main body 122 and prevent direct contact between the pusher tip 2018 and the ventricular anchor 126 to reduce the risk of damage to the ventricular anchors.

When the inner sheath 2014 is retracted relative to the prosthetic valve 100, the distal, or upper, portion of the prosthetic valve comprising the downwardly folded atrial sealing member 124 is uncovered first. With reference to FIGS. 59 and 60, when the inner sheath 2014 has been retracted beyond the outer rim of the atrial sealing member 124 of the prosthetic valve 100, the atrial sealing member can spring radially outward away from the main body 122, pivoting about the distal end of the main body.

As the inner sheath 2014 is retracted relative to the prosthetic valve 100, the end portions of the ventricular anchors 126 passing through the rounded proximal end portion 2020 of the slots 2028 are forced through the narrower distal portions of the slots 2028 toward the retaining band 2022, as shown in FIGS. 59 and 60. The end portions of the ventricular anchors are initially side-by-side in the wider proximal end portion 2020 of the slot. When forced into the narrower portion of a slot 2028, the two end portions of each ventricular anchor 126 can be radially overlapping, or oriented one on top of the other, as opposed to side-by-side. In other embodiments, the slots 2028 can be wider such that the two end portions of the ventricular anchor 126 can move about the slots 2028 side-by-side. As the ventricular anchor 126 moves toward the distal end of a slot 2028, the ventricular anchor can contact the notch 2026 in the retaining band 2022, as shown in FIG. 60, and can cut the band 2022 or otherwise cause the band to tear or split apart at the notched location, as shown in FIG. 61. When the inner sheath 2014 is retracted beyond the proximal, or lower, end of the prosthetic valve 100, the compressed body of the prosthetic valve can resiliently self-expand to the expanded state, as shown in FIG. 61. As the prosthetic valve expands, the gaps between the ventricular anchors 126 and the outer surface of the main body 122 decreases, capturing the leaflets 10, 12 between the ventricular anchors 126 and the main body 122, as shown in FIGS. 23 and 62. The expansion of the main body 122 of the prosthetic valve 100 can force open the native mitral leaflets 10, 12, holding the native mitral valve 2 in an open position. The prosthetic valve 100 can then replace the functionality of the native mitral valve 2. After the prosthetic valve 100 is expanded, the inner shaft 2006 of the delivery system can be retracted, pulling the nose cone 2030 back through the prosthetic valve, and the whole delivery system 2000 can be retracted out of the body.

In some embodiments, the delivery system 2000 can be guided in and/or out of the body using a guide wire (not shown). The guide wire can be inserted into the heart and through the native mitral orifice, and then a proximal end of the guidewire can be threaded through the lumen 2008 of the inner shaft 2006. The delivery system 2000 can then be inserted through the body using the guidewire to direct the path of the delivery system.

Atrial Approaches

The prosthetic valve 100 can alternatively be delivered to the native mitral valve region from the left atrium 4. Referring to FIGS. 63-67, one approach for delivering the prosthetic valve from the atrial side of the mitral valve region utilizes a delivery catheter 2100. The prosthetic valve 100 is first crimped from the expanded state to the radially compressed state and loaded into a primary sheath 2102, and optionally also a secondary sheath, at the distal end portion of the delivery catheter 2100, as shown in FIG. 63. The delivery catheter 2100 is used to guide the prosthetic valve 100 through the body and into the left atrium 4. The prosthetic valve 100 is oriented within the sheath 2102 such that the outflow end 112 of the prosthetic valve 100 (the end supporting the ventricular anchors 126) is closest to the distal end of the sheath and thus enters the left atrium 4 first and the inflow end 110 (the atrial sealing member 124) of the prosthetic valve enters last. The sheath 2102 can then be inserted into the left atrium 4 in various manners, one example being the transatrial approach shown in FIG. 66, and another example being the transeptal approach shown in FIG. 67. When the delivery catheter 2100 is used to access the heart via the patient's vasculature, such as shown in FIG. 67, the catheter 2100 can comprise a flexible, steerable catheter.

Once in the left atrium 4, the distal end 2104 of the primary sheath 2102 can be moved across the mitral annulus 8 such that the ventricular anchors 126 are positioned beyond the mitral leaflets 10, 12 prior to deploying the ventricular anchors from the sheath.

The prosthetic valve 100 can then be partially expelled from of the distal end 2104 of the primary sheath 2102 using a rigid pusher shaft 2106 (see FIG. 64) that is positioned within the sheath 2102 and can slide axially relative to the sheath. When the sheath 2102 is retracted proximally relative to the pusher shaft 2106 and the prosthetic valve 100, the pusher shaft 2106 urges the prosthetic valve distally out of the sheath 2102, as shown in FIG. 64. Alternatively, the pusher shaft 2106 can be moved distally while the sheath 2102 is held in place, thereby pushing the prosthetic valve 100 distally out of the sheath.

Figure 68:
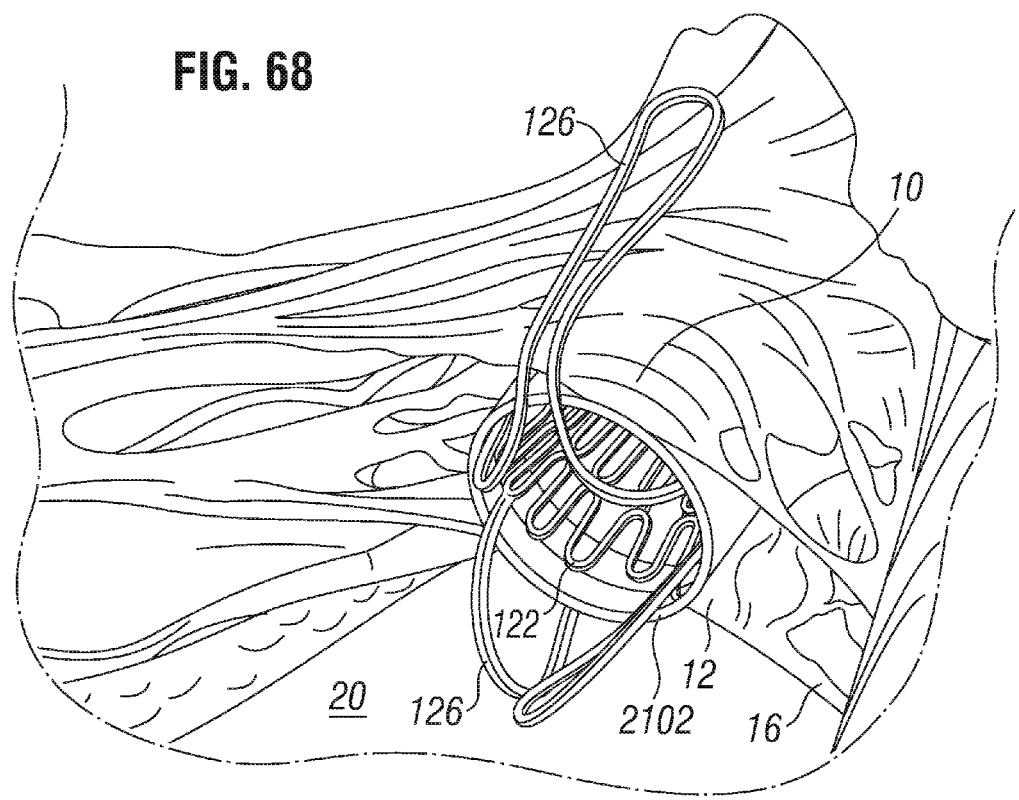
FIG. 68 is a view of the mitral valve region from the left ventricle showing an embodiment of an atrially delivered prosthetic valve having ventricular anchors extending free of a sheath and positioned between the native mitral valve leaflets and the ventricular walls.

When the primary sheath 2102 is inserted across the mitral annulus 8 and past the lower ends of the leaflets 10, 12, the prosthetic valve 100 can be partially expelled to free the ventricular anchors 126, as shown in FIG. 64. The freed ventricular anchors 126 can spring outwardly when they are freed from the sheath 2102. Optionally, the sheath 2102 can then be slid back over the exposed portion of the main body 122, such that only the ventricular anchors are showing, as shown in FIG. 65. To accomplish this step, the atrial end of the frame can comprise features (not shown), such as mechanical locking features, for releasably attaching the prosthetic valve 100 to the pusher shaft 2106, such that the pusher shaft can pull the prosthetic valve back into the sheath 2102. The sheath 2102 and the prosthetic valve 100 are then retracted atrially, proximally, such that the outwardly protruding ventricular anchors 126 move between respective leaflets 10, 12, and the ventricular walls 20, as shown in FIGS. 66-68. In other embodiments, such as those shown in FIGS. 44 and 45, the ventricular anchors can elastically deflect upward or bend around respective leaflets 10, 12 when the ventricular anchors are freed from the sheath 2102.

Optionally, the delivery catheter 2100 can also include a secondary sheath (not shown) within the outer sheath 2102 and can contain the pusher shaft 2106, the atrial sealing member 124 and the main body 122 of the frame, but not the anchors 126. In the position shown in FIG. 63, the distal end of the secondary sheath can be positioned between the anchors 126 and the main body 122. As the outer primary sheath 2102 is retracted, as in FIG. 64, the secondary sheath can remain in a position compressing the main body 122 of the frame while the anchors 126 are freed to extend outward. Because the secondary sheath remains covering and compressing the main body 122, there is no need recover the main body with the primary sheath 2102, as in FIG. 65. Instead, the prosthetic valve 100 is moved proximally by moving the secondary sheath and pusher shaft proximally in unison. Then, to expel the prosthetic valve 100 from the secondary sheath, the secondary sheath is retracted proximally relative to the pusher shaft 2106.

Figure 69:
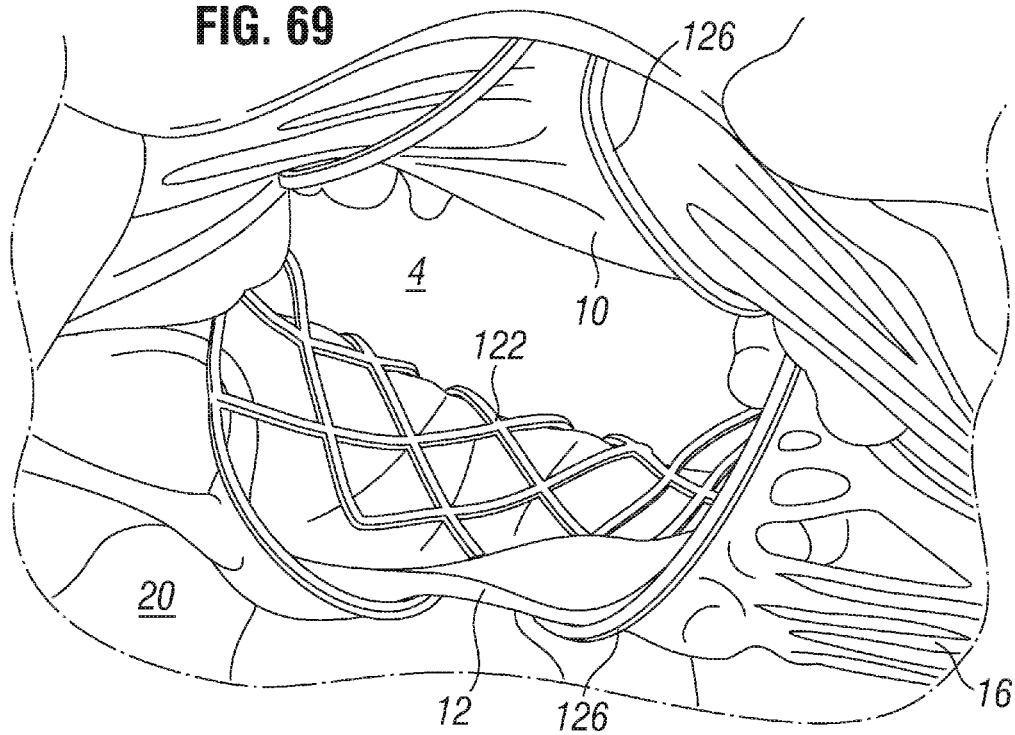
FIG. 69 is a view of the mitral valve region from the left ventricle showing the prosthetic valve of FIG. 68 fully expanded and anchored to the native mitral valve leaflets.

After the ventricular anchors 126 are positioned behind the leaflets 10, 12 and the remaining portion of the prosthetic valve 100 is expelled from the primary sheath 2102, the prosthetic valve 100 can expand to its functional size, as shown in FIGS. 62 and 69, thereby capturing the leaflets 10, 12 between the ventricular anchors 126 and the main body 122. Once the prosthetic valve 100 is implanted, the delivery catheter 2100 can be retracted back out of the body.

In alternative prosthetic valve embodiments, the main body and the atrial sealing member of the frame can be plastically expandable and can be expanded by a balloon of a balloon catheter (not shown) when the prosthetic valve is positioned at the desired location. The ventricular anchors in such an embodiment can exhibit a desired amount of elasticity to assist in positioning the leaflets 10, 12 between the ventricular anchors and the main body during deployment. Once the prosthetic valve is fully expanded, the balloon can be retracted through the expanded prosthetic valve and out of the body.

Mitral Regurgitation Reduction

Mitral regurgitation (MR) occurs when the native mitral valve fails to close properly and blood flows into the left atrium from the left ventricle during the systole phase of heart contraction. MR is the most common form of valvular heart disease. MR has different causes, such as leaflet prolapse, dysfunctional papillary muscles and/or stretching of the mitral valve annulus resulting from dilation of the left ventricle. MR at a central portion of the leaflets can be referred to as central jet MR and MR nearer to one commissure of the leaflets can be referred to as eccentric jet MR.

Rather than completely replacing the native mitral valve, another way to treat MR is by positioning a prosthetic spacer between the leaflets that decreases the regurgitant orifice area, allowing the mitral valve to function with little or no regurgitation, while minimizing impact to the native valve and left ventricle function and to the surrounding tissue. Additional information regarding treatment of MR can be found in U.S. Pat. No. 7,704,277 and U.S. Publication No. 2006/0241745 A1, both of which are incorporated by reference herein.

Figure 71:
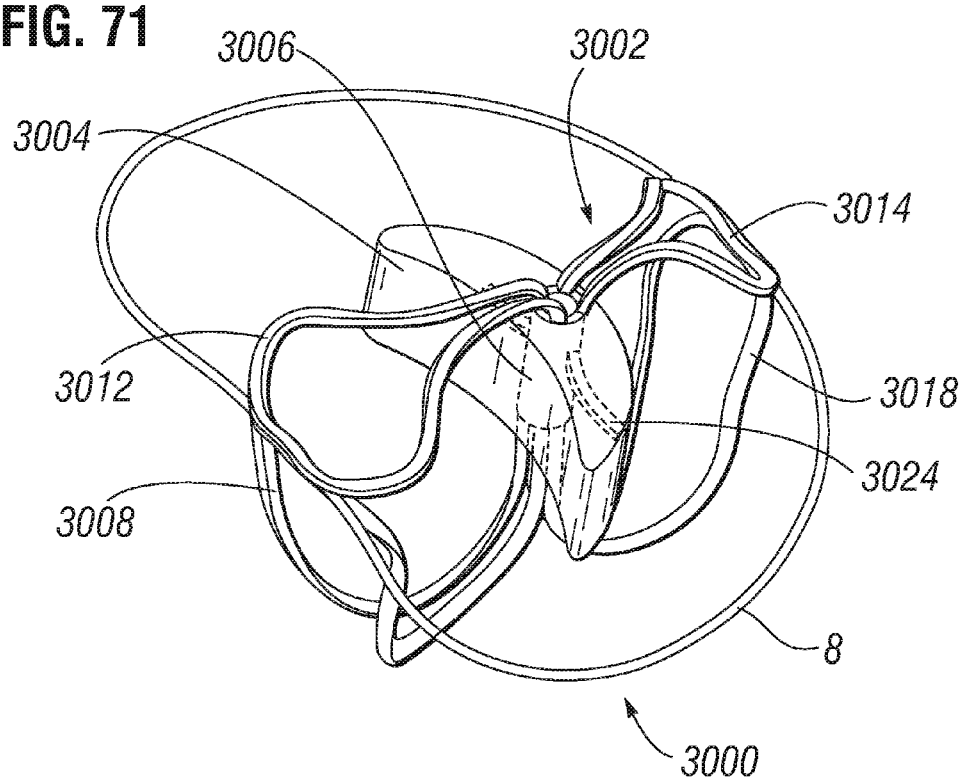
FIG. 71 a perspective view of an embodiment of a prosthetic apparatus for implanting at the native mitral valve region to treat mitral regurgitation.
Figure 72:
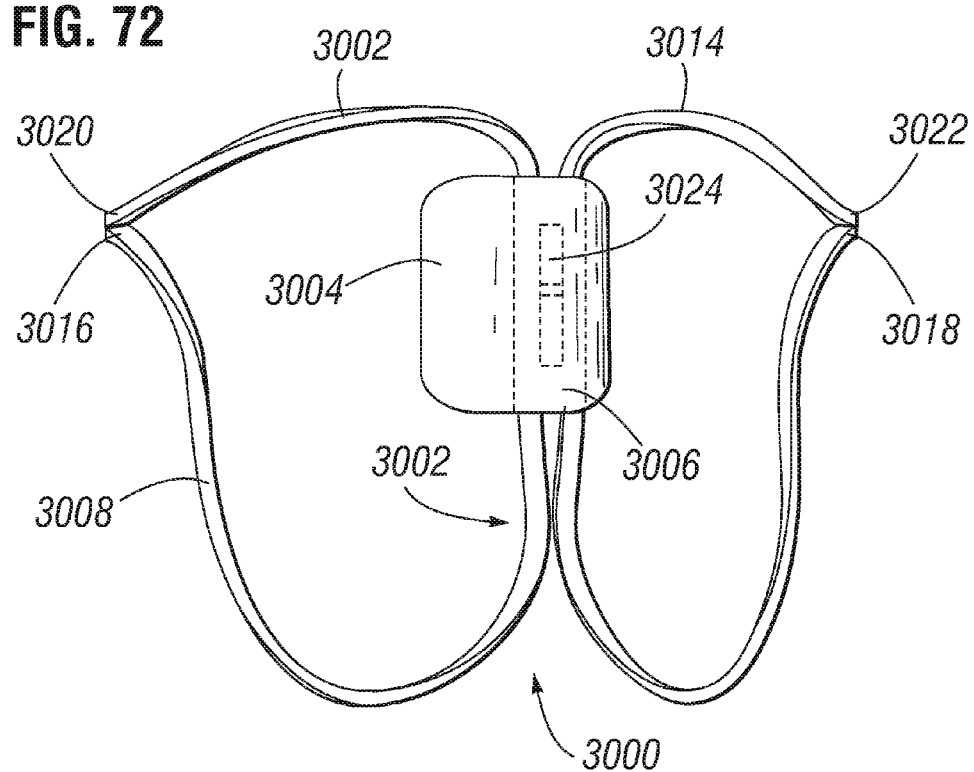
FIG. 72 is a side view of the prosthetic apparatus of FIG. 71.
Figure 73:
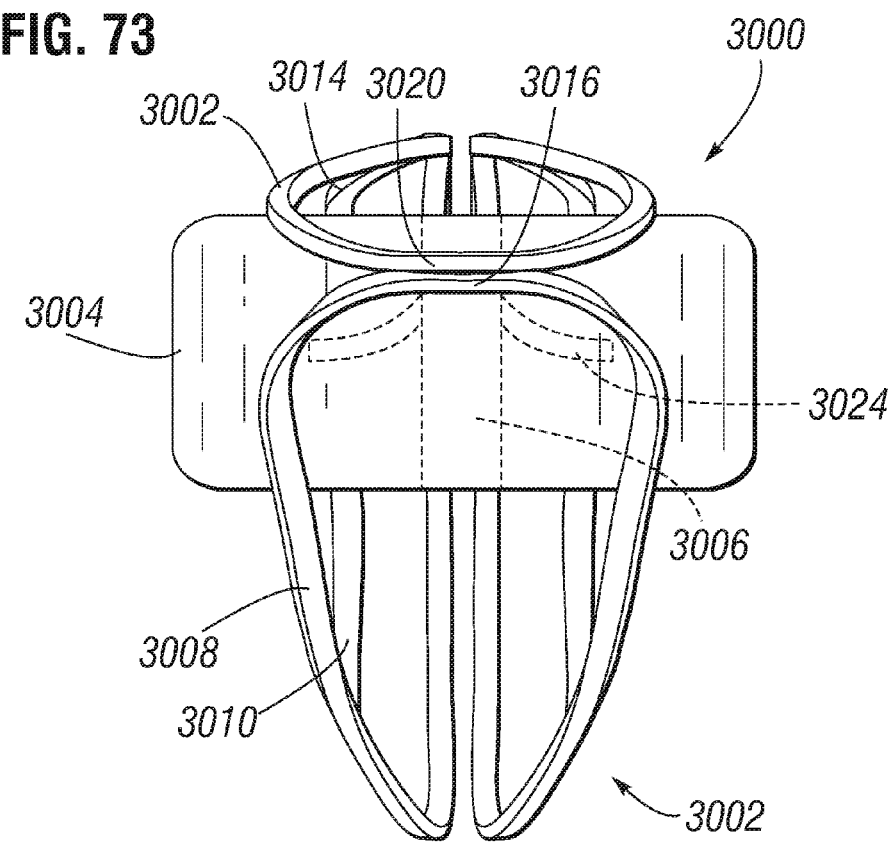
FIG. 73 is another side view of the prosthetic apparatus of FIG. 71.

FIG. 71 shows an exemplary prosthetic spacer embodiment 3000 with which a spacer, or other body, can be suspended or "floated" between the leaflets using anchoring concepts described herein. The prosthetic spacer 3000 can comprise a frame 3002 and spacer body 3004. The spacer body 3004 can comprise polyurethane, foam, and/or other suitable material(s) and can optionally be coated with Teflon and/or other suitable material(s). The spacer body 3004 can comprise a crescent shape that conforms to the crescent shaped juncture between the anterior leaflet 10 and the posterior leaflet 12 (see FIGS. 4A and 4B), or the spacer body can comprise other suitable shapes, such as an ellipse, circle, hourglass, etc. Depending on the shape of the spacer body 3004 and the positioning of the spacer body relative to the native structure, embodiments of the prosthetic spacer 3000 can help treat central jet MR, eccentric jet MR, or both.

Furthermore, the spacer body 3004 can comprise a minimal transverse cross-sectional area and tapered edges. This shape can reduce diastolic forces from blood flowing through the mitral valve from the left atrium to the left ventricle. This shape can also reduce systolic forces on the spacer body 3004 when the native valve is closed around the spacer body and naturally place a larger portion of the systolic forces on the native leaflets and chordae. The shape of the spacer body 3004 can therefore reduce the forces transferred to the native valve tissue at anchor engagement locations, which can reduce the likelihood of perforation and erosion at the engagement locations and rupture of the native chordae that support the leaflets. The overall minimal size of the prosthetic spacer 3000 can further provide an opportunity to decrease the required cross-sectional size of a delivery system, allowing for delivery via narrower vasculature and/or less invasive incisions in the body and heart.

The frame 3002 can be made of a strong, flexible material, such as Nitinol. As shown in FIG. 71, the frame 3002 can comprise a frame body 3006, an anterior ventricular anchor 3008, a posterior ventricular anchor 3010, an anterior atrial anchor 3012 and a posterior atrial anchor 3014. The frame body 3006 can comprise a generally longitudinal column extending through the spacer body 3004. Various embodiments of the frame body 3006 are described in detail below.

The frame 3002 can further comprise one or more spacer expanders 3024 extending laterally from the frame body 3006 through the spacer body 3004. The expanders 3024 can resiliently expand away from the frame body and assist in the expansion of the spacer body 3004 during deployment. In some embodiments, the spacer expanders 3024 can be rectangular cut-out portions of a cylindrical frame body 3006, as shown in FIG. 71, that are bent radially away from the frame body.

The anterior ventricular anchor 3008 is configured to extend from the ventricular end of the frame body 3006, around the A2 edge of the anterior leaflet 10 and extend upward behind the leaflet to a location on the ventricular surface of the mitral annulus 8 and/or the annulus connection portion of the anterior leaflet, while the anterior atrial anchor 3012 is configured to extend radially from the atrial end of the frame body 3006 to a location on the atrial surface of the mitral annulus 8 opposite the anterior ventricular anchor 3008. Similarly, the posterior ventricular anchor 3010 is configured to extend from the ventricular end of the frame body 3006, around the P2 edge of the posterior leaflet 12 and extend upward behind the leaflet to a location on the ventricular surface of the mitral annulus 8 and/or the annulus connection portion of the posterior leaflet, while the posterior atrial anchor 3014 is configured to extend radially from the atrial end of the frame body 3006 to a location on the atrial surface of the mitral annulus 8 opposite the posterior ventricular anchor 3010.

The ventricular anchors 3008, 3010 and the atrial anchors 3012, 3014 can comprise broad engagement portions 3016, 3018, 3020 and 3022, respectively, that can be configured to compress the mitral annulus 8 and/or annulus connection portions of the leaflets 10, 12 to retain the prosthetic spacer 3000 from movement in both the atrial and ventricular directions. The broad engagement portions can provide a greater area of contact between the anchors and the native tissue to distribute the load and reduce the likelihood of damaging the native tissue, such as perforation or erosion at the engagement location. The ventricular anchors 3008, 3010 in the illustrated configuration loop around the native leaflets 10, 12 and do not compress the native leaflets against the outer surface of the spacer body 3004, allowing the native leaflets to naturally open and close around the spacer body 3004.

Figure 74:
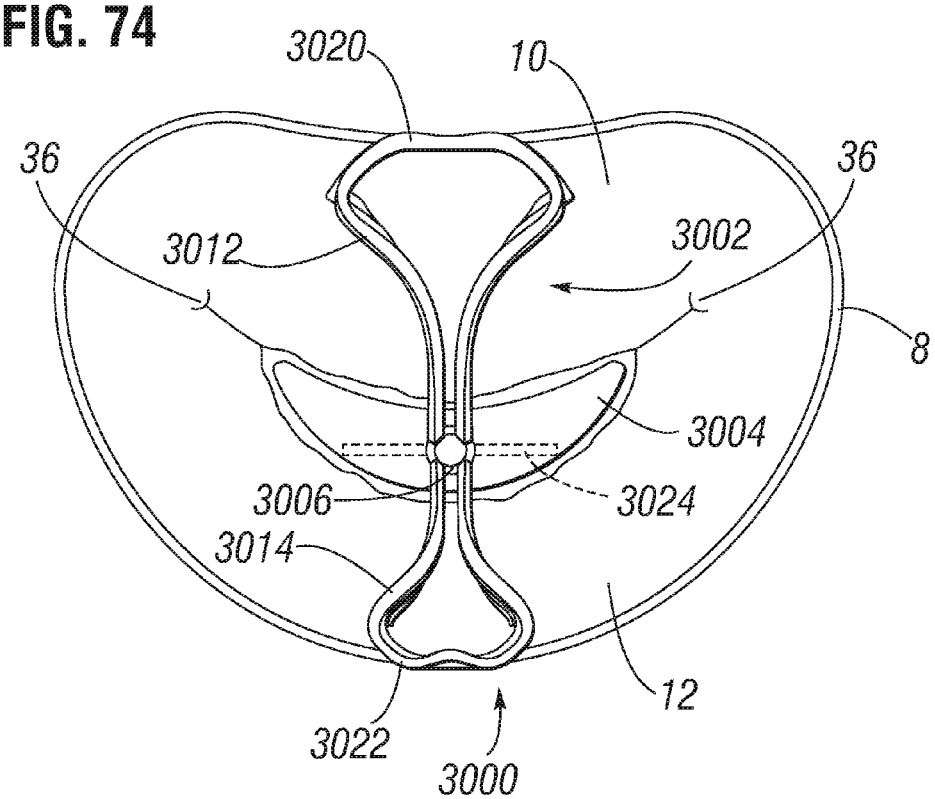
FIG. 74 is an end view of the prosthetic apparatus of FIG. 71.

As shown in FIG. 74, the mitral annulus 8 is generally kidney shaped such that the anterior-posterior dimension is referred to as the minor dimension of the annulus. Because the prosthetic spacer 3000 can anchor at the anterior and posterior regions of the native mitral valve 2, the prosthetic spacer can be sized according to the minor dimension of the annulus 8. Echo and CT measuring of the minor dimension of the mitral annulus 8 are exemplary methods of sizing the prosthetic spacer 3000.

Figure 75:
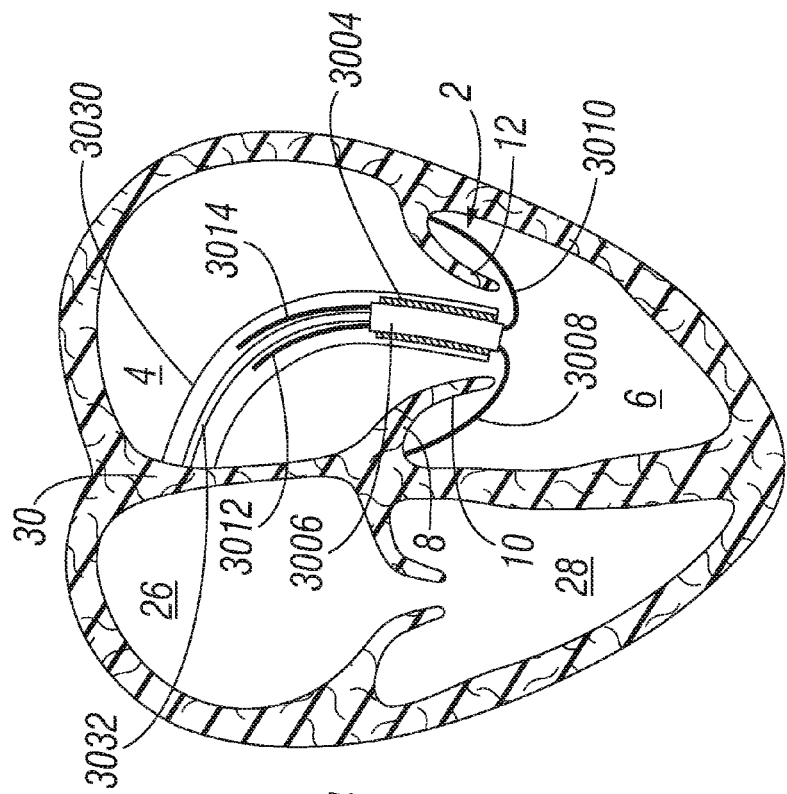

FIGS. 75-79 illustrate an exemplary method for delivering the prosthetic spacer 3000 to the native mitral valve region of the heart. The prosthetic spacer 3000 can be delivered into the heart using a delivery system comprising an outer sheath 3030 and inner torque shaft 3032. The prosthetic spacer 3000 is compressed and loaded into a distal end of the outer sheath 3030 with the atrial anchors 3012, 3014 loaded first. As shown in FIG. 75, the atrial anchors are resiliently extended proximally and the ventricular anchors 3008, 3010 are resiliently extended distally such that the prosthetic spacer 3000 assumes a sufficiently narrow cross-sectional area to fit within the lumen of the outer sheath 3030. Within the outer sheath 3030, the prosthetic spacer 3000 is positioned such that the atrial end of the frame body 3006 abuts the distal end of the torque shaft 3032, the atrial anchors 3012, 3014 are between the torque shaft and the inner wall of the outer shaft, the compressed spacer 3004 abuts the inner wall of the outer sheath, and the distal ends of the ventricular anchors 3008, 3010 are adjacent to the distal opening of the outer sheath. The torque shaft 3032 can be releasably coupled to the atrial end of the prosthetic spacer 3000, such as at the proximal end of the frame body 3006.

Once loaded, the delivery system can be introduced into the left atrium 4, such as via the atrial septum 30, and the distal end of the outer sheath 3030 can be passed through the native mitral valve 2 and into the left ventricle 6, as shown in FIG. 75.

Figure 76:
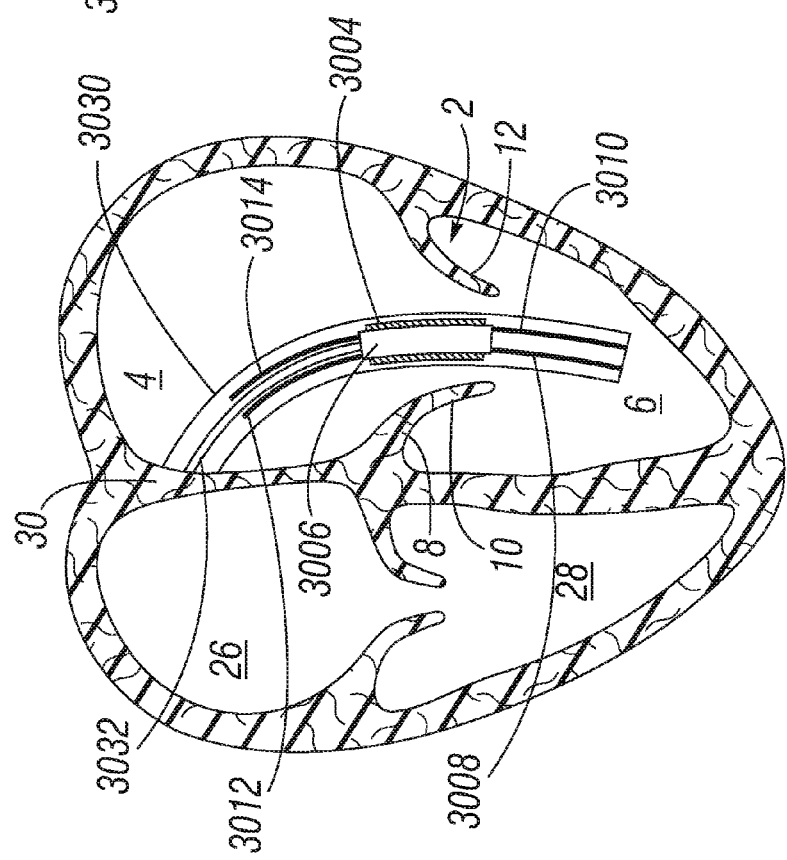

Next, the outer sheath 3030 can be retracted relative to the torque shaft 3032 to expel the ventricular anchors 3008, 3010 from the distal opening of the outer sheath. At this point, the torque shaft 3032 can be rotated to rotate the prosthetic spacer 3000 within the outer sheath 3030 (or optionally, the torque shaft and the outer sheath can both be rotated) as needed to align the ventricular anchors with the A2/P2 aspects of the native valve 2. The releasable attachment between the torque shaft 3032 and the prosthetic spacer 3000 can be sufficient to transfer torque from the torque shaft to the prosthetic in order to rotate the prosthetic as needed. The ventricular anchors 3008, 3010 can be pre-formed such that, as they are gradually expelled from the outer sheath 3030, they begin to curl apart from each other and around the A2/P2 regions of the leaflets. This curling movement can be desirable to avoid entanglement with the ventricular walls. When the outer sheath 3030 is retracted to the ventricular end of the frame body 3006, as shown in FIG. 76, the ventricular anchors 3008, 3010 are fully expelled from the outer sheath and positioned behind the leaflets. The entire delivery system and prosthetic can them be moved proximally until the engagement portions 3016, 3018 of the ventricular anchors abut the ventricular side of the mitral annulus 8 and/or the annulus connection portions of the leaflets 10, 12.

Next, the outer sheath 3030 can be further retracted to relative to the torque shaft 3032 such that the distal end of the outer sheath is even with the atrial end of the frame body 3006, as shown in FIG. 77, which allows the compressed spacer expanders 3024 and the compressed spacer body, or other body, 3004 to resiliently self-expand radially outward to the fully expanded, functional state. Note that the spacer body 3004 expands mostly in a direction perpendicular to the minor dimension of the annulus, or toward the commissures 36 (see FIG. 74). In some embodiments, the spacer body 3004 can unfold or unfurl from the compressed state to the expanded state and in some embodiments the spacer body can be inflated, such as with saline or with an epoxy that hardens over time.

Once the spacer body is expanded within the valve, as shown in FIG. 77, hemodynamic evaluation of the spacer can be performed to assess the effectiveness of the prosthetic spacer 3000 in reducing MR. Depending on the result of the evaluation, deployment can continue or the prosthetic spacer 3000 can be recovered, retracted and/or repositioned for deployment.

From the position shown in FIG. 77, the outer sheath 3030 can be advanced back over the spacer body 3004 (by advancing the outer sheath 3030 relative to the torque shaft 3032), causing the spacer body to re-compress, as shown in FIG. 76. In some embodiments, the ventricular anchors are not recoverable, though in some embodiments the ventricular anchors can be sufficiently pliable to be re-straightened and recovered, in which case then entire delivery process can be reversed and restarted. From the position shown in FIG. 76, the delivery system can be repositioned and the spacer body 3004 can be redeployed and reassessed.

Once the ventricular anchors 3008, 3010 and the spacer body 3004 are acceptably deployed, the outer sheath 3030 can be further retracted relative to the prosthetic spacer 3000 and the torque shaft 3032 to expel the atrial anchors 3012, 3014 from the outer sheath, as shown in FIG. 78. Once fully expelled, the atrial anchors resiliently curl into their final deployment position shown in FIG. 78 with their engagement portions 3020, 3022 pressed against the atrial side of the annulus 8 and/or the annulus connection portions of the leaflets 10, 12 opposite the engagement portions 3016, 3018, respectively, of the ventricular anchors, thereby compressing the annulus and/or the annulus connection portions of the leaflets at the A2 and P2 regions to retain the prosthetic spacer 3000 within the native mitral valve region 2.

Figure 79:
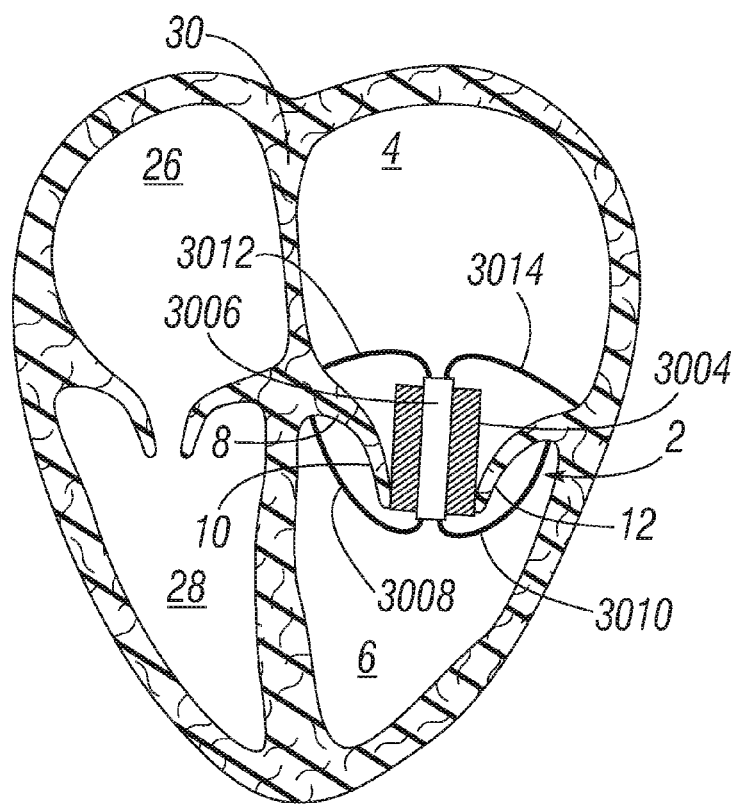

Once the atrial anchors 3012, 3014 are deployed, the torque shaft 3032 can be released from the atrial end of the frame body 3006. The delivery system can then be retracted back out of the body, leaving the prosthetic spacer 3000 implanted, as shown in FIG. 79.

Figure 80:
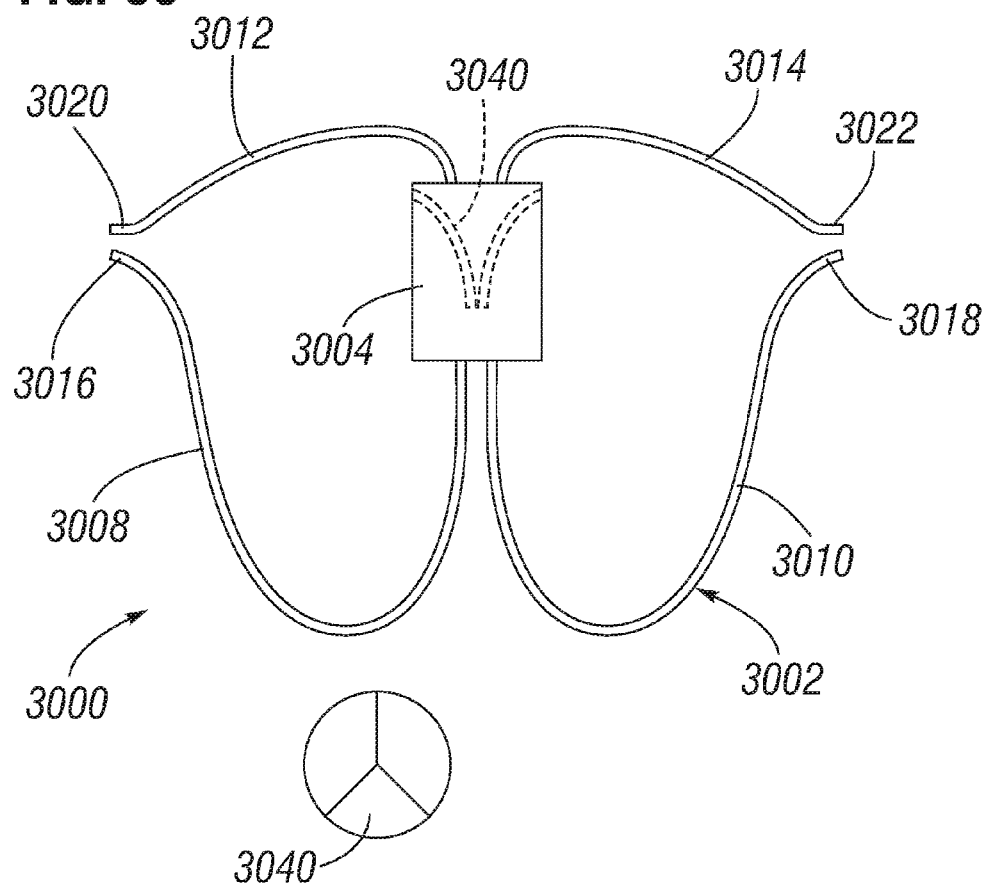
FIG. 80 is a side view of an alternative embodiment of a prosthetic apparatus of FIG. 71, comprising prosthetic valve.
Figure 82:
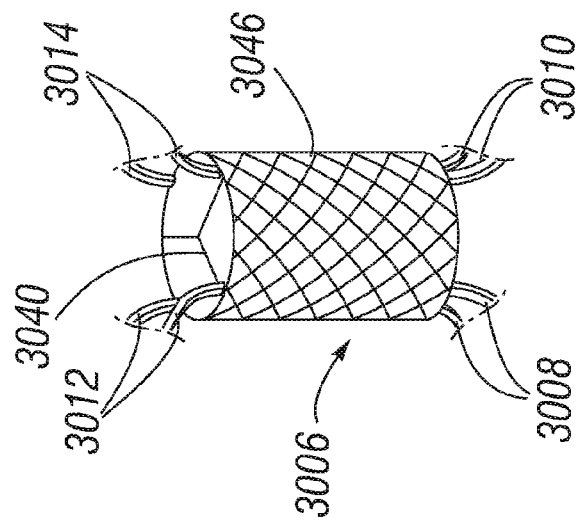
FIG. 82 is a partial side view of an alternative embodiment of a prosthetic apparatus of FIG. 71, comprising a lattice frame body and a prosthetic valve.

In some embodiments, the spacer body 3004 can comprise a valve structure 3040, such the embodiments shown in FIGS. 80 and 82. The valve structure 3040 can function in conjunction with the native mitral valve 2 to regulate blood flow between the left atrium 4 and the left ventricle 6. For example, the valve structure 3040 can be positioned between the native leaflets such that the native leaflets close around the outside of the valve structure such that some blood flows through the valve structure while other blood flows between the outside of the valve structure and the native leaflets. The valve structure 3040 can comprise a three-leaflet configuration, such as is described herein with reference to the valve structure 104 and shown in FIGS. 5-7.

In some embodiments, the frame body 3006 can comprise a cylinder, which can optionally comprise solid-walled tube, such as in FIGS. 71-74, a mesh-like wire lattice 3046, such as in FIG. 82, or other cylindrical configurations. With reference to FIGS. 71-75, the frame body 3006 and optionally one or more of the anchors can be formed from a solid-walled tube, such as of Nitinol, wherein the atrial anchors are formed, such as by laser cutting, from one portion of the tube and the ventricular anchors are formed from a second portion of the tube and the frame body is formed from a portion of the tube between the first and second portions. The anchors can then be formed, such as by heat treatment, to a desired implantation configuration. In such embodiments, the anchors and the frame body can be a unibody, or monolithic, structure.

Figure 83:
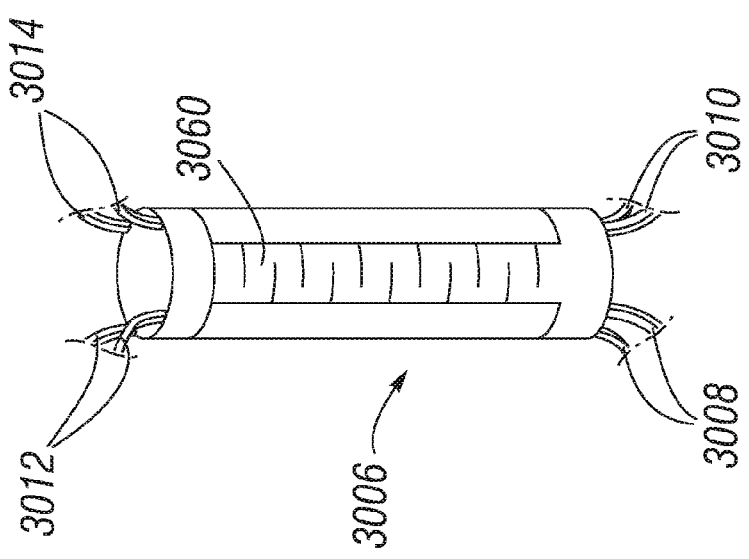
FIG. 83 is a partial side view of an alternative embodiment of a prosthetic apparatus of FIG. 71 comprising a helical frame body.

In other embodiments, the frame body 3006 can comprise a spring-like helically coiled wire column 3050, as shown in FIG. 83. Such a coiled column 3050 can be made from wire having a round or rectangular cross-section and can comprise a resiliently flexible material, such as Nitinol, providing lateral flexibility for conforming to the native valve structure while maintaining longitudinal column stiffness for delivery. In some of these embodiments, the frame body 3006 can comprise a quadrahelical coil of four wires having four atrial ends that extend to form the atrial anchors 3012, 3014 and four ventricular ends that extend to form the four ventricular anchors 3008, 3010.

In other embodiments, the frame body 3006 can comprise a plurality of longitudinal members (not shown). In one such example, the frame body 3006 can comprise four longitudinal members: two longitudinal members that extend to form the anterior anchors 3012, 3014 and two longitudinal members that extend to from the posterior anchors 3008, 3010.

Figure 81:
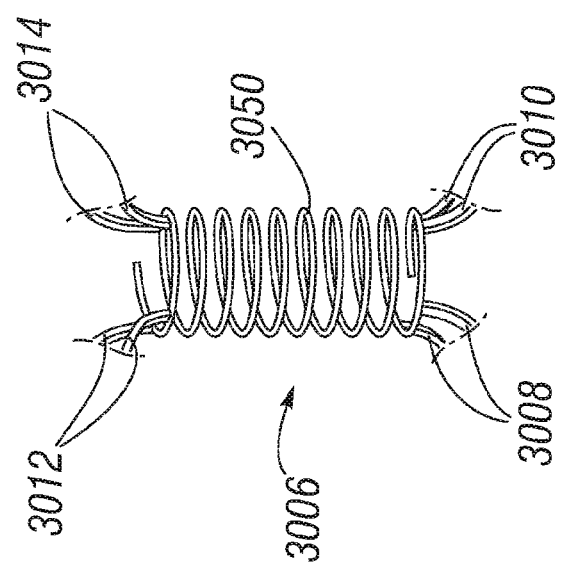
FIG. 81 is a partial side view of an alternative embodiment of a prosthetic apparatus of FIG. 71, comprising a Z-cut frame body.

In other embodiments, the frame body 3006 can comprise a zig-zag cut pattern 3050 along the longitudinal direction of the body, as shown in FIG. 81, that can also provide lateral flexibility while maintaining column strength.

In some embodiments, the prosthetic spacer 3000 can have additional anchors. In some embodiment (not shown), the prosthetic spacer 3000 can have three pairs of anchors: one pair of anchors centered around the posterior leaflet 12, such as the posterior anchors 3010 and 3014 described above, and one pair of anchors at each commissure 36 between the native leaflets 10, 12. These commissure anchors pairs can similarly comprise a ventricular anchor and an atrial anchor and can similarly compress the native annulus 8. In other embodiments, the anterior anchors 3008 and 3012 can also be included as a fourth pair of anchors. Other embodiments can comprise other combinations of these four pairs of anchors and/or additional anchors.

In addition to filling the regurgitant orifice area and blocking blood from flowing toward the left atrium, the prosthetic spacer 3000 can also add tension to the chordae tendineae to prevent further enlargement of the left ventricle and prevent further dilation of the mitral valve annulus.

Anchoring Beneath the Mitral Valve Commissures

Some embodiments of prosthetic devices comprising ventricular anchors, including both prosthetic valves and prosthetic spacers, can be configured such that the ventricular anchors anchor beneath the commissures 36 of the native mitral valve 2 instead of, or in addition to, anchoring behind the A2/P2 regions of the native mitral leaflets 10, 12. FIGS. 84-87 show exemplary prosthetic device embodiments that comprise ventricular anchors that anchor beneath the two commissures 36 of the native mitral valve 2, and related delivery methods. These commissure-anchoring concepts are primarily for use with prosthetic valves, but can be used with other prosthetic devices, including prosthetic spacers.

Figure 88:
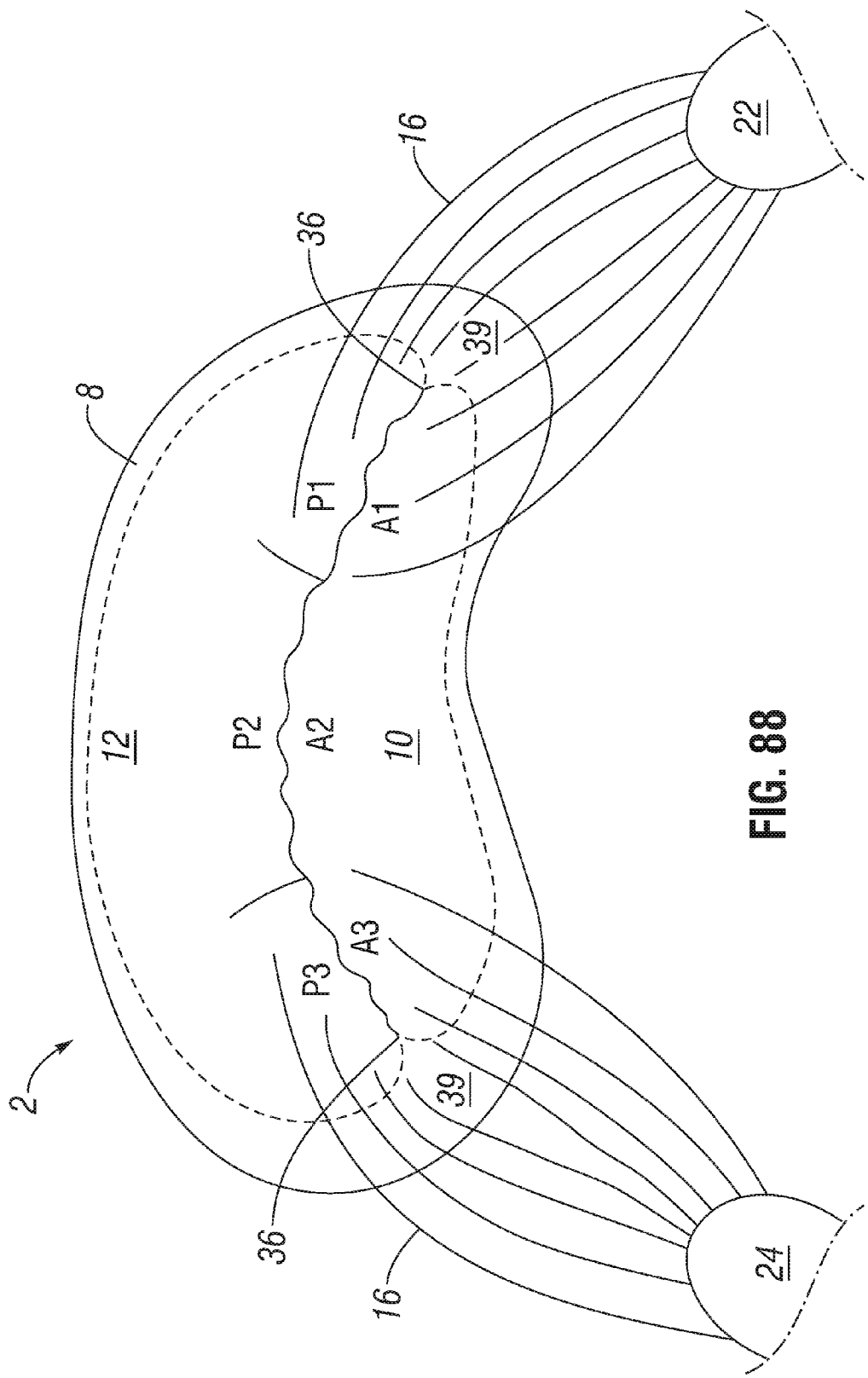
FIG. 88 is ventricular view of the native mitral valve region.

As shown in FIGS. 3, 4 and 88, the commissures 36 are the areas of the native mitral valve 2 where the anterior leaflet 10 and the posterior leaflet 12 are joined. Portions 39 of the native mitral annulus 8 adjacent to each commissure 36, as shown in FIG. 88, can be relatively thicker and/or stronger than the portions of the mitral annulus 8 adjacent to the intermediate portions of the leaflets A2/P2, providing a rigid, stable location to anchor a prosthetic apparatus. These annulus regions 39 can comprise tough, fibrous tissue that can take a greater load than the native leaflet tissue, and can form a natural concave surface, or cavity.

FIGS. 84 and 85 show an exemplary prosthetic apparatus 4000 being implanted at the native mitral valve region 2 by positioning a ventricular anchor 4002 at one of the cavities 39. The prosthetic apparatus 4000 can be a prosthetic valve having a leaflet structure or a spacer device having a spacer body 3004 for reducing MR. The chordae tendineae 16 attach to the leaflets 10, 12 adjacent to the commissures 36, which can present an obstacle in positioning ventricular anchors in the cavities 39 behind the chordae. It is possible, however, to deliver anchors, such as anchor 4002, around the chordae 16 to reach the cavities 39. Positioning engagement portions, such as the engagement portion 4004, of the ventricular anchors behind the chordae 16 in these natural cavities 39 can be desirable for retaining a prosthetic apparatus at the native mitral valve region 2. However, to avoid entanglement with and/or damage to the native chordae 16, it can be desirable to first guide the engagement portions of the anchors vertically behind the leaflets 10, 12 at the A2/P2 regions, between the chordae 16 from the postero-medial papillary muscle 22 and the chordae 16 from the antero-lateral papillary muscle 24, as shown in FIG. 84, and then move or rotate the engagement portions of the anchors horizontally around behind the chordae 16 toward the commissure cavities 39, as shown in FIG. 85.

In some such methods, the ventricular anchors are first deployed behind the A2/P2 regions of the leaflets and then the entire prosthetic apparatus is rotated or twisted to move the engagement portions of the anchors horizontally toward the cavities 39, as shown in FIGS. 84 and 85. For example, a first anchor deployed behind the anterior leaflet 10 can move toward one of the cavities 39 while a second anchor deployed behind the posterior leaflet 12 can move toward the other cavity 39. This method can also be referred to as a "screw method" because the entire prosthetic is rotated to engage the anchors with the native tissue.

As shown in FIGS. 84 and 85, a prosthetic apparatus 4000 comprising bent, curved, hooked, or generally "L" shaped, anchors 4002 can be used with the screw method. The "L" shaped anchors 4002 can comprise a leg portion 4006 the extends vertically upward from the body of the apparatus 4000, a knee portion 4008, and a foot portion 4010 extending horizontally from the knee portion and terminating in the engagement portion 4004. In some of these embodiments, the "L" shaped anchor 4002 can comprise a looped wire that attaches to the body of the apparatus 4000 at two locations, such that the wire forms a pair of leg portions 4006, a pair of knee portions 4008 and a pair of foot portions 4010. In other embodiments, the anchor 4002 can have other similar shapes, such as a more arced shape, rather than the right angle shape shown in FIG. 84. During delivery into the heart, the foot portion 4010 can be curled or wrapped around the outer surface of the body of the apparatus 4000.

As shown in FIG. 84, in order to move the foot portion 4010 vertically behind the leaflet 10 without entanglement with the chordae, the leg portion 4006 can be positioned slightly off center from the A2 region, closer to the chordae opposite the cavity 39 of desired delivery. As shown in FIG. 84, the leg portion 4006 is positioned to the right such that the foot portion 4010 can pass between the chordae 16.

After the foot portion 4010 clears the chordae 16 and is positioned behind the leaflet, the apparatus 4000 can be rotated to move the engagement portion 4004 horizontally into the cavity 39, as shown in FIG. 85. Note that in FIG. 85 the leg portion 4006 can end up positioned at the A2/P2 region between the chordae 16 to avoid interference with the chordae.

While FIGS. 84 and 85 show a single anchor 4002, both an anterior and a posterior anchor can be delivery in symmetrical manners on opposite sides of the native valve 2, one being anchored at each cavity 39. The feet 4010 of the two anchors 4002 can point in opposite directions, such that the twisting motion shown in FIG. 85 can move them simultaneously to the two cavities 39. During delivery of two anchor embodiments, the two foot portions 4010 can wrap around the outer surface of the body of the apparatus 4000 such that the two foot portions 4010 overlap one another.

In similar embodiments, the anchors 4002 can comprise a paddle shape (see FIG. 37 for example) having two foot portions 4010 extending in opposite directions. While more difficult to move between the chordae, these paddle shaped anchors can allow the apparatus 4000 to be rotated in either direction to engage one of the foot portions 4010 at a cavity 39. In some embodiments, the paddle shaped anchors can be wide enough such that one foot portion 4010 can be positioned at one cavity 39 while the other foot portion is positioned at the other cavity.

Because the anchors 4002 each attach to the body of the apparatus 4000 at two locations, the anchors can spread apart from the main body of the apparatus when the main body is compressed, forming a gap to receive a leaflet, as described in detail above with reference to FIGS. 11-22. In some embodiments, the anchors can separate from the main body when the main body is compressed and either remain separated from the main body, such that the leaflets are not pinched or compressed between the anchors and the main body of the apparatus, or close against the main body during expansion to engage the leaflets. In some embodiments, the main body can move toward the anchors to reduce the gap when then main body expands while maintaining the distance between the foot portions 4010 of the opposing anchors.

Figure 86:
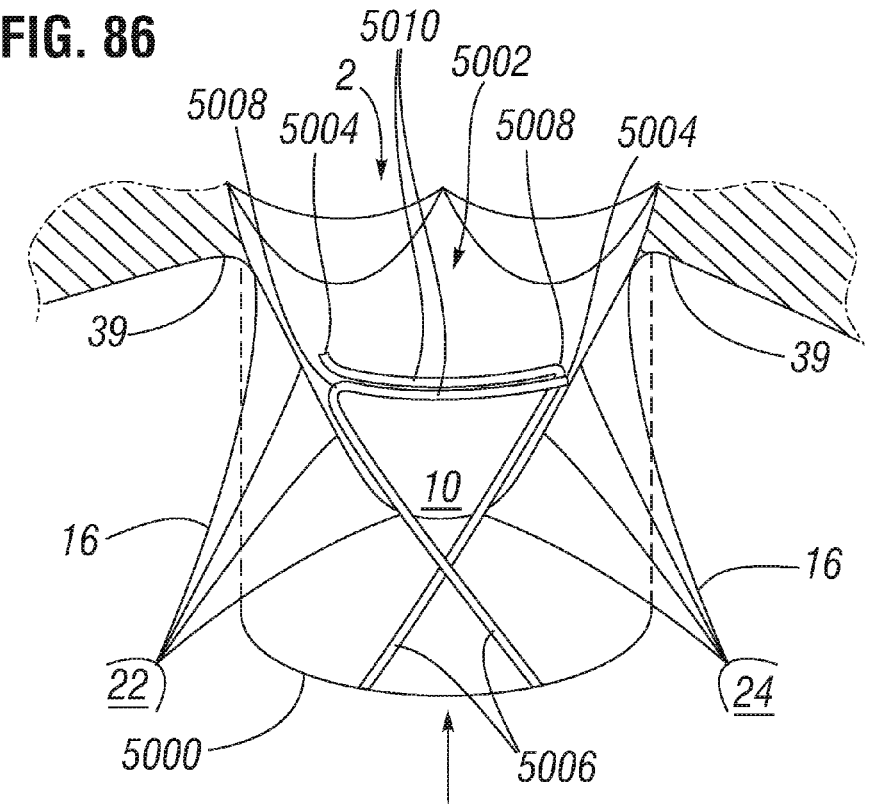
FIGS. 86 and 87 show another exemplary method for implanting another prosthetic apparatus having "L" shaped ventricular anchors.
Figure 87:
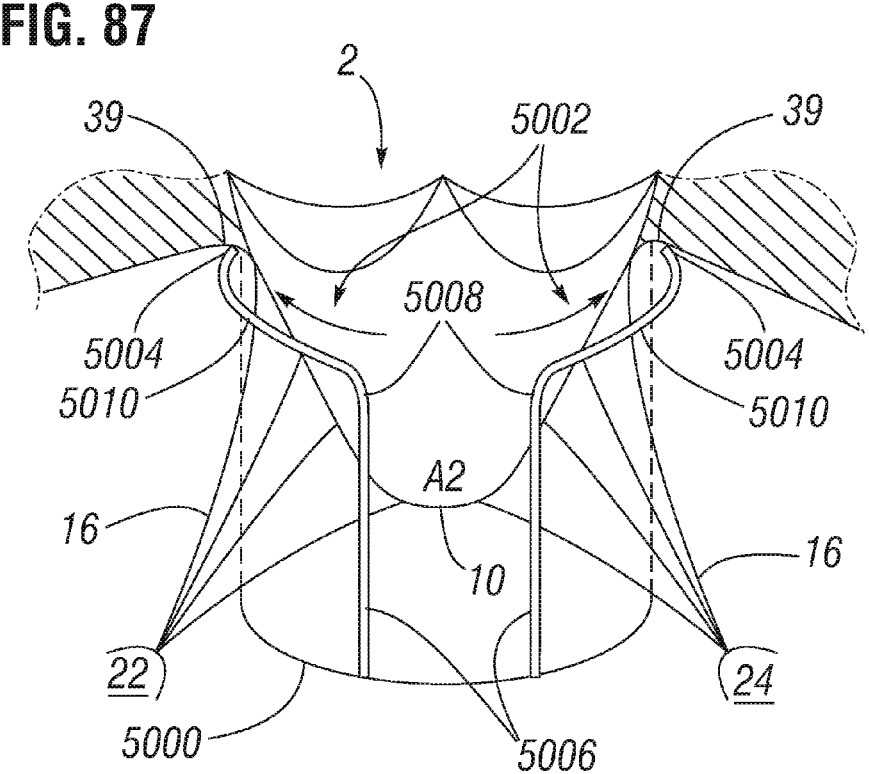

FIGS. 86 and 87 shown another exemplary prosthetic apparatus 5000 being implanted at the native mitral valve region 2 by positioning ventricular anchors 5002 at the cavities 39 and a corresponding method for do so. In this embodiment, the apparatus 5000 can comprise a pair of "L" shaped anchors 5002 on each side (only one pair is visible in FIGS. 86 and 87), with each pair comprising one anchor for positioning in one of the cavities 39 and another anchor for positioning in the other cavity. Each of the anchors can comprise a leg portion 5006 extending vertically from the body of the apparatus 5000 to a knee portion 5008, and a foot portion 5010 extending horizontally from the knee portion 5008 to an engagement portion 5004. In other embodiments, the anchors 5002 can have other similar shapes, such as a more arced shape, rather than the angled shape shown in FIG. 86.

Each pair of anchors 5002 can comprise a resiliently flexible material, such as Nitinol, such that they can be pre-flexed and constrained in a cocked position for delivery behind the leaflets, as shown in FIG. 86, and then released to resiliently spring apart to move the engagement portions 5004 in opposite directions toward the two cavities 39, as shown in FIG. 87. Any suitable constraint and release mechanisms can be used, such as a releasable mechanical lock mechanism. Once released, one anterior anchor and one posterior anchor can be positioned at one cavity 39 from opposite directions, and a second anterior anchor and a second posterior anchor can be positioned at the other cavity from opposite directions. Some embodiments can include only one anchor on each side of the apparatus 5000 that move in opposite directions toward opposite cavities 39 when released.

Because each pair of anchors 5002 are initially constrained together, as shown in FIG. 86, each pair of anchors can act like a single anchor having two attachment points to the main body of the apparatus 5000. Thus, the anchor pairs can separate, or expand away, from the main body when the main body is compressed, and either remain spaced from the main body, such that the leaflets are not pinched or compressed between the anchors and the main body of the apparatus, or close against the main body during expansion to engage the leaflets. In some embodiments, the main body can move toward the anchor pairs to reduce the gap when then main body expands while maintaining the distance between the foot portions 5010 of the opposing anchor pairs.

In the embodiments shown in FIGS. 84-87, the prosthetic apparatus 4000 or 5000 can have a main frame body similar to the embodiments shown in FIG. 5, from which the ventricular anchors 4002, 5002 can extend, and can further comprise one or more atrial anchors, such as an atrial sealing member similar to the atrial sealing member 124 shown in FIG. 5 or a plurality of atrial anchors similar to the atrial anchors 3012 and 3014 shown in FIG. 71, for example. The atrial anchors can extend radially outward from an atrial end of the prosthetic apparatus and contact the native tissue opposite the cavities 39 and thereby compress the tissue between the atrial anchors and the engagement portions 4004, 5004 of the ventricular anchors 4002, 5002 to retain the prosthetic apparatus at the native mitral valve region. The atrial anchors and the ventricular anchors can comprise a broad contact area to distribute the load over a wider area and reduce the likelihood of damaging the native tissue.

Atrial Portion of Prosthetic Mitral Valves

Some embodiments of prosthetic devices disclosed herein comprise atrial portions that extend radially outward from an atrial end of the main body, while other embodiments do not. As explained above, an atrial portion which extends radially from the atrial end of the main body of a prosthetic mitral valve can provide several advantages. The atrial portion can create a fully annular contact area, or seal, with the native tissue on the atrial side of the mitral annulus, thereby preventing or reducing the flow of blood between the outside of the prosthetic valve and the native valve tissue. This can help to reduce paravalvular leakage. The atrial portion can also act to retain the prosthetic valve against migration toward the left ventricle. The atrial portion can also promote tissue in-growth, which can further reduce paravalvular leakage and increase retention of the prosthetic valve.

In some embodiments, the atrial portion can be formed integrally with the main body and can be radially collapsible and expandable to facilitate delivery. The shape of the atrial portion can be selected to accommodate a patient's anatomy. The atrial portion (like the main body) can be covered by at least one biocompatible layer to block the flow of blood, further promote tissue in-growth, and/or further accommodate a patient's anatomy.

The configuration of the atrial portion can depend on several factors, including the structure of the patient's mitral valve region and the patient's medical condition(s). Several alternative configurations are described below, each of which varies in one or more respects. For example, the configuration of the atrial portion as viewed from above (i.e., along a longitudinal center axis extending through the center of the main body), referred to herein as the "radial configuration," can vary from embodiment to embodiment. Furthermore, the configuration of the atrial portion as viewed from the side (i.e., along an axis perpendicular to the longitudinal axis), referred to herein as the "axial configuration," can vary from embodiment to embodiment. Additional features of the atrial portion can also vary from embodiment to embodiment depending on various factors. These additional features can include, without limitation, the manner in which the atrial portion is connected to the main body, the location on the main body at which the atrial portion is connected, the type of fabric used to cover the atrial portion, the symmetry (or asymmetry) of the radial configuration, the inclusion of arms having serpentine or coiled configurations, and the method(s) by which the atrial portion is fabricated. Except where such a combination would be structurally impossible, any of the alternative radial configurations disclosed herein can be used in combination with any of the alternative axial configurations disclosed herein, and further in combination with any of the additional variations described herein.

The radial configuration of the atrial portion can affect several properties of the atrial portion, such as the radial stiffness, axial stiffness, circumferential stiffness, and/or circumferential dependence of the atrial portion. Radial stiffness is the stiffness of the atrial portion in the radial direction. In some cases, radial stiffness can be defined more specifically as the radial distance a point on the circumference of the atrial portion travels in response to a radial force exerted against that point on the atrial portion. Axial stiffness is the stiffness of the atrial portion in the axial direction. In some cases, the axial stiffness can be defined more specifically as the axial distance a point on the circumference of the atrial portion travels with respect to the main body in response to an axial force exerted against that point on the atrial portion. Circumferential stiffness is the stiffness of the atrial portion in a circumferential direction. In some cases, the circumferential stiffness can be defined more specifically as the angular distance a point on the circumference of the atrial portion travels about the central longitudinal axis of the main body in response to a circumferential force (i.e., a force exerted in a direction perpendicular to a radial force and an axial force) exerted against that point on the atrial portion. The circumferential dependence of the atrial portion is the degree to which the displacement of one point on the circumference of the atrial portion is affected by displacement of a neighboring point on the circumference of the atrial portion.

Other properties of the atrial portion can also vary depending on the radial configuration of the atrial portion. For example, the radial configuration can affect the tendency of the atrial portion to cause trauma to the native tissue. Also, the radial configuration can affect the resistance to fatigue failure of the atrial portion, its components, and their connections to the main body, especially fatigue failure due to cyclic forces of a beating heart. Further, the radial configuration can affect the ability of the atrial portion to be bent or flex relative to the main body, such as from an axially extending configuration into a radially extending configuration during manufacturing or between a crimped configuration and a deployed configuration during deployment. Furthermore, the radial configuration of the atrial portion can affect the performance of the overall prosthetic valve, such as with regard to preventing paravalvular leakage, anchoring the prosthetic valve, and facilitating tissue ingrowth. Additionally, the radial configuration of the atrial portion can affect various other properties, including some of those described below with respect to the axial configuration. The properties of various different radial configurations are described below in relation to several alternative embodiments of the atrial portion.

The axial configuration of the atrial portion can similarly affect several properties of the atrial portion, including some of those described above with respect to the radial configuration. For example, introduction of a prosthetic valve at the native mitral valve can cause trauma to the native tissue, particularly in the locations where the prosthetic valve is anchored. The axial configuration of the atrial portion can affect the degree and/or type of such trauma. Further, the axial configuration can affect the total surface area of contact between the native tissue and the atrial portion, thereby affecting tissue in-growth. In addition, the axial configuration can also affect the force exerted by the atrial portion against the native tissue, thereby affecting the tightness of the seal. Furthermore, the axial configuration can also affect how well the prosthetic valve conforms to the anatomy of the native mitral valve and adjacent structures.

Various exemplary axial configurations are illustrated schematically in FIGS. 100A-100F, each of which shows a cross-sectional view of one half of a main body 7018 and a different atrial portion, along with the longitudinal axis 7016 of the main body. As shown in FIG. 100A, an atrial portion 7000 can extend radially away from an atrial end of the main body 7018 approximately perpendicular to the axis 7016. As shown in FIG. 100B, an atrial portion 7002 can extend both radially and ventricularly away from an atrial end of the main body 7018, such that the atrial portion 7002 forms an acute angle with the side of the main body 7018. In related axial configurations, an atrial portion can extend away from the main body at any desired angle Θ or range of angles Θ (where the angle Θ is measured between the atrial portion and a side surface of the main body). For example, an atrial portion can extend away from the main body at any suitable acute angle, at any suitable obtuse angle, or any angle ranging generally from 0° to 180° from the side of the main body. As shown in FIG. 100C, the atrial portion 7004 can extend generally radially away from the main body 7018 to a radial periphery, curl ventricularly from the radial periphery, and then extend back toward the main body. As shown in FIG. 100D, the atrial portion 7006 can extend radially from the main body 7018, come to a point at a radial periphery, and then extend back toward the main body from the radial periphery. As shown in FIGS. 100E and 100F, the atrial portion 7008 can include a frame which is not directly fastened to the main body 7018. In embodiments of the atrial portion having such a configuration, the atrial portions can be coupled to the main body 7018 with a fabric. As shown in FIG. 100E, the atrial portion 7008 can extend radially outwardly relative to the main body 7018. As shown in FIG. 100F, the atrial portion 7010 can comprise a single element encircling the main body 7018. Other axial configurations are possible, though not illustrated in FIGS. 100A-100F. For example, in some embodiments, the atrial portion extends away from the main body 7018 and curls atrially near the radial periphery.

Axial configurations having a frame not directly connected to the main body 7018 can exhibit less axial stiffness than other axial configurations, as there can be less resistance against the atrial portion moving axially with respect to the main body 7018. The axial configurations illustrated in FIGS. 100A, 100C, and 100D may reduce expected tissue trauma, provide greater surface area of contact with the native tissue, and/or fit the mitral valve anatomy more naturally, but may provide looser and/or less continuous contact with the native tissue than, for example, the axial configuration illustrated in FIG. 100B.

The axial configuration is also modified in some embodiments by changing the location of the points of connection of the atrial portion to the main body 7018. While FIGS. 100A-100D illustrate the point of connection at the atrial end of the main body 7018, the point of connection need not be at the end, and in some embodiments is axially displaced in the direction of the ventricular end of the main body 7018. Such a configuration is illustrated in FIG. 100F, which shows the atrial body axially displaced to a location that is below the atrial end of the main body 7018.

Figure 101A:
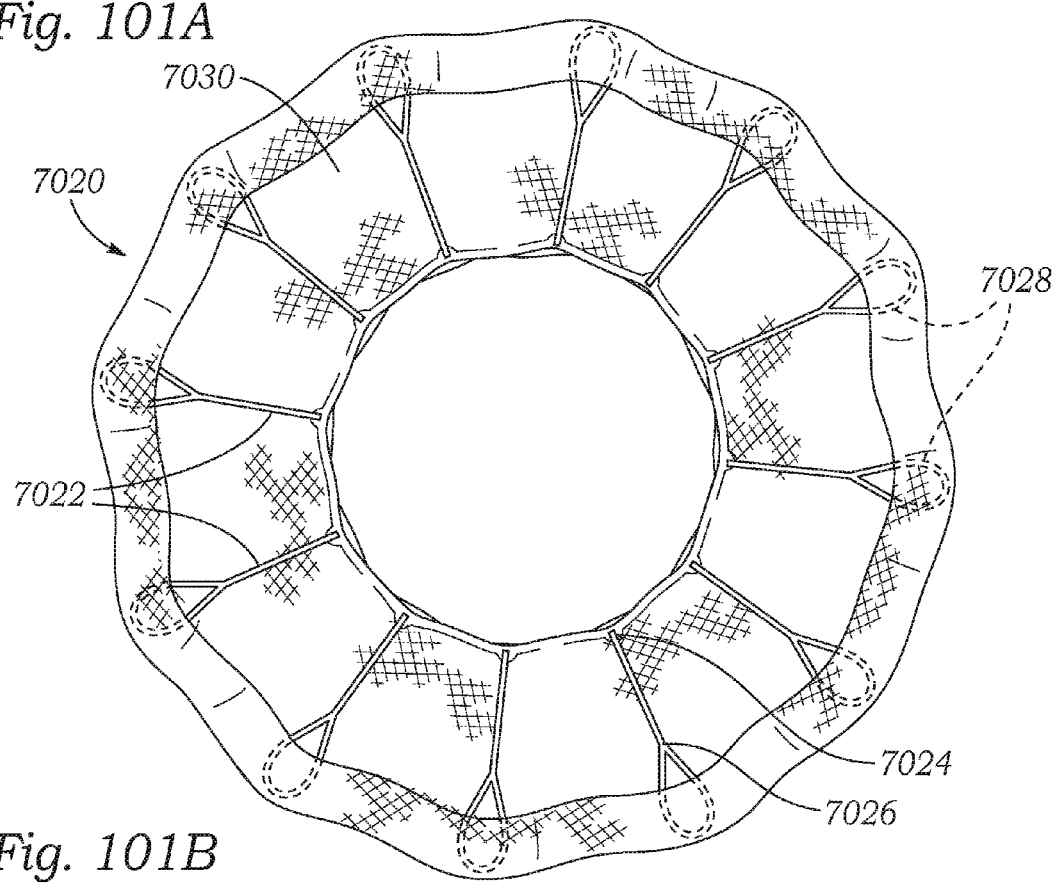
Figure 101B:
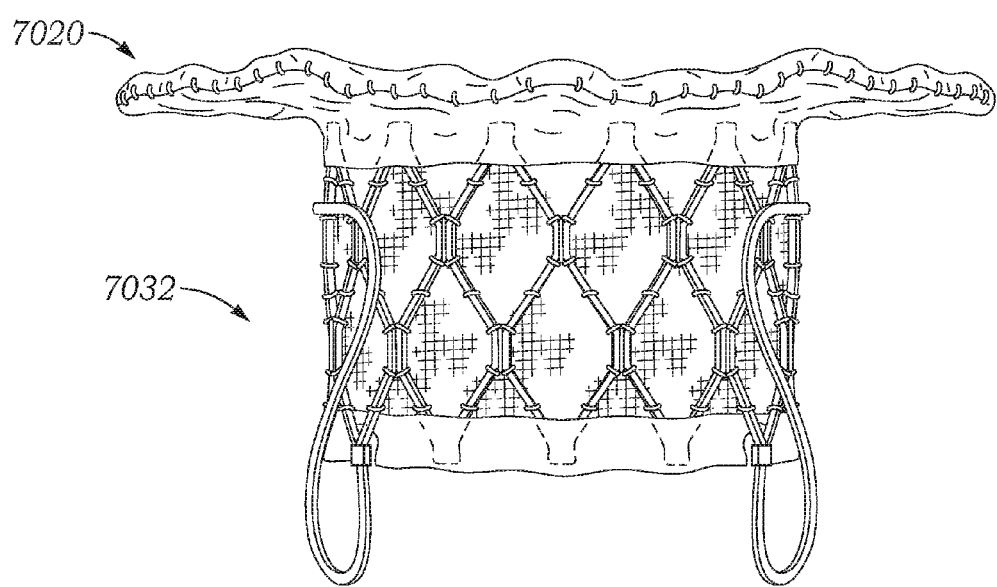

FIGS. 101A-140 show several exemplary embodiments of atrial portions of different axial and/or radial configurations. While several of the embodiments of atrial portions are shown in combination with a prosthetic mitral valve, various embodiments of atrial portions can be used in combination with various other devices to be implanted in the region of the native mitral valve. While several of the embodiments of atrial portions are shown with a specific number of various components, e.g., radially extending arms, the number of the various components provided in each of the illustrated embodiments can be different in alternative embodiments. FIGS. 101A-101B show an exemplary atrial portion 7020 having a radial configuration comprising twelve arms 7022, each connected at an originating end 7024 to a main body 7032, extending radially outward, and connected at a terminal end 7026 to a respective loop 7028. A fabric cover 7030 is connected to the arms 7022, loops 7028, and main body 7032, and spans gaps between these components. The atrial portion 7020 has an axial configuration resembling that illustrated in FIG. 100A: the arms extend radially away from the main body 7018 approximately perpendicular to the axis 7016. Each arm 7022 is independent of each neighboring arm 7022, that is, each arm 7022 can flex or bend independently of the others. As a result, this radial configuration and other radial configurations having independent arms exhibit low circumferential dependence. The loops 7028 connected to the terminal ends 7026 of each arm 7022 help to reduce to trauma experienced by the patient's tissue as a result of contact between the atrial portion 7000 and the native tissue.

Figure 102A:
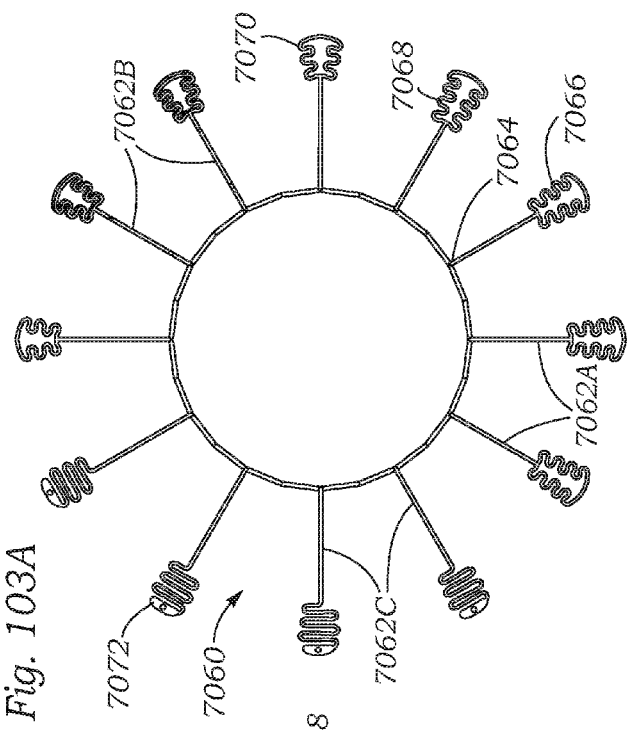
Figure 102B:
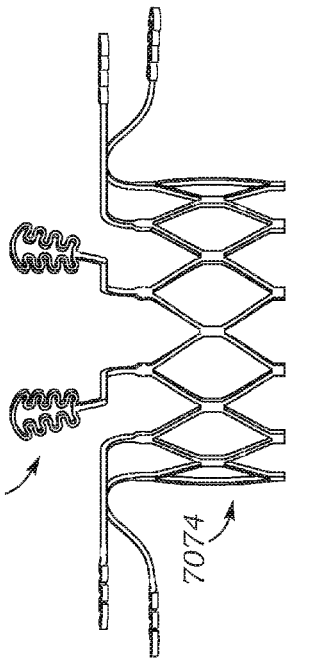

FIGS. 102A-102B show an exemplary atrial portion 7040 having a radial configuration which also comprises twelve arms 7042, each connected at an originating end 7044 to a main body 7052 and extending radially outward. The atrial portion 7040 has an axial configuration in which the terminal end 7046 of each arm 7042 curves atrially away from the main body 7052 in the axial direction. The terminal end 7046 of each arm can be connected to a horseshoe shaped element 7048. The terminal end 7046 of each arm 7042 is connected to the horseshoe element 7048 such that the ends of the horseshoe shaped element 7048 point radially inward toward the main body 7052. At each end of the horseshoe shaped element 7048 can be a small loop 7050 having a hole formed therethrough.

Figure 103A:
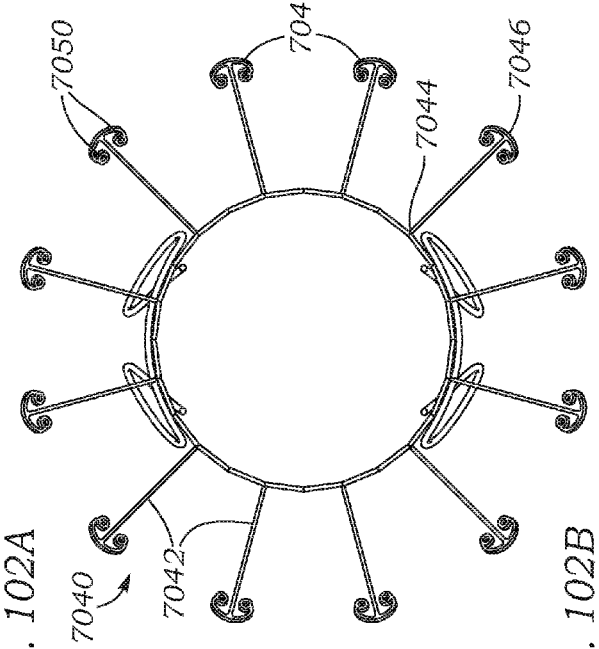
Figure 103B:
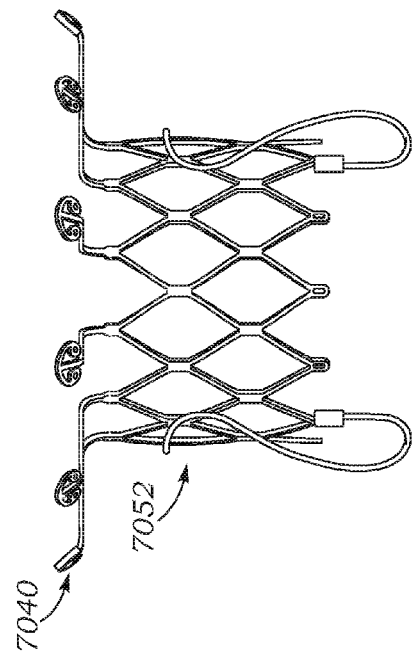

FIGS. 103A-103B show an exemplary atrial portion 7060 having a radial configuration which also comprises twelve arms, each connected at an originating end 7064 to a main body 7074 and extending radially outward. Four of the arms 7062A are connected at their terminal ends 7066 to loops 7068 whose shape includes six inward pointing projections; four of the arms 7062B are connected at their terminal ends 7066 to loops 7070 whose shape includes four inward pointing projections; and four of the arms 7062C are connected at their terminal ends 7066 to a serpentine portion 7072. The atrial portion 7060 has an axial configuration in which some of the arms 7062A, 7062B, 7062C extend both radially and ventricularly away from the atrial end of the main body 7074, such that they form an acute angle with the side of the main body 7074, and in which other arms 7062A, 7062B, 7062C extend both radially and atrially away from the atrial end of the main body 7074, such that they form an obtuse angle with the side of the main body 7074.

In an alternative embodiment, an atrial portion can be similar to atrial portion 7060 but have twelve arms connected at their terminal ends to loops whose shape includes six inward pointing projections. In another alternative embodiment, an atrial portion can be similar to atrial portion 7060 but have twelve arms connected at their terminal ends to loops whose shape includes four inward pointing projections. In yet another alternative embodiment, an atrial portion can be similar to atrial portion 7060 but have twelve arms connected at their terminal ends to a serpentine portion. These alternative embodiments can be selected for the effect the loops or serpentine portions have on the properties of the atrial portion, including its tendency to cause trauma to native tissue.

Figure 104:
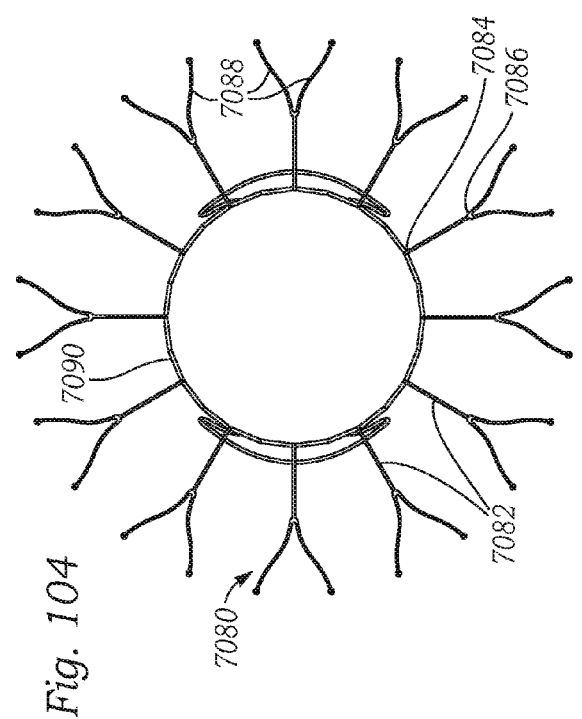

FIG. 104 shows an exemplary atrial portion 7080 having a radial configuration which also comprises twelve arms 7082, each connected at an originating end 7084 to a main body 7090 and extending radially outward. Each of the arms 7082 splits at a terminal end 7086 to form two radially outwardly extending extensions 7088. The atrial portion 7080 has an axial configuration wherein the originating end 7084 of each of the arms 7082 is connected to the main body 7090 at a point displaced from its atrial end (as shown in FIG. 125B). The arms 7082 first extend atrially away from their originating ends 7084 and curl radially so they extend radially outward from the main body 7090 (as shown in FIG. 102B). The extensions 7088 curl atrially so the periphery of the atrial portion 7080 extends both radially and atrially away from an atrial end of the main body 7090 (also as shown in FIG. 102B). Elements of the atrial portion 7080 can be curved to match the anatomy of a patient's native mitral valve region.

Figure 105:
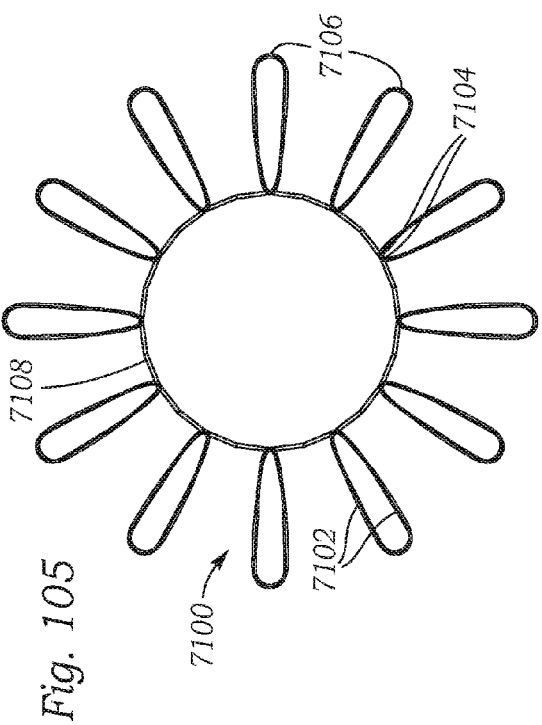

FIG. 105 shows an exemplary atrial portion 7100 having a radial configuration comprising twenty four arms 7102. The twenty four arms 7102 are arranged to form twelve pairs of arms, each pair forming a continuous loop attached to a main body 7108 at the originating ends 7104 of each of the pair of arms, extending away from the main body 7108, and connecting again at a connection location 7106 radially displaced from the main body 7108. Because each arm 7102 is connected to another, this radial configuration provides greater stiffness than other radial configurations. The atrial portion 7100 has an axial configuration resembling that illustrated in FIG. 100A.

Figure 106:
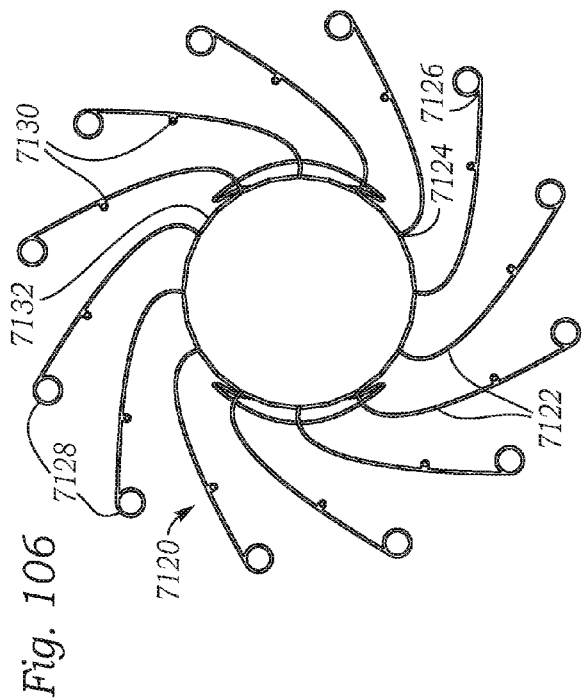

FIG. 106 shows an exemplary atrial portion 7120 having a radial configuration comprising twelve arms 7122, each connected at an originating end 7124 to a main body 7132, extending radially outward and connected at a terminal end 7126 to a loop 7128. This radial configuration differs from the previous radial configurations in that the arms 7122, in addition to extending radially away from the main body 7132, also extend angularly away from their originating end 7124, such that the arms 7122 form a spiral pattern. Atrial portion 7120, like other atrial portions having independent arms, exhibits low circumferential dependence. Unlike many of the other configurations however, this configuration exhibits low radial stiffness due to the spiral configuration of the arms 7122. When one of the arms 7122 experiences a radial force, it can flex relatively easily in the radial direction because it experiences primarily bending, rather than compression or tension. The atrial portion 7120 also includes several connection points 7130 near the midpoints of the arms 7122, which can be used to facilitate the attachment of a fabric cover (not pictured) to the arms 7122. The atrial portion 7020 has an axial configuration resembling that illustrated in FIG. 100A.

Figure 107:
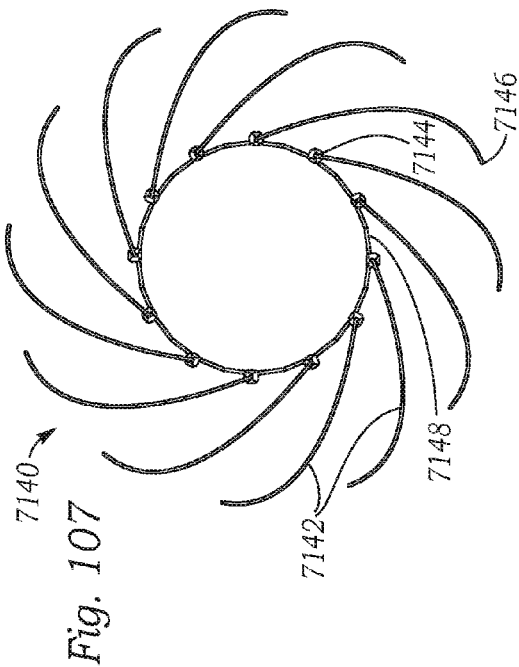

FIG. 107 shows an exemplary atrial portion 7140 having a radial configuration comprising twelve arms 7142, each connected at an originating end 7144 to a main body 7148 and extending radially outward. Atrial portion 7140 is similar to atrial portion 7120, but the arms 7142 are not connected at their terminal ends 7146 to loops, and the arms 7142 are not integrally formed with the main body 7148, but are instead mechanically fastened to the main body 7148 at the originating ends 7144. As a result, atrial portion 7140 is less likely to experience fatigue failure than other similar atrial portions. The atrial portion 7140 has an axial configuration resembling that illustrated in FIG. 100A.

FIG. 108 shows an exemplary atrial portion 7160 having a radial configuration comprising twelve arms 7162, each connected at an originating end 7164 to a main body 7172, extending radially outward, and connected at their terminal end 7166 to a horseshoe shaped element 7168, the ends of which point back toward the main body 7172, similar to the embodiment shown in FIGS. 102A-102B. A fabric 7170 is connected to the arms 7162, horseshoe shaped elements 7168, and main body 7172, and spans gaps between these components. This radial configuration differs from the previous configurations in that the arms 7162 are formed in a serpentine shape, rather than as a straight section of material.

As illustrated in FIGS. 109A-109E, the serpentine shape of the arms 7162 can comprise a plurality of substantially straight, parallel segments interconnected by a plurality of curved segments or bends (such as in FIGS. 109A, 109B, and 109E), substantially curved portions (such as in FIG. 109C), and/or straighter portions nearer the main body 7172 and more curved portions nearer the terminal ends 7166 of the arms 7162 (such as in FIG. 109D). As illustrated in FIG. 109E, in some embodiments the serpentine shape can be thicker nearer the main body 7172 and thinner nearer the terminal end 7166 of the arms 7162. Including a serpentine shape in the arms 7162 can decrease their stiffness and can decrease the chance they will fail due to fatigue. The atrial portion 7160 has an axial configuration resembling that illustrated in FIG. 100A. An important characteristic of serpentine arms is their thickness: by increasing their thickness, their flexibility is decreased, and by decreasing their thickness, their flexibility is increased.

Figure 110A:
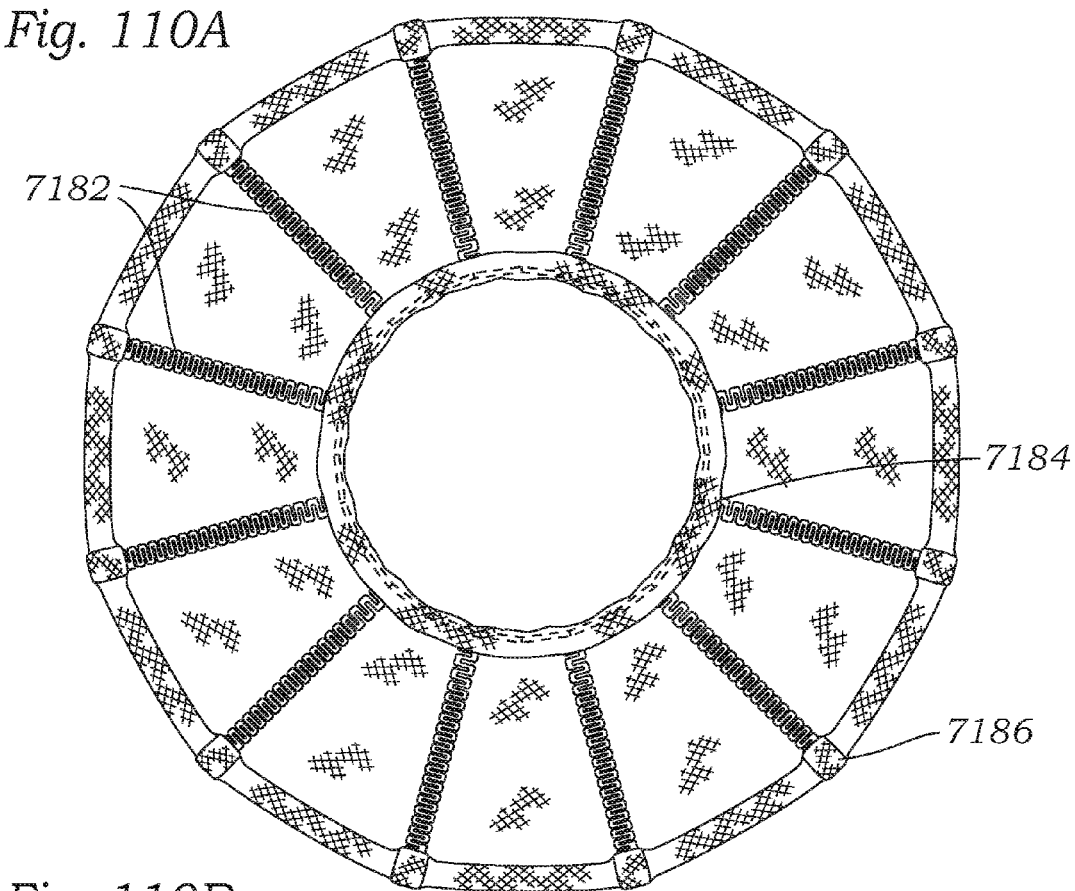
Figure 110B:
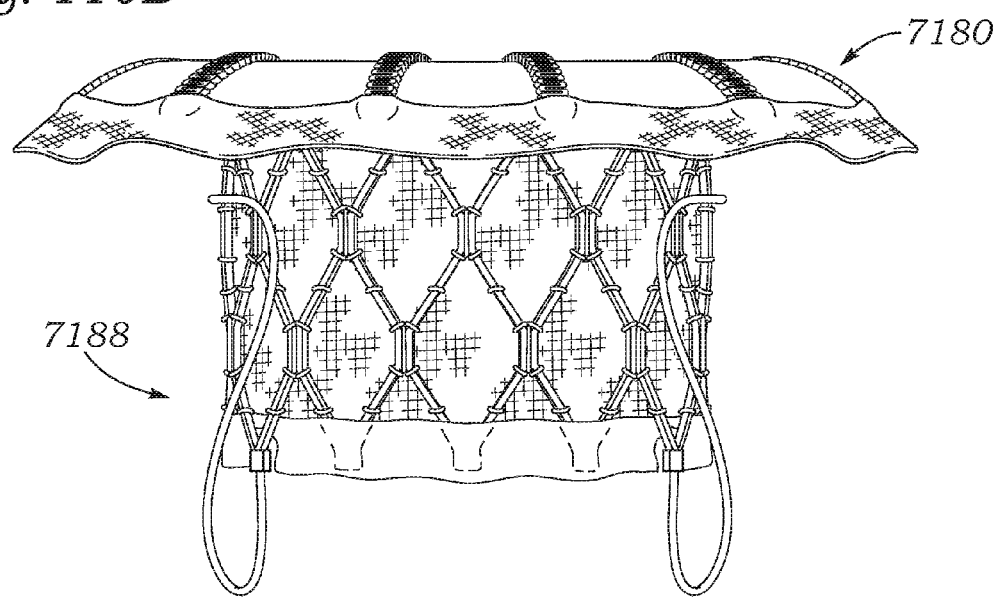

FIGS. 110A-110B show an exemplary atrial portion 7180 having a radial configuration comprising twelve arms 7182, each connected at an originating end 7184 to a main body 7188 and extending radially outward. Atrial portion 7180 is similar to atrial portion 7160 except that the arms 7182 are formed without an additional element attached to their terminal ends 7186. Atrial portion 7180 has an axial configuration resembling that illustrated in FIG. 100B: the arms 7182 curve ventricularly, moving radially away from the main body 7188, such that they extend at an acute angle to the side of the main body 7188. As a result, atrial portion 7180 provides less surface area of contact with native tissue, but can provide a tighter seal when implanted than some other atrial portions.

Figure 111:
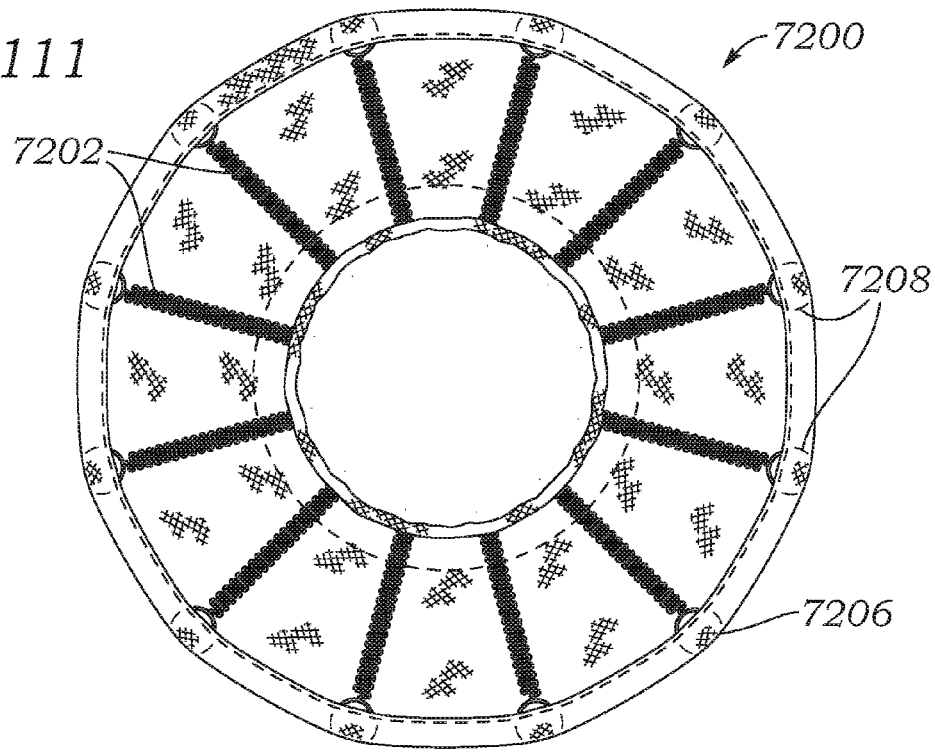

FIG. 111 shows an exemplary atrial portion 7200 having a radial configuration similar to that of atrial portions 7160 and 7180 except that the arms 7202 are connected at their terminal ends 7206 to loops 7208. In addition to atrial portions 7160, 7180, and 7200, many of the other atrial portion embodiments described herein can be altered to incorporate arm elements having a serpentine shape, and doing so can in many cases decrease the stiffness and/or the chance of fatigue failure in the altered element(s). The atrial portion 7200 has an axial configuration resembling that illustrated in FIG. 100A.

Figure 112:
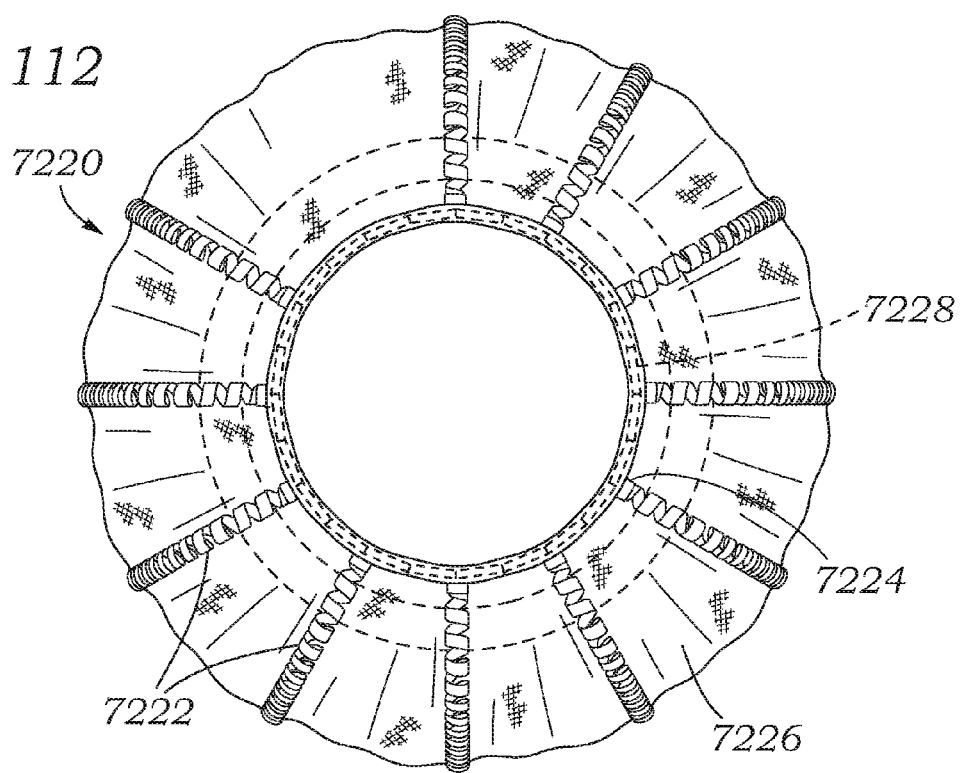

FIG. 112 shows an exemplary atrial portion 7220 having a radial configuration comprising eleven arms 7222, each connected at an originating end 7224 to a main body 7228 and extending radially outward. The eleven arms 7222 are configured such that a larger space exists between two neighboring arms 7222 than between other neighboring arms 7222, the advantage of which is described below with regard to FIGS. 126-130. Atrial portion 7220 differs from the previous configurations in that the arms 7222 are formed in a coiled or helical configuration rather than as a straight section of material. Like the serpentine shape used in atrial portions 7160, 7180, and 7200, including a coil shape in the configuration of the arms 7222 can decrease their stiffness and/or the chance of fatigue failure. Atrial portion 7220 has an axial configuration resembling that illustrated in FIG. 100B: the arms 7222 curve ventricularly, extending radially outward, such that they extend at an acute angle to the side of the main body 7228. As a result, atrial portion 7220 can provide less surface area of contact with native tissue, but provide a tighter seal when implanted than some other atrial portions. A fabric 7226 is connected to the arms 7222 and the main body 7228, and spans gaps between these components.

FIG. 113 shows an exemplary atrial portion 7240 having a radial configuration similar to that of atrial portion 7220 except that it comprises coiled arms 7242 which extend angularly as well as radially away from their originating end 7244 at the main body 7246, such that the arms 7242 form a spiral pattern, as in atrial portion 7120. Like with atrial portions 7220 and 7240, many of the other atrial portion embodiments described herein can be altered to incorporate elements having a coiled configuration, and doing so can in many cases decrease the stiffness and/or the chance of fatigue failure in the altered element(s). The atrial portion 7240 has an axial configuration resembling that illustrated in FIG. 100A.

Figure 114:
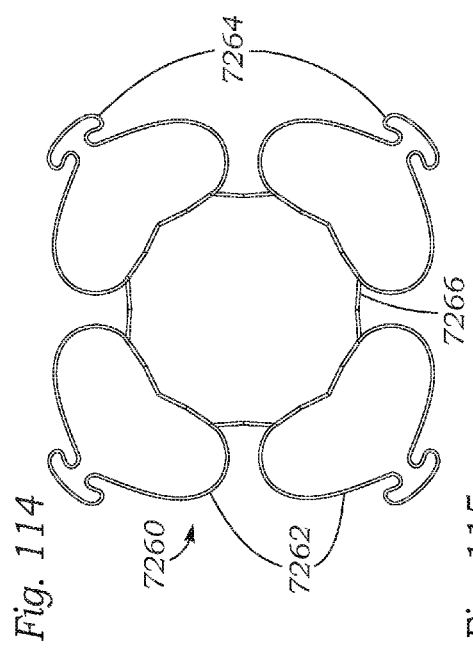

FIG. 114 shows an exemplary atrial portion 7260 having a radial configuration comprising four loops 7262 extending radially away from a main body 7266. While the atrial portion 7260 is shown with four loops 7262, the number of loops provided can vary in alternative embodiments. Each of the four loops 7262 includes a smaller sub-loop 7264 at its point farthest from the main body 7266. Together, each loop 7262 and sub-loop 7264 form one larger interrupted loop of material. This particular configuration can help when crimping or otherwise bending the atrial portion 7160, as the interruption in the larger loop can make it more flexible. The atrial portion 7260 has an axial configuration resembling that illustrated in FIG. 100A.

Figure 115:
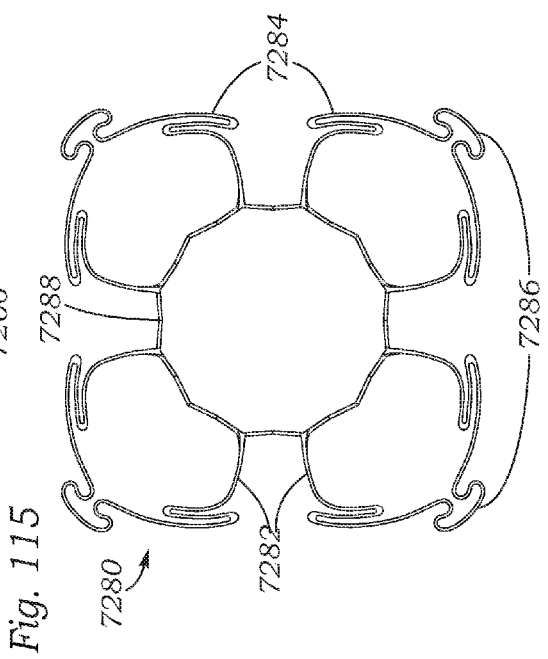

FIG. 115 shows an exemplary atrial portion 7280 having a radial configuration comprising four loops 7282 extending radially away from a main body 7288. Each of the four loops 7282 includes a secondary loop 7284 at its point farthest from the main body 7288, and each secondary loop 7284 includes a tertiary loop 7286 at its point farthest from the main body 7288. Together, each loop 7282, secondary loop 7284, and tertiary loop 7286 form one larger interrupted loop of material. In the illustrated configuration, the secondary loops 7284 have a first radial dimension which is smaller than their corresponding first angular dimension. Also as illustrated, the tertiary loops have a second radial dimension that is smaller than their corresponding second angular dimension, wherein the first radial dimension is smaller than the second radial dimension and the first angular dimension is larger than the second angular dimension. This configuration can help when crimping or otherwise bending atrial portion 7180, as the interruptions in the loop can make it more flexible. The atrial portion 7280 has an axial configuration resembling that illustrated in FIG. 100A.

Figure 116A:
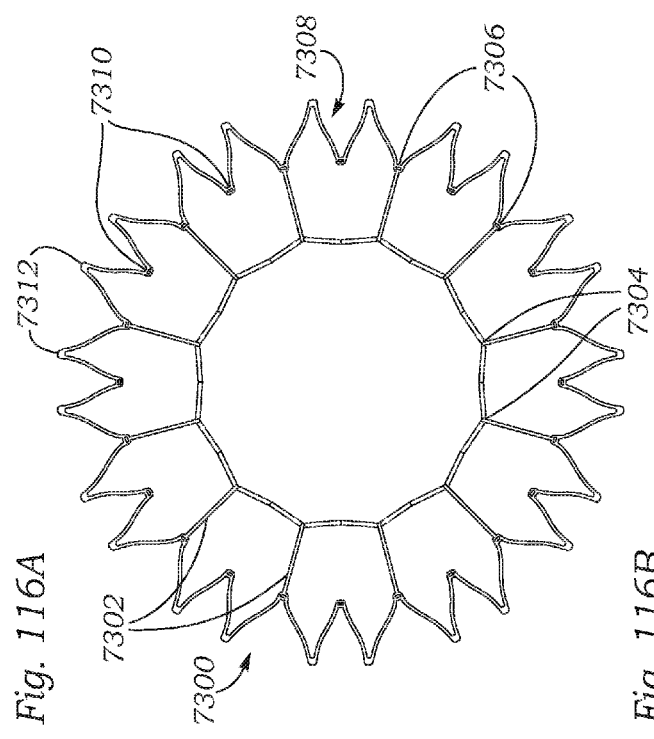
Figure 116B:
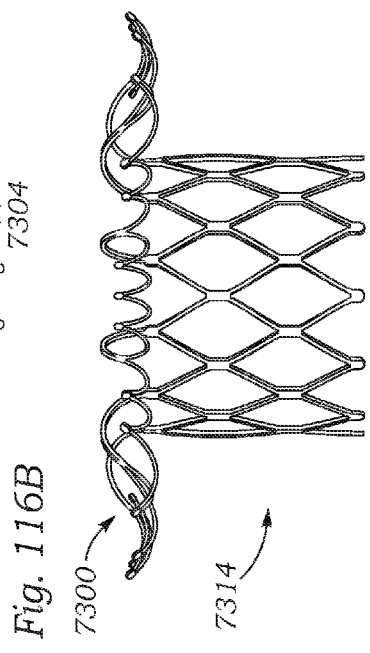

FIGS. 116A-116B show an exemplary atrial portion 7300 having a radial configuration comprising twelve arms 7302, each connected at an originating end 7304 to a main body 7314, extending radially outward from the main body 7314, and connecting at a terminal end 7306 to an inward pointing apex 7310 of an annular circumferential portion 7308 having a zig-zag configuration. The zig-zag portion 7308 extends around the main body 7314 and can comprise two or more zig-zags for each arm. For example, the illustrated zig-zag portion includes twenty four outward pointing apexes 7312 pointing radially outward from the main body 7314 and twenty four inward pointing apexes 7310 pointing radially inward toward the main body 7314. Because each of the arms 7302 is connected via the zig-zag portion 7308 to each of its neighbors, this configuration exhibits higher circumferential dependence than configurations having independent arms. The atrial portion 7300 has an axial configuration in which the arms 7302 extend atrially away from their originating ends 7304 at the main body 7314, and then curl radially and ventricularly. The zig-zag portion 7308 curls radially and atrially so that it extends both radially and atrially away from the arms 7302.

Figure 117A:
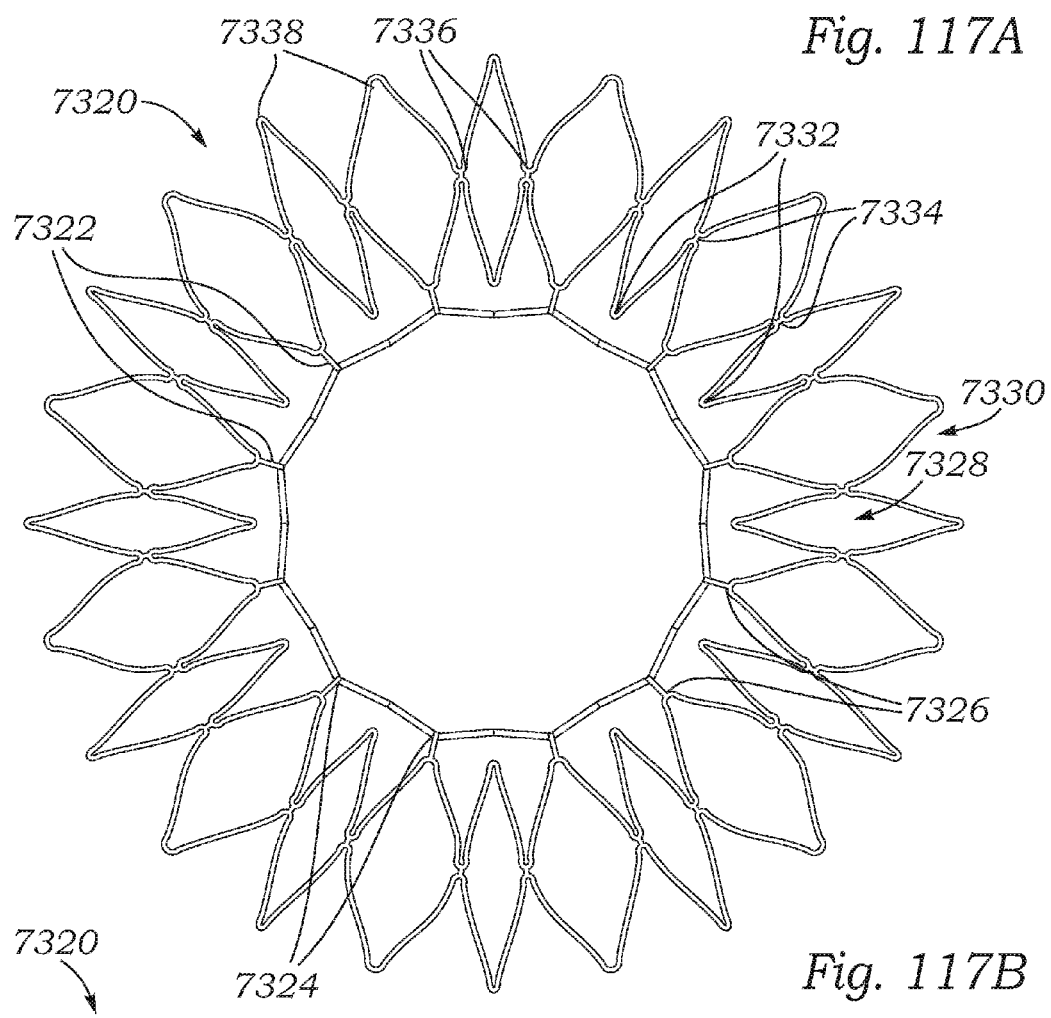
Figure 117B:
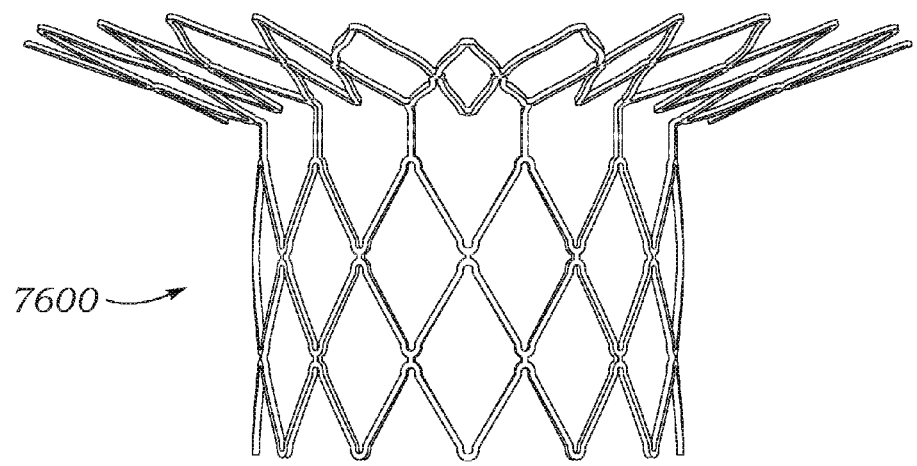

FIGS. 117A-117B show an exemplary atrial portion 7320 having a radial configuration comprising twelve arms 7322, each connected at an originating end 7324 to a main body 7600, extending radially outward from the main body 7600, and connecting at a terminal end 7326 to an inward pointing apex 7332 of a first circumferential zig-zag portion 7328. The first zig-zag portion 7328 extends around the main body 7600 and includes 24 outward pointing apexes 7334 pointing radially outward from the main body 7600 and 24 inward pointing apexes 7332 pointing radially inward toward the main body 7600. Atrial portion 7320 further includes a second zig-zag portion 7330 extending around the first and including 24 outward pointing apexes 7338 and 24 inward pointing apexes 7336. Each of the inward pointing apexes 7336 of the second zig-zag portion 7330 is connected to one of the outward pointing apexes 7334 of the first zig-zag portion 7328. Due to the second zig-zag portion 7330, atrial portion 7320 has greater axial and radial stiffness and greater circumferential dependence than atrial portion 7300. The atrial portion 7320 has an axial configuration resembling that illustrated in FIG. 100A.

Figure 118:
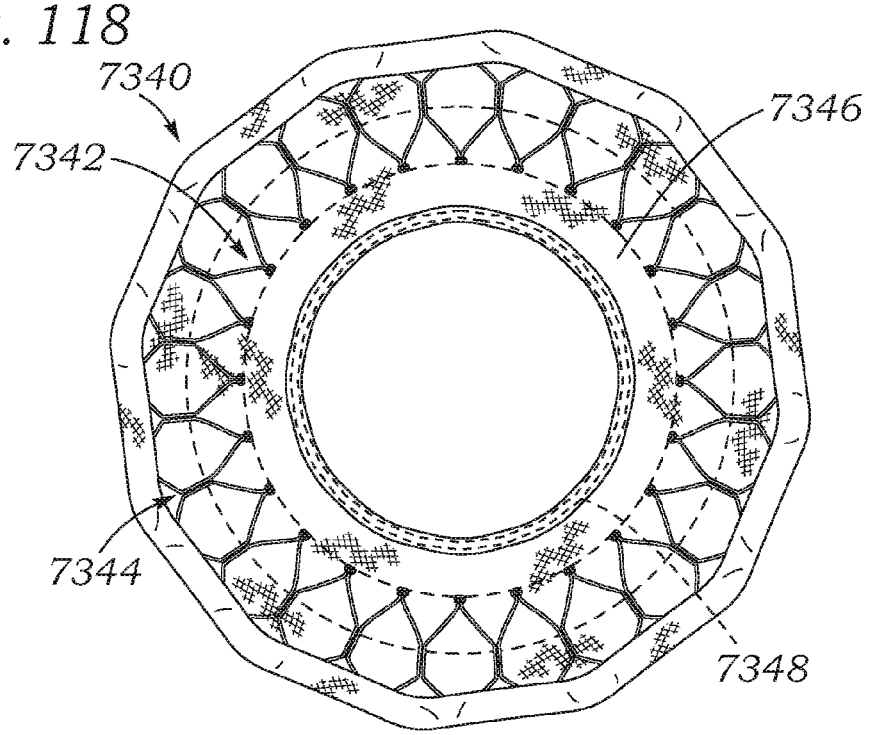

FIG. 118 shows an exemplary atrial portion 7340 having a radial configuration similar to that of atrial portion 7320. The atrial portion 7340 has an axial configuration which resembles that illustrated in FIG. 100E. Atrial portion 7340 does not include the arms present in atrial portion 7320 and thus the inner zig-zag portion 7342 and the outer zig-zag portion 7344 are only connected to the main body portion 7348 via the fabric 7346. Because the zig-zag portions are only connected to the main body portion 7348 by the fabric 7346, the atrial portion 7340 has low axial stiffness.

FIGS. 119A-119B show an exemplary atrial portion 7360 having a radial configuration comprising a single portion of material 7362 forming a series of loops around the main body 7366. As illustrated, these loops may overlap each other in some places but not in other places as they wind around the main body 7366. The connection of atrial portion 7360 to the main body 7366 can be at a location displaced from the atrial end of the main body 7366, and the connection can be made by sutures 7364, as shown. Atrial portion 7360 has high circumferential dependence, low axial stiffness due to its connection to the main body 7366, and low radial stiffness because a radial force exerted against the portion of material 7362 causes bending of the loops of the material 7362. The atrial portion 7360 has an axial configuration resembling that illustrated in FIG. 100A, except that the point of connection between the atrial portion 7360 and the main body 7366 is at a point which is ventricularly displaced from the atrial end of the main body 7366.

Figure 120:
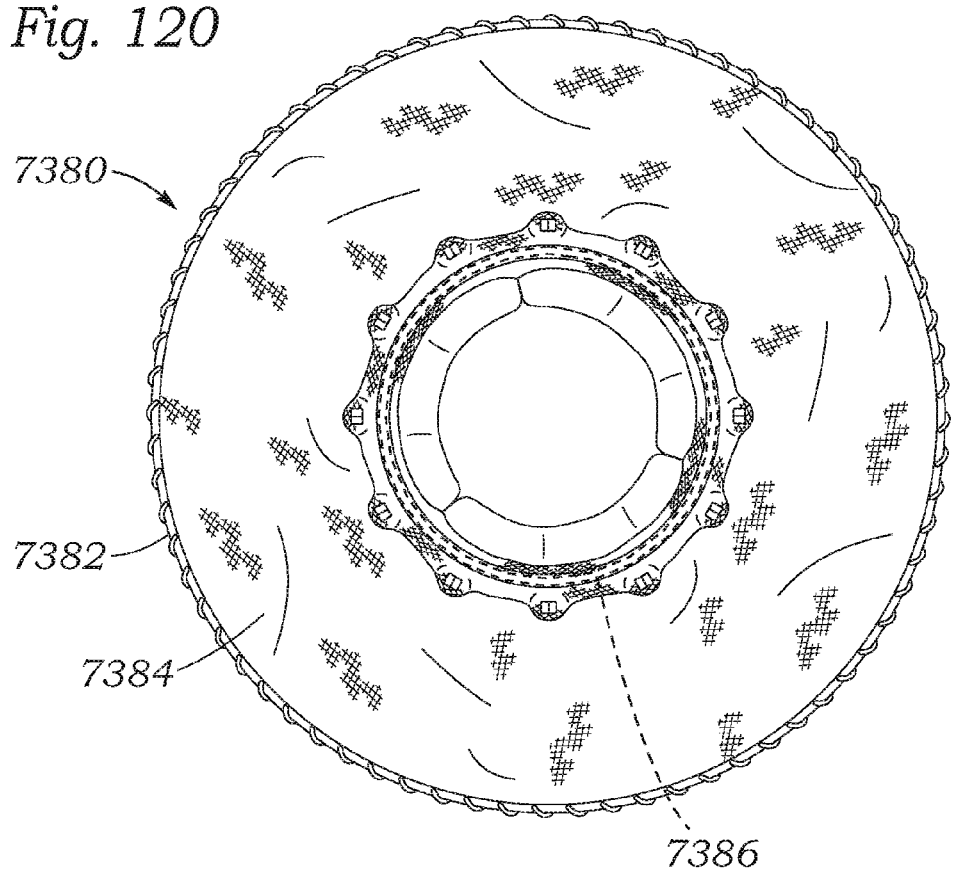

FIG. 120 shows an exemplary atrial portion 7380 having a radial configuration comprising a single ring of material 7382 extending around a main body 7386, and thus has an axial configuration resembling that illustrated in FIG. 100F. The single ring of material 7382 is not connected to the main body 7386 except via the fabric 7384. Atrial portion 7380 has high circumferential dependence, low radial stiffness because a radial force exerted against the ring 7382 causes the ring 7382 to shift radially and/or collapse, and low axial stiffness because material 7382 can move independently of the main body 7386.

FIG. 121 shows an exemplary atrial portion 7400 having a radial configuration similar to that of atrial portion 7100 except that it includes only twelve arms 7402 forming six pairs of arms, each pair forming a single loop 7406. In other embodiments, not illustrated, any number of pairs of arms could be used. Atrial portion 7400 has spaces 7404 between adjacent pairs of arms which can be used to accommodate various features of a patient's mitral valve anatomy. As one example, atrial portion 7400 could be implanted such that the aortic valve structure is positioned in one of the spaces 7404.

FIG. 122 shows an exemplary atrial portion 7420 having a radial configuration similar to that of atrial portion 7400 except that each of the loops 7424 formed by the pairs of arms 7422 is larger and wider than those in atrial portion 7400. Though not shown in FIG. 122, the loops 7424 can be sized such that neighboring loops 7424 are in contact with one another.

Figure 123A:
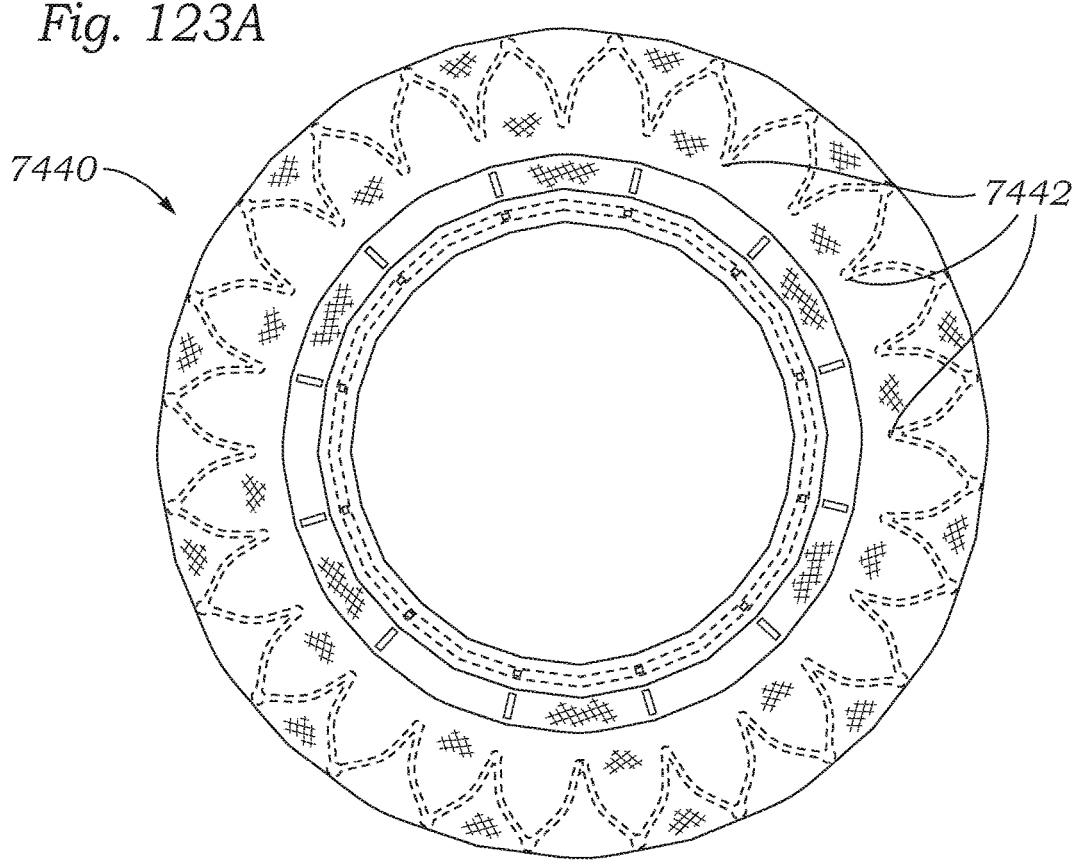
Figure 123B:
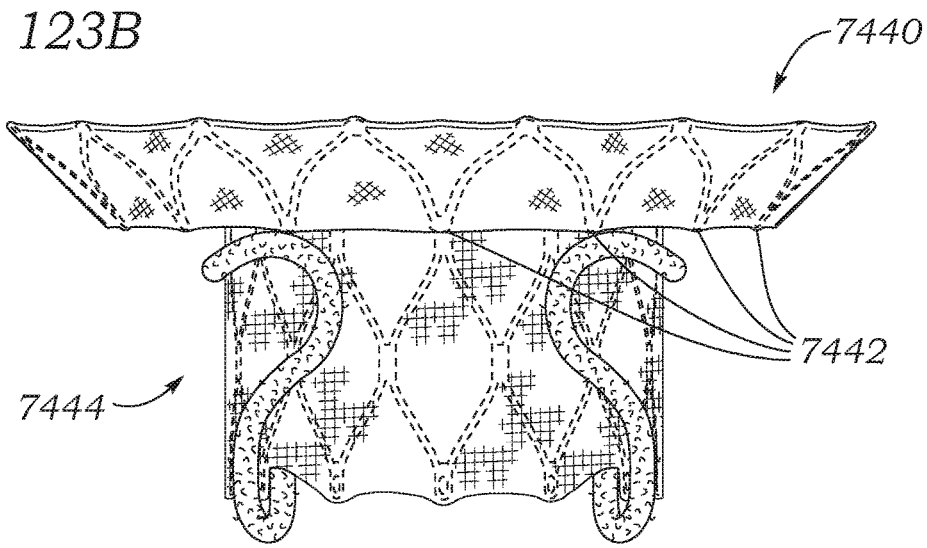

FIGS. 123A-123B show an exemplary atrial portion 7440 which is similar to atrial portion 7300 except that it has an axial configuration resembling that illustrated in FIG. 100D: the inward pointing apexes 7442 point in toward the main body 7444 but also at a slight angle in the direction of the ventricular end 130 of the main body 7444.

FIGS. 124A-124B show an exemplary atrial portion 7460 which is similar to atrial portion 7300 except that it has an axial configuration resembling that illustrated in FIG. 100C: the atrial portion curls ventricularly and radially inwardly such that the apexes 7462 point back toward the main body 7468.

FIGS. 125A-125B show an exemplary atrial portion 7480 which is similar to atrial portion 7460 except that it is not connected to the main body 7482 at its atrial end. Rather, atrial portion 7480 is connected to the main body 7482 at a point displaced from the atrial end toward the ventricular end of the main body 7482.

Figure 128:
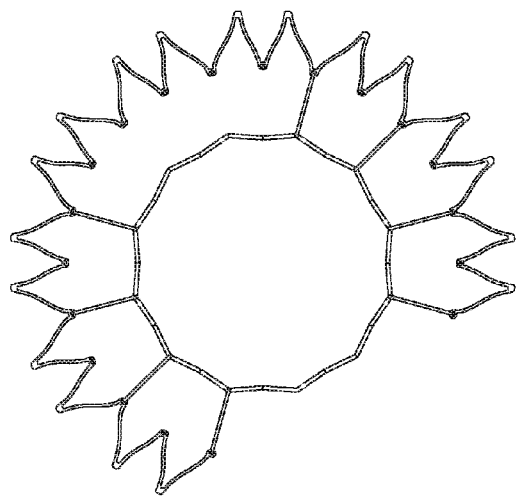
FIGS. 126-130 show additional atrial portions of prosthetic devices having asymmetrical radial configurations.
Figure 130:
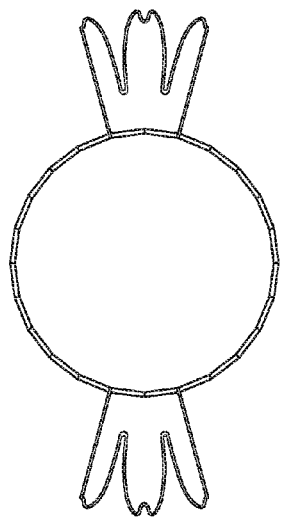
Figure 126:
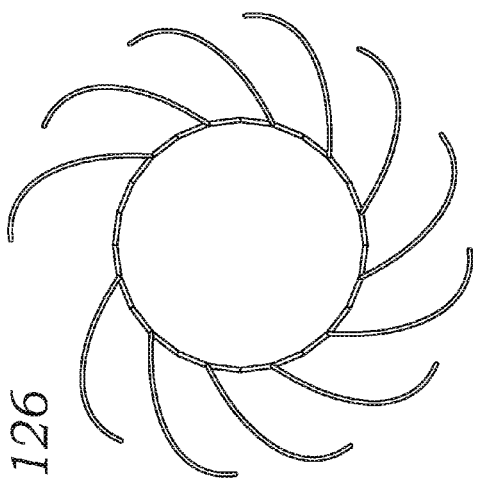
Figure 127:
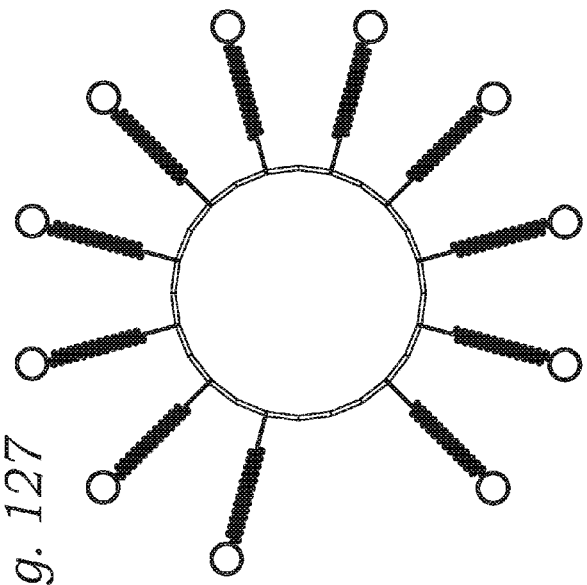
Figure 129:
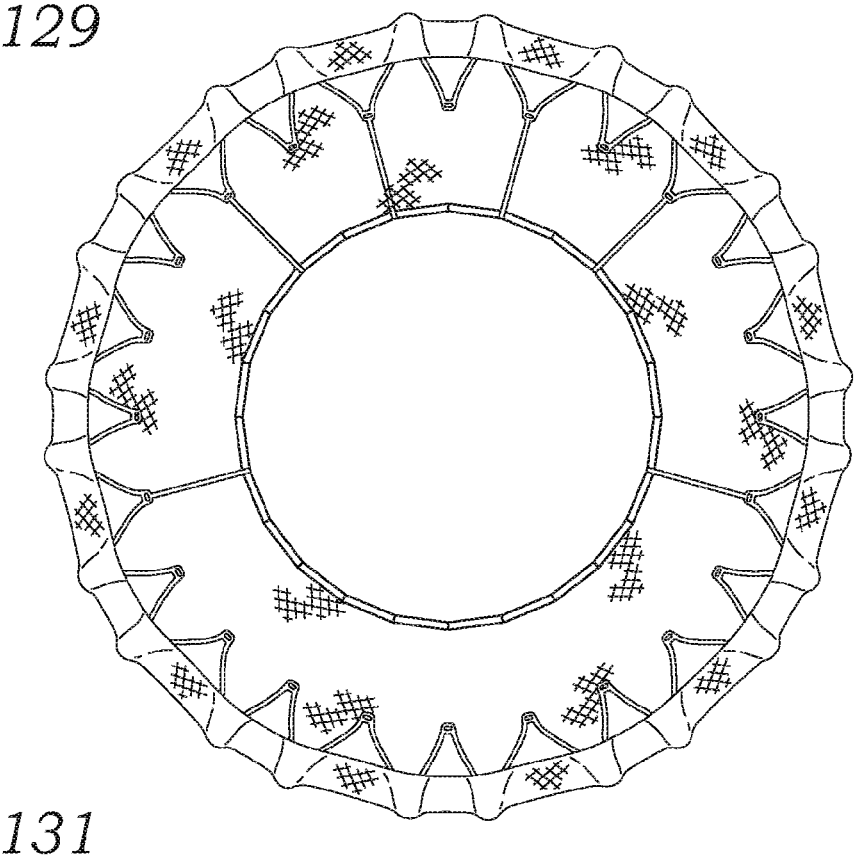

Any of the radial configurations described above may be modified to accommodate the anatomy of the mitral valve region of a patient. FIGS. 112 and 126-130 illustrate examples of atrial portions modified for this purpose. FIG. 126 illustrates atrial portion 7140 with one of the twelve arms 7142 removed. FIG. 127 illustrates atrial portion 7200 with one of the twelve arms 7202 removed. FIG. 128 illustrates atrial portion 7300 with two arms 7302 removed from one side, and two arms 7302 and a segment of the zig-zag portion 7308 removed from the opposite side. FIG. 129 illustrates atrial portion 7300 with six of the twelve arms 7302 removed. FIG. 130 illustrates atrial portion 7460 with eight of the twelve arms 7464 and two sections of the zig-zag portion 7466 removed. As one example of a use of this technique, an arm or other portion of an atrial portion expected to be oriented in the direction of the aortic valve 14 after implantation of the prosthetic valve can be removed, thereby allowing additional space for and relieving pressure against this anatomical feature. Similarly, these modifications can be used to change the stiffness or circumferential dependence of the configuration.

Figure 131:
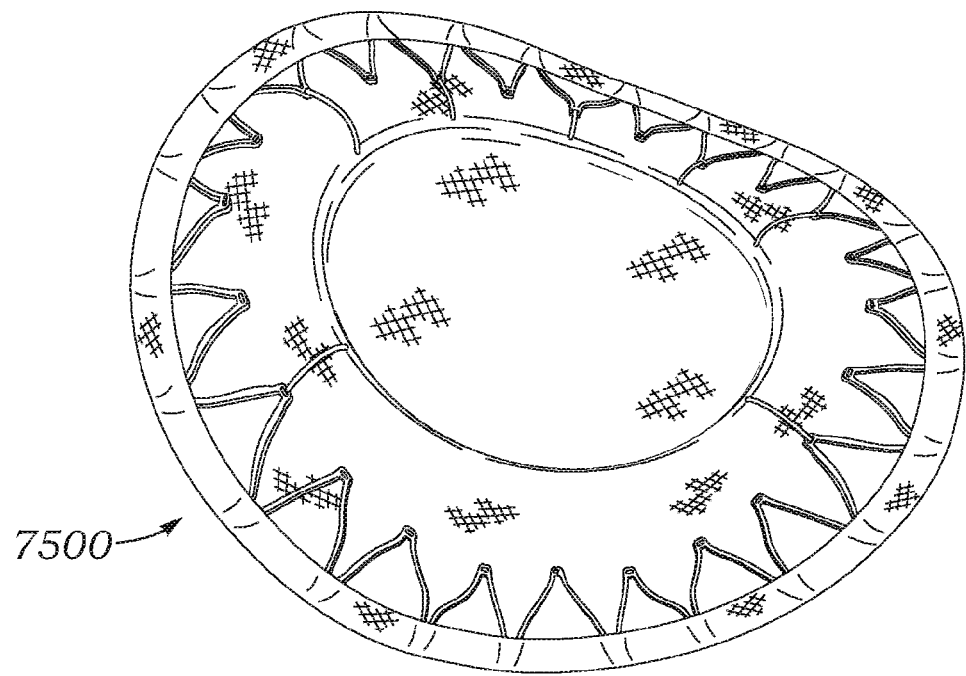
FIG. 131 shows an additional atrial portion of a prosthetic device having a generally saddle shaped configuration.

Similarly, the configuration of any of the atrial portions described above can be further varied in three dimensions. The axial position of the atrial body can be dependent on the angular and/or radial position about the longitudinal axis. As one example, an atrial portion can include a saddle shape to accommodate the natural shape of the annulus of the mitral valve. Such a configuration is shown in FIG. 131, illustrating atrial portion 7500, which is similar to atrial portion 7300 except that it is generally saddle shaped. Further, any of the atrial portions described above can be varied such that its shape in plan view is not a circle or even substantially circular. As one example, any of the atrial portions described above can be generally kidney shaped to accommodate the natural shape of the annulus of the native mitral valve.

Figure 132A:
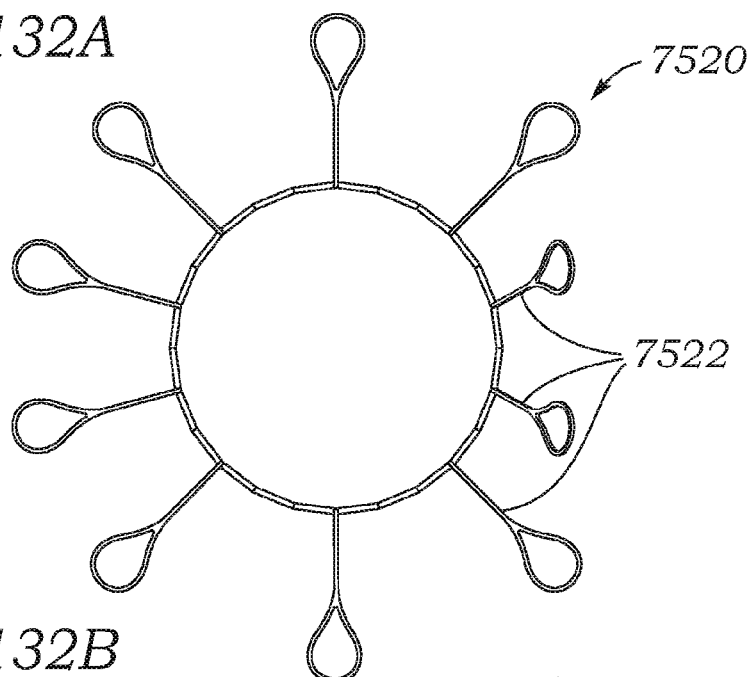
FIGS. 132A-132C show another atrial portion of a prosthetic device.
Figure 132B:
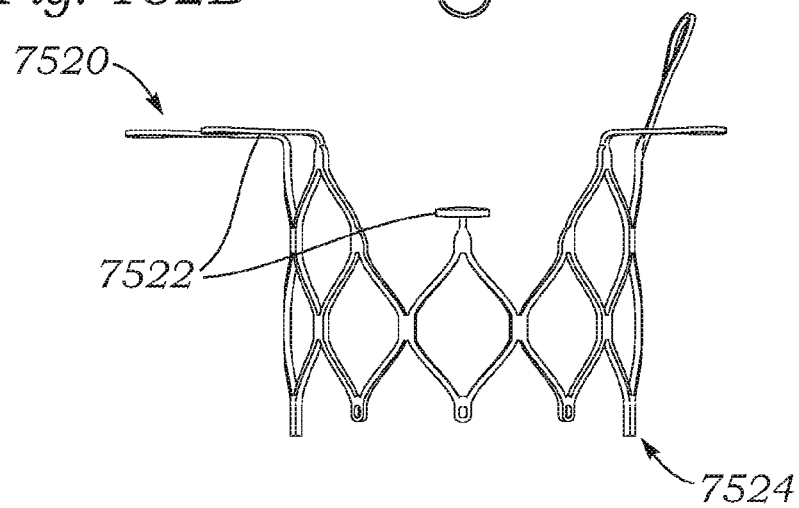
Figure 132C:
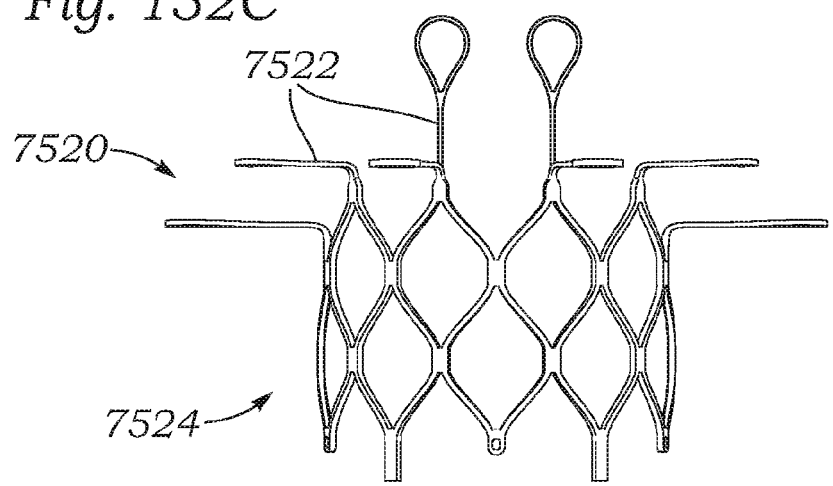

FIGS. 132A-132C show an exemplary atrial portion 7520 having a radial configuration similar to that of atrial portion 7020. The illustrated atrial portion 7520 comprises ten arms 7522. The atrial portion 7520 has an axial configuration in which some of the arms 7522 are attached to the main body 7524 at the atrial end of the main body 7524, while other arms are attached to the main body 7524 at a location ventricularly displaced from the atrial end of the main body 7524. Additionally, some of the arms 7522 extend radially away from the main body 7524 while others extend both radially and ventricularly away from the main body 7524.

Figure 133B:
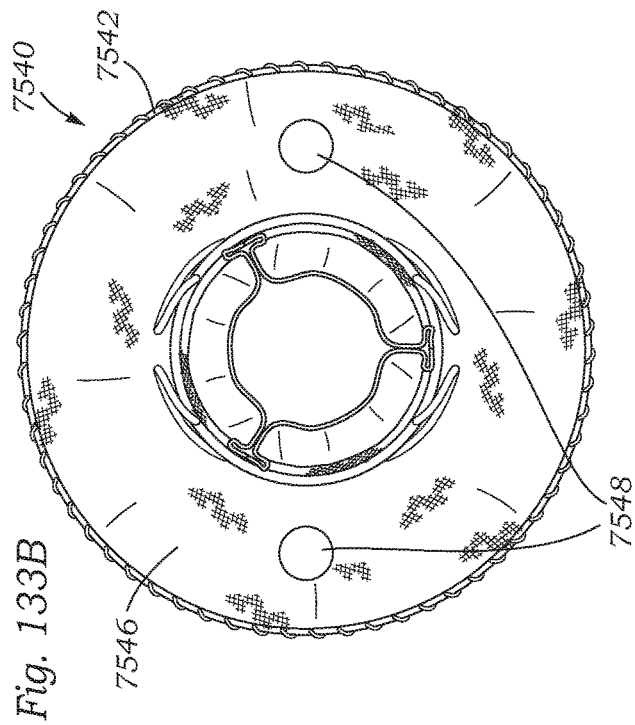
FIGS. 133A-133C show another atrial portion of a prosthetic device having holes.
Figure 133C:
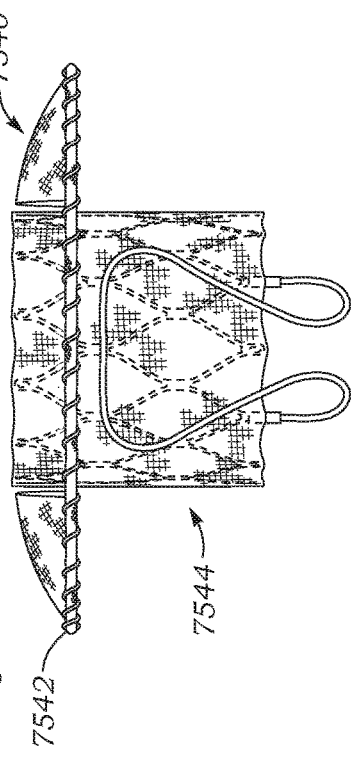
Figure 133A:
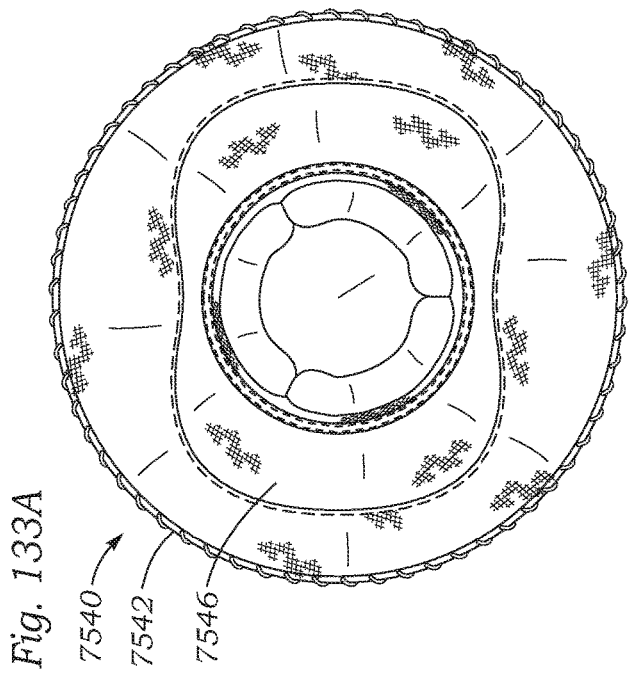

FIGS. 133A-133C show top, bottom, and side views, respectively, of an exemplary atrial portion 7540 having a radial configuration similar to that of atrial portion 7380. Atrial portion 7540 comprises a single portion of material 7542 encircling the main body 7544, and coupled to the main body 7544 by a fabric 7546. The fabric 7546 comprises two bypass holes 7548 which can allow blood to flow more rapidly through the fabric in either direction, thus reducing pressure exerted against the fabric. Of particular importance is the ability of the bypass holes to reduce the systolic pressure exerted against the fabric by allowing some blood to flow from the left ventricle to the left atrium through the holes when the prosthetic valve is initially implanted. If too high, the systolic pressure can cause separation of the atrial portion from the native tissue, thereby preventing sustainable tissue in-growth. Thus, by allowing some blood to flow through the atrial portion 7540 and thereby reducing the systolic pressure against the atrial portion 7540, the bypass holes 7548 can promote tissue in-growth, particularly in the regions of the commissures 36. In some embodiments, once sustainable tissue in-growth has occurred, the patient can undergo a follow-up procedure in which the bypass holes are sealed, thereby further reducing mitral regurgitation.

Figure 134:
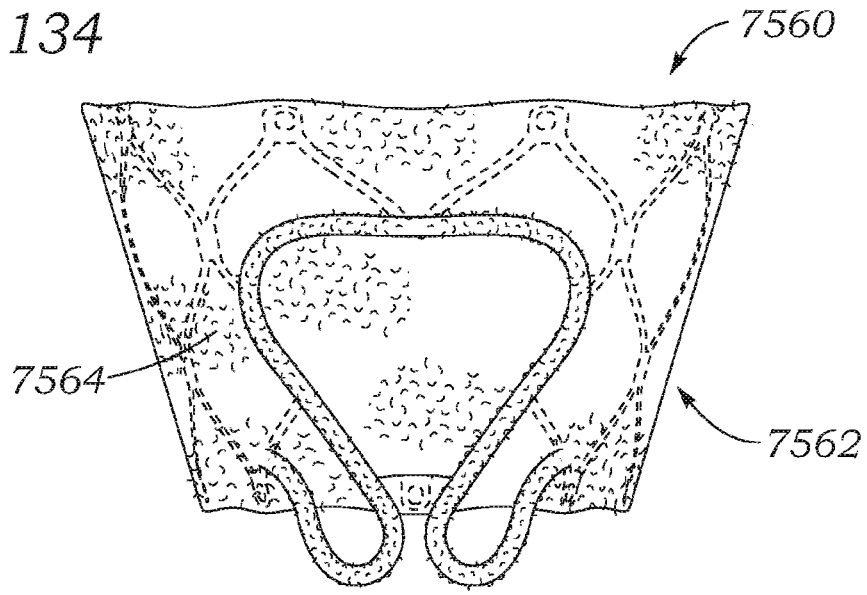
FIG. 134 shows a prosthetic device having a generally frustoconical main body.

FIG. 134 shows an exemplary prosthetic valve 7560 having a main body 7562 which has a generally frustoconical shape which tapers from a first diameter near the atrial end of the main body 7562 to a relatively smaller diameter near the ventricular end of the main body 7562. The tapered shape of the main body 7562 can help the valve 7560 conform to the shape of the native mitral valve, thereby providing a greater surface area of contact between the prosthetic valve and the native tissue and thus can help to improve sealing, tissue in-growth, and stability of the device when implanted. The tapered shape of the main body 7562 can also help to improve coaptation of edges of leaflets provided within the prosthetic valve 7560. Providing a valve having a smaller ventricular end can also help to reduce interference between the valve 7560 and the chordae 16 or papillary muscles 22, 24.

Valve 7560 includes a flexible fabric 7564 extending from the atrial end to the ventricular end of the main body 7562. The fabric 7564 can help the valve 7560 conform to the shape of native tissues, thereby further improving sealing and tissue in-growth, and reducing trauma to the native tissue. The flexible fabric 7564 can comprise various biocompatible materials, such as, for example, an elastic material such as spandex or a non-elastomeric fabric, such as PET. In another embodiment, an alternative valve can have a generally frustoconical shape resembling that of valve 7560, and the atrial end of the alternative valve can be provided with a relatively flat edge such that the shape of the atrial end is non-circular. One advantage of this configuration is that the relatively flat edge of the alternative valve can help to accommodate a patient's mitral valve anatomy and thus can improve stability of the device when implanted.

Figure 135:
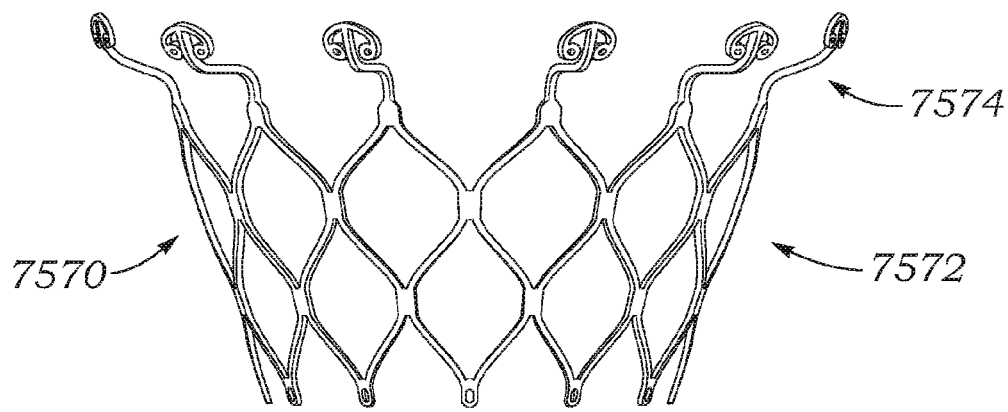
FIG. 135 shows a frame of a prosthetic device having a generally frustoconical main body.

FIG. 135 shows an exemplary frame 7570 for use in a prosthetic valve and having a main body 7572 and an atrial portion 7574. The main body 7572 has a configuration generally resembling the frustoconical shape of the main body 7562, and the atrial portion 7574 has a configuration similar to that of the atrial portion 7040. The frame 7570 can be enclosed in a flexible fabric (not shown) extending from the periphery of the atrial portion 7574 to the ventricular end of the main body 7572, which can help improve sealing and tissue in-growth, and reduce trauma to the native tissue. In another embodiment, an alternative frame can have a generally frustoconical shape resembling that of frame 7570, and the atrial end of the alternative frame can be provided with a relatively flat edge such that the shape of the atrial end is non-circular. One advantage of this configuration is that the relatively flat edge of the alternative frame can help to accommodate a patient's mitral valve anatomy and thus can improve stability of the device when implanted.

Figure 136:
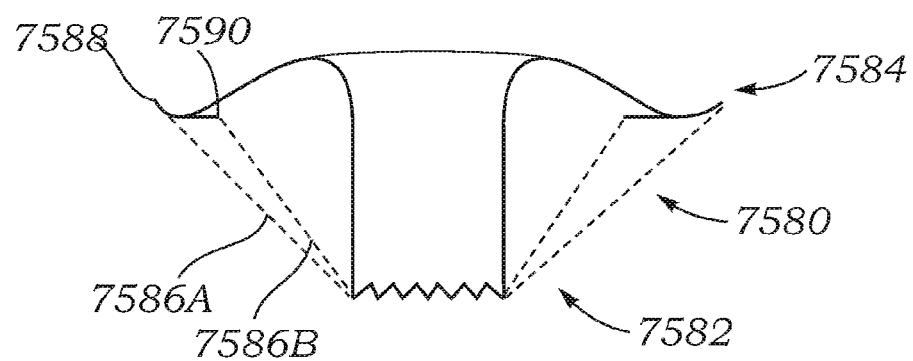
FIG. 136 shows another prosthetic device having two fabrics spanning between the atrial portion and the ventricular end of the main body.

FIG. 136 shows an exemplary frame 7580 of a prosthetic valve having a main body 7582 and an atrial portion 7584 which has a configuration similar to that of atrial portion 7440. Similar to atrial portion 7440, atrial portion 7584 comprises an outer ring of zig-zag struts having a plurality of inwardly pointed apices 7590 and outwardly pointed apices 7588. Frame 7580 includes a first flexible frustoconical fabric cover 7586A extending from the outwardly pointed apices 7588 on the atrial portion 7584 to the ventricular end of the main body 7582. The frame 7580 also includes a second flexible frustoconical fabric cover 7586B extending from the inwardly pointed apices 7590 to the ventricular end of the main body 7582. The two layers of fabric 7586 can help the frame 7580 conform to the shape of native tissues, thereby improving sealing and tissue in-growth, and reducing trauma to the native tissue. The two layers of flexible fabric 7586 can comprise various biocompatible materials, such as, for example, an elastic material such as spandex.

Figure 137A:
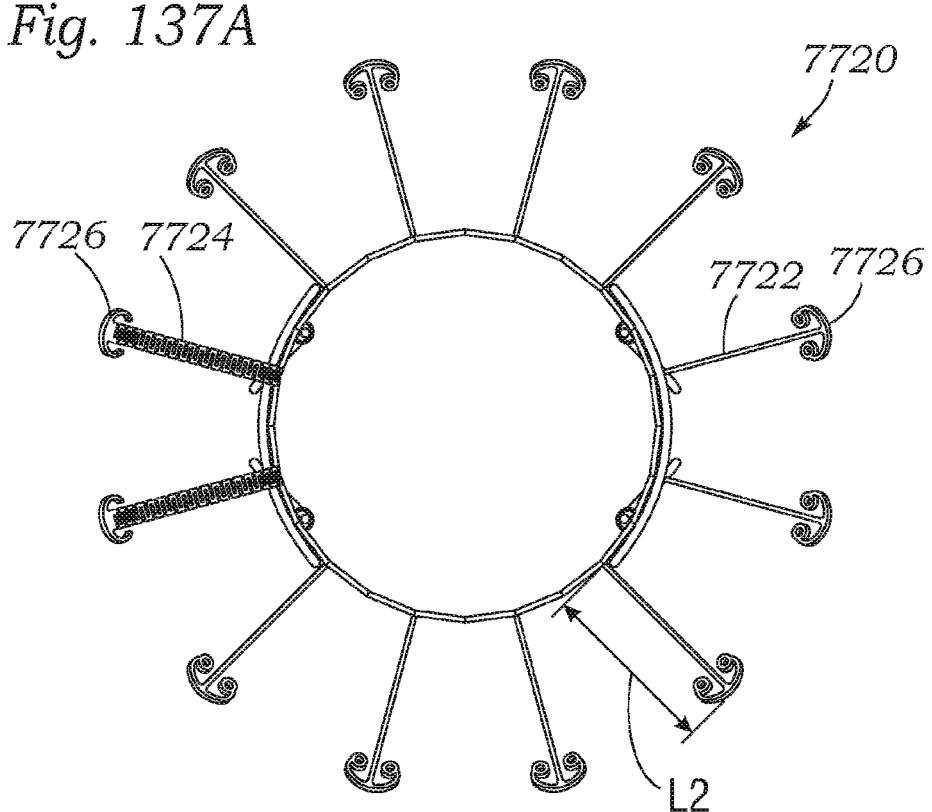
FIGS. 137A-137B show an exemplary frame having another exemplary atrial portion.
Figure 137B:
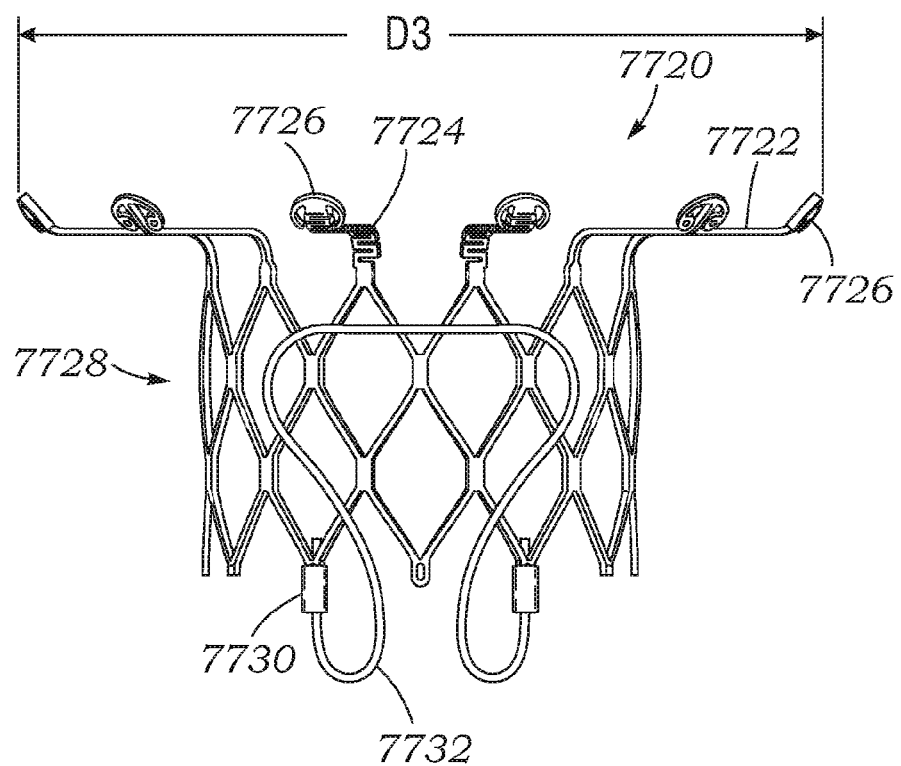

FIGS. 137A-137B show top and side views, respectively, of another exemplary atrial portion 7720 of a frame for use in a prosthetic valve. More specifically, atrial portion 7720 comprises ten relatively stiff (relative to arms 7724), radially extending arms 7722, each having the same configuration as the arms 7042 of FIGS. 102A-102B (including the horseshoe-shaped elements 7726). Atrial portion 7720 also includes two relatively flexible (relative to arms 7722) radially extending arms 7724, each having the same configuration as the arms 7162 of FIG. 108 (including the horseshoe-shaped elements 7726). As used with regard to FIGS. 137A-137B, stiffness can refer to radial, axial, and/or circumferential stiffness, as those terms were defined above. In the embodiment shown in FIGS. 137A-137B, the two arms 7724 can comprise a generally zig-zag, serpentine, or similar configuration, or can have a small cross sectional profile as compared to the cross sectional profile of arms 7722, to effect the relative flexibility. FIGS. 137A-137B also show that the radial end portions of the arms 7722 and 7724 (including the respective horseshoe-shaped elements 7726) can curve atrially away from a main body 7728 of the frame, and that the main body 7728 of the frame can be coupled to at least one ventricular anchor 7732 by a cylindrical coupling element 7730 similar to sleeves 1506, 1606. In some cases, the atrial portion 7720 can have a diameter D3 between about 40 mm and 70 mm, with 55 mm being one exemplary suitable diameter for the atrial portion. In some cases, the arms 7722 and/or 7724 can have a length L2 between about 5 mm and 25 mm, with 13 mm being one exemplary suitable length for the arms.

Figure 138:
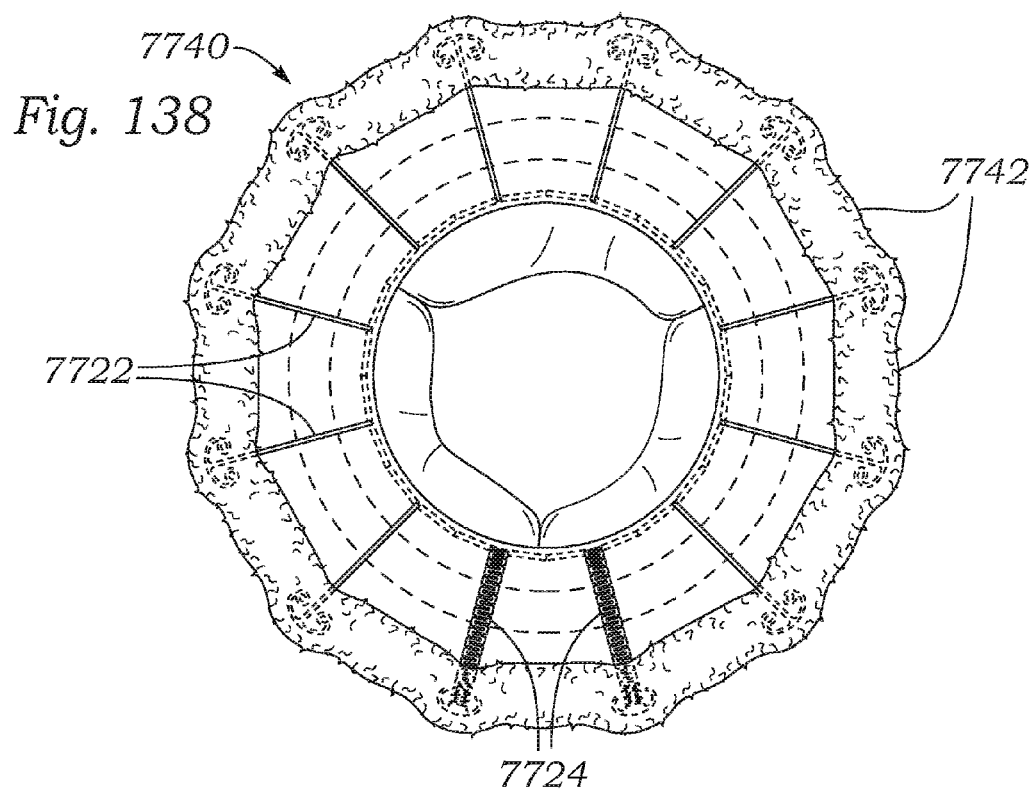
FIG. 138 shows another exemplary prosthetic device.
Figure 139:
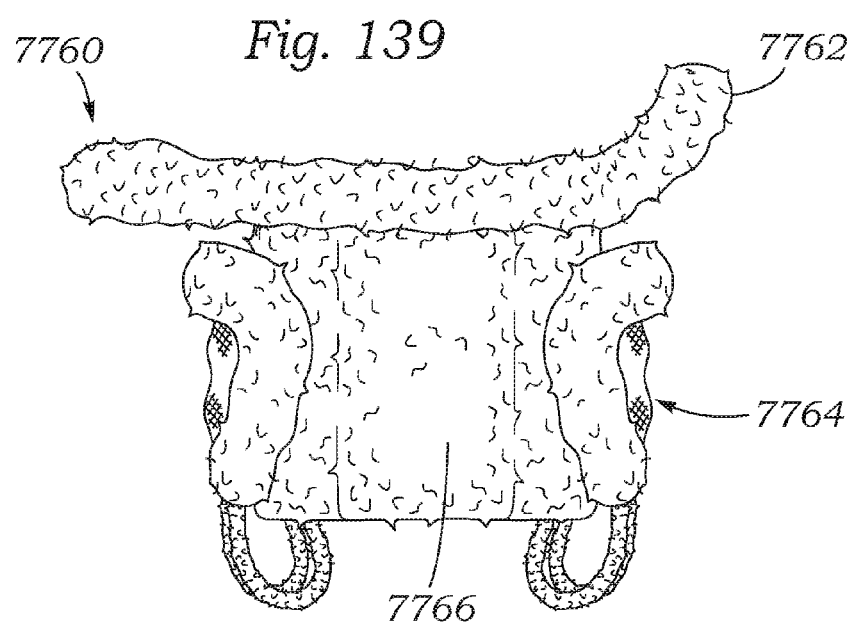
FIG. 139 shows another exemplary prosthetic device.

FIG. 138 shows a top view of a prosthetic valve 7740 including a frame having an atrial portion resembling that of FIGS. 137A-137B. FIG. 138 shows that the frame can be covered in a fabric 7742 (e.g., as described elsewhere in this application). FIG. 139 shows a prosthetic valve 7760 having a configuration similar to that of prosthetic valve 7740. Prosthetic valve 7760 can have an atrial portion including an atrially curved portion 7762 which curls atrially away from a main body 7764 of the prosthetic valve 7760. In some cases, the atrially curved portion 7762 can include two relatively flexible radially-extending arms (such as arms 7724 or any arm having properties effecting a relative flexibility, as described elsewhere herein (e.g., arms having serpentine shapes as shown in FIGS. 109A-109E and described in the corresponding text of this application, or coiled configurations, as shown in FIGS. 112-113 and described in the corresponding text of this application)) covered in a fabric 7766. In some cases, the atrially curved portion 7762 can include only two such arms covered in a fabric, although the curved portion 7762 can include a larger or a smaller number of relatively flexible radially-extending arms.

Any of the embodiments shown in FIGS. 137A-139 can be modified in various ways, e.g., by including additional or fewer arms (e.g., including one or three or more relatively flexible arms or including eleven or more, or nine or fewer, relatively stiff arms), or by incorporating any other features as described herein. Further, the atrial portions illustrated in FIGS. 137A-139 can have an overall circular shape, as shown in FIG. 138, or can have arms having variable lengths and therefore can have alternative shapes such as an oval shape, an elliptical shape, a D shape, or a kidney shape. Such alternative shapes can be used in some cases to better conform to the anatomy of the left atrium. For example, the lengths of the arms can be varied such that the ends of each of the arms are in contact with the walls of the left atrium when the prosthetic valve is implanted within a native mitral valve.

The embodiments illustrated in FIGS. 137A-139 can provide certain advantages. For example, when a prosthetic valve is implanted within a native mitral valve, the atrial portion of the prosthetic valve (e.g., one of those shown in FIGS. 137A-139 can be oriented such that the relatively flexible arms, or the atrially curved portion 7762, or both, are positioned adjacent to the aortic sinus within the left atrium (i.e., at the A2 position by Carpentier nomenclature), thereby reducing trauma to the native tissue in this region of the left atrium, reducing pressure exerted against the aortic sinus, and reducing the chance of abrasion and/or perforation of the aortic sinus by the arms. In some cases, the atrial portions shown in FIGS. 137A-139 can have relatively flexible arms at both the A2 and the P2 positions, or can have various other arrangements of relatively stiff and relatively flexible arms.

Any of the various atrial portions described above can be fitted with any one of various biocompatible fabrics, which can span the open spaces between arms or other components of the configurations described. Several examples of suitable fabric material are described above, and include synthetic materials such as PET and biological materials such as bovine pericardium. Fabric material can be selected based on the desired porosity, permeability to blood, or other relevant characteristics.

The atrial portions described above can be fabricated by a variety of methods, but in one exemplary method, they are laser cut from a single tube of metallic material (e.g., nitinol). In other embodiments, the various components (e.g., the several arms) may be fabricated separately and connected to other components later to form a single prosthetic unit. Similarly, any of the atrial portions can be attached to the main body of a prosthetic unit by various methods, including by being formed integrally (i.e., cut from the same piece of base material) or by being formed separately and connected later (e.g., by welding or tying with sutures).

Figure 140:
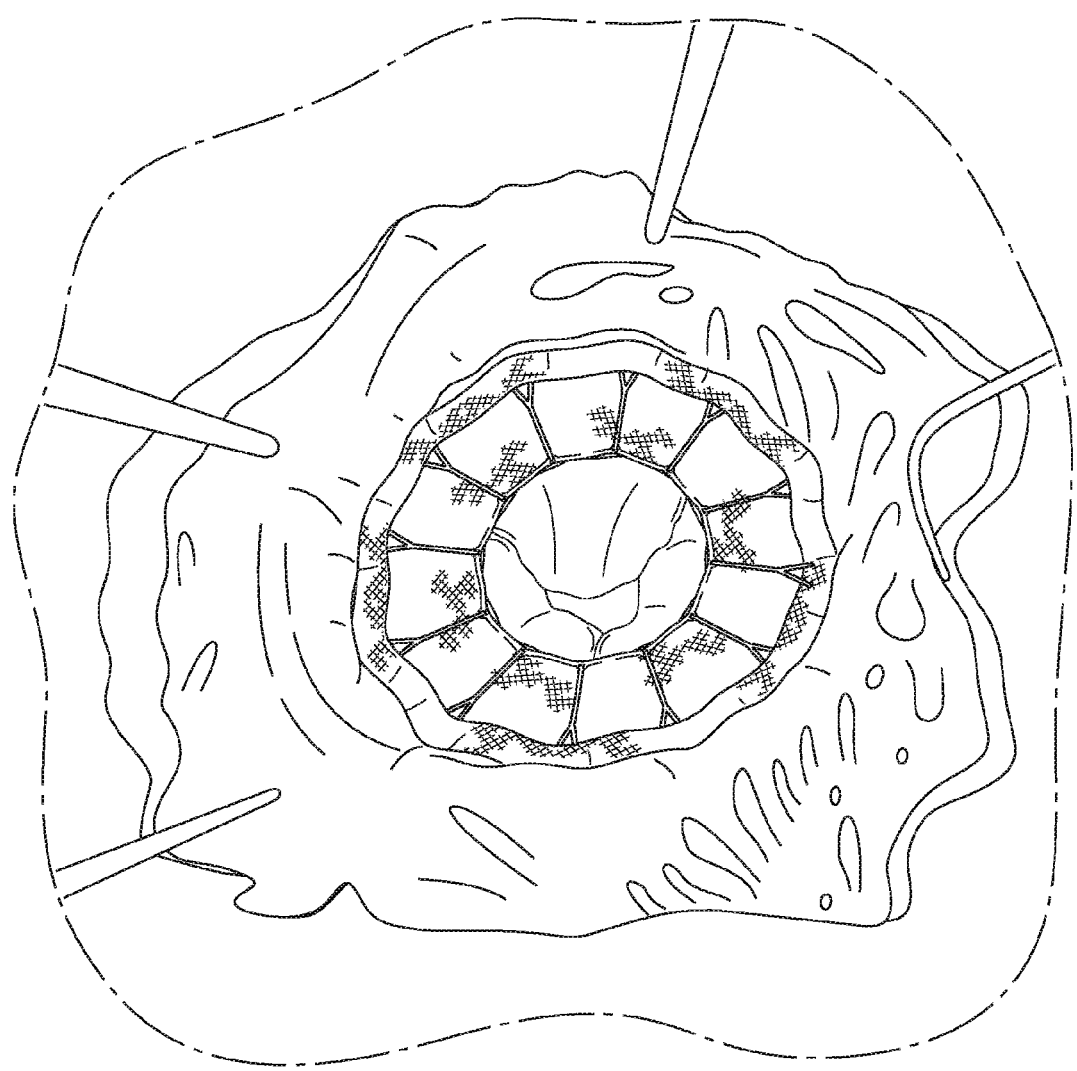
FIG. 140 shows a prosthetic device situated in native tissue.

Once a prosthetic valve has been implanted in the native mitral valve, as illustrated in FIG. 140, paravalvular leakage is initially prevented primarily by the pressure of the native mitral valve leaflets against the exterior of the prosthetic valve, which acts as a prosthetic spacer, such as with embodiment 3000 described above. Over time, however, tissue in-growth occurs and increases the occlusion of blood around the prosthetic valve by forming a solid barrier of biological tissue and prosthetic material, thus reducing the reliance on pressure between native leaflets and the prosthetic material.

Orientation of Prostheses in the Heart

Referring again to FIGS. 1-4, the native mitral valve 2 of the human heart has a very different structure than the other native heart valves, and includes an annulus portion 8, an anterior leaflet 10, a posterior leaflet 12, and chordae tendineae 16 which tether the leaflets 10 and 12 to the postero-medial and antero-lateral papillary muscles 22 and 24. As also noted above, the chordae 16 attach to the leaflets 10 and 12 in regions A1, A3, P1, and P3, leaving regions A2 and P2 relatively free of chordae attachment points. These anatomical features provide a desirable approach path for delivery of a prosthesis to the vicinity of the native mitral valve 2. Further, these anatomical features make it desirable to anchor a prosthesis in the A2 and P2 regions rather than the A1, A3, P1, or P3 regions, to reduce the chance of interference between the anchors of the prosthesis and the chordae 16.

While the overall structure of the heart is well known, the specific dimensions of the components of each human heart are sufficiently variable to make determining the exact orientation of an individual's mitral valve and the location of chordae and respective chordae attachment points difficult. Thus, it can be challenging to determine the proper orientation with which to introduce a prosthesis into the native mitral valve 2, and to determine the proper locations for anchoring the prosthesis. This problem is exacerbated by the fact that mitral valve prostheses are often delivered under fluoroscopy, which allows a physician to see the metallic components of the prosthesis, but not the soft tissue of the patient's heart (including the chordae 16).

Figure 89:
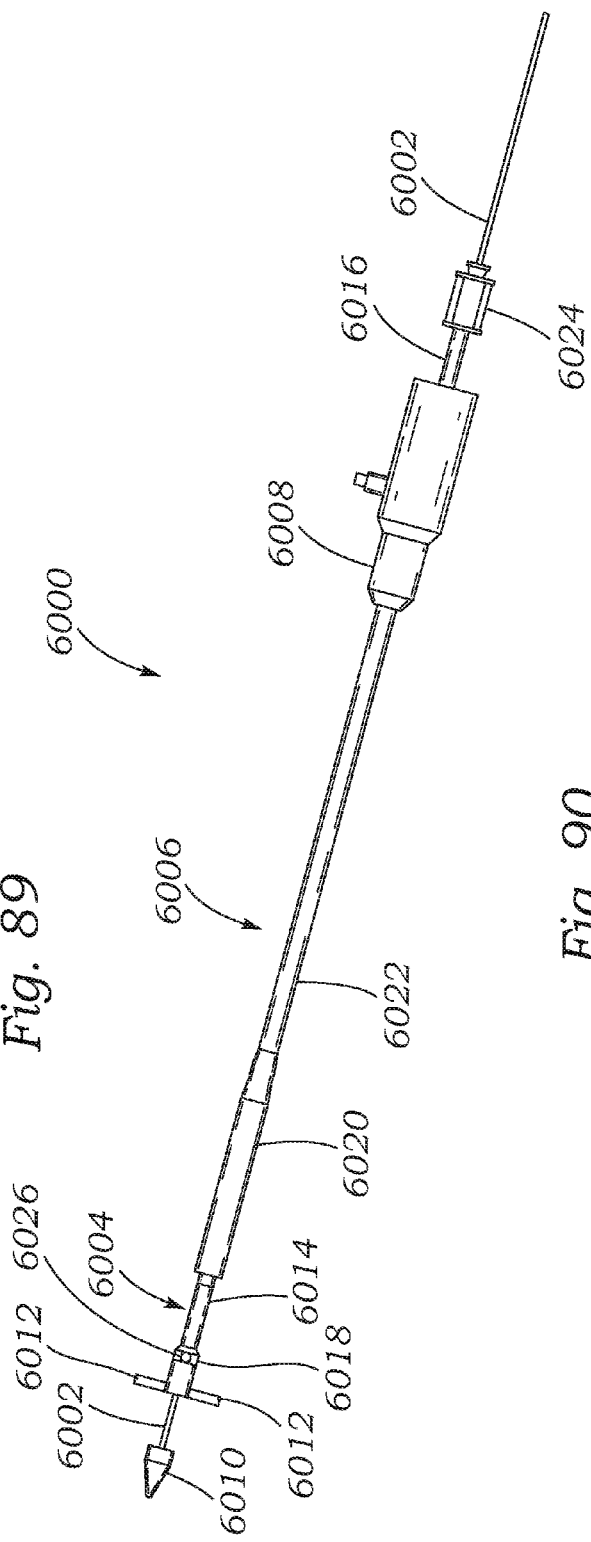
FIG. 89 shows an exemplary embodiment of an orientation device.

FIG. 89 illustrates a fluoroscopy orientation device 6000 which can be used to improve a physician's ability to orient a prosthesis on a desirable axis for delivery and anchoring. The device can be used in advance of the delivery of a mitral valve prosthesis (e.g., a prosthetic mitral valve) to increase the physician's ability to orient the prosthetic anchors in the A2 and P2 regions.

As illustrated in FIG. 89, the orientation device 6000 comprises a guidewire shaft 6002, an inner shaft 6004, an outer shaft 6006, and a handle 6008. Each of the shafts 6002, 6004, and 6006 comprises an elongate, tubular shape, and has an internal lumen within which other components can be positioned. The guidewire shaft 6002 includes an internal lumen through which a guidewire can be provided. The inner shaft 6004 comprises an internal lumen within which the guidewire shaft 6002 can be positioned, and the outer shaft 6006 comprises an internal lumen within which the inner shaft 6004 can be positioned.

A nosecone 6010 can be fastened to the distal end of the guidewire shaft 6002. The nosecone 6010 facilitates passage of the orientation device 6000 through a human body. The nosecone 6010 includes an internal lumen in communication with the guidewire lumen so that a guidewire provided through the guidewire shaft 6002 can continue through the nosecone 6010 and into the human body. The inner shaft 6004 comprises a distal portion 6014 and a proximal portion 6016. As illustrated, the distal portion 6014 of the inner shaft 6004 can comprise a non-metallic material, while the proximal portion 6016 of the inner shaft 6004 can comprise a metallic material. The outer shaft 6006 similarly comprises a distal portion 6020, which can comprise a non-metallic material, and a proximal portion 6022, which can comprise a metallic material. The advantages of these combinations of materials are discussed below.

As also illustrated in FIG. 89, the proximal portion 6016 of the inner shaft 6004 extends beyond the proximal portion 6022 of the outer shaft 6006, and a proximal end of the guidewire shaft 6002 extends beyond the proximal portion 6016 of the inner shaft 6004. Thus, by adjusting the proximal portions of the respective shafts with respect to each other, a physician can control the locations of the distal portions of each of the shafts with respect to each other, thereby controlling the deployment of the device, as further explained below.

As further illustrated in FIG. 89, coupled to the proximal portion 6016 of the inner shaft 6004 is a sealing element 6024 which prevents fluid flowing out of the human body through the lumen of the inner shaft 6004. As also illustrated, two echogenic arms 6012 and a fluoroscopic marker band 6018 are coupled to the distal portion 6014 of the inner shaft 6004. The echogenic arms 6012 extend outward from the inner shaft 6004 in opposing directions in a deployed configuration and the marker band 6018 includes two apertures 6026 disposed on opposing sides of the marker band 6018. The positions of the opposing arms 6012 and opposing apertures 6026 can be displaced from each other by any angle, but in the illustrated configuration, each arm 6012 is angularly displaced from each of the apertures 6026 by 90 degrees. The advantages of these features and angular dimensions are described below.

Figure 90:
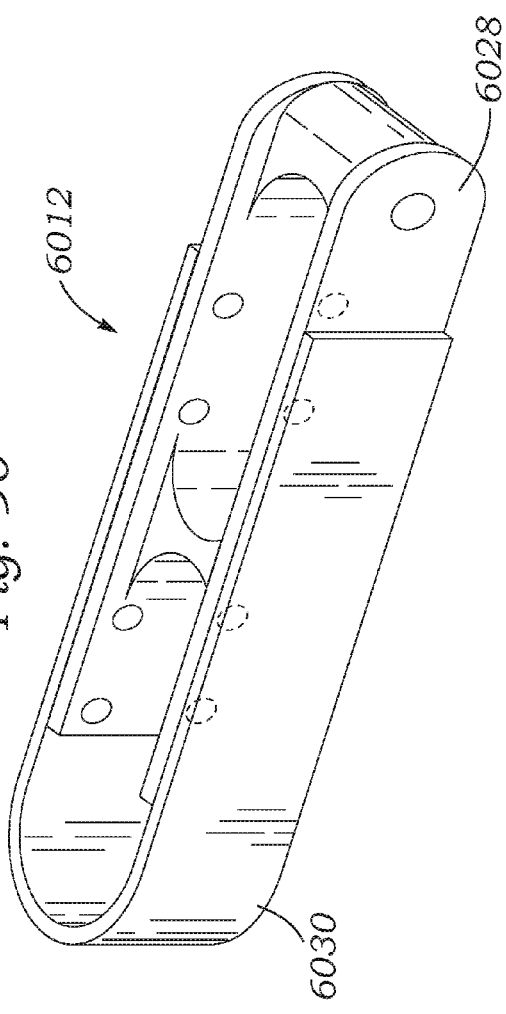
FIG. 90 shows details of an arm component of the orientation device of FIG. 89.

An exemplary echogenic arm 6012 is shown in FIG. 90. The echogenic arm 6012 can include a connector portion 6028 and an extension portion 6030. The connector portion 6028 is adapted to be pivotably connected to the distal portion 6014 of the inner shaft 6004 by any one of various mechanisms, such as by a hinge, by flexible materials, etc. The extension portion 6030 comprises an echogenic material which allows the arms 6012 to be viewed via echocardiography (ultrasound imaging of the heart).

A variety of mechanisms can be used to induce the arms 6012 to transition from an axially oriented position in the delivery configuration to an outwardly oriented position in the deployed configuration. For example, the arms may be configured to self-expand under the force of, e.g., a spring, elastic material, or a metal having shape memory, such as nitinol. The device 6000 can also be provided with actuation lines (e.g., wires) (not pictured) which run through the body of the device and allow the physician to control the extension and/or retraction of the arms 6012. While the embodiment illustrated in FIG. 89 allows one dimensional rotation of the arm with respect to the inner shaft 6004, in alternative embodiments, the arms 6012 are rotatable in two or three dimensions, such as by a gimble or universal joint connection.

Figure 91:
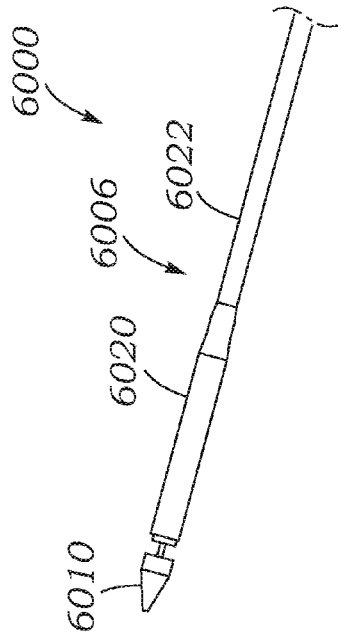
FIGS. 91-94 show an exemplary deployment sequence of the orientation device of FIG. 89.
Figure 92:
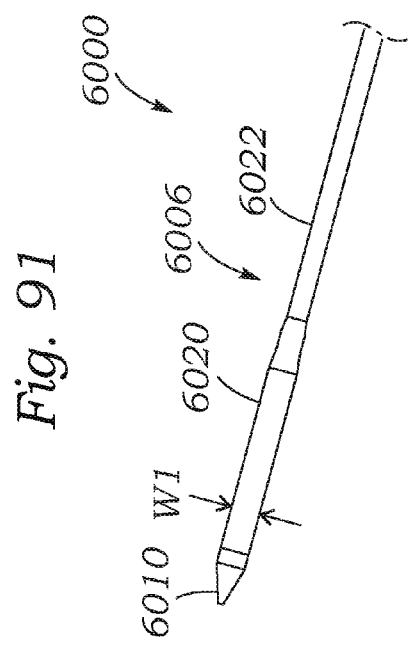
Figure 93:
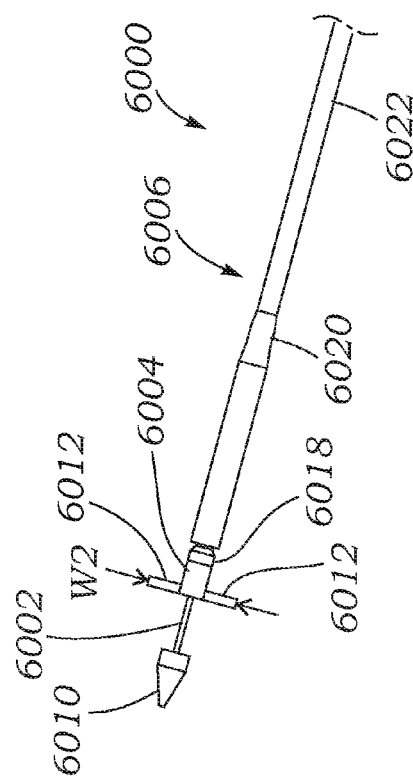
Figure 94:
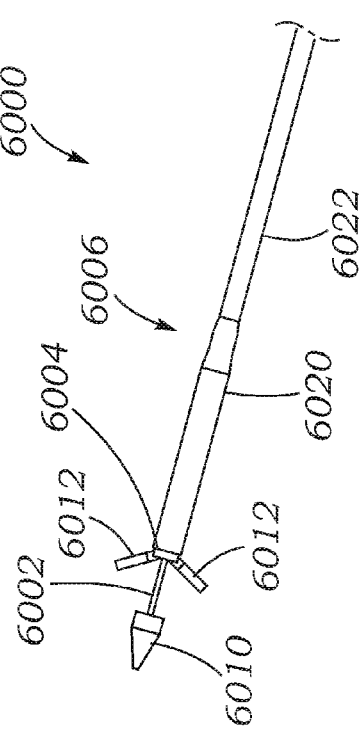

FIGS. 91-94 illustrate the deployment sequence of the fluoroscopy orientation device 6000 from a delivery configuration to a deployed configuration. As illustrated in FIG. 91, in the delivery configuration, the outer shaft 6006 and the nosecone 6010 form a contiguous cylindrical body, which allows passage of the device 6000 through a patient's body and into the heart. As illustrated in FIG. 92, deployment of the device begins by retracting the outer shaft 6006 from the nosecone 6010 (or, alternatively, advancing the nosecone 6010 from the outer shaft 6006). As illustrated in FIG. 93, deployment of the device 6000 continues by further separating the nosecone 6010 and the outer shaft 6006, and by advancing the inner shaft 6004 distally through the outer shaft 6006 until the echogenic arms 6012 begin to extend outward from the device 6000. As illustrated in FIG. 94, in the deployed configuration, the nosecone 6010 is separated from the outer shaft 6006, and the inner shaft 6004 has been advanced distally through the outer shaft 6006 to the point where the arms 6012 are fully extended outward from the device 6000 and the marker band 6018 is fully exposed.

As described above, the proximal portion of each of the shafts 6002, 6004, and 6006, is accessible to a physician. Thus, a physician can control the deployment sequence by advancing and retracting the guidewire shaft 6002 within the inner shaft 6004 and the inner shaft 6004 within the outer shaft 6006. By advancing the proximal end of the guidewire shaft 6002 with respect to the proximal portion 6022 of the outer shaft 6006, the physician can advance the nosecone 6010 from the distal portion 6020 of the outer shaft 6006. Similarly, by advancing the proximal portion 6016 of the inner shaft 6004 with respect to the outer shaft 6006, the physician can advance the distal portion 6014 of the inner shaft 6004 (to which the arms 6012 and marker band 6018 are coupled) with respect to the distal portion 6020 of the outer shaft 6006.

When the physician has finished using the device 6000, it can be withdrawn from the patient's body by reversing the deployment sequence. That is, the physician begins withdrawal with the device 6000 in its deployed configuration. The physician can retract the inner shaft 6004 with respect to the outer shaft 6006 until the marker band 6018 and arms 6012 are enclosed within the outer shaft 6006. The physician can then retract the guidewire shaft 6002 with respect to the outer shaft 6006 until the nosecone 6010 and the distal portion 6020 of the outer shaft 6006 come into contact, forming a contiguous cylindrical body. The physician can then remove the device 6000 from the patient's body.

In one specific embodiment, the width (W1) of the device 6000 in its delivery configuration is 33 French and the maximum width of the device 6000 (W2) in the deployed configuration (i.e., the distance between the opposing ends of the two echogenic arms 6012) is 33.5 mm.

FIGS. 95A-99 illustrate the device 6000 in various stages of operation. The device 6000 can be introduced into a patient's body and advanced to the vicinity of the mitral valve using various approaches, including via a transapical or a transeptal approach. FIG. 95A illustrates the device 6000 in the deployed configuration in the vicinity of a native mitral valve 2 using a transapical approach. As can be seen, the nosecone 6010 is separated from the distal portion 6014 of the inner shaft, and the echogenic arms 6012 extend away from the distal portion 6014 of the inner shaft 6004. Also illustrated are the chordae tendineae 16, the papillary muscles 22 and 24, and the leaflets 10 and 12 of the mitral valve.

Figure 95B:
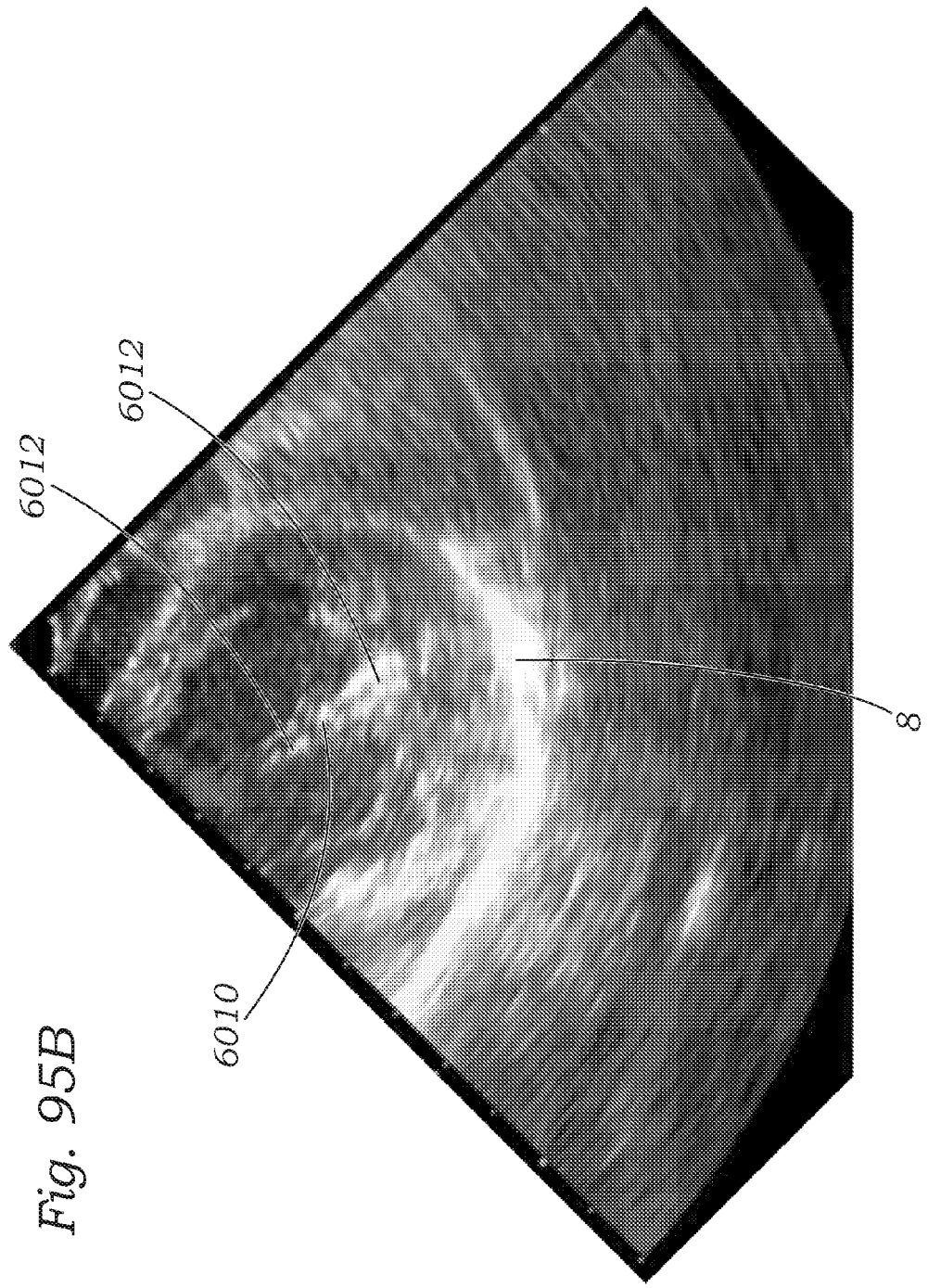

FIG. 95B is an echocardiographic image that illustrates the device 6000 from an end view in its deployed configuration in the vicinity of the native mitral valve 2. Because soft tissue of the mitral valve and the echogenic arms 6012 of the device 6000 are both visible during echocardiography, a physician can use echocardiography to orient the arms 6012 of the device 6000 into a position which corresponds to the locations A2 and P2 where there are relatively few attachment points of chordae 16 to the leaflets 10, 12. That is, a physician can orient the arms 6012 in the orientation it is desired to anchor a prosthesis.

Once the echogenic arms 6012 have been oriented to align with the locations A2 and P2, echocardiography can be concluded and a fluoroscope can be used to view the patient's heart under fluoroscopy. FIG. 96 illustrates an exemplary C-Arm Fluoroscope 6032, comprising a transmitter 6034, receiver 6036, and a flat surface 6038, on which a patient can rest. The path between the transmitter 6034 and receiver 6036 defines the fluoroscope axis 6040.

Figure 97:
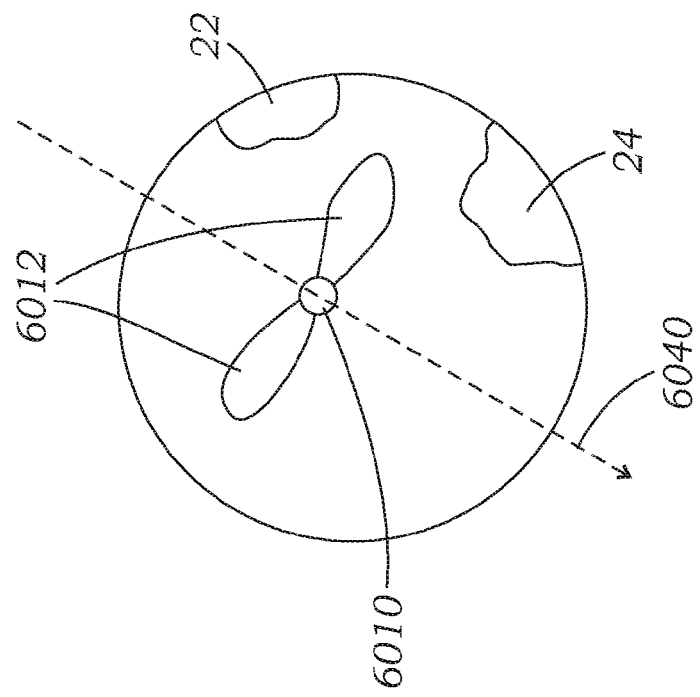
FIGS. 97 and 98 are end views of the orientation device of FIG. 89 showing steps in an exemplary process of orientating the orientation device.
Figure 98:
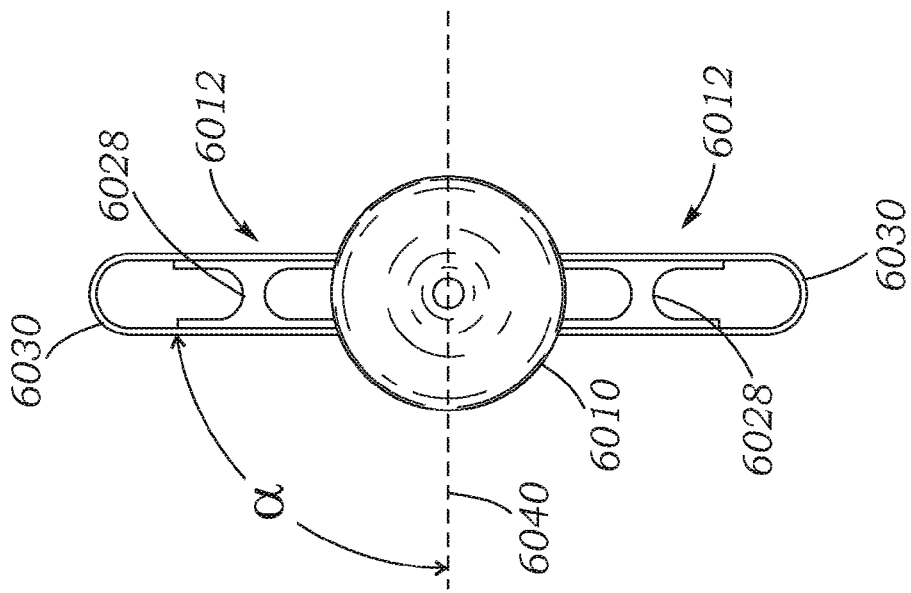
Figure 99:
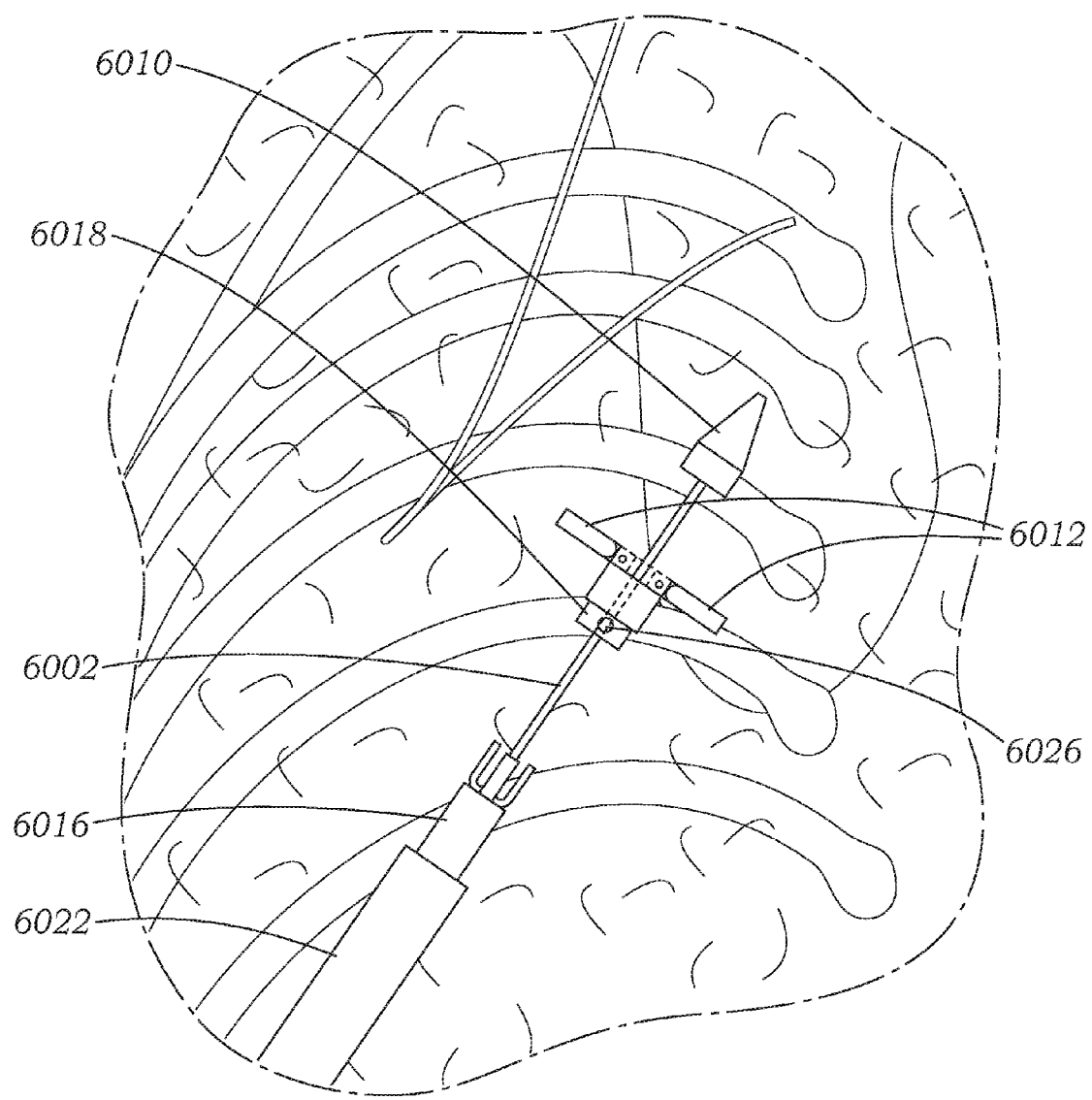
FIG. 99 shows the orientation device of FIG. 89 deployed in the native mitral valve region of a heart, as seen under fluoroscopy.

As illustrated in FIGS. 97-99, the device 6000 can be used to position the fluoroscope 6032 in a desired orientation relative to the patient. The marker band 6018 of the device 6000 is visible under fluoroscopy and, as illustrated in FIG. 89, has two apertures 6026 displaced angularly from the echogenic arms 6012 by known angles, such as about 90 degrees. Thus, the orientation of the arms 6012 within the patient's heart can be determined by rotating the fluoroscope 6032 until the apertures 6026 are visible, and thus aligned with the fluoroscope axis 6040. As illustrated in FIG. 97, the apertures 6026 are known to be displaced angularly from the arms 6012 by 90 degrees. As also illustrated in FIG. 97, the fluoroscope axis 6040 has been aligned with the apertures 6026. Thus, it is known that the fluoroscope axis 6040 is angularly displaced from the arms 6012 by 90 degrees.

As illustrated in FIG. 98, the fluoroscope axis 6040 is aligned with the apertures 6026 and perpendicular to the arms 6012. Because the arms were initially aligned with the locations A2 and P2 under echocardiography, it is now known that the axis 6040 is perpendicular to an axis between these locations and that items delivered to the vicinity of the native mitral valve 2 and aligned along an axis perpendicular to the fluoroscope axis 6040 are less likely to experience interference with the chordae 16 or papillary muscles 22, 24. Thus, by rotating the fluoroscope 6032 until the apertures 6026 in the marker band 6018 are visible under fluoroscopy, and thus aligned with the axis 6040, a desired orientation of the fluoroscope 6032 relative to the patient's heart can be obtained.

FIG. 99 illustrates the device 6000 in the deployed configuration in the vicinity of a mitral valve, as viewed under fluoroscopy. Neither the distal portion 6020 of the outer shaft 6006, nor the distal portion 6014 of the inner shaft 6004, is visible in this view, as they comprise a non-fluoroscopic material. In contrast, the nosecone 6010, the guidewire shaft 6002, and the marker band 6018 are visible, as they comprise fluoroscopic materials. Thus, the selection of non-fluoroscopic materials for the distal portions of the inner and outer shafts 6004 and 6006 allows the physician a better view of the components relevant to orienting the fluoroscope 6032 on a desired axis. As illustrated in FIG. 99, the echogenic arms 6012 can be visible under fluoroscopy, for example, where the arm connector portion 6028 and the arm extension portion 6030 are made of different materials, one being echogenic and the other being fluoroscopic. In this illustrated embodiment, the arms 6012 can supplement the marker band 6018 in allowing the physician to orient the device 6000 under fluoroscopy. Locating the apertures 6026 on the marker band 6018 rather than another component of the device 6000 (e.g., the arms 6012) increases the distance between them, thereby allowing more accurate orientation of the fluoroscope.

Once the fluoroscope 6032 has been oriented to align the axis 6040 with the apertures 6026 (and thus a known angle from the arms 6012 and a known angle from the axis between the locations A2 and P2), the device 6000 can be removed from the patient's body. By maintaining the patient's position on the flat surface 6038 and maintaining the orientation of the fluoroscope 6032 relative to the patient's heart, the axis 6040 can be used to orient a prosthesis during implantation. A mitral valve prosthesis (e.g., a prosthetic mitral valve) can be advanced to the vicinity of the patient's native mitral valve 2 and rotated under fluoroscopy until its anchors are seen to extend laterally away from the body of the prosthesis and delivery apparatus, or generally perpendicular to the fluoroscope axis 6040. Because the anchors of the prosthesis are now oriented on the same axis as the echogenic arms 6012 were when the device 6000 was in the patient's heart, a physician can be more confident that the anchors are now aligned with the regions A2 and P2 of the native leaflets.

To summarize some advantages that the orientation device 6000 can provide, it is first noted that the delivery and anchoring location of mitral prostheses is a relevant factor in their successful implantation. Further, determining the proper orientation for delivery and anchoring is difficult due to the nature of the relevant materials: soft human tissue (e.g., the tissue of the human heart) is visible under echocardiography but not under fluoroscopy. Materials used for fabricating mitral prostheses are often visible under fluoroscopy but not under echocardiography. Thus, the orientation device 6000 utilizes the advantages of echocardiography and fluoroscopy, allowing a physician to determine a desirable orientation with which to deliver and anchor a prosthesis.

Expansion-Assisted Delivery Systems

For embodiments of prosthetic devices having anchors which are not independently expandable relative to the main body (as may be the case for embodiments having frames in which the main body is not formed integrally with the ventricular anchors, such as those illustrated in FIGS. 47 and 48), a delivery system having a mechanism for forcibly expanding the anchors can be used. Illustrated in FIGS. 141-156 is one embodiment of an expansion-assisted delivery system 8000 configured to deliver and implant an exemplary prosthetic mitral valve 8050 (see FIG. 151) having anchors 8052, a main body 8054, and an atrial portion 8056, and including a mechanism for forcibly expanding components of the prosthetic valve 8050. The delivery system 8000 is described herein with respect to the exemplary prosthetic valve 8050 and delivery via a transapical approach, though it should be understood that similar systems can be used to deliver alternative prostheses via alternative delivery approaches to the native mitral valve region, and/or via alternative deployment sequences. For example, a prosthesis having any of the atrial portion embodiments described in FIGS. 101A-140 can be used with the delivery system 8000 with appropriate modifications to the delivery system and associated delivery methods. The atrial portion embodiments of FIGS. 101A-140 are therefore collectively represented by the exemplary prosthetic valve 8050 below for simplicity of description.

Figure 141:
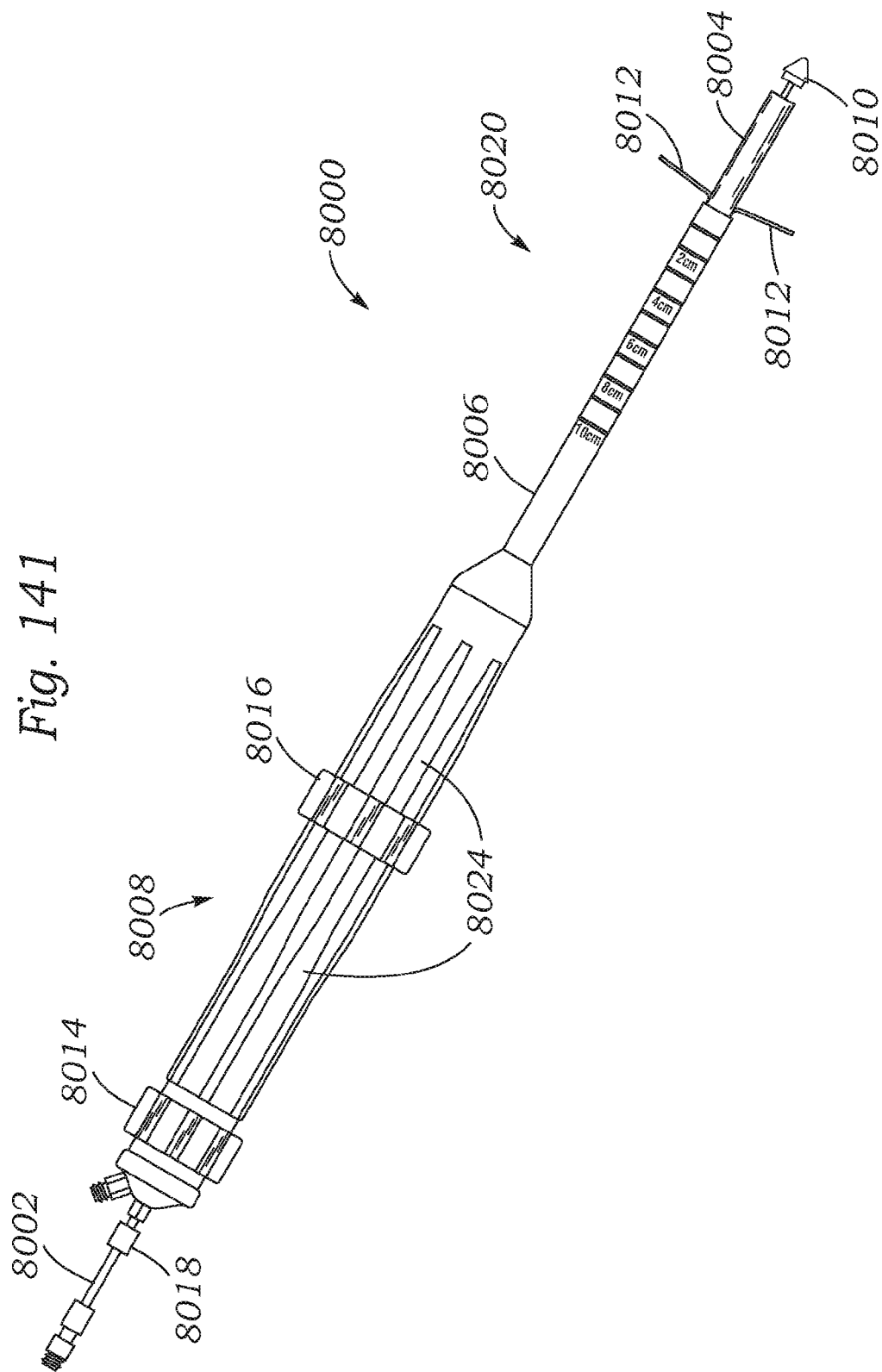
FIG. 141 shows an exemplary embodiment of an expansion assisted delivery device.

As illustrated in FIG. 141, the delivery system 8000 can include a series of concentric sheaths aligned about a central axis and slidable relative to one another in the axial directions. The delivery system 8000 can comprise a proximal handle portion 8008 having controlling mechanisms for physician manipulation outside of a patient's body while a distal portion 8020 is inserted into the patient's body.

The delivery system 8000 can include a guidewire sheath 8002 that runs the length of the delivery system and comprises a lumen through which a guidewire (not shown) can pass. The guidewire sheath 8002 can be positioned within an inner sheath 8004 and can have a length that extends proximally beyond the proximal end of the inner sheath 8004 and distally beyond the distal end of the inner sheath 8004. The inner sheath 8004 can be positioned within an outer sheath 8006. The distal portion 8020 of the delivery system 8000 can also include a pair of anchor spreaders 8012 attached to the inner sheath 8004 and a nosecone attached to the distal end of the guidewire sheath 8002. The anchor spreaders 8012 can be formed from any suitable material (e.g., nitinol) such that the anchor spreaders 8012 resiliently extend radially from the inner sheath 8004 when they are not constrained by the outer sheath 8006, as further explained below.

Figure 143:
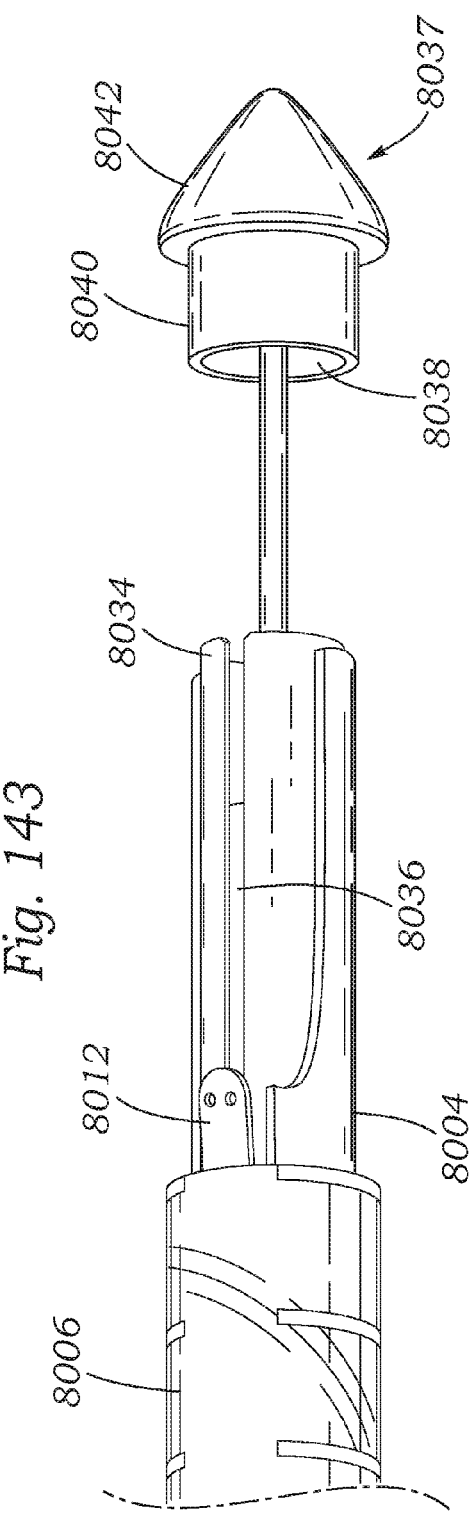

As illustrated in FIGS. 141,143,147-151, and 154-156, the nosecone can comprise various configurations. As illustrated in FIG. 141, a conical nosecone 8010 is generally conically shaped and formed from a solid piece of material. As illustrated in FIG. 143, a hollow nosecone 8037 comprises a hollow, generally cylindrically shaped proximal portion 8040 having a cavity 8038, and a generally conically shaped distal portion 8042. As illustrated in FIGS. 147-151, a diamond nosecone 8046 comprises a solid, generally diamond shaped configuration. Each of the nosecones 8010, 8037, and 8046 provides a tapered distal end to the system 8000, which can act as a wedge to guide the distal portion 8020 of the system 8000 into a patient's body and reduce trauma incurred by the surrounding tissue as the system 8000 is advanced through the body. Additional advantages of these configurations are explained below.

As illustrated, the handle portion 8008 includes at least three controller mechanisms: an inner sheath controller 8014, an outer sheath controller 8016, and a guidewire sheath controller 8018. Using these three mechanisms, the guidewire sheath 8002, the inner sheath 8004, the outer sheath 8006, and the handle portion 8008 are each axially slidable relative to one another. Due to the axial adjustability of these components, various configurations are possible. As can be seen in the configuration illustrated in FIG. 146, in which the inner sheath 8004 and the outer sheath 8006 have been retracted in the proximal direction with respect to the handle 8008, a prosthetic support 8022 is positioned within the inner sheath 8004. The support 8022 is rigidly connected to the handle portion 8008 and is thus axially slidable with respect to any of the guidewire sheath 8002, inner sheath 8004, and/or outer sheath 8006, but not with respect to the handle 8008.

The handle 8008 can be structurally similar to the handle portion 2002 of the delivery system 2000, described above and illustrated in FIGS. 49-55. Accordingly, the handle 8008 comprises components which facilitate the axial adjustment of the various sheaths with respect to each other and with respect to the handle 8008 itself. Specifically, the handle

8008 comprises a housing 8024 that provides a grip for a physician to hold the system steady while actuating the sheaths using the controllers. The handle 8008 also includes a first sliding lead screw fixed to the end of the inner sheath 8004 and a second sliding lead screw fixed to the end of the outer sheath 8006. Each of the sliding lead screws is rotationally fixed and axially slidable with respect to the housing 8024. A first rotatable sleeve can be positioned concentrically between the housing 8024 and the first sliding lead screw, and have a helical groove which interacts with a helical ridge protruding from the lead screw. A second rotatable sleeve can be positioned concentrically between the housing 8024 and the second sliding lead screw, and have a helical groove which interacts with a helical ridge protruding from the second sliding lead screw. The first rotatable sleeve includes the inner sheath controller 8014 which extends free of the housing 8024, and the second rotatable sleeve includes the outer sheath controller 8016, which extends free of the housing 8024.

Whereas the sliding lead screws are rotationally fixed and axially slidable relative to the housing 8024, the rotatable sleeves are each rotatable but axially fixed relative to the housing 8024. In this configuration, by rotating the outer sheath controller 8016 with respect to the housing 8024, a physician can cause the second lead screw to slide axially with respect to the housing 8024 and thereby cause the outer sheath to slide axially with respect to the handle portion 8024. Similarly, by rotating the inner sheath controller 8014 with respect to the housing 8024, a physician can cause the first lead screw to slide axially with respect to the housing 8024 and thereby cause the inner sheath to slide axially with respect to the handle portion 8024. In the illustrated configuration, the first sliding lead screw can have fewer ridges per inch than the second sliding lead screw. Thus, one rotation of the inner sheath controller (which interacts with the first sliding lead screw) can cause greater axial displacement of the inner sheath than one rotation of the outer sheath controller causes for the outer sheath.

In alternative embodiments, various numbers of ridges per inch can be used for both lead screws, and those numbers can be the same for the two lead screws, or can be different (as in the illustrated configuration). Further, rotation of the controllers 8014, 8016 in either direction may cause displacement of the sheaths 8004, 8006 in either axial direction. For example, in one embodiment, clockwise rotation of the inner sheath controller 8014 can cause the distal end of the inner sheath 8004 to move distally, while in another embodiment, clockwise rotation of the inner sheath controller 8014 can cause the distal end of the inner sheath 8004 to move proximally. In some embodiments, rotation of the controllers 8014, 8016 in the same direction can cause the distal ends of the sheaths 8004, 8006 to move in the same direction, while in other embodiments, rotation of the controllers 8014, 8016 in the same direction can cause the distal ends of the sheaths 8004, 8006 to move in opposing directions.

In alternative embodiments, alternative methods of actuating the sheaths can be employed. For example, the advancing and/or retracting of the various sheaths can be controlled by a hydraulic system, an electric motor, a pulley system, or various other methods.

Figure 142:
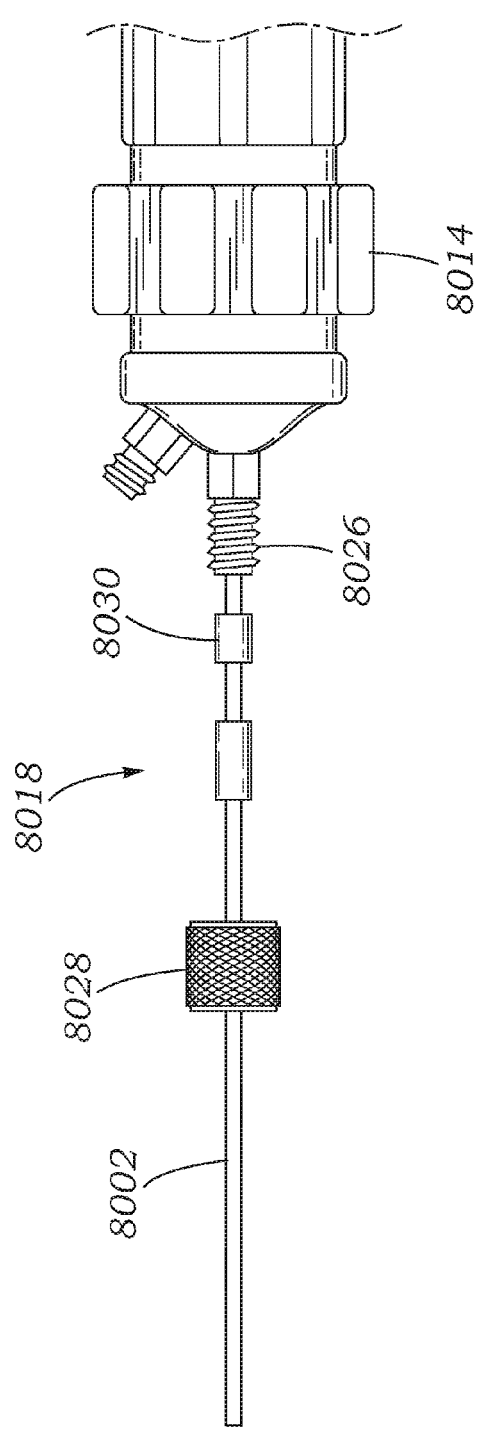
FIG. 142 shows a partial side view of the proximal end portion of the delivery device of FIG. 141.

FIG. 142 illustrates the proximal end portion of the system 8000 in greater detail and the guidewire sheath controller 8018 in a disassembled configuration. As illustrated in FIG. 142, the guidewire sheath controller 8018 comprises an inner threaded rod 8026 and an outer nut 8028 configured to fit on the threaded rod 8026. By tightening the nut 8028 on the rod 8026, an elastic material 8030 mounted on the guidewire sheath 8002 is compressed axially, thus expanding radially and exerting a radial force on the guidewire sheath 8002, thereby retaining the position of the guidewire sheath 8002 with respect to the handle 8008 by friction.

FIG. 143 illustrates the distal end portion 8020 of the system 8000 in greater detail. In the configuration illustrated in FIG. 143, the outer sheath 8006 contains the inner sheath 8004 and retains the attached anchor spreaders 8012 in a substantially axial orientation. As also illustrated in FIG. 143, the inner sheath 8004 includes two opposing recessed portions, or grooves, 8034 (only one is visible in FIG. 143) and two opposing slots 8036 (only one is visible in FIG. 143). The grooves 8034 allow more space for portions of the prosthetic valve 8050 to fit within the outer sheath 8006 by reducing the profile of the inner sheath 8004, while retaining some additional strength by not reducing the profile of the inner sheath 8004 throughout its entire cross section. The slots 8036 allow a prosthetic valve to be mounted within the inner sheath 8004 and the anchors 8052 to extend outside the inner sheath 8004 so the anchors 8052 can be deployed before the main body 8054 of the prosthetic valve 8050.

FIG. 143 also illustrates the nosecone 8037 in greater detail. The cavity 8038 within the nosecone 8037 allows a distal portion of a frame (e.g., an atrial portion) to be retained within the nosecone 8037. The diameter of the proximal portion 8040 of the nosecone 8037 is slightly smaller than the diameter of the proximal end of the distal portion 8042, and is configured such that when the nosecone 8037 is brought to within the vicinity of the outer sheath 8006, the outer sheath 8006 can extend over the proximal portion 8040 of the nosecone 8037 until it comes into contact with the proximal end of the distal portion 8042 of the nosecone 8037.

Figure 146:
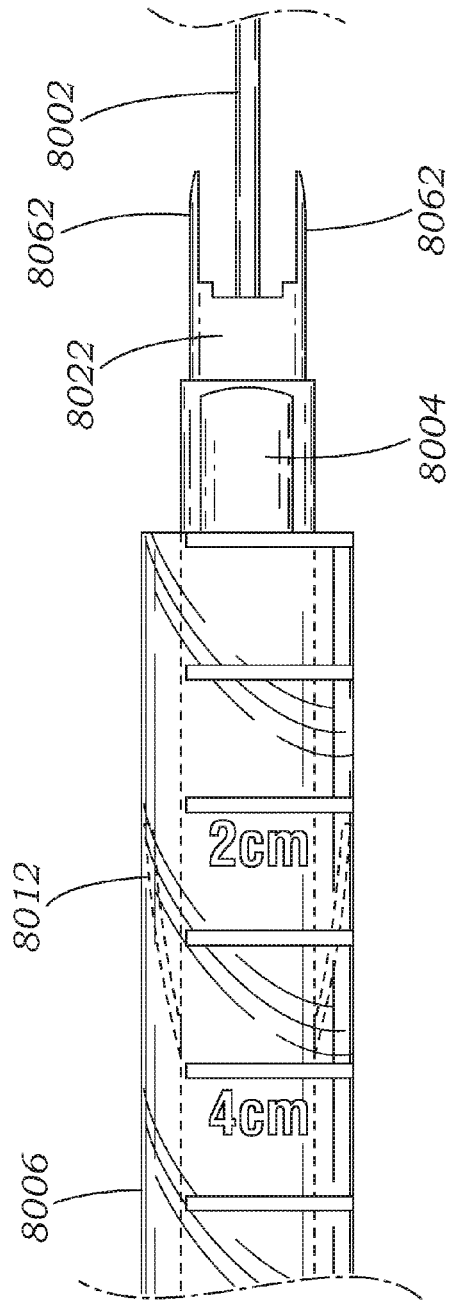

FIGS. 144-146 illustrate three possible configurations of the system 8000 in which the guidewire sheath 8002 has been extended distally with respect to the inner sheath 8004 and the outer sheath 8006, and in which the inner sheath 8004 has been extended beyond the distal end of the outer sheath 8006. As seen in FIG. 144, as the inner sheath 8004 extends beyond the outer sheath 8006, the anchor spreaders 8012 (which are self-expanding in this embodiment) begin to extend radially outward from the inner sheath 8004. FIG. 145 illustrates the inner sheath 8004 extended fully beyond the outer sheath 8006 and the anchor spreaders 8012 fully radially extended. FIG. 146 illustrates a configuration in which the inner sheath 8004 and the outer sheath 8006 have been retracted with respect to the handle 8008, thereby exposing the prosthetic support 8022, the purpose of which is explained further below.

FIGS. 147-151 illustrate an exemplary deployment sequence using the system 8000 with the prosthetic valve 8050. As used with regard to FIGS. 147-151, the phrases "proximally" and "distally" are used to indicate motion of an element relative to the handle 8008. Elements moved proximally are moved toward the handle 8008 and elements moved distally are moved away from the handle 8008.

Figure 147:
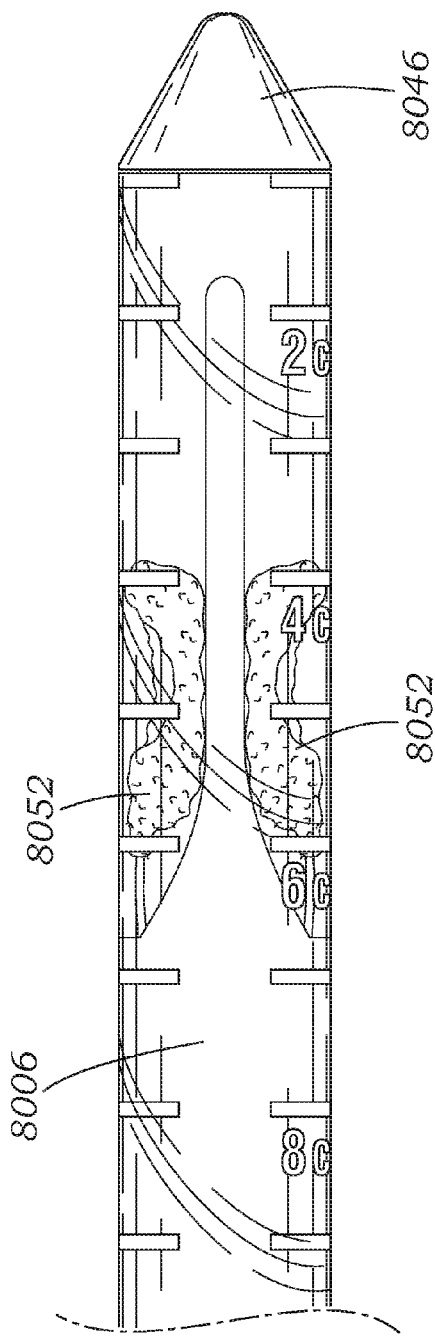

FIG. 147 illustrates the system 8000 in a delivery configuration. As illustrated in FIG. 147, a prosthetic valve 8050 having anchors 8052, main body 8054, and atrial portion 8056 has been loaded into the delivery system 8000 in a delivery configuration. In order to load the prosthetic valve 8050 into the system 8000, the nosecone 8046 is extended distally, and the outer sheath 8006 is retracted proximally in order to expose the lumen within the inner sheath 8004. The prosthetic valve 8050 is then positioned so that it surrounds the guidewire sheath 8002 in a radially expanded state, and is compressed to a radially compressed state. The radially compressed main body 8054 and atrial portion 8056 are then inserted into the inner sheath 8004, and the anchors 8052 are positioned within the slots 8036 and grooves 8034 outside the inner sheath. The main body 8054 is advanced proximally through the inner sheath until it rests against the support 8022. The outer sheath 8006 can then be extended over the inner sheath 8004 and anchors 8052. Thus, in the delivery configuration illustrated in FIG. 147, the main body 8054 and atrial portion 8056 are retained within the inner sheath 8004 while the anchors 8052 are retained within the outer sheath 8006.

FIG. 148 illustrates the system 8000 in a leaflet capture configuration. As illustrated in FIG. 148, once the distal end of the delivery system 8000 has been delivered to the native mitral valve region (e.g., the left ventricle), a physician can retract the outer sheath 8006, allowing the anchor spreaders 8012 to extend radially outward from the inner sheath 8004, in preparation for leaflet capture. As illustrated in FIG. 148, the anchors 8052 can be covered in a cloth 8058 which is configured to be relatively thick, strong, and soft. In particular embodiments, the cloth 8058 can be made from a knitted lofty cloth. The cloth 8058 covers the anchors 8052 in order to provide a softer surface for contact with the native tissue, thus reducing trauma. The cloth 8058 also increases the surface area of contact between the prosthetic valve 8050 and the native tissue, thereby facilitating tissue in-growth and providing a more secure installation. As also illustrated in FIG. 148, the cloth can be configured to create a cavity or pocket into which the anchor spreaders 8012 can extend for transferring force from the anchor spreaders 8012 to the anchors 8052. In this configuration, as the outer sheath 8006 is retracted, the anchor spreaders 8012 expand radially and pull on the cloth 8058, which in turn pulls the anchors 8052 into an open configuration shown in FIG. 148.

In alternative embodiments, the anchors 8052 can be forced apart by other mechanisms. For example, in one alternative embodiment, the anchor spreaders 8012 are fastened directly to the anchors 8052. In another alternative embodiment, there are no anchor spreaders, and instead sutures are provided which are fastened to the anchors 8012, run along the length of the system 8000 (e.g., between the inner sheath 8004 and the outer sheath 8006), and exit the system 8000 at the handle 8008. In this alternative embodiment, by pulling on the sutures, a physician can force the anchors 8012 into an open configuration. In another alternative embodiment, the hollow portion 8040 of the nosecone 8037 can extend proximally between the anchors 8052 and the inner sheath 8004. In this alternative embodiment, the nosecone 8037 can be retracted proximally between the anchors 8052 and inner sheath 8004 such that the proximal end portion of the hollow portion 8040 forces the anchors 8052 to extend radially away from the inner sheath 8004.

Once the anchors 8052 have been radially expanded as illustrated in FIG. 148, a fluoroscope which was oriented to align with a patient's anatomy using the method described above can be used to orient the anchors 8052 with the regions A2 and P2 of the patient's native mitral valve leaflets. With the delivery system 8000 in place near the native mitral valve and the anchors 8052 in a radially expanded configuration, a physician can use the fluoroscope device to view the system 8000 as it is rotated. When the physician views the anchors 8052 at their maximum width under fluoroscopy, which indicates that the anchors 8052 are aligned along an axis perpendicular to the fluoroscopy axis 6040, the anchors are aligned with the A2 and P2 regions, thereby reducing the chance of interference between the anchors 8052 and the chordae as the leaflets are captured by the anchors 8052.

Once the anchors 8052 have been radially expanded and angularly oriented using a fluoroscope, the distal end of the system 8000 can be advanced through the patient's native mitral valve so that the expanded anchors 8052 move behind the native leaflets 10, 12, as described above. FIG. 149 illustrates the system 8000 in a closed configuration. As illustrated in FIG. 149, once the anchors 8052 are positioned behind the native leaflets 10, 12, the outer sheath 8006 can be advanced distally to partially re-cover the anchor spreaders 8012, thereby forcing the anchors back toward a closed configuration, thereby capturing the native leaflets 10, 12 between the anchors 8052 and the inner sheath 8004.

Once the anchors 8052 have returned to a closed configuration and captured the leaflets, the inner sheath 8004 can be retracted proximally so that the atrial portion 8056 can expand radially outward, the anchor spreaders 8012 retract from within the cloth 8058, and the inner sheath 8004 slides out from between the leaflets and the main body 8054. The inner sheath is shown slightly retracted in FIG. 149. FIG. 150 illustrates the system 8000 in a further retracted configuration. As illustrated in FIG. 150, the inner sheath 8004 is further retracted so that the atrial portion 8056 is partially expanded radially outward and the anchor spreaders are fully retracted from the cloth 8058 and anchors 8052. As can also be seen in FIG. 150, the diamond shape of the nosecone 8046, and particularly the proximal portion of the nosecone 8046, positioned within the atrial portion 8056, can help to guide the atrial portion 8046 as it expands radially outward.

The support 8022 (FIG. 146) serves to maintain the position of the prosthetic valve 8050 as the inner sheath 8004 is retracted. As the inner sheath 8004 is further retracted toward the position shown in FIG. 151, the atrial portion 8056 continues to expand radially outward within the left atrium and the main body 8054 begins to expand radially outward within the native mitral valve orifice. As the distal end of the inner sheath 8004 approaches the support 8022, the main body continues to expand, but the ventricular loops 8060 of the anchors 8052, which connect to the main body 8054, continue to be retained within the inner sheath 8004.

In order to ensure the radial expansion of the main body 8054 continues in a controlled fashion once the main body 8054 is fully outside the inner sheath 8004, and thereby prevent damage to the loops 8060, the support 8022 (FIG. 146) is provided with two distally projecting arms 8062, each of which is positioned along the exterior of the main body 8054 in its radially compressed state. In this configuration, the arms 8062 act to partially retain the ventricular end of the main body 8054 until the loops 8060 are fully outside the inner sheath 8004, at which point the prosthetic valve 8050 will finish radially expanding into a fully expanded configuration, as illustrated in FIG. 151. In alternative embodiments, alternative mechanisms can be used to ensure the radial expansion of the main body 8054 continues in a controlled fashion. In one particular alternative embodiment, a pair of hooks or grasping elements can be used to partially retain the ventricular end of the main body 8054 until the loops 8060 are fully outside the inner sheath 8004, thereby ensuring controlled radial expansion of the main body 8054.

FIG. 151 illustrates the system 8000 in a fully retracted configuration and the prosthetic valve 8050 in a fully radially expanded configuration. Once implanted in the native mitral valve region, the prosthetic valve 8050 can be positioned generally as shown in any of FIGS. 23, 33, 34, 39, and 70. The atrial portion 8056 is positioned within the left atrium and is positioned in contact with the native tissue of the mitral annulus. The main body 8054 is positioned within the native mitral valve orifice, and can include leaflets, as described above. The anchors 8052 are positioned such that the native mitral valve leaflets are captured between the anchors 8052 and the main body 8054.

Once the system 8000 reaches the fully retracted configuration and the prosthetic valve 8050 reaches a fully expanded and deployed configuration, the outer shaft 8006 can be extended distally toward the nosecone 8046, or the guidewire shaft 8002 can be retracted proximally such that the nosecone 8046 moves toward the outer shaft 8006, thereby bringing the nosecone 8046 into contact with the outer shaft 8006. The device 8000 can then be retracted from the patient's body, leaving the prosthetic valve 8050 implanted at the native mitral valve region.

Various alternative deployment sequences can be used. In one alternative deployment sequence, an atrial portion can be deployed before the anchors are allowed to extend radially outward from the delivery system. In this alternative embodiment, the distal end of the delivery system is advanced transapically through the left ventricle and into the left atrium where the atrial portion is deployed, then the delivery system is retracted far enough to allow the anchors to be deployed within the left ventricle and capture the leaflets. In another alternative deployment sequence, an atrial portion which is retained within a nosecone can be deployed after the anchors and main body. In another alternative deployment sequence, the hollow portion 8040 of the nosecone 8037 can extend proximally and retain the atrial portion, main body, and anchors of the prosthesis. In this alternative embodiment, the nosecone can be advanced away from the prosthesis, thereby allowing the prosthesis to radially expand. In various embodiments, various delivery approaches can be used, and modifications to the delivery system can allow use of transeptal, transapical, femoral, or aortic approaches (see, e.g., FIGS. 63-67).

Figure 152D:
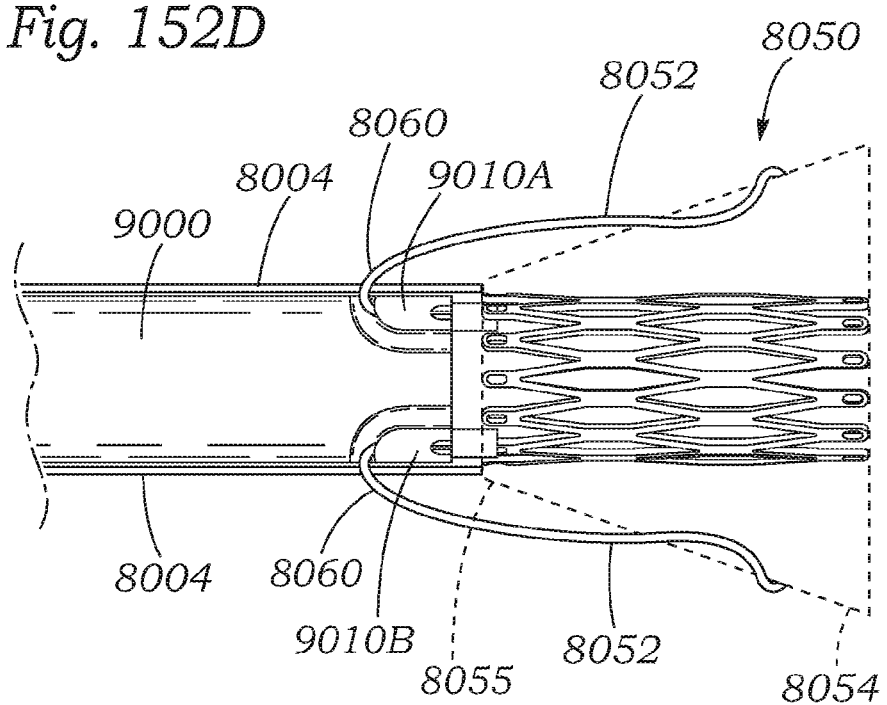

FIGS. 152A-152C illustrate a harness 9000 which can be used in a delivery system such as system 8000, for example, in place of the support 8022. The harness 9000 can include a main body portion 9002, a proximal connection portion 9004 at a proximal end of the main body portion 9002, and a distal connection portion 9006 at a distal end of the main body portion 9002. The proximal connection portion 9004 can couple the harness 9000 to the delivery system 8000 (such as to the distal end of a shaft that extends from the handle and through the inner sheath 8004), and the distal connection portion 9006 can be releasably coupled to a proximal portion of a prosthetic valve, such as the loops 8060 of prosthetic valve 8050 (for illustrative purposes, portions of the bare frame of valve 8050 are shown in FIGS. 152B-152E). The main body portion 9002 can have a generally cylindrical shape. The distal connection portion 9006 can be formed integrally with the main body portion 9002 and can comprise an extension of the cylindrical shape of the main body portion 9002, with four spaces or recesses 9016A-9016D formed therein.

The structure of the distal connection portion 9006 formed by the spaces 9016A-9016D within the cylindrical shape can include a central, tapered extension 9008, which tapers in width from the diameter of the cylindrical shape of the main body 9002 toward the distal end of the harness 9000. A pair of retaining elements 9010A, 9010B can extend radially outward from the extension 9008. Each retaining element 9010A, 9010B can include a relatively narrow neck portion 9012A, 9012B coupled to the extension 9008 and a relatively wide head portion 9014A, 9014B coupled to the neck portion 9012A, 9012B. In some cases, a pair of ridges 9020 (only one is shown) can separate the spaces 9016A-9016D from one another. For example, the illustrated ridge 9020 separates the space 9016A from the space 9016C. A lumen 9018 can extend through the harness 9000 and can be configured to house a guidewire sheath 8002, as described above.

FIGS. 152B and 152C illustrate the loops 8060 of prosthetic valve 8050 being cradled within the distal connection portion 9006 of the harness 9000. In embodiments where the harness 9000 is used in place of the support 8022 in system 8000, the inner and outer sheaths can be retracted to expose the harness 9000, and a prosthetic valve such as valve 8050 can be loaded into the harness 9000 as shown in FIGS. 152B-152C. The inner and outer sheaths can then be extended over the harness 9000 and the valve retained thereby. The inner sheath can extend over a main body 8054 of the valve 8050, while anchors 8052 can be allowed to extend through slots in the inner sheath 8004, as explained above. The outer sheath 8006 can then be extended over the inner sheath 8004 and the anchors 8052, as also explained above.

In embodiments where the harness 9000 is used in place of the support 8022 in system 8000, delivery sequences similar to those described above (including those using the anchor spreaders 8012) can be used to expand the anchors 8052 away from the main body 8054. One exemplary advantage of the harness 9000 is that it can allow forcible expansion of the anchors after the main body of a prosthetic valve has been deployed. This can be advantageous in cases where deployment of the main body of the prosthetic valve does not result in optimal placement of the valve on a first attempt. For example, when a prosthetic valve is released from a delivery device, it can spring open, causing movement within the native valve. Thus, the ability to force expansion of the anchors after the deployment of the main body can allow a physician to adjust the position of the prosthetic valve within the native valve to achieve a more desirable placement.

Figure 152E:
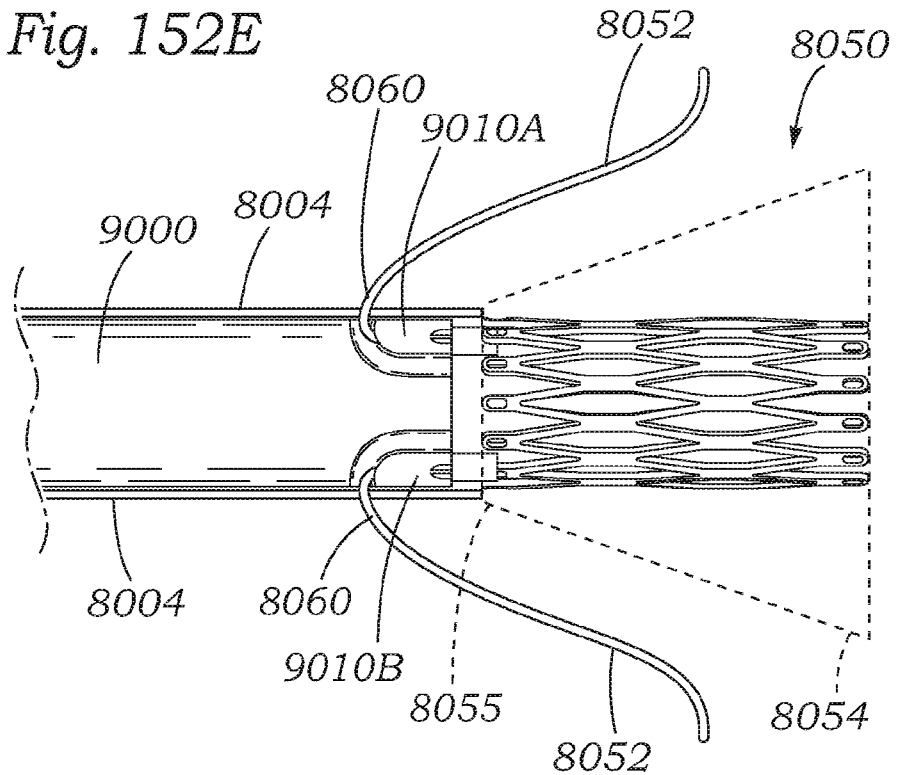

In one embodiment, the delivery sequence illustrated in FIGS. 147-151 can proceed to the configuration shown in FIG. 150. At that point, the inner sheath 8004 can be retracted until the main body 8054 of the prosthetic valve 8050 is completely uncovered by the sheaths 8004, 8006, but the loops 8060 are still retained by the harness 9000 within the inner sheath 8004, as shown in FIG. 152D (showing the deployed main body in dashed lines). The inner sheath 8004 can then be advanced distally over the harness 9000, until it approaches a proximal end 8055 of the main body 8054. The inner sheath 8004 in some cases cannot be extended to once again cover the main body, as the diameter of the main body 8054 cannot be sufficiently reduced once inside the patient's body. Thus, as the inner sheath 8004 is extended toward and comes into contact with the proximal end 8055 of the main body 8054, it will exert a distally directed force against a proximal portion of the main body 8054. Because the loops 8060 are still retained by the harness 9000 within the inner sheath 8004, the distally directed force on the prosthetic valve pulls the loops 8060 against retaining elements 9010A and 9010B. This causes the anchors 8052 to flex radially away from the main body 8054, as shown in FIG. 152E (also showing the deployed main body 8054 in dashed lines), allowing a physician to further manipulate the prosthetic valve 8050 as needed.

Once the prosthetic valve 8050 has been desirably positioned within the native valve, the inner sheath can be retracted to uncover the harness 9000. At that point, the loops 8060 are no longer restrained within the system 8000, and the prosthetic valve is completely released from the system 8000, as shown in FIG. 151.

Figure 153C:
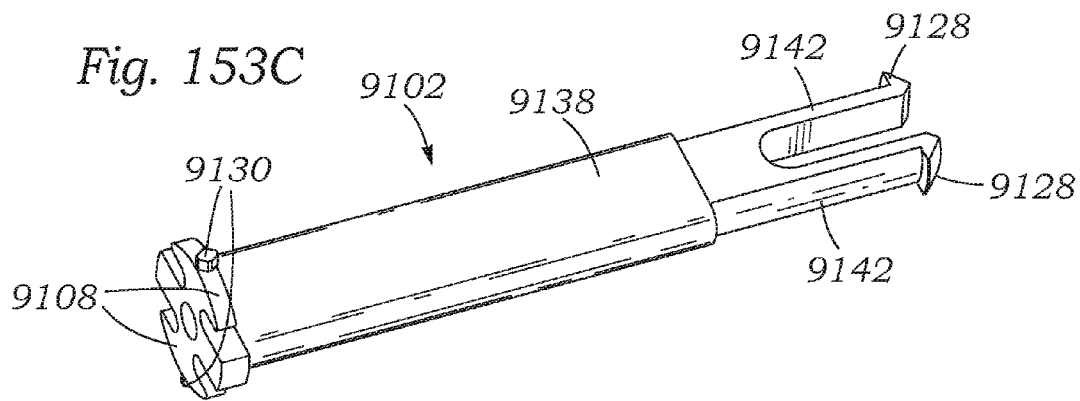

FIGS. 153A and 153B illustrate another embodiment of a harness device 9100 which can be used in place of support 8022 or harness 9000. The harness 9100 can include an inner anchor control portion 9102 (shown in more detail in FIG. 153C), an outer anchor control portion 9104 (shown in more detail in FIG. 153D), a spacing ring 9126 (shown in more detail in FIG. 153E), and a hollow adjustment control shaft 9106 coupled to the handle portion 8008. As shown in FIG. 153C, the inner portion 9102 can include a main body 9138, a pair of distal retaining elements 9108 extending radially away from a distal end portion of the inner portion 9102, a pair of distal aligning protrusions 9130 extending radially away from respective retaining elements 9108, and a pair of locking elements 9128 disposed at the proximal end of and extending radially away from respective proximal extensions 9142.

Figure 153D:
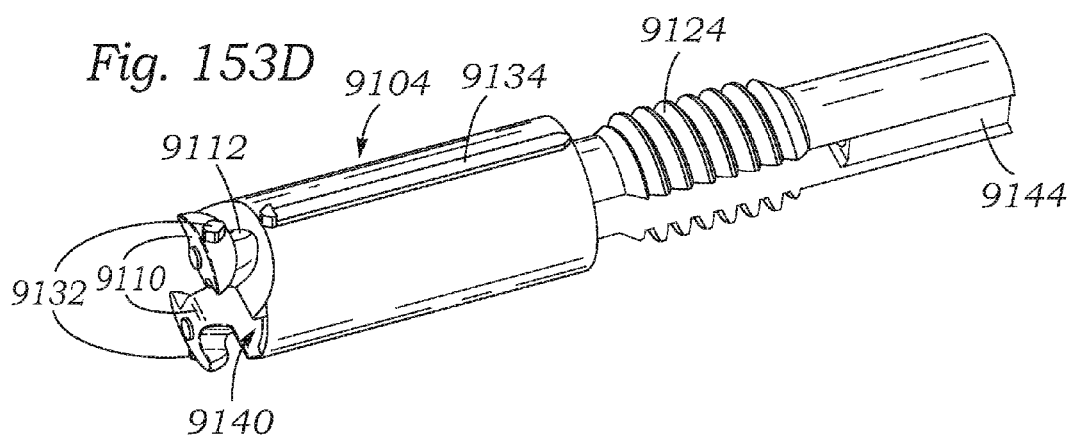
Figure 153E:
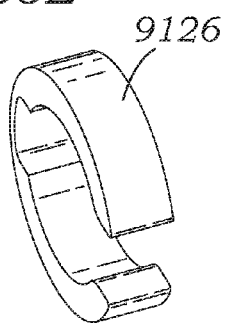
Figure 153F:
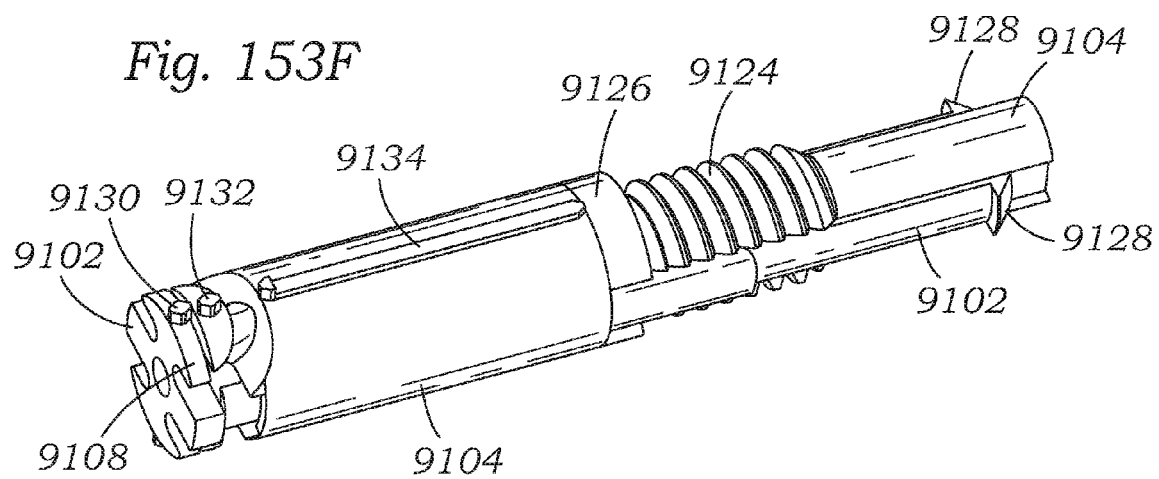
Figure 153G:
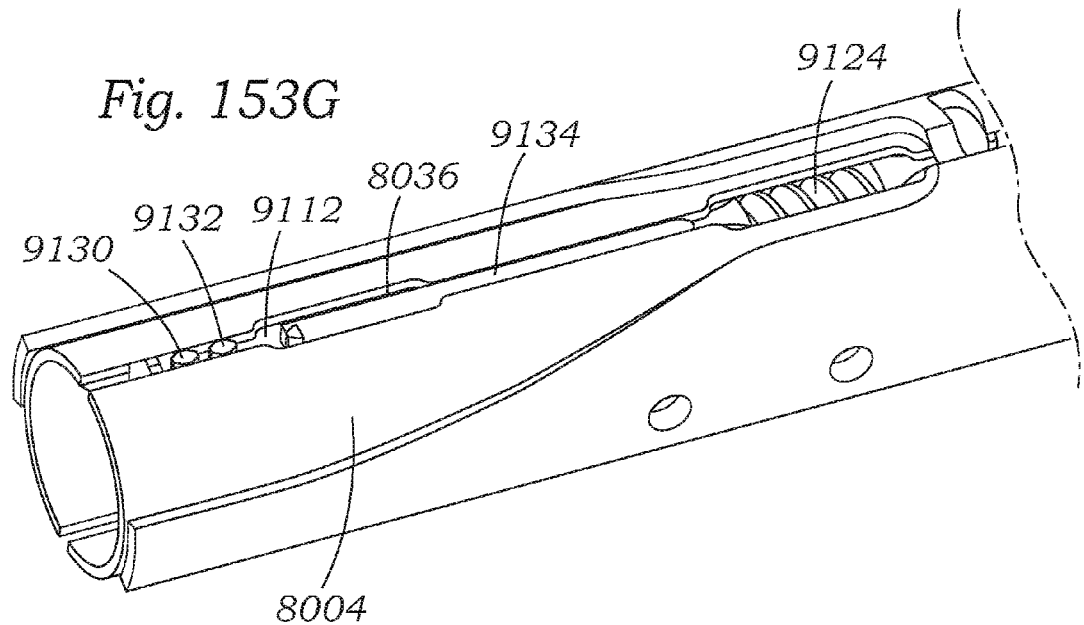

As illustrated in FIG. 153D, the outer portion 9104 can include a central lumen 9140, a pair of distal retaining elements 9110, a pair of distal aligning protrusions 9132 extending radially away from respective retaining elements 9110, a pair of loop-receiving channels 9112, a pair of aligning ridges 9134 (only one is illustrated), a threaded portion 9124, and a locking member 9144 at its proximal end. The inner portion 9102 (e.g., the main body 9138) and the outer portion 9104 (e.g., the locking portion 9144) can include respective central lumen to accommodate the passage of a guidewire lumen and a guidewire passing therethrough. The inner portion 9102, outer portion 9104, and ring 9126 can be formed from various suitable materials, such as one of various suitable plastics or metals. FIG. 153F shows the inner portion 9102, the outer portion 9104, and the ring 9126 in an assembled unit. FIG. 153G shows the harness 9100 situated within the inner shaft 8004.

When the harness 9100 is used in a system such as system 8000, e.g., in place of the support 8022 or the harness 9000, the outer portion 9104 can be axially adjustable but rotationally fixed with respect to the inner portion 9102. For example, the main body 9138 of the inner portion 9102 can have a non-circular cross section configured to be inserted into the lumen 9140 of the outer portion 9104, which can have a matching non-circular cross section. As shown in FIGS. 153A-153B, the inner and outer portions 9102, 9104 can have proximal end portions configured to fit within a distal end portion of the shaft 9106. For example, the threaded portion 9124 of the outer portion 9104 can be configured to engage with complementary threads formed in an interior surface of the shaft 9106, and the locking elements 9128 of the inner portion 9102 can be configured to engage with an annular groove 9136 formed in the interior surface of the shaft 9106.

Assembly of the harness 9100 can begin by threading the outer portion 9104 in a proximal direction completely into the shaft 9106. The inner portion 9102 can then be inserted into the shaft 9106 through the lumen 9140 of the outer portion 9104, until the locking elements 9128 engage with the groove 9136. The main body 9138 of the inner portion 9102 can have a staggered width which decreases from a first width larger than the interior of the shaft to a second width smaller than the interior of the shaft such that the inner portion 9102 cannot be inserted into the shaft 9106 such that the locking portions 9128 are proximal to the groove 9136.

The outer portion 9104 can then be threaded in a distal direction so that it moves distally until the locking portion 9144 is situated between the extensions 9142, preventing the locking elements 9128 coming loose from the groove 9136. The ring 9126 can then be mounted over the outer portion 9104 at a location distal to the threads 9124 and proximal to the ridges 9134. In this configuration, the spacing ring 9126 can prevent the outer portion being threaded far enough in a proximal direction so that the locking portion 9144 no longer engages the extensions 9142.

FIG. 153G shows the assembled harness 9100 situated within the inner sheath 8004, and that the protrusions 9130, 9132, and ridges 9134 can be situated within the slots 8036 of the extended inner sheath 8004. The adjustment shaft 9106 can be actuated (e.g. by a physician using a respective control element at the handle portion 8008) to rotate with respect to the inner and outer sheaths 8004, 8006, and inner and outer portions 9102, 9104. The protrusions 9130, 9132, and ridges 9134 are situated within the slot 8036, restraining the inner and outer portions 9102, 9104 against rotation with respect to the sheath 8004. Thus, as the adjustment shaft rotates, the inner portion 9102 remains stationary, restrained against axial motion by the locking elements 9128 in the groove 9136, and against rotation by the protrusions 9130 in the slot 8036. As the adjustment shaft rotates, the outer portion 9104 is restrained against rotation by the protrusions 9132 and ridges 9134 in the slot 8036, and is caused to translate axially by the engagement of the threads 9124 with the complementary threads formed in the interior surface of the shaft 9106. Thus, actuation of the shaft 9106 can cause axial movement of the outer portion 9104 with respect to the inner portion 9102.

Once the harness 9100 has been assembled, the inner and outer sheaths 8004, 8006 can be retracted to expose the harness 9100, and a prosthetic valve such as valve 8050 can be loaded into the harness 9100 such that a proximal end of the main body 8054 rests against a distal surface of the retaining element 9108 and the loops 8060 extend through the loop-receiving channel 9112. The inner and outer sheaths 8004, 8006 can then be extended over the harness 9100 and the valve 8050 retained thereby. The inner sheath 8004 can extend over the main body 8054 of the valve 8050, while anchors 8052 can be allowed to extend through the slots 8036 in the inner sheath, as explained above. The outer sheath can then be extended over the inner sheath and the anchors 8052, as also explained above.

When the valve 8050 has been loaded in the harness 9100 within the sheath 8004, the loops 8060 pass through the channel 9112 and the anchors 8052 pass through the slots 8036 in the region of the loop-receiving channel 9112 (as best seen in FIG. 153G). In such a configuration, the loops 8060 and anchors 8052 can restrain the inner and outer portions 9102, 9104 against rotation with respect to the inner sheath 8004. Thus, the process of deploying the valve 8050 does not require the protrusions 9130, 9132, or ridges 9134, though they can help by providing additional restraint. These components can also help in restraining the inner and outer portions 9102, 9104 against rotation with respect to the inner sheath 8004 when the valve 8050 is not loaded in the harness 9100, e.g., during demonstrations of the device without the valve 8050, or during the process of loading the valve 8050 into the device 8000.

The harness 9100 can eliminate the need for the anchor spreaders 8012 by allowing a physician to control the expansion and contraction of the anchors 8052 at any stage of delivery after retraction of the outer sheath 8006 and before the valve 8050 is completely released from the device 8000. That is, in one embodiment, the delivery sequence illustrated in FIGS. 147-151 can proceed without use of the anchor spreaders 8012. In order to cause the anchors 8052 to spread radially away from the system 8000 and the main body 8054 of the valve 8050, a physician can actuate the adjustment shaft 9106 to cause the retaining elements 9108, 9110 to move away from each other. The distal end of the inner portion 9102 exerts a distally directed force against the proximal end 8055 of the main body 8054 and the retaining elements 9110 of the outer portion 9104, which is moved in the proximal direction, exert a proximally directed force on the loops 8060 of anchors 8052. This causes the anchors 8052 to flex radially away from the main body 8054. To cause the anchors 8060 to move radially inward toward the system 8000 and the main body 8054, a physician can actuate the adjustment shaft 9106 in the opposite direction, causing the retaining elements 9108, 9110 to move toward one another and thus allowing the anchors to return to positions adjacent the main body 8054 under their own resiliency.

Figure 154:
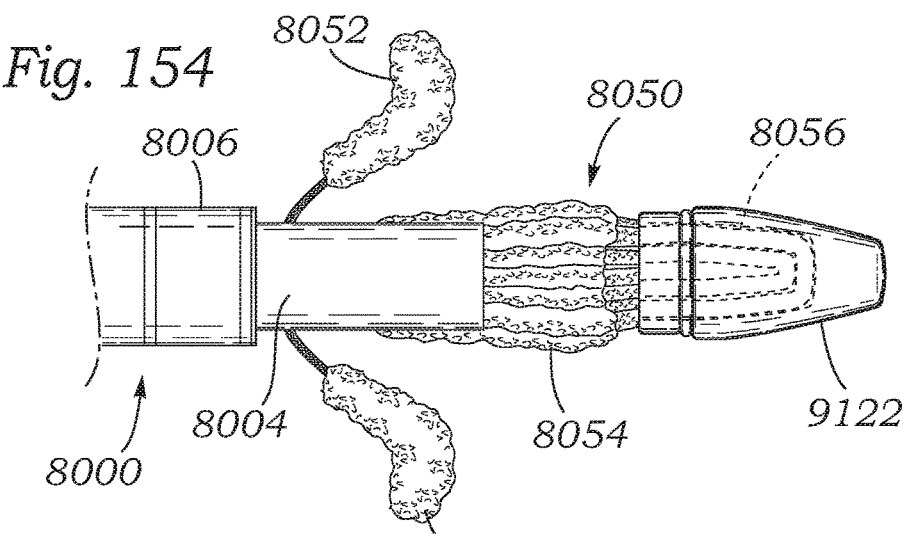
FIGS. 154-156 show an exemplary deployment sequence of a delivery device including the harness device of FIGS. 153A-G.
Figure 155:
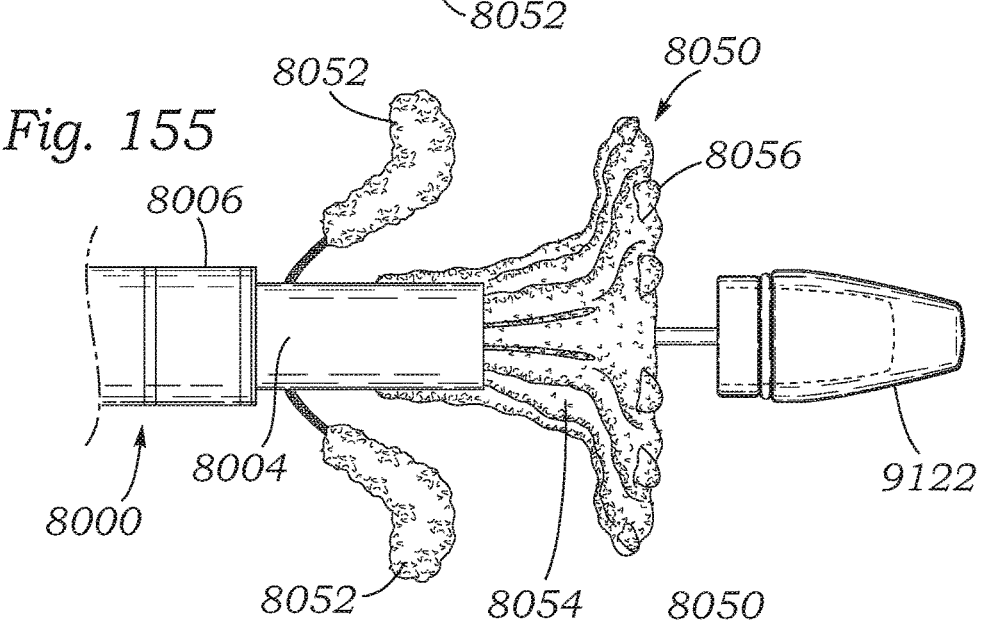
Figure 156:
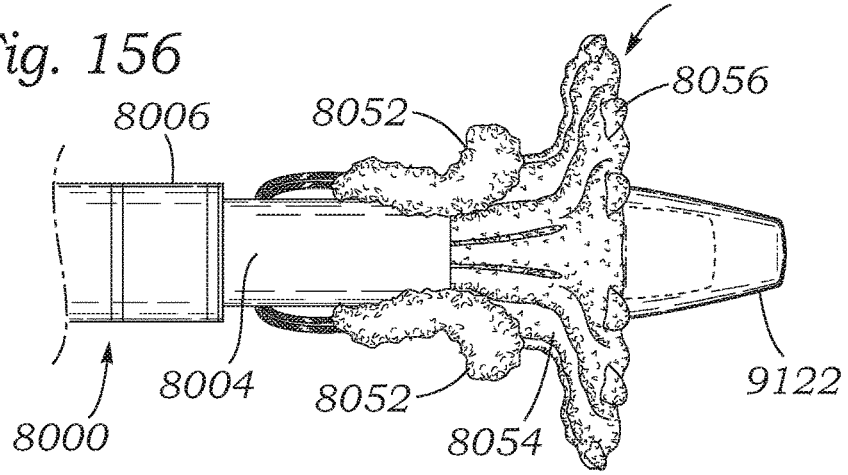

FIGS. 154-156 illustrate a deployment sequence of a valve 8050 from a system similar to system 8000, including harness 9100 and a hollow nosecone 9122. As shown in FIG. 154, the valve 8050 is loaded within the system 8000 with a main body portion 8054 situated within the inner sheath 8004, anchors 8052 situated within the outer sheath 8006, and an atrial portion 8056 situated at least partially within the hollow nosecone 9122. The system 8000 with the valve 8050 can be advanced through various delivery approaches (with appropriate modifications, transeptal, transapical, femoral, aortic, or other approaches can be used) to the region of a native valve of a patient, such as the native mitral valve of a patient. The outer sheath 8006 can then be retracted to allow the anchors 8052 to be expanded by actuation of the harness 9100. In the configuration shown in FIG. 154, the shaft 9106 has been actuated to cause the outer portion 9104 to move proximally relative to the inner portion 9102 (FIG. 153B), which in turn causes the anchors 8052 to expand radially away from the system 8000 and the main body 8054 (as shown in FIG. 154).

Once the anchors 8052 have expanded radially away from the system 8000, the system 8000 and valve 8050 can be advanced through the native mitral valve so that the anchors 8052 are positioned at locations opposite the native mitral valve leaflets from the main body 8054 (at the A2 and P2 positions), and so that the atrial portion 8056 is positioned within the patient's left atrium. As shown in FIG. 155, the nosecone 9122 can then be extended distally away from the rest of the system 8000 and the valve 8050, thereby releasing the atrial portion 8056 and allowing it to expand within the patient's left atrium. As shown in FIG. 156, the shaft 9106 can then be actuated to bring the retaining elements 9108, 9110 toward each other, allowing the anchors to return to their positions adjacent the inner sheath 8004 (against the native leaflets). The inner sheath 8004 can then be retracted proximally until the main body 8054 is completely released but the loops 8060 are still retained by the harness 9100 within the distal end of the inner sheath 8004, at which point, the harness 9100 can be used by a physician to adjust the final placement of the valve 8050 as needed (in a manner similar to that described above with regard to harness 9000 (FIGS. 152D-152E)). Finally, the inner sheath 8004 can be fully retracted proximally until the valve 8050 is completely released from the system 8000. Retracting the inner sheath 8004 proximally past the loops 8060 allows the loops 8060 to expand radially outwardly from the loop-receiving channels 9112, allowing the prosthetic valve 8050 to assume its fully expanded, functional size (as shown in FIG. 151).

In view of the many possible embodiments to which the principles disclosed herein may be applied, it should be recognized that the illustrated embodiments are only preferred examples and should not be taken as limiting the scope of the disclosure. Rather, the scope of the invention is defined by the following claims. We therefore claim as our invention all that comes within the scope and spirit of these claims.

We claim:

1. A prosthetic heart valve comprising:
a radially collapsible and radially expandable frame having a main body, an atrial portion, and at least one ventricular anchor, wherein the main body has an atrial end and a ventricular end, the atrial portion extending radially outwardly relative to the main body and comprising a continuous wire form that extends around the main body, the ventricular anchor extending from the ventricular end of the main body;
wherein the main body and the atrial portion are separate metal components that are coupled to each other via sutures or a fabric member; and
a valve structure having a plurality of leaflets and configured for regulating the flow of blood in one direction through the prosthetic heart valve, wherein the valve structure is supported in the main body of the frame.

2. The prosthetic heart valve of claim 1, wherein the main body and the atrial portion are coupled together by the fabric member.

3. The prosthetic heart valve of claim 2, wherein the fabric member comprises a sealing member that is configured to seal against native tissue surrounding the prosthetic valve upon implantation of the prosthetic valve within a native heart valve of a patient.

4. The prosthetic heart valve of claim 1, wherein the main body and the atrial portion are coupled together by sutures.

5. The prosthetic heart valve of claim 1, wherein the atrial portion is spaced radially outwardly from the main body.

6. The prosthetic heart valve of claim 1, wherein the atrial portion has an axial stiffness, the main body has an axial stiffness, and the axial stiffness of the atrial portion is less than the axial stiffness of the main body.

7. The prosthetic heart valve of claim 1, wherein the atrial portion has a radial stiffness, the main body has a radial stiffness, and the radial stiffness of the atrial portion is less than the radial stiffness of the main body.

8. The prosthetic heart valve of claim 1, wherein the atrial portion is axially spaced from the atrial end of the main body toward the ventricular end of the main body.

9. The prosthetic heart valve of claim 1, wherein the atrial portion comprises a plurality of projections distributed circumferentially around the main body.

10. The prosthetic heart valve of claim 1, wherein the main body has a plurality of interconnected struts that form vertices at connection points, and the projections of the atrial portion extend from respective vertices of the main body.

11. The prosthetic heart valve of claim 1, wherein the wire form comprises a plurality of loops distributed circumferentially around the main body.

12. A prosthetic heart valve comprising:
a collapsible and expandable frame having a first portion and a second portion, wherein the first portion has at least one ventricular anchor and is at least partially disposed radially inwardly relative to the second portion, and the second portion comprises an atrial portion extending radially outwardly away from the first portion;

wherein the first portion and the second portion are separate metal components;

a fabric member covering at least a portion of the second portion of the frame, wherein the first and the second portions of the frame are connected together by the fabric member; and a valve structure having a plurality of leaflets and configured for regulating the flow of blood in one direction through the prosthetic heart valve, wherein the valve structure is coupled to the frame.

13. The prosthetic heart valve of claim 12, wherein the first portion comprises an inflow end and an outflow end, and the second portion is axially spaced from the inflow end of the first portion toward the outflow end of the first portion.

14. The prosthetic heart valve of claim 12, wherein the first portion comprises has a radial stiffness that is greater than a radial stiffness of the atrial portion.

15. The prosthetic heart valve of claim 12, wherein the first portion comprises has an axial stiffness that is greater than an axial stiffness of the atrial portion.

16. The prosthetic heart valve of claim 12, wherein the first portion is an annular main body portion and the valve structure is supported in the main body portion.

17. The prosthetic heart valve of claim 12, wherein the fabric member blocks blood from flowing through openings in the second portion.

18. A prosthetic heart valve comprising:

a collapsible and expandable frame having an annular first portion and a separate, annular second portion, wherein the first portion has at least one ventricular anchor and is at least partially disposed radially inwardly relative to the second portion, and the second portion comprises an atrial portion extending radially outwardly away from the first portion, and wherein the second portion is not directly attached to the first portion;

a fabric member covering at least a portion of the second portion of the frame, wherein the first and the second portions of the frame are coupled to the fabric member; and a valve structure having a plurality of leaflets and configured for regulating the flow of blood in one direction through the prosthetic heart valve, wherein the valve structure is supported in the first portion.

19. The prosthetic heart valve of claim 18, wherein the second portion is more flexible than the first portion.

20. The prosthetic heart valve of claim 18, wherein the frame comprises a gap extending radially between the first and second portions and extending annularly around an inflow end portion of the first portion, and wherein the fabric member extends radially over the gap and to the first and second portions.

* * * * *